US011717539B2

(12) United States Patent
Novik et al.

(10) Patent No.: US 11,717,539 B2
(45) Date of Patent: *Aug. 8, 2023

(54) COMBINATION IMMUNE THERAPY AND CYTOKINE CONTROL THERAPY FOR CANCER TREATMENT

(71) Applicant: Enlivex Therapeutics RDO Ltd, Nez-Ziona (IL)

(72) Inventors: Shai Novik, Ramat Hasharon (IL); Dror Mevorach, Jerusalem (IL)

(73) Assignee: Enlivex Therapeutics RDO Ltd., Nes-Ziona (IL)

( * ) Notice: Subject to any disclaimer, the term of this patent is extended or adjusted under 35 U.S.C. 154(b) by 819 days.

This patent is subject to a terminal disclaimer.

(21) Appl. No.: 16/576,676

(22) Filed: Sep. 19, 2019

(65) Prior Publication Data

US 2020/0009191 A1 Jan. 9, 2020

Related U.S. Application Data

(63) Continuation-in-part of application No. PCT/IL2018/050916, filed on Aug. 20, 2018, which is a continuation of application No. 15/685,086, filed on Aug. 24, 2017, now Pat. No. 11,000,548, which is a continuation-in-part of application No. 15/551,284, filed as application No. PCT/IL2016/050194 on Feb. 18, 2016, now Pat. No. 11,512,289, said application No. 15/685,086 is a continuation-in-part of application No. PCT/IL2017/050196, filed on Feb. 15, 2017, said application No. 15/685,086 is a continuation-in-part of application No. PCT/IL2016/050430, filed on Apr. 21, 2016.

(60) Provisional application No. 62/117,752, filed on Feb. 18, 2015, provisional application No. 62/127,218, filed on Mar. 2, 2015, provisional application No. 62/148,227, filed on Apr. 16, 2015, provisional application No. 62/159,365, filed on May 11, 2015, provisional application No. 62/296,622, filed on Feb. 18, 2016, provisional application No. 62/370,741, filed on Aug. 4, 2016, provisional application No. 62/150,305, filed on Apr. 21, 2015.

(51) Int. Cl.
| | | |
|---|---|---|
| A61K 35/17 | (2015.01) | |
| A61K 45/06 | (2006.01) | |
| A61K 39/00 | (2006.01) | |
| A61K 39/395 | (2006.01) | |
| C07K 16/28 | (2006.01) | |
| C12N 5/0783 | (2010.01) | |

(52) U.S. Cl.
CPC .......... *A61K 35/17* (2013.01); *A61K 39/0011* (2013.01); *A61K 39/39541* (2013.01); *A61K 39/39558* (2013.01); *A61K 45/06* (2013.01); *C07K 16/2887* (2013.01); *C12N 5/0636* (2013.01); *A61K 2039/505* (2013.01); *A61K 2039/5158* (2013.01); *C12N 2501/04* (2013.01); *C12N 2501/91* (2013.01); *C12N 2523/00* (2013.01); *C12N 2529/00* (2013.01)

(58) Field of Classification Search
CPC ................ A61K 35/17; A61K 39/0011; A61K 39/39541; A61K 39/39558; A61K 45/06; A61K 2039/505; A61K 2039/5158; C07K 16/2887; C12N 5/0636; C12N 2501/04; A61P 35/00
USPC ...................................................... 424/133.1
See application file for complete search history.

(56) References Cited

U.S. PATENT DOCUMENTS

| | | | |
|---|---|---|---|
| 4,816,567 | A | 3/1989 | Cabilly et al. |
| 4,956,778 | A | 9/1990 | Naito |
| 5,091,513 | A | 2/1992 | Huston et al. |
| 5,132,405 | A | 7/1992 | Huston et al. |
| 5,906,936 | A | 5/1999 | Eshhar et al. |
| 5,912,172 | A | 6/1999 | Eshhar et al. |
| 7,056,660 | B1 | 6/2006 | Giesing et al. |
| 7,521,197 | B2 | 4/2009 | Savage et al. |

(Continued)

FOREIGN PATENT DOCUMENTS

| | | | |
|---|---|---|---|
| WO | WO 1993/019163 A1 | 9/1993 | |
| WO | WO 1997/015669 A1 | 5/1997 | |

(Continued)

OTHER PUBLICATIONS

Byers, T. (CA Cancer Journal, 1999, 49: 353-361).*

(Continued)

*Primary Examiner* — Yan Xiao
(74) *Attorney, Agent, or Firm* — Mark S. Cohen; Pearl Cohen Zedek Latzer Baratz LLP

(57) ABSTRACT

Compositions disclosed herein, and methods of use thereof included those for inhibiting or reducing the incidence of cytokine release syndrome or cytokine storm in a subject undergoing CAR T-cell therapy, methods of treating a cancer or tumor, methods of reducing tumor load, methods of reducing the size or growth rate of a cancer or a tumor, and methods of extending of the survival of a subject suffering from a cancer or tumor, wherein the subjects are administered compositions comprising apoptotic cells or apoptotic cell supernatants. Compositions and methods of use thereof may increase the efficacy of a CAR T-cell cancer therapy. Disclosed herein are also compositions and methods of use thereof for decreasing or inhibiting cytokine production in a subject experiencing cytokine release syndrome or cytokine storm. In certain instances compositions may include additional chemotherapeutic or immunomodulatory agents.

17 Claims, 48 Drawing Sheets

(56) References Cited

U.S. PATENT DOCUMENTS

| | | | |
|---|---|---|---|
| 7,652,065 B2 | 1/2010 | Albeck et al. | |
| 7,771,715 B2 | 8/2010 | Schlom et al. | |
| 7,772,373 B2 | 8/2010 | Hansen et al. | |
| 7,931,903 B2 | 4/2011 | Hansen et al. | |
| 8,119,101 B2 | 2/2012 | Byrd et al. | |
| 8,147,800 B2 | 4/2012 | Mcbride et al. | |
| 8,211,422 B2 | 7/2012 | Eshhar et al. | |
| 8,268,317 B2 | 9/2012 | Govindan et al. | |
| 8,481,003 B2 | 7/2013 | Griffiths et al. | |
| 8,506,954 B2 | 8/2013 | Strober et al. | |
| 8,834,886 B2 | 9/2014 | Govindan et al. | |
| 8,846,026 B2 | 9/2014 | Plebanski et al. | |
| 8,889,616 B2 | 11/2014 | Peterson et al. | |
| 10,077,426 B2 | 9/2018 | Mevorach et al. | |
| 10,857,181 B2 * | 12/2020 | Mevorach | A61K 35/17 |
| 10,927,343 B2 * | 2/2021 | Mevorach | A61K 31/194 |
| 11,000,548 B2 | 5/2021 | Novik et al. | |
| 11,304,976 B2 | 4/2022 | Novik et al. | |
| 11,318,163 B2 | 5/2022 | Novik et al. | |
| 11,512,289 B2 | 11/2022 | Novik et al. | |
| 2001/0033839 A1 | 10/2001 | Barbera-Guillem | |
| 2002/0044924 A1 | 4/2002 | Bolton et al. | |
| 2002/0137697 A1 | 9/2002 | Eshhar et al. | |
| 2002/0193569 A1 | 12/2002 | Hanna | |
| 2003/0036505 A1 | 2/2003 | Barash et al. | |
| 2003/0207287 A1 | 11/2003 | Short | |
| 2004/0009939 A1 | 1/2004 | Chada et al. | |
| 2004/0018557 A1 | 1/2004 | Qu et al. | |
| 2004/0019195 A1 | 1/2004 | Scholm et al. | |
| 2004/0053348 A1 | 3/2004 | Faris et al. | |
| 2004/0072288 A1 | 4/2004 | Collas et al. | |
| 2004/0083497 A1 | 4/2004 | Raitano et al. | |
| 2004/0115193 A1 | 6/2004 | Hansen et al. | |
| 2004/0192597 A1 | 9/2004 | Raitano et al. | |
| 2004/0202666 A1 | 10/2004 | Griffiths | |
| 2004/0213778 A1 | 10/2004 | Challita-Eid et al. | |
| 2004/0214212 A1 | 10/2004 | Raitano et al. | |
| 2004/0214783 A1 | 10/2004 | Terman et al. | |
| 2004/0219156 A1 | 11/2004 | Goldenberg et al. | |
| 2004/0253245 A1 | 12/2004 | Briend et al. | |
| 2005/0079184 A1 | 4/2005 | Hsing-Chang et al. | |
| 2005/0084913 A1 | 4/2005 | Punnonen et al. | |
| 2005/0113297 A1 | 5/2005 | Francois et al. | |
| 2005/0136435 A1 | 6/2005 | Kanner et al. | |
| 2005/0191311 A1 | 9/2005 | Raitano et al. | |
| 2005/0191312 A1 | 9/2005 | Raitano et al. | |
| 2005/0191313 A1 | 9/2005 | Barbera-Guillem | |
| 2005/0196754 A1 | 9/2005 | Drmanac et al. | |
| 2005/0202098 A1 | 9/2005 | Mevorach | |
| 2005/0276822 A1 | 12/2005 | Wiseman et al. | |
| 2006/0029940 A1 | 2/2006 | Ge et al. | |
| 2006/0052295 A1 | 3/2006 | Terman | |
| 2006/0140936 A1 | 6/2006 | Goldenberg et al. | |
| 2006/0193865 A1 | 8/2006 | Govindan et al. | |
| 2006/0228357 A1 | 10/2006 | Chang et al. | |
| 2007/0059729 A1 | 3/2007 | Faris et al. | |
| 2007/0086942 A1 | 4/2007 | Chang et al. | |
| 2007/0298051 A1 | 12/2007 | Barouch et al. | |
| 2008/0004287 A1 | 1/2008 | Ma et al. | |
| 2008/0081791 A1 | 4/2008 | Huang et al. | |
| 2008/0108794 A1 | 5/2008 | Goldenberg | |
| 2008/0138333 A1 | 6/2008 | Hansen et al. | |
| 2008/0159993 A1 | 7/2008 | Stauss | |
| 2008/0166342 A1 | 7/2008 | Hansen | |
| 2008/0166363 A1 | 7/2008 | Govindan et al. | |
| 2008/0181885 A1 | 7/2008 | Raitano et al. | |
| 2008/0241141 A1 | 10/2008 | Goldenberg | |
| 2008/0241145 A1 | 10/2008 | Goldenberg | |
| 2009/0041804 A1 | 2/2009 | Schlom et al. | |
| 2009/0123467 A1 | 5/2009 | Bedi et al. | |
| 2009/0155166 A1 | 6/2009 | Mcbride et al. | |
| 2009/0162315 A1 | 6/2009 | Terman et al. | |
| 2009/0192114 A1 | 7/2009 | Ovcharenko et al. | |
| 2009/0214550 A1 | 8/2009 | Sahin et al. | |
| 2009/0215895 A1 | 8/2009 | Ferrante et al. | |
| 2009/0298195 A1 | 12/2009 | Ruker et al. | |
| 2010/0015046 A1 | 1/2010 | Govindan et al. | |
| 2010/0040589 A1 | 2/2010 | Spetz-holmgren et al. | |
| 2010/0104589 A1 | 4/2010 | Govindan et al. | |
| 2010/0119511 A1 | 5/2010 | Wang et al. | |
| 2010/0135974 A1 | 6/2010 | Eshhar et al. | |
| 2010/0233251 A1 | 9/2010 | Von et al. | |
| 2010/0266496 A1 | 10/2010 | Hansen et al. | |
| 2010/0266497 A1 | 10/2010 | Hansen et al. | |
| 2010/0272636 A1 | 10/2010 | Byrd et al. | |
| 2011/0008393 A1 | 1/2011 | Kanner et al. | |
| 2011/0027295 A1 | 2/2011 | Powell et al. | |
| 2011/0038869 A1 | 2/2011 | Van Den et al. | |
| 2011/0183870 A1 | 7/2011 | Pan et al. | |
| 2011/0280801 A1 | 11/2011 | Mcbride et al. | |
| 2011/0293513 A1 | 12/2011 | Govindan et al. | |
| 2011/0300156 A1 | 12/2011 | Verploegen et al. | |
| 2011/0311450 A1 | 12/2011 | Levine et al. | |
| 2012/0082725 A1 | 4/2012 | Plebanski | |
| 2012/0093842 A1 | 4/2012 | Eshhar et al. | |
| 2012/0196762 A1 | 8/2012 | Paradis et al. | |
| 2012/0201746 A1 | 8/2012 | Liu et al. | |
| 2012/0219617 A1 | 8/2012 | Peterson et al. | |
| 2012/0328564 A1 | 12/2012 | Govindan et al. | |
| 2013/0039911 A1 | 2/2013 | Bedi et al. | |
| 2013/0045191 A1 | 2/2013 | Weinschenk et al. | |
| 2013/0095034 A1 | 4/2013 | Griffiths et al. | |
| 2013/0101590 A1 | 4/2013 | Arnett et al. | |
| 2013/0136718 A1 | 5/2013 | Chien et al. | |
| 2013/0156794 A1 | 6/2013 | Eshhar et al. | |
| 2013/0171064 A1 | 7/2013 | Hans et al. | |
| 2013/0177498 A1 | 7/2013 | Goldenberg et al. | |
| 2013/0259891 A1 | 10/2013 | Harn et al. | |
| 2013/0280220 A1 | 10/2013 | Ahmed et al. | |
| 2013/0287857 A1 | 10/2013 | Von et al. | |
| 2014/0030273 A1 | 1/2014 | Verploegen et al. | |
| 2014/0050660 A1 | 2/2014 | Chang et al. | |
| 2014/0050709 A1 | 2/2014 | Leen et al. | |
| 2014/0099254 A1 | 4/2014 | Chang et al. | |
| 2014/0099258 A1 | 4/2014 | Govindan et al. | |
| 2014/0099309 A1 | 4/2014 | Powell et al. | |
| 2014/0134265 A1 | 5/2014 | Buggy et al. | |
| 2014/0271582 A1 | 9/2014 | Forman et al. | |
| 2014/0294765 A1 | 10/2014 | Cojocaru et al. | |
| 2014/0336105 A1 | 11/2014 | Shai et al. | |
| 2014/0341917 A1 | 11/2014 | Nastri et al. | |
| 2015/0023937 A1 | 1/2015 | Vera et al. | |
| 2015/0025812 A1 | 1/2015 | Paradis et al. | |
| 2015/0275175 A1 | 10/2015 | Mevorach et al. | |
| 2016/0017048 A1 | 1/2016 | Dotti et al. | |
| 2017/0360836 A1 | 12/2017 | Novik et al. | |
| 2018/0094244 A1 | 4/2018 | Novik et al. | |
| 2018/0104277 A1 | 4/2018 | Mevorach et al. | |
| 2019/0083535 A1 | 3/2019 | Novik et al. | |
| 2019/0175649 A1 | 6/2019 | Novik et al. | |
| 2020/0009191 A1 | 1/2020 | Novik et al. | |
| 2020/0009192 A1 | 1/2020 | Novik et al. | |
| 2020/0061116 A1 | 2/2020 | Novik et al. | |
| 2020/0121718 A1 | 4/2020 | Novik et al. | |
| 2020/0289557 A1 | 9/2020 | Novik et al. | |
| 2021/0038644 A1 | 2/2021 | Mevorach et al. | |
| 2021/0228633 A1 | 7/2021 | Novik et al. | |
| 2022/0133799 A1 | 5/2022 | Novik et al. | |

FOREIGN PATENT DOCUMENTS

| | | | |
|---|---|---|---|
| WO | WO 2000/031239 A1 | 6/2000 | |
| WO | WO 2001/089536 A2 | 11/2001 | |
| WO | WO 2001/089537 A2 | 11/2001 | |
| WO | WO 2001/097844 A1 | 12/2001 | |
| WO | WO 2002/082041 A2 | 10/2002 | |
| WO | WO 2003/029293 A2 | 4/2003 | |
| WO | WO 2003/033654 A2 | 4/2003 | |
| WO | WO 2003/074567 A2 | 9/2003 | |
| WO | WO 2003/074569 A2 | 9/2003 | |
| WO | WO 2004/016734 A2 | 2/2004 | |
| WO | WO 2004/016736 A2 | 2/2004 | |
| WO | WO 2004/016762 A2 | 2/2004 | |
| WO | WO 2004/016799 A2 | 2/2004 | |

(56) References Cited

FOREIGN PATENT DOCUMENTS

| | | |
|---|---|---|
| WO | WO 2004/039412 A2 | 5/2004 |
| WO | WO 2004/058298 A1 | 7/2004 |
| WO | WO 2004/061113 A1 | 7/2004 |
| WO | WO 2004/067038 A1 | 8/2004 |
| WO | WO 2004/067716 A2 | 8/2004 |
| WO | WO 2004/076644 A2 | 9/2004 |
| WO | WO 2004/093808 A2 | 11/2004 |
| WO | WO 2004/098515 A2 | 11/2004 |
| WO | WO 2004/108753 A1 | 12/2004 |
| WO | WO 2005/014618 A2 | 2/2005 |
| WO | WO 2005/014780 A2 | 2/2005 |
| WO | WO 2005/019429 A2 | 3/2005 |
| WO | WO 2005/049852 A2 | 6/2005 |
| WO | WO 2005/052119 A2 | 6/2005 |
| WO | WO 2005/073164 A1 | 8/2005 |
| WO | WO 2005/117846 A2 | 12/2005 |
| WO | WO 2005/123908 A2 | 12/2005 |
| WO | WO 2006/000787 A2 | 1/2006 |
| WO | WO 2006/004620 A2 | 1/2006 |
| WO | WO 2006/022722 A1 | 3/2006 |
| WO | WO 2006/055004 A1 | 5/2006 |
| WO | WO 2006/063150 A2 | 6/2006 |
| WO | WO 2006/072620 A1 | 7/2006 |
| WO | WO 2006/120439 A2 | 11/2006 |
| WO | WO 2006/107617 A2 | 12/2006 |
| WO | WO 2006/135454 A1 | 12/2006 |
| WO | WO 2007/046893 A2 | 4/2007 |
| WO | WO 2008/005268 A1 | 1/2008 |
| WO | WO 2008/056174 A2 | 5/2008 |
| WO | WO 2008/095141 A2 | 8/2008 |
| WO | WO 2008/137901 A2 | 11/2008 |
| WO | WO 2010/070105 A1 | 6/2010 |
| WO | WO 2011/088226 A2 | 7/2011 |
| WO | WO 2011/109440 A1 | 9/2011 |
| WO | WO 2011/109789 A2 | 9/2011 |
| WO | WO 2011/110642 A2 | 9/2011 |
| WO | WO 2011/139629 A2 | 11/2011 |
| WO | WO 2011/140170 A1 | 11/2011 |
| WO | WO 2011/144358 A1 | 11/2011 |
| WO | WO 2011/147986 A1 | 12/2011 |
| WO | WO 2012/024543 A2 | 2/2012 |
| WO | WO 2012/088302 A2 | 6/2012 |
| WO | WO 2012/104344 A1 | 8/2012 |
| WO | WO 2012/115885 A1 | 8/2012 |
| WO | WO 2012/116225 A2 | 8/2012 |
| WO | WO 2012/138858 A1 | 10/2012 |
| WO | WO 2012/174282 A2 | 12/2012 |
| WO | WO 2013/022995 A2 | 2/2013 |
| WO | WO 2013/025972 A1 | 2/2013 |
| WO | WO 2013/079174 A1 | 6/2013 |
| WO | WO 2013/105089 A2 | 7/2013 |
| WO | WO 2013/112801 A1 | 8/2013 |
| WO | WO 2013/130683 A2 | 9/2013 |
| WO | WO 2013/136334 A2 | 9/2013 |
| WO | WO 2013/155375 A1 | 10/2013 |
| WO | WO 2014/011984 A1 | 1/2014 |
| WO | WO 2014/028560 A2 | 2/2014 |
| WO | WO 2014/055657 A1 | 4/2014 |
| WO | WO 2014/071231 A1 | 5/2014 |
| WO | WO 2014/071379 A1 | 5/2014 |
| WO | WO 2014/080251 A1 | 5/2014 |
| WO | WO 2014/082083 A1 | 5/2014 |
| WO | WO 2014/087408 A1 | 6/2014 |
| WO | WO 2014/106666 | 7/2014 |
| WO | WO 2014/068408 A2 | 8/2014 |
| WO | WO 2014/122467 A1 | 8/2014 |
| WO | WO 2014/138704 A1 | 9/2014 |
| WO | WO 2014/144622 A2 | 9/2014 |
| WO | WO 2014/145578 A1 | 9/2014 |
| WO | WO 2014/151085 A1 | 9/2014 |
| WO | WO 2014/153114 A1 | 9/2014 |
| WO | WO 2014/163684 A1 | 10/2014 |
| WO | WO 2014/164554 A1 | 10/2014 |
| WO | WO 2014/172584 A1 | 10/2014 |
| WO | WO 2014/186773 A1 | 11/2014 |
| WO | WO 2014/193999 A2 | 12/2014 |
| WO | WO 2014/197638 A2 | 12/2014 |
| WO | WO 2014/201021 A2 | 12/2014 |
| WO | WO 2015/010096 A1 | 1/2015 |
| WO | WO 2015/089495 A2 | 6/2015 |
| WO | WO 2015/117846 A1 | 8/2015 |
| WO | WO 2016/132366 A1 | 8/2016 |
| WO | WO 2016/170541 | 10/2016 |
| WO | WO 2017/141243 | 8/2017 |

OTHER PUBLICATIONS

Amarilyo et al. "iC3b-opsonized apoptotic cells mediate a distinct anti-inflammatory response and transcriptional NF-κB-dependent blockade." European Journal of Immunology 40(3):699-709, 2010.

Barrett et al. "Treatment of advanced leukemia in mice with mRNA engineered T cells." Human Gene Therapy 22(12) 1575-1586, 2011.

Barrett et al. "Chimeric antigen receptor therapy for cancer." Annual Review of Medicine 65: 333-347, 2014.

Bittencourt et al. "Intravenous injection of apoptotic leukocytes enhances bone marrow engraftment across major histocompatibility barriers" Blood, 98(1), 224-230, 2001.

Brentjens et al. "Eradication of systemic B-cell tumors by genetically targeted human T lymphocytes co-stimulated by CD80 and interleukin-15." Nature Medicine 9(3): 279, 2003.

Brentjens et al. "Genetically targeted T cells eradicate systemic acute lymphoblastic leukemia xenografts." Clinical Cancer Research 13(18): 5426-5435, 2007.

Brentjens et al. "Safety and persistence of adoptively transferred autologous CD19-targeted T cells in patients with relapsed or chemotherapy refractory B-cell leukemias." Blood 118.18: 4817-4828, 2011.

Brentjens et al. "CD19-targeted T cells rapidly induce molecular remissions in adults with chemotherapy-refractory acute lymphoblastic leukemia." Science Translational Medicine 5(177): 138-177, 2013.

Brigham et al. "Rapid communication: In vivo transfection of murine lungs with a functioning prokaryotic gene using a liposome vehicle." The American Journal of the Medical Sciences 298(4): 278-281, 1989.

Brocks et al. "A TNF receptor antagonistic scFv, which is not secreted in mammalian cells, is expressed as a soluble mono-and bivalent scFv derivative in insect cells." Immunotechnology 3(3):173-184, 1997.

Canna et al. "Making sense of the cytokine storm: a conceptual framework for understanding, diagnosing, and treating hemophagocytic syndromes." Pediatric Clinics 59(2): 329-344, 2012.

Cartellieri, M, "Chimeric antigen receptor-engineered T cells for immunotherapy of cancer". Journal of Biomedicine and Biotechnology, Article ID 956304, doi:10.1155/2010/956304, 2010.

Champlin et al. "Selective depletion of CD8+ T lymphocytes for prevention of graft-versus-host disease after allogeneic bone marrow transplantation." Blood 76(2): 418-423, 1990.

Cheadle et al. "Differential role of Th1 and Th2 cytokines in autotoxicity driven by CD19-specific second-generation chimeric antigen receptor T cells in a mouse model." The Journal of Immunology 192(8): 3654-3665, 2014.

Chekmasova et al. "Successful eradication of established peritoneal ovarian tumors in SCID-Beige mice following adoptive transfer of T cells genetically targeted to the MUC16 antigen." Clinical Cancer Research 16(14): 3594-3606, 2010.

Cheng et al. "NK cell-based immunotherapy for malignant diseases." Cellular & Molecular Immunology 10(3): 230, 2013.

Clair et al. "The calm after the cytokine storm: lessons from the TGN1412 trial." The Journal of clinical investigation 118(4): 1344-1347, 2008.

Cooke et al. "An experimental model of idiopathic pneumonia syndrome after bone marrow transplantation: I. The roles of minor H antigens and endotoxin." Blood 88(8): 3230-3239, 1996.

Curran et al. "Chimeric antigen receptors for T cell immunotherapy: current understanding and future directions." The Journal of Gene Medicine 14(6): 405-415, 2012.

(56) References Cited

OTHER PUBLICATIONS

Davila et al. "How do CARs work? Early insights from recent clinical studies targeting CD19." Oncoimmunology 1(9): 1577-1583, 2012.
Davila et al. "CD19 CAR-targeted T cells induce long-term remission and B Cell Aplasia in an immunocompetent mouse model of B cell acute lymphoblastic leukemia." PLOS one 8(4): e61338, 2013.
Davila et al. "Efficacy and toxicity management of 19-28z CAR T cell therapy in B cell acute lymphoblastic leukemia." Science Translational Medicine 6(224): 224-225, 2014.
Essand et al. "Genetically engineered T cells for the treatment of cancer." Journal of Internal Medicine 273(2): 166-181, 2013.
European Search report issued for European Application No. 17752797.5 dated Feb. 5, 2020.
Felgner et al. "Lipofection: a highly efficient, lipid-mediated DNA-transfection procedure." Proceedings of the National Academy of Sciences 84(21): 7413-7417, 1987.
Fife et al. "Inhibition of T cell activation and autoimmune diabetes using a B cell surface-linked CTLA-4 agonist." The Journal of Clinical Investigation 116(8): 2252-2261, 2006.
Gallardo et al. "Low-dose donor CD8+ cells in the CD4-depleted graft prevent allogeneic marrow graft rejection and severe graft-versus-host disease for chronic myeloid leukemia patients in first chronic phase." Bone Marrow Transplantation 20(11): 945, 1997.
Ganss et al. "Combination of T-cell therapy and trigger of inflammation induces remodeling of the vasculature and tumor eradication." Cancer Research 62: 1462-1470, (Mar. 2002).
Giomarelli et al. "Inhibition of thrombin-induced platelet aggregation using human single-chain Fv antibodies specific for TREM-like transcript-1." Thrombosis and Haemostasis 97(06): 955-963, 2007.
Goding, James W. Monoclonal antibodies: principles and practice. Elsevier, pp. 59-103, 1996.
Gong et al. "Cancer patient T cells genetically targeted to prostate-specific membrane antigen specifically lyse prostate cancer cells and release cytokines in response to prostate-specific membrane antigen." Neoplasia 1(2): 123-127, 1999.
Grau et al. "Apoptotic cells induce NF-κB and inflammasome negative signaling." PloS one 10(3): e0122440, 2015.
Haji-Fatahaliha et al. "CAR-modified T-cell therapy for cancer: an updated review." Artificial Cells, Nanomedicine, and Biotechnology 44(6): 1339-1349,2016.
Han et al. "Chimeric antigen receptor-engineered T cells for cancer immunotherapy: progress and challenges." Journal of Hematology & Oncology 69(47), 2013.
Ho et al. "Inhibition of cocaine binding to the human dopamine transporter by a single chain anti-idiotypic antibody: its cloning, expression, and functional properties." Biochimica et Biophysica Acta (BBA)-Molecular Basis of Disease 1638(3): 257-266, 2003.
Hoffman et al. "Mutation of a new gene encoding a putative pyrin-like protein causes familial cold autoinflammatory syndrome and Muckle-Wells syndrome." Nature genetics 29.3: 301, 2001.
Huston et al. "Protein engineering of antibody binding sites: recovery of specific activity in an anti-digoxin single-chain Fv analogue produced in *Escherichia coli*." Proceedings of the National Academy of Sciences 85(16): 5879-5883, 1988.
Inoue et al. "Dose dependent effect of anti-CTLA-4 on survival in sepsis" Shock (Augusta, Ga.). Jul. 2011;36(1):38.
International Search Report and Written opinion issued for International Application No. PCT/IL2016/050194 dated May 18, 2016.
International Search Report and Written opinion issued for International Application No. PCT/IL2017/050196 dated Jun. 11, 2017.
International Search Report and Written opinion issued for International Application No. PCT/IL2016/050430 dated Jul. 13, 2016.
International Search Report and Written opinion issued for International Application No. PCT/IL2019/051250 dated Jul. Mar. 26, 2020.
Jagasia et al. "National Institutes of Health consensus development project on criteria for clinical trials in chronic graft-versus-host disease: I. The 2014 Diagnosis and Staging Working Group report." Biology of Blood and Marrow Transplantation 21(3): 389-401, 2015.
Jensen et al. "Design and implementation of adoptive therapy with chimeric antigen receptor-modified T cells." Immunological Reviews 257(1): 127-144, 2014.
Kalinski, Pawel. "Regulation of immune responses by prostaglandin E2." The Journal of Immunology 188(1): 21-28, 2012.
Karlsson et al. "Combining CAR T cells and the Bcl-2 family apoptosis inhibitor ABT-737 for treating B-cell malignancy." Cancer Gene Therapy 20(7): 386, 2013.
Kobayashi et al. "A chimeric antigen receptor for TRAIL-receptor 1 induces apoptosis in various types of tumor cells." Biochemical and Biophysical Research Communications 453(4): 798-803, 2014.
Kobayashi Y. "The regulatory role of nitric oxide in proinflammatory cytokine expression during the induction and resolution of inflammation" Journal of leukocyte biology. Dec. 2010;88(6):1157-62.
Kochenderfer et al. "B-cell depletion and remissions of malignancy along with cytokine-associated toxicity in a clinical trial of anti-CD19 chimeric-antigen-receptor-transduced T cells." Blood 119(12): 2709-2720, 2012.
Köhler et al. "Continuous cultures of fused cells secreting antibody of predefined specificity." Nature 256 (5517): 495, 1975.
Krispin et al. "Apoptotic cell thrombospondin-1 and heparin-binding domain lead to dendritic-cell phagocytic and tolerizing states" Blood 108: 3580-3589, 2006.
Ledbetter et al. "Agonistic activity of a CD40-specific single-chain Fv constructed from the variable regions of mAb G28-5." Critical Reviews in Immunology 17.5-6: 427-435, 1997. Abstract only.
Lee et al. "Current concepts in the diagnosis and management of cytokine release syndrome." Blood 124, pp. 188-195, 2014.
Levy et al. "The surviving sepsis campaign bundle: 2018 update" Intensive care medicine. Jun. 1, 2018;44(6):925-8.
Magenau et al. "Next generation treatment of acute graft-versus-host disease." Leukemia 28 (12): 2283, 2014.
Maldarelli, Frank, et al. "Specific HIV integration sites are linked to clonal expansion and persistence of infected cells." Science vol. 345 Issue 6193: 179-183, 2014.
Malinin TI. "Injury of human polymorphonuclear granulocytes frozen in the presence of cryoprotective agents" Cryobiology. Apr. 1, 1972;9(2):123-30.
Marcondes et al. "α-1-Antitrypsin (AAT)-modified donor cells suppress GVHD but enhance the GVL effect: a role for mitochondrial bioenergetics." Blood 124 (18): 2881-2891, 2014.
Martínez et al. "Graft-versus-host disease therapy: something else beyond glucocorticoids?" Haematologica, Journal of the Ferrata Stori Foundation, vol. 96, Issue 9:1249-1251, 2011.
Maude et al. "Managing cytokine release syndrome associated with novel T cell-engaging therapies." Cancer Journal (Sudbury, Mass.) 20 (2): 119, 2014.
McClain et al. "Clinical features and diagnosis of hemophagocytic lymphohistiocytosis." UpToDate p. 1-22, 2016. https://www.uptodate.com/contents/clinical-features-and-diagnosis-of-hemophagocytic-lymphohistiocytosis.
Mevorach et al. "Single infusion of donor mononuclear early apoptotic cells as prophylaxis for graft-versus-host disease in myeloablative HLA-matched allogeneic bone marrow transplantation: a phase I/IIa clinical trial." Biology of Blood and Marrow Transplantation 20 (1): 58-65, 2014.
Mevorach et al. "Early Apoptotic Cells (ApoCell) as Prophylaxis of Graft-Versus-Host Disease is Safe and Effective: 1 Year Follow-up and Mechanism of Action." Biology of Blood and Marrow Transplantation 21 (2): S339-S340, 2015.
Mevorach et al., Apoptotic Cells for the Prevention of Cytokine Release Syndrome (CRS) in CAR T-Cell Therapy, Blood 128:1626, 2016.
Mevorach, Dror "Inflammation and Immunity—Friends or Foes? Synergism between human apoptotic cell infusion and human chimeric antigen receptor (CAR)-T therapy in fighting solid human tumor in SCID Bg mice" The joint meeting of the Israeli Immunological Society (IIS) and the Israel Society for Cancer Research (ISCR) Sep. 23, 2019 at the Dan Panorama Hotel, Israel; p. 144.

(56) References Cited

OTHER PUBLICATIONS

Moosmayer et al. "A single-chain TNF receptor antagonist is an effective inhibitor of TNF mediated cytotoxicity." Therapeutic Immunology 2 (1): 31-40, 1995.
Munson et al. "Ligand: A versatile computerized approach for characterization of ligand-binding systems", Analytical Biochemistry, vol. 107, Issue1 pp. 220-239, Sep. 1980.
Nelson J. Lee. "The Otherness of Self: Microchimerism in Heath and Disease", Trends in Immunology, vol. 33, Issue 8, pp. 421-427, Aug. 2012.
Neven et al. "Cryopyrinopathies: update on pathogenesis and treatment." Nature Reviews Rheumatology 4 (9): 481, 2008.
Ono et al. "Plasmid DNAs directly injected into mouse brain with lipofectin can be incorporated and expressed by brain cells." Neuroscience Letters 117 (3): 259-263, 1990.
Peter et al. "scFv single chain antibody variable fragment as inverse agonist of the β2-adrenergic receptor." Journal of Biological Chemistry 278 (38): 36740-36747, 2003.
Peter et al. "Protective effects of an anti-melanocortin-4 receptor scFv derivative in lipopo lysaccharide-induced cachexia in rats." Journal of Cachexia, Sarcopenia and Muscle 4(1): 79-88, 2013.
Poon et al. "Apoptotic cell clearance: basic biology and therapeutic potential." Nature Reviews Immunology 14(3): 166, 2014.
Pupjalis et al. "Annexin A1 released from apoptotic cells acts through formyl peptide receptors to dampen inflammatory monocyte activation via JAK/STAT/SOCS signaling." EMBO Molecular Medicine 3(2): 102-114, 2011.
Ren Y. et al., "Apoptotic Cells Protect Mice against Lipopolysaccharide-Induced Shock", The Journal of Immunology, J Immunol Apr. 1, 180 (7) 4978-4985, 2008.
Rhodes et al. "Surviving sepsis campaign: international guidelines for management of sepsis and septic shock: 2016" Intensive care medicine. Mar. 1, 2017;43(3):304-77.
Ruella et al. "Treatment of leukemia antigen-loss relapses occurring after CD19-targeted immunotherapies by combination of anti-CD123 and anti-CD19 chimeric antigen receptor T cells" Journal for ImmunoTherapy of Cancer. Dec. 1, 2015;3(S2):O5.
Saas et al. "Prospects of apoptotic cell-based therapies for transplantation and inflammatory diseases" Immunotherapy, 5(10), 1055-1073, 2013.
Sadelain et al. "The basic principles of chimeric antigen receptor design" Cancer Discovery 3(4): pp. 388-398, 2013.
Sharpe et al. "Genetically modified T cells in cancer therapy: opportunities and challenges." Disease Models & Mechanisms 8 (4): 337-350, 2015.
Shieh et al. "Transgenic expression of single-chain anti-CTLA-4 Fv on β cells protects nonobese diabetic mice from autoimmune diabetes." The Journal of Immunology 183 (4): 2277-2285, 2009.
Shrum et al. "A robust scoring system to evaluate sepsis severity in an animal model" BMC research notes, 7(1), 233, 2014.
Stebbings, R. et al. "After TGN1412: recent developments in cytokine release assays." Journal of Immunotoxicology 10 (1): 75-82, 2013.
Supplementary European Search Report issued for European Application No. 16752041 dated Jun. 14, 2018.
Supplementary European Search Report issued for EP 16782737 dated Oct. 15, 2018.
Supplementary European search report issued for EP Application No. 17752797.5 dated Oct. 10, 2019.
Tarrant et al. "Blood cytokines as biomarkers of in vivo toxicity in preclinical safety assessment: considerations for their use." Toxicological Sciences 117 (2): 4-16, 2010.
Tawara, Isao et al. "Alpha-1-antitrypsin monotherapy reduces graft-versus-host disease after experimental allogeneic bone marrow transplantation." Proceedings of the National Academy of Sciences 109 (2): 564-569, 2012.
Teachey et al. "Cytokine release syndrome after blinatumomab treatment related to abnormal macrophage activation and ameliorated with cytokine-directed therapy." Blood 121(26): 5154-5157, 2013.
Themeli et al. "New cell sources for T cell engineering and adoptive immunotherapy." Cell stem cell 16(4): 357-366, 2015.
Tisoncik et al. "Into the eye of the cytokine storm" Microbiology and Molecular Biology Reviews. Mar. 1, 2012;76(1):16-32.
Tschopp et al. "NALPs: a novel protein family involved in inflammation." Nature reviews Molecular cell biology 4 (2): 95,2003.
Verbovetski et al. "Opsonization of apoptotic cells by autologous iC3b facilitates clearance by immature dendritic cells, down-regulates DR and CD86, and up-regulates CC chemokine receptor 7." Journal of Experimental Medicine 196 (12): 1553-1561, 2002.
Van Der Stegen et al. "Preclinical in vivo modeling of cytokine release syndrome induced by ErbB-retargeted human T cells: identifying a window of therapeutic opportunity?" The Journal of Immunology 191(9): 4589-4598, 2013.
Van Der Stegen et al. "The pharmacology of second-generation chimeric antigen receptors." Nature reviews Drug discovery 14 (7): 499, 2015.
Wagner et al. "Proliferation of cells with HIV integrated into cancer genes contributes to persistent infection." Science 345.6196: 570-573, 2014.
Wahl et al. "Improved radioimaging and tumor localization with monoclonal F(ab')2", Journal of Nuclear Medicine: Official Publication, Society of Nuclear Medicine, 24(4): 316-325, Apr. 1983.
Wahl et al. "Molecular Hybridization of Immobilized Nucleic Acids: Theoretical Concepts and Practical Considerations", Methods in Enzymology, vol. 152, pp. 399-407, 1987.
Wilkie et al. "Selective Expansion of Chimeric Antigen Receptor-targeted T-cells with Potent Effector Function using Interleukin-4", The Journal of Biological Chemistry, 285, 25538-25544, 2010.
Wilkie et al. "Retargeting of human T cells to tumor-associated MUC1: the evolution of a chimeric antigen receptor." The Journal of Immunology 180(7): 4901-4909, 2008.
Wolff et al., "Direct gene transfer into mouse muscle in vivo", Science Mar. 1990: vol. 247, Issue 4949, pp. 1465-1468.
Wu et al. "Targeting genes: delivery and persistent expression of a foreign gene driven by mammalian regulatory elements in vivo" Journal of Biological Chemistry, vol. 264, 16985-16987, 1989.
Wu et al., "Receptor-mediated gene delivery and expression in vivo" Journal of Biological Chemistry, vol. 263: 14621-14624, 1988.
Xu et al. "Cytokine release syndrome in cancer immunotherapy with chimeric antigen receptor engineered T cells." Cancer letters 343 (2): 172-178, 2014.
Zhao et al., "Characteristics of an scFv Antibody Fragment That Binds to Immunoglobulin G of Graves' Disease Patients and Inhibits Autoantibody-Mediated Thyroid-Stimulating Activity" Hybridoma vol. 27 Issue 6: Dec. 2008.
Henson et al. "Antiinflammatory effects of apoptotic cells" The Journal of Clinical Investigation. Jul. 1, 2013;123(7):2773-4.
Bonini et al. "Adoptive T-cell therapy for cancer: The era of engineered T cells"European journal of immunology. Sep. 2015;45(9):2457-69.
Butterfield LH. "Cancer vaccines" Bmj. Apr. 22, 2015;350.
European Search Report for European Application No. 21164060.2 dated Jun. 5, 2021.
Griffith et al. "Cell death in the maintenance and abrogation of tolerance: the five Ws of dying cells" Immunity. Oct. 28, 2011;35(4):456-66.
Higuchi et al. "CTLA-4 blockade synergizes therapeutically with PARP inhibition in BRCA1-deficient ovarian cancer" Cancer immunology research. Nov. 1, 2015;3(11):1257-68.
Iagăru et al. "Macrophage Activation Syndrome in Two Girls with Systemic Lupus Erythematosus" Therapeutics, Pharmacology & Clinical Toxicology. Sep. 1, 2010;14(3).
International Search Report for PCT Application No. PCT/IL2020/051011 dated Mar. 24, 2021.
Lorusso et al. "Accelerating cancer therapy development: the importance of combination strategies and collaboration. Summary of an Institute of Medicine workshop" Clinical Cancer Research. Nov. 15, 2012;18(22):6101-9.
Mohebtash et al. "Therapeutic prostate cancer vaccines: a review of the latest developments" Current opinion in investigational drugs (London, England: 2000). Dec. 2008;9(12):1296.

(56) References Cited

OTHER PUBLICATIONS

Morelli et al. "Apoptotic cell-based therapies against transplant rejection: role of recipient's dendritic cells" Apoptosis. Sep. 2010;15(9):1083-97.
Murthy et al. "Cytokine release syndrome: current perspectives" ImmunoTargets and therapy. 2019;8:43.
Saas et al. "Intravenous apoptotic cell infusion as a cell-based therapy toward improving hematopoietic cell transplantation outcome" Annals of the New York Academy of Sciences. Oct. 2010;1209(1):118-26.
Supplementary European Search Report for European Patent Application No. 18848045.3 dated Apr. 19, 2021.
Tagliamonte et al. "Antigen-specific vaccines for cancer treatment" Human vaccines & immunotherapeutics. Nov. 2 2014;10(11):3332-46.
Voll et al. "Immunosuppressive effects of apoptotic cells" Nature. Nov. 1997;390(6658):350-1.
Wang et al. "Use of the inhibitory effect of apoptotic cells on dendritic cells for graft survival via T-cell deletion and regulatory T cells" American Journal of Transplantation. Jun. 2006;6(6):1297-311.
Wolchok et al. "Nivolumab plus ipilimumab in advanced melanoma" N Engl J Med. Jul. 11, 2013:369:122-33.
Wood et al. "Understanding stem cell immunogenicity in therapeutic applications" Trends in immunology. Jan. 1, 2016;37(1):5-16.
Yang et al. "Challenges and opportunities of allogeneic donor-derived CAR T cells" Current opinion in hematology. Nov. 2015;22(6):509.
Qi et al. "Research Progress in Apoptosis and Tumor Microenvironment" Medical Recapitulate 2017 22 4433-4442. Abstract.
Sun et al. "Effects of apoptotic colorectal cancer CT26 cells on serum levels of immunological factor" Guangxi Medical Journal 2016 10:1337-1342. Abstract.

* cited by examiner

COMBINATION IMMUNE THERAPY AND CYTOKINE CONTROL THERAPY FOR CANCER TREATMENT

CROSS-REFERENCE TO RELATED APPLICATIONS

This application is a Continuation in Part of PCT International Application No. PCT/IL2018/050916, filed Aug. 20, 2018, which claims the priority of U.S. application Ser. No. 15/685,086, filed Aug. 24, 2017; and this application is a Continuation in Part of U.S. application Ser. No. 15/685,086, filed Aug. 24, 2017 which is a Continuation in Part of U.S. application Ser. No. 15/551,284, which is a National Filing of PCT International Application No. PCT/IL2016/050194, filed Feb. 18, 2016, which claims benefit of U.S. Provisional Applications Nos. 62/117,752, filed Feb. 18, 2015, 62/127,218, filed Mar. 2, 2015, 62/148,227, filed Apr. 15, 2016 and 62/159,365, filed May 11, 2015; U.S. application Ser. No. 15/685,086, filed Aug. 24, 2017 is a Continuation in Part of PCT International Application No. PCT/IL2017/050196, filed Feb. 15, 2017, which claims benefit of U.S. Provisional Applications Nos. 62/296,622, filed Feb. 18, 2016 and 63/370,741, filed Aug. 4, 2016; and U.S. application Ser. No. 15/685,086, filed Aug. 24, 2017 is a Continuation in Part of PCT International Application No. PCT/IL2016/050430, filed Apr. 21, 2016, which claims benefit of U.S. Provisional Application No. 62/150,305, filed Apr. 21, 2015; which are all hereby incorporated by reference in their entirety.

FIELD OF INTEREST

Disclosed herein are compositions and methods thereof for inhibiting or reducing the incidence of cytokine release syndrome (CRS) or a cytokine storm in a subject undergoing CAR T-cell cancer therapy. Further, disclosed herein are compositions and methods thereof for decreasing or inhibiting cytokine production in a subject experiencing cytokine release syndrome or a cytokine storm. Further, compositions disclosed herein may be used for treating, preventing, inhibiting the growth of, or reducing the incidence of, a cancer or a tumor in a subject. Compositions may be used for increasing survival of a subject suffering from a cancer or a tumor. Compositions used may be administered alone or in combination with other chemotherapies. Methods disclosed herein include those comprising administration of a composition comprising apoptotic cells or an apoptotic cell supernatant alone or in combination with a CAR T-cell therapy.

BACKGROUND

While standard treatments for cancer are surgery, chemotherapy, and radiation therapy, improved methods, such as targeted immunological therapies, are currently being developed and tested. One promising technique uses adoptive cell transfer (ACT), in which immune cells are modified to recognize and attack their tumors. One example of ACT is when a patient's own cytotoxic T-cells, or a donor's, are engineered to express a chimeric antigen receptor (CAR T-cells) targeted to a tumor specific antigen expressed on the surface of the tumor cells. These CAR T-cells are then cytotoxic only to cells expressing the tumor specific antigen. Clinical trials have shown that CAR T-cell therapy has great potential in controlling advanced acute lymphoblastic leukemia (ALL) and lymphoma, among others.

However, some patients given CAR T-cell therapy and other immune therapies experience a dangerous and sometimes life-threatening side effect called cytokine release syndrome (CRS), in which the infused, activated T-cells produce a systemic inflammatory response in which there is a rapid and massive release of cytokines into the bloodstream, leading to dangerously low blood pressure, high fever and shivering.

In severe cases of CRS, patients experience a cytokine storm (a.k.a. cytokine cascade or hypercytokinemia), in which there is a positive feedback loop between cytokines and white blood cells with highly elevated levels of cytokines. This can lead to potentially life-threatening complications including cardiac dysfunction, adult respiratory distress syndrome, neurologic toxicity, renal and/or hepatic failure, pulmonary edema and disseminated intravascular coagulation.

For example, six patients in a recent phase I trial who were administered the monoclonal antibody TGN1412, which binds to the CD28 receptor on T-cells, exhibited severe cases of cytokine storm and multi-organ failure. This happened despite the fact that the TGN1412 dose was 500-times lower than that found to be safe in animals (St. Clair E W: The calm after the cytokine storm: Lessons from the TGN1412 trial. J Clin Invest 118: 1344-1347, 2008).

To date, corticosteroids, biological therapies such as anti-IL6 therapies and anti-inflammatory drugs are being evaluated to control cytokine release syndrome in patients administered CAR T-cell therapy. However, steroids may affect CAR T-cells' activity and/or proliferation and put the patients in danger of sepsis and opportunistic infections. Anti-inflammatory drugs may not be effective in controlling cytokine release syndromes or cytokine storms, because the cytokine storm includes a very large number of cytokines while there is limited ability to infuse patients with anti-inflammatory drugs. Novel strategies are needed to control cytokine release syndromes, and especially cytokine storms, in order to realize the potential of CAR T-cell therapy.

Cytokine storms are also a problem after other infectious and non-infectious stimuli. In a cytokine storm, numerous proinflammatory cytokines, such as interleukin-1 (IL-1), IL-6, g-interferon (g-IFN), and tumor necrosis factor-α (TNFα), are released, resulting in hypotension, hemorrhage, and, ultimately, multiorgan failure. The relatively high death rate in young people, with presumably healthy immune systems, in the 1918 H1N1 influenza pandemic and the more recent bird flu H5N1 infection are attributed to cytokine storms. This syndrome has been also known to occur in advanced or terminal cases of severe acute respiratory syndrome (SARS), Epstein-Barr virus-associated hemophagocytic lymphohistiocytosis, gram-negative sepsis, malaria and numerous other infectious diseases, including Ebola infection.

Cytokine storm may also stem from non-infectious causes, such as acute pancreatitis, severe burns or trauma, or acute respiratory distress syndrome. Novel strategies are therefore needed to control cytokine release syndrome, and especially cytokine storms.

Cancer is an abnormal state in which uncontrolled proliferation of one or more cell populations interferes with normal biological functioning. The proliferative changes are usually accompanied by other changes in cellular properties, including reversion to a less differentiated, more developmentally primitive state. The in vitro correlate of cancer is called cellular transformation. Transformed cells generally display several or all of the following properties: spherical morphology, expression of fetal antigens, growth-factor independence, lack of contact inhibition, anchorage-independence, and growth to high density.

The primary cause of lethality of malignant diseases such as lung and skin cancer arises from metastatic spread. In many cases, it is not possible to prevent the onset of metastatic disease since cancers are often metastatic by the time of diagnosis, and even in cases where cancers are diagnosed prior to this stage, complete surgical removal or destruction of primary lesion tissues which are capable of eventually generating metastases may not be feasible. Metastatic disease may be impossible to diagnose at early stages due to the small size of metastatic lesions, and/or the absence of reliable markers in primary lesions upon which to reliably predict their existence. Such lesions may be difficult or impossible to treat via ablative methods due to their being inaccessible, disseminated, and/or poorly localized. Chemotherapy/radiotherapy, the current methods of choice for treatment of certain metastatic malignancies are often ineffective or suboptimally effective, and have the significant disadvantage of being associated with particularly harmful and/or potentially lethal side-effects.

Immunotherapeutic cancer treatment methods, such as those involving antigen presenting cell (APC) vaccinations, have the potential to be optimally effective for treatment of inaccessible, disseminated, microscopic, recurrent and/or poorly localized cancer lesions. One promising immunotherapy avenue involves the use of professional APCs, such as dendritic cells (DCs), to elicit systemic anti-cancer immunity.

Dendritic cells are antigen-producing and presenting cells of the mammalian immune system that process antigen material and present it on the cell surface to the T-cells of the immune system and are thereby capable of sensitizing T-cells to both new and recall antigens. DCs are the most potent antigen-producing cells, acting as messengers between the innate and the adaptive immune systems. DC cells may be used, to prime specific antitumor immunity through the generation of effector cells that attack and lyse tumors.

Apoptotic cells present one pathway of physiological cell death, most commonly occurring via apoptosis, which elicits a series of molecular homeostatic mechanisms comprising recognition, an immune response and a removal processes. Moreover, apoptotic cells are immunomodulatory cells capable of directly and indirectly inducing immune tolerance to dendritic cells and macrophages. Apoptotic cells have been shown to modulate dendritic cells and macrophages and to render them tolerogenic and inhibit proinflammatory activities such as secretion of proinflammatory cytokines and expression of costimulatory molecules.

There remains an unmet need for compositions and methods for treating, preventing, inhibiting the growth of, or reducing the incidence of, a cancer or a tumor in a subject. The apoptotic cell preparations, compositions and uses thereof, described herein below, address this need by providing a population of early apoptotic cells that may be used to treat, prevent, inhibit the growth or, or reduce the incidence of a cancer or tumor in a subject. Further, the methods of use described herein address the need to increasing survival of a subject suffering from a cancer and tumor, including increasing remission of the cancer or tumor.

SUMMARY

In one aspect disclosed herein is a method of treating, preventing, inhibiting the growth of, delaying disease progression, reducing the tumor load, or reducing the incidence of a cancer or a tumor in a subject, or any combination thereof, comprising a step of administering a composition comprising an early apoptotic cell population to said subject, wherein said method treats, prevents, inhibits the growth of, delays the disease progression, reduces the tumor load, or reduces the incidence of the cancer or a tumor in said subject, or any combination thereof, compared with a subject not administered the early apoptotic cell population.

In a related aspect, the size or the growth rate, or a combination thereof, of said cancer or tumor is reduced. In another related aspect, the survival of said subject is increased.

In a related aspect, the early apoptotic cell population comprises a mononuclear enriched cell population, or an apoptotic population stable for greater than 24 hours, or an apoptotic population devoid of cell aggregates, or an apoptotic population irradiated following apoptotic induction, or any combination thereof. In another related aspect, the early apoptotic cell population comprises a pooled population of early apoptotic cells.

In a related aspect, the subject is a human subject.

In a related aspect, the cancer or tumor comprises a solid tumor or non-solid tumor. In another related aspect, the non-solid cancer or tumor comprises a hematopoietic malignancy, a blood cell cancer, a leukemia, a myelodysplastic syndrome, a lymphoma, a multiple myeloma (a plasma cell myeloma), an acute lymphoblastic leukemia, an acute myelogenous leukemia, a chronic myelogenous leukemia, a Hodgkin lymphoma, a non-Hodgkin lymphoma, or plasma cell leukemia. In another related aspect, the solid tumor comprises a sarcoma or a carcinoma, a fibrosarcoma, a myxosarcoma, a liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, an Ewing's tumor, a leiomyosarcoma, a rhabdomyosarcoma, a colon carcinoma, a pancreatic cancer or tumor, a breast cancer or tumor, an ovarian cancer or tumor, a prostate cancer or tumor, a squamous cell carcinoma, a basal cell carcinoma, an adenocarcinoma, a sweat gland carcinoma, a sebaceous gland carcinoma, a papillary carcinoma, a papillary adenocarcinomas, a cystadenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilm's tumor, a cervical cancer or tumor, a uterine cancer or tumor, a testicular cancer or tumor, a lung carcinoma, a small cell lung carcinoma, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodenroglioma, a schwannoma, a meningioma, a melanoma, a neuroblastoma, or a retinoblastoma. In another related aspect, the tumor or cancer comprises a metastasis of a tumor or cancer.

In a related aspect, the administering comprises a single infusion of said early apoptotic cell population. In another related aspect, the administering comprises multiple infusions of said apoptotic cell population. In another related aspect, the method further comprises administering an additional immune therapy, a chemotherapeutic agent, or an immune modulator to said subject, or any combination thereof. In another related aspect, the additional immune therapy, a chemotherapeutic agent, or an immune modulator is administered prior to, concurrent with, or following administration of said early apoptotic cells. In another related aspect, the immune therapy comprises administration of CAR T-cells. In another related aspect, the immune modulator comprises an antibody or a functional fragment thereof. In another related aspect, the antibody or functional fragment thereof comprises a rituximab (RtX) antibody or functional fragment thereof.

In a related aspect, the method increases the efficacy of said CAR T-cells, compared with a subject administered CAR T-cells and not administered early apoptotic cells In a related aspect, the method comprises a first-line therapy.

In a related aspect, the method comprises an adjuvant therapy.

In a related aspect, the method reduces the minimal residual disease, increases remission, increases remission duration, reduces tumor relapse rate, prevents metastasis of said tumor or said cancer, or reduces the rate of metastasis of said tumor or said cancer, or any combination thereof.

In one aspect, disclosed herein is a population of mononuclear apoptotic cell comprising mononuclear cells in an early-apoptotic state, wherein said mononuclear apoptotic cell population comprises: a decreased percent of non-quiescent non-apoptotic viable cells; a suppressed cellular activation of any living non-apoptotic cells; or a reduced proliferation of any living non-apoptotic cells; or any combination thereof.

In a related aspect, the decreased percent of non-quiescent non-apoptotic viable cells is less than 10%. In another related aspect, the mononuclear apoptotic cell population comprises no viable non-apoptotic cells.

In a related aspect, the mononuclear cell population is selected from the group consisting of: lymphocytes, monocytes, dendritic cells, and natural killer cells.

In a related aspect, the population of mononuclear apoptotic cells is irradiated after production of early apoptotic cells. In another related aspect, irradiation comprises gamma irradiation or UV irradiation. In another related aspect, the irradiated cell population comprises a decreased percent of non-quiescent non-apoptotic cells per population compared with a non-irradiated apoptotic cell population.

In one aspect, disclosed herein is a pharmaceutical composition, comprising a population of mononuclear apoptotic cell comprising mononuclear cells in an early-apoptotic state, wherein said mononuclear apoptotic cell population comprises: a decreased percent of non-quiescent non-apoptotic viable cells; a suppressed cellular activation of any living non-apoptotic cells; or a reduced proliferation of any living non-apoptotic cells; or any combination thereof. and a pharmaceutically acceptable excipient.

In one aspect, disclosed herein is a method for producing a population of mononuclear apoptotic cell comprising a decreased percent of non-quiescent non-apoptotic viable cells; a suppressed cellular activation of any living non-apoptotic cells; or a reduced proliferation of any living non-apoptotic cells; or any combination thereof, said method comprising the following steps, obtaining a mononuclear-enriched cell population of peripheral blood; freezing said mononuclear-enriched cell population in a freezing medium comprising an anticoagulant; thawing said mononuclear-enriched cell population; incubating said mononuclear-enriched cell population in an apoptosis inducing incubation medium comprising methylprednisolone at a final concentration of about 10-100 μg/mL and an anticoagulant; resuspending said apoptotic cell population in an administration medium; and inactivating said mononuclear-enriched population, wherein said inactivation occurs following step (e), wherein said method produces a population of mononuclear apoptotic cell comprising a decreased percent of non-quiescent non-apoptotic cells; a suppressed cellular activation of any living non-apoptotic cells; or a reduced proliferation of any living non-apoptotic cells; or any combination thereof.

In a related aspect, the inactivating step comprises decreasing the percent of non-quiescent non-apoptotic cells, suppressing cellular activation of any living non-apoptotic cells, or reducing the proliferation of any living non-apoptotic cells, or any combination thereof within said mononuclear apoptotic cell preparation. In another related aspect, the percent of non-quiescent non-apoptotic cells is decreased to about 10%. In another related aspect, the percent of non-quiescent non-apoptotic cells is decreased to about 0%.

In a related aspect, mononuclear-enriched cell population is selected from the group consisting of lymphocytes, monocytes, dendritic cells, and natural killer cells.

In a related aspect, the incubating is for about 2-12 hours.

In a related aspect, the step (f) inactivating of said mononuclear-enriched population comprises suppressing or eliminating an immune response, suppressing or eliminating cross-reactivity of cells, or reducing or eliminating T-cell receptor activity, and wherein said population comprises a decreased the percent of living non-apoptotic cells, a suppress cellular activation of any living non-apoptotic cells, or a reduced proliferation of any living non-apoptotic cells, or any combination thereof. In another related aspect, the said step (f) inactivating comprises irradiating a mononuclear-enriched apoptotic cell population produced in step (e). In another related aspect, the irradiation comprises gamma irradiation or UV irradiation. In another related aspect, the irradiation comprises about 25-50 Grey units (Gy).

BRIEF DESCRIPTION OF THE DRAWINGS

The subject matter disclosed herein is particularly pointed out and distinctly claimed in the concluding portion of the specification. The compositions and methods disclosed herein, however, both as to organization and method of operation, together with objects, features, and advantages thereof, may best be understood by reference to the following detailed description when read with the accompanying drawings.

FIG. 4A shows the reduction of LPS induced IL-10 levels in the macrophage activation syndrome model in the presence of cancer following administration of Apocells at a macrophage/monocyte:Apocell ratio of 1:8 and 1:16, at two time periods (6 hours and 24 hours). FIG. 4B shows the reduction of LPS induced IL-6 levels in the macrophage activation syndrome model following administration of Apocells in the presence of cancer and CAR-19, at a macrophage/monocyte:Apocell ratio of 1:8 and 1:16, at two time periods (6 hours and 24 hours). FIG. 4C shows the reduction of LPS induced MIP-1a levels in the macrophage activation syndrome model in the presence of cancer and CAR-19, following administration of Apocells at a macrophage/monocyte:Apocell ratio of 1:8 and 1:16, at two time periods (6 hours and 24 hours). FIG. 4D shows the reduction of LPS induced IL-8 levels in the macrophage activation syndrome model in the presence of cancer and CAR-19, following administration of Apocells at a macrophage/monocyte:Apocell ratio of 1:8 and 1:16, at two time periods (6 hours and 24 hours). FIG. 4E shows the reduction of LPS induced TNF-α levels in the macrophage activation syndrome model in the presence of cancer and CAR-19, following administration of Apocells at a macrophage/monocyte:Apocell ratio of 1:8 and 1:16, at TWO time periods (6 hours and 24 hours).

FIG. 4F shows the reduction of LPS induced MIP-1β levels in the macrophage activation syndrome model in the presence of cancer and CAR-19, following administration of Apocells at a macrophage/monocyte:Apocell ratio of 1:4, 1:8, 1:16, 1:32, and 1:64 at 24 hours. FIG. 4G shows the reduction of LPS induced MCP-1 levels in the macrophage activation syndrome model in the presence of cancer and CAR-19, following administration of Apocells at a macrophage/monocyte:Apocell ratio of 1:4, 1:8, 1:16, 1:32, and 1:64 at 24 hours. FIG. 4H shows the reduction of LPS induced IL-9 levels in the macrophage activation syndrome model in the presence of cancer and CAR-19, following administration of Apocells at a macrophage/monocyte:Apocell ratio of 1:8 and 1:16, at two time periods (6 hours and 24 hours).

FIG. 4I shows the increase of LPS induced IL-2R levels in the macrophage activation syndrome model in the presence of cancer and CAR-19, following administration of Apocells at a macrophage/monocyte:Apocell ratio of 1:4, 1:8, 1:16, 1:32, and 1:64 at 24 hours. FIG. 4J shows that apoptotic cells do not down regulate IL-2 release from cells. Apoptotic cells were incubated with macrophages/monocytes in the presence of cancer and CAR-19, over a 24 hour time period with increasing doses of apoptotic cells (n=3). Empty bar (outline only)—$2.5 \times 10^6$ apoptotic cells per well; Black—$5 \times 10^6$ apoptotic cells per well; Grey—$10 \times 10^6$ apoptotic cells per well.

FIG. 11A shows Weight change over the experimental time period. Blue-control no $4.5 \times 10^6$ SKOV3-luc cells administrated. Red-$0.5 \times 10^6$ SKOV3-luc cells. Green-$1.0 \times 10^6$ SKOV3-luc cells. Purple-$4.5 \times 10^6$ SKOV3-luc cells FIG. 11B presents a representative SKOV3-luc tumor for a mouse receiving $4.5 \times 10^6$ SKOV3-luc cells, 39 days after injection.

FIG. 13A, mice inoculated with $0.5 \times 10^6$ SKOV3-luc. FIG. 13B, mice inoculated with $1 \times 10^6$ SKOV3-luc. FIG. 13C, mice inoculated with $4.5 \times 10^6$ SKOV3-luc. FIG. 13D, Average SKOV3-luc tumor growth.

FIG. 18A presents the experimental scheme to analyze the influence of apoptotic cells on CAR T-cell therapy. SCID mice were injected on day 1 with Raji cancer cells, followed on day 6 by administration of CAR T-CD19 cells (CAR T-cell therapy) and Apoptotic cells. FIG. 18B shows that CAR T-cell therapy was not negatively influenced by co-administration of ApoCells. Survival Curve: SCID mice were injected with CD19+ Raji cells with or without addition of early apoptotic cells.

FIG. 19A shows slight increase of IL-6 released from a solid tumor present in the peritoneum of BALB/c and SCID mice, wherein the IL-6 release is significantly increased in the presence of HeLa CAR-CD-19 CAR T-cells. Similarly, FIG. 19B shows a slight increase of IP-10 released from a solid tumor present in the peritoneum of BALB/c and SCID mice, wherein the IP-10 release is significantly increased in the presence of HeLa CAR-CD-19 CAR T-cells, and FIG. 19C shows that surprisingly even TNF-α release is increased by in the presence of HeLa CAR-CD-19 CAR T-cells.

FIG. 20A was with $0.5 \times 10^6$ CAR-T positive cells. FIG. 20B was with $2.2 \times 10^6$ CAR-T positive cells.

FIG. 22B. Apoptotic cell infusions increased the percentage of mice surviving up to 12% of the expected life-span post leukemia induction. FIG. 22C. Apoptotic cell infusions increased the percentage of mice surviving up to 30% of the expected life-span post leukemia induction. FIG. 22D. Apoptotic cell infusions increased the percentage of mice surviving up to 100% of the expected life-span post leukemia induction and attaining complete remission.

FIG. 23B. Apoptotic cell infusions increased the percentage of mice surviving up to 24% longer than the expected life-span post leukemia induction. FIG. 23C. Apoptotic cell infusions increased the percentage of mice surviving up to 59% longer than the expected life-span post leukemia induction and enhanced the anti-CD20 mAb effect on the life-span of leukemic mice. FIG. 23D. Apoptotic cell infusions increased the percentage of mice surviving up to 76% longer than the expected life-span post leukemia induction and enhanced the anti-CD20 mAb effect on the life-span of leukemic mice. FIG. 23E. Apoptotic cell infusions increased the percentage of mice attaining complete remission.

FIG. 25A presents data from a study wherein female SCID-Bg mice, 7-weeks-old (ENVIGO, Jerusalem, Israel), were injected IV with $0.1 \times 10^6$ Raji cells per mouse (n=10 per group, three groups). Mice received three IV doses (days 5, 8, 11) of $30 \times 10^6$ ApoCell. (RPMI-light blue; Raji-orange; and Raji+ApoCell—dark blue) FIG. 25B presents data from a study wherein female SCID-Bg mice, 7-weeks-old (ENVIGO, Jerusalem, Israel), were injected IV with $0.1 \times 10^6$ Raji cells per mouse (n=10 per group, three groups). Mice received three IV doses (days 5, 8, 11) of $30 \times 10^6$ ApoCell. (RPMI-black; Raji-orange; and Raji+ApoCell—dark blue) FIG. 25C presents data from a study wherein female SCID-Bg mice, 8-9-weeks-old (ENVIGO, Jerusalem, Israel), were injected IV with $0.1 \times 10^6$ Raji cells per mouse (n=10 per group, 2 groups). Mice received three IV doses (days 5, 8, 12) of $30 \times 10^6$ ApoCell. (Raji-orange; and Raji+ApoCell—dark blue)

FIG. 28 presents a graph showing the clear effect (p<0.01) of a single apoptotic cell preparation injection from multiple individual donors (blue) on survival. The graph presented is a Kaplan-Meier survival curve in a GvHD mouse model that was treated with a single dose irradiated pooled apoptotic cell preparation from multiple individual donors.

FIG. 29 presents a graph showing the clear effect (p<0.01) of a single apoptotic cell preparation injection from multiple individual donors (blue) on percentage of weight loss of the 2 compared groups.

FIG. 30 presents a graph showing comparison between the administration of a single dose of single-donor and multiple-donor apoptotic cell preparations +/− irradiation on % survival using a mouse model of induced GvHD.

FIGS. 31A-31B present the results of a potency test that shows the inhibition of maturation of dendritic cells (DCs) following interaction with apoptotic cells, measured by expression of HLA-DR. FIG. 31A. HLA DR mean fluorescence of fresh final product A (t0). FIG. 31B. HLA DR mean fluorescence of final product A, following 24 h at 2-8° C.

FIGS. 32A-32B present the results of a potency test that shows the inhibition of maturation of dendritic cells (DCs) following interaction with apoptotic cells, measured by expression of CD86. FIG. 32A. CD86 Mean fluorescence of fresh final product A (t0). FIG. 32B. CD86 Mean fluorescence of final product A, following 24 h at 2-8° C.

FIG. 34A shows survival curves of peritoneal solid tumor Hela-CD19, treated by CAR T-cell therapy alone (SCID-Bg-HeLa-CD19: control no treatment; SCID-Bg-HeLa-CD19+ CAR-T: includes treatment with CAR T-cells; SCID-Bg-HeLa-CD19+Mock-T: control addition of Mock T-cells. FIG. 34B is representative of 5 separate experiments, as described in Example 17 and shows survival curves of peritoneal solid tumor Hela-CD19, treated by CAR T-cell therapy alone or CAR T-cell therapy plus co-administration of apoptotic cells. (HeLa-CD19: control no treatment; HeLa-CD19+ CAR-T: includes treatment with CAR T-cells; HeLa-CD19+ Mock-T: control addition of Mock T-cells; Hela-CD19+ CAR-T+OTS-ALC-4K: treatment was with CAR T-cells and "off the shelf" apoptotic cells irradiated with 4000 rad). FIG. 34C presents representative results, as described in Example 17 and shows survival curves of peritoneal solid tumor Hela-CD19, treated by CAR T-cell therapy alone or CAR T-cell therapy plus co-administration of apoptotic cells. (SCID-Bg-HeLa-CD19: control no treatment; SCID-Bg-HeLa-CD19+ CAR-T: includes treatment with CAR T-cells; SCID-Bg-HeLa-CD19+Mock-T: control addition of Mock T-cells; SCID-Bg-Hela-CD19+CAR-T+Allocetra-OTS: treatment was with CAR T-cells and "off the shelf" apoptotic cells irradiated with 4000 rad). FIG. 34D (Luciferase in vivo imaging system (IVIS) results) shows progression of tumor as visualized by IVIS representing the development leading to the survival curve results presented in FIG. 34B. Spread of the tumor can already be visualized on day 15 (Hela-CD19-Luc; control no treatment) whereas mice treated with CAR T-cells did not show any tumor spread until day 43. When mice receive apoptotic cells in conjunction with CAR T-cell treatment, unexpectedly most mice did not show tumor spread until day 50 and tumor size (see scale for correlation) was clearly smaller.

FIG. 35A shows survival curves of peritoneal solid tumor Hela-CD19, treated by CAR T-cell therapy alone. FIG. 35B shows survival curves of peritoneal solid tumor Hela-CD19, treated by CAR T-cell therapy alone or CAR T-cell therapy plus co-administration of apoptotic cells. (SCID-Bg-HeLa-CD19: control no treatment; SCID-Bg-HeLa-CD19+ CAR-T: includes treatment with CAR T-cells; SCID-Bg-Hela-CD19+CAR-T+Allocetra-OTS: treatment was with CAR T-cells and "off the shelf" apoptotic cells irradiated with 4000 rad).

FIG. 36A shows FACS analysis of resident peritoneal macrophage markers F4/80, CD11b, Tim4, and MerTK, in the SCID-bg mice (control, no tumor), in SCID-bg-Hela-CD19 mice (control with tumor, no treatment), and in SCID-bg-HeLa-CD19-CART (includes treatment with CAR T-cells). The results seen in the SCID-bg mice provide a resident macrophage signature. Comparison of the data shows that resident peritoneal macrophages disappear during tumor progression. FIG. 36B shows FACS analysis of tumor associated macrophage (TAM) markers CCR2, Ly6c, CD206, CD64, CD169, and CD74 during tumor progression in the SCID-bg mice (control, no tumor), in SCID-bg-Hela-CD19 mice (control with tumor, no treatment), and in SCID-bg-HeLa-CD19-CART (includes treatment with CAR T-cells). The results seen in the SCID-bg-CD19 provide a infiltrating macrophage signature. Comparison of the data shows that TAM infiltrate during tumor progression. FIG. 36C presents FACs results showing that resident macrophages in SCID mice are mostly large peritoneal macrophages (LPM), and that during tumor progression, most resident macrophages disappear, and TAM, monocytes, and dendritic cells appear. Macrophage markers F4/80, CD11b, TIM4, MER-TK, rIgG2b, and rIgG2a were measured, as was the percent of MHCII positive cells.

DETAILED DESCRIPTION

Figure 1A:
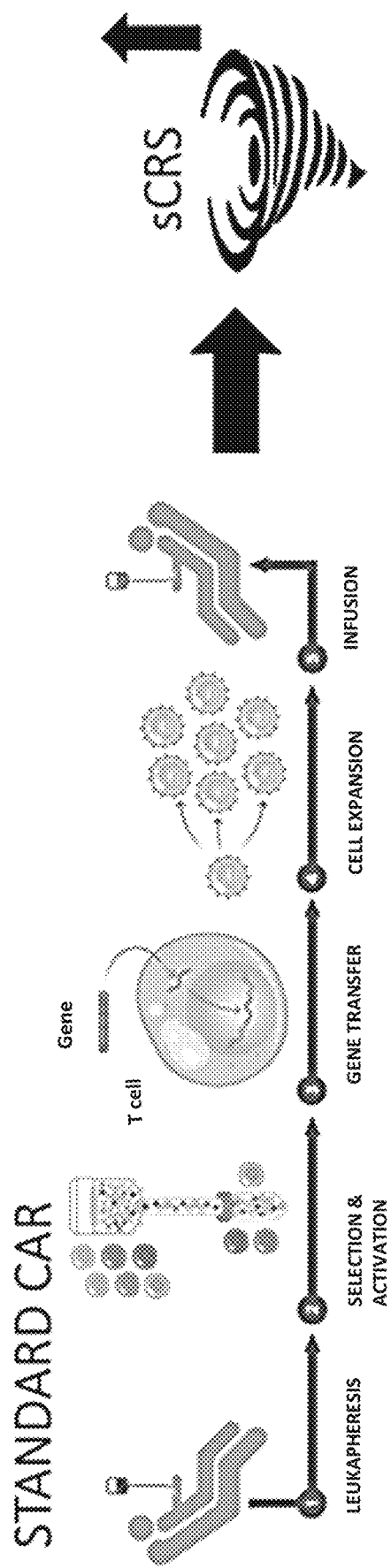
FIGS. 1A-1B. Schematic showing standard CAR T-cell therapy (FIG. 1A) and embodiments of a method of safe and efficacious CAR T-cell cancer therapy in a patient using patients' own cells (autologous) (FIG. 1B) to produce apoptotic cells or an apoptotic cell supernatant.

In the following detailed description, numerous specific details are set forth in order to provide a thorough understanding of the methods disclosed herein. However, it will be understood by those skilled in the art that these methods may be practiced without these specific details. In other instances, well-known methods, procedures, and components have not been described in detail so as not to obscure the methods disclosed herein.

Genetic modification of immune cells is well known as a strategy for immune-cell therapies against cancer. These immune-cell therapies are based on the manipulation and administration of autologous or allogeneic immune cells to a subject in need Immune-cell based therapies include natural killer cells therapies, dendrite cell therapies, and T-cell immunotherapies including those utilizing naïve T-cells, effector T-cells also known as T-helper cells, cytotoxic T-cells, and regulatory T-cells (Tregs).

In some embodiments, disclosed herein are compositions comprising genetically modified immune cells. In another embodiment, the genetically modified immune cell is a T-cell. In another embodiment, a T-cell is a naïve T-cell. In another embodiment, a T-cell is a naïve CD4$^+$ T-cell. In another embodiment, a T-cell is a naïve T-cell. In another embodiment, a T-cell is a naïve CD8$^+$ T-cell. In another embodiment, the genetically modified immune cell is a natural killer (NK) cell. In another embodiment, the genetically modified immune cell is a dendritic cell. In still another embodiment, the genetically modified T-cell is a cytotoxic T lymphocyte (CTL cell). In another embodiment, the genetically modified T-cell is a regulatory T-cell (Treg). In another embodiment, the genetically modified T-cell is a chimeric antigen receptor (CAR) T-cell. In another embodiment, the genetically modified T-cell is a genetically modified T-cell receptor (TCR) cell.

In some embodiments, disclosed herein are compositions comprising genetically modified immune cells and apoptotic cells. In another embodiment, disclosed herein are compositions comprising genetically modified immune cells and supernatants from apoptotic cells. In another embodiment, the genetically modified immune cell is a T-cell. In another embodiment, the genetically modified immune cell is a natural killer (NK) cell. In still another embodiment, the genetically modified immune cell is a cytotoxic T lymphocyte (CTL cell). In another embodiment, the genetically modified immune cell is a regulatory T lymphocyte (Treg cell).

In some embodiments, disclosed herein is a method of maintaining or increasing the proliferation rate of chimeric antigen receptor-expressing T-cells (CAR T-cell) during CAR T-cell cancer therapy, the method comprising the step of administering a composition comprising apoptotic cells or an apoptotic cell supernatant to said subject, and wherein said proliferation rate is maintained or increased in the subject compared with a subject undergoing CAR T-cell cancer therapy and not administered said apoptotic cells or said apoptotic cell supernatant.

In a related embodiment, the method does not reduce or inhibit the efficacy of said CAR T-cell cancer therapy. In a related embodiment, the method improves the efficacy of said CAR T-cell cancer therapy. In another related embodiment the incidence of cytokine release syndrome (CRS) or a cytokine storm in said subject is inhibited or reduced compared with a subject not administered said apoptotic cells or said apoptotic cell supernatant.

In some embodiments, CRS occurs spontaneously. In another embodiment, CRS occurs in response to LPS. In another embodiment, CRS occurs in response to IFN-γ.

In some embodiments, disclosed herein is a method of increasing the efficacy of chimeric antigen receptor T-cell (CAR T-cell) cancer therapy, the method comprising the step of administering CAR T-cells and an additional agent selected from the group comprising apoptotic cells, an apoptotic cell supernatant, a CTLA-4 blocking agent, an alpha-1 anti-trypsin or fragment thereof or analogue thereof, a tellurium-based compound, or an immune modulating agent, or any combination thereof, wherein said efficacy said CAR T-cells is increased in the subject compared with a subject undergoing CAR T-cell cancer therapy and not administered said additional agent. In a related embodiment, the level of production of at least one pro-inflammatory cytokine is reduced compared with the level of said pro-inflammatory cytokine in a subject received CAR T-cell cancer therapy and not administered a composition comprising said agent. In another related embodiment, the pro-inflammatory cytokine comprises IL-6.

In a related embodiment, when apoptotic cells or an apoptotic cell supernatant is administered, said method increases the levels of IL-2 in the subject compared with a subject undergoing CAR T-cell cancer therapy and not administered said apoptotic cells or said apoptotic cell supernatant. In another embodiment, when apoptotic cells or an apoptotic cell supernatant is administered, said method maintains the levels of IL-2 in the subject compared with a subject undergoing CAR T-cell cancer therapy and not administered said apoptotic cells or said apoptotic cell supernatant. In another embodiment, when apoptotic cells or an apoptotic cell supernatant is administered, said method maintains or increases the levels of IL-2 in the subject compared with a subject undergoing CAR T-cell cancer therapy and not administered said apoptotic cells or said apoptotic cell supernatant. In another related embodiment, the incidence of cytokine release syndrome (CRS) or a cytokine storm in said subject is inhibited or reduced compared with a subject not administered said additional agent.

In a related embodiment, CAR T-cells and said additional agent or any combination thereof are comprised in a single composition. In another related embodiment, said CAR T-cell and said additional agent or any combination thereof are comprised in at least two compositions.

In some embodiments, disclosed herein is a method of treating, preventing, inhibiting, reducing the incidence of, ameliorating, or alleviating a cancer or a tumor in a subject, comprising the step of administering chimeric antigen receptor-expressing T-cells (CAR T-cell) and an additional agent, said additional agent comprising apoptotic cells, apoptotic supernatants or a CTLA-4 blocking agent, an alpha-1 anti-trypsin or fragment thereof or analogue thereof, a tellurium-based compound, or an immune modulating agent, or any combination thereof, wherein said method treats, prevents, inhibits, reduces the incidence of, ameliorates or alleviates a cancer or a tumor in said subject compared with a subject administered CAR T-cells and not administered said additional agent.

In a related embodiment, said method has increased efficacy treating, preventing, inhibiting, reducing the incidence of, ameliorating or alleviating said cancer or said tumor in said subject compared with a subject administered CAR T-cells and not administered said additional agent.

In another related embodiment, the level of production of at least one pro-inflammatory cytokine is reduced compared with the level of said pro-inflammatory cytokine in a subject administered said CAR T-cells and not administered a composition comprising said agent. In another related embodiment, said pro-inflammatory cytokine comprises IL-6. In another related embodiment, said additional agent comprises apoptotic cells or an apoptotic cell supernatant, said method increases the levels of IL-2 in the subject compared with a subject administered said CAR T-cells and not administered said apoptotic cells or said apoptotic cell supernatant. In another related embodiment, said CAR T-cells and said additional agent or any combination thereof are comprised in a single composition. In yet another related embodiment, said CAR T-cells and said additional agent or any combination thereof are comprised in at least two compositions.

In a related embodiment, the administration of said additional agent occurs prior to, concurrent with, or following the administration of said CAR T-cells. In another related embodiment, said apoptotic cells comprise apoptotic cells in an early-apoptotic state. In another related embodiment, said apoptotic cells are autologous to said subject or are pooled third-party donor cells.

In a related embodiment, said apoptotic cell supernatant is obtained by a method comprising the steps of (a) providing apoptotic cells, (b) culturing the cells of step (a), and (c) separating the supernatant from the cells. In another related embodiment, said apoptotic cell supernatant is an apoptotic cell-white blood cell supernatant and said method further comprises the steps of: (d) providing white blood cells, (e) optionally, washing the apoptotic cells and the white blood cells, (f) co-culturing the apoptotic cells and the white blood cells, wherein steps (d)-(f) are in place of step (b). In another related embodiment, the provided white blood cells are selected from the group consisting of phagocytes, macrophages, dendritic cells, monocytes, B cells, T cells, and NK cells. Thus, in some embodiments, apoptotic supernatants comprise a supernatant produced by culturing apoptotic cells with macrophages, wherein the macrophage ingests the apoptotic cells and the supernatant produced from this co-culturing is used. In some embodiments, apoptotic supernatants comprise a supernatant produced by culturing apoptotic cells, wherein the supernatant is produced from materials secreted by the apoptotic cells.

In some embodiments, disclosed herein are compositions comprising early apoptotic cells. In some embodiments, disclosed herein are compositions comprising early apoptotic cells in combination with an additional agent. In some embodiments, the additional agent may be a CAR T-cell. In some embodiments, the additional agent may be an antibody. In some embodiments, the antibody comprises rituximab or a functional fragment thereof.

In some embodiments, compositions of early apoptotic cells comprise a population of mononuclear apoptotic cell comprising mononuclear cells in an early-apoptotic state, wherein said mononuclear apoptotic cell population comprises: a decreased percent of non-quiescent non-apoptotic viable cells; a suppressed cellular activation of any living non-apoptotic cells; or a reduced proliferation of any living non-apoptotic cells; or any combination thereof.

In some embodiments, disclosed herein are compositions comprising genetically modified T-cells and apoptotic cells. In another embodiment, disclosed herein are compositions comprising genetically modified T-cells and supernatants of apoptotic cells. In another embodiment, the genetically modified T-cell is a chimeric antigen receptor (CAR) T-cell. In another embodiment, the genetically modified T-cell is a genetically modified T-cell receptor (TCR) cell.

In some embodiments, disclosed herein are compositions comprising CAR T-cells and apoptotic cells. In another embodiment, disclosed herein are compositions comprising genetically modified T-cell receptor cells (TCRs) and apoptotic cells. In another embodiment, disclosed herein are compositions comprising CAR T-cells and supernatants from apoptotic cells. In another embodiment, disclosed herein are compositions comprising genetically modified T-cell receptor cells (TCRs) and supernatant of apoptotic cells.

In certain embodiments, genetically modified immune cells and apoptotic cells or apoptotic cell supernatants are comprised within a single composition. In other embodiments, genetically modified immune cells and apoptotic cells or apoptotic cell supernatants are comprised in separate compositions.

This disclosure provides in some embodiments, a pooled mononuclear apoptotic cell preparation comprising mononuclear cells in an early-apoptotic state, wherein said pooled mononuclear apoptotic cells preparation comprises pooled individual mononuclear cell populations, and wherein said pooled mononuclear apoptotic cell preparation comprises a decreased percent of living non-apoptotic cells, a suppressed cellular activation of any living non-apoptotic cells, or a reduced proliferation of any living non-apoptotic cells, or any combination thereof. In another embodiment, the pooled mononuclear apoptotic cells have been irradiated. In another embodiment, this disclosure provides a pooled mononuclear apoptotic cell preparation that in some embodiments, uses the white blood cell fraction (WBC) obtained from donated blood. Often this WBC fraction is discarded at blood banks or is targeted for use in research.

In some embodiments, a cell population disclosed herein is inactivated. In another embodiment, inactivation comprises irradiation. In another embodiment, inactivation comprises T-cell receptor inactivation. In another embodiment, inactivation comprises T-cell receptor editing. In another embodiment, inactivation comprises suppressing or eliminating an immune response in said preparation. In another embodiment, inactivation comprises suppressing or eliminating cross-reactivity between multiple individual populations comprised in the preparation. In other embodiment, inactivation comprises reducing or eliminating T-cell receptor activity between multiple individual populations comprised in the preparation. In another embodiment, an inactivated cell preparation comprises a decreased percent of living non-apoptotic cells, suppressed cellular activation of any living non-apoptotic cells, or a reduce proliferation of any living non-apoptotic cells, or any combination thereof.

In another embodiment, an inactivated cell population comprises a reduced number of non-quiescent non-apoptotic cells compared with a non-radiated cell preparation. In some embodiments, an inactivated cell population comprises 50 percent (%) of living non-apoptotic cells. In some embodiments, an inactivated cell population comprises 40% of living non-apoptotic cells. In some embodiments, an inactivated cell population comprises 30% of living non-apoptotic cells. In some embodiments, an inactivated cell population comprises 20% of living non-apoptotic cells. In some embodiments, an inactivated cell population comprises 100% of living non-apoptotic cells. In some embodiments, an inactivated cell population comprises 0% of living non-apoptotic cells.

In some embodiments, disclosed herein is a method of preparing an inactivated early apoptotic cell population. In some embodiments, disclosed herein is a method for producing a population of mononuclear apoptotic cell comprising a decreased percent of non-quiescent non-apoptotic viable cells; a suppressed cellular activation of any living non-apoptotic cells; or a reduced proliferation of any living non-apoptotic cells; or any combination thereof, said method comprising the following steps, obtaining a mononuclear-enriched cell population of peripheral blood;

freezing said mononuclear-enriched cell population in a freezing medium comprising an anticoagulant;

thawing said mononuclear-enriched cell population;

incubating said mononuclear-enriched cell population in an apoptosis inducing incubation medium comprising methylprednisolone at a final concentration of about 10-100 µg/mL and an anticoagulant;

resuspending said apoptotic cell population in an administration medium; and inactivating said mononuclear-enriched population, wherein said inactivation occurs following induction, wherein said method produces a population of mononuclear apoptotic cell comprising a decreased percent of non-quiescent non-apoptotic cells; a suppressed cellular activation of any living non-apoptotic cells; or a reduced proliferation of any living non-apoptotic cells; or any combination thereof.

In another embodiment, the irradiation comprises gamma irradiation or UV irradiation. In yet another embodiment, the irradiated preparation has a reduced number of non-quiescent non-apoptotic cells compared with a non-irradiated cell preparation.

In another embodiment, the pooled mononuclear apoptotic cells have undergone T-cell receptor inactivation. In another embodiment, the pooled mononuclear apoptotic cells have undergone T-cell receptor editing.

In some embodiments, pooled blood comprises $3^{rd}$ party blood from HLA matched or HLA unmatched sources, with respect to a recipient.

In some embodiments, disclosed herein are compositions comprising genetically modified immune cells, for example but not limited to CAR T-cells and an additional agent selected from the group comprising apoptotic cells, an apoptotic cell supernatant, a CTLA-4 blocking agent, an alpha-1 anti-trypsin or fragment thereof or analogue thereof, a tellurium-based compound, or an immune modulating agent, or any combination thereof.

In some embodiments, this disclosure provides methods of production of a pharmaceutical composition comprising a pooled mononuclear apoptotic cell preparation comprising pooled individual mononuclear cell populations in an early apoptotic state, wherein said composition comprises a decreased percent of living non-apoptotic cells, a preparation having a suppressed cellular activation of any living non-apoptotic cells, or a preparation having reduced proliferation of any living non-apoptotic cells, or any combination thereof. In another embodiment, the methods provide a pharmaceutical composition comprising a pooled mononuclear apoptotic cell preparation comprising pooled individual mononuclear cell populations in an early apoptotic state, wherein said composition comprises a decreased percent of non-quiescent non-apoptotic cells.

In some embodiments, disclosed herein is a method of treating, preventing, inhibiting the growth of, reducing the incidence of, or any combination thereof, a cancer or a tumor in a subject, comprising a step of administering an early apoptotic cell population to said subject, wherein said method treats, prevents, inhibits the growth of, reduces the incidence of, or any combination thereof, a cancer or a tumor in said subject. In some embodiments, methods herein comprise treating, preventing, inhibiting the growth of, delaying disease progression, reducing the tumor load, or reducing the incidence of a cancer or a tumor in a subject, or any combination thereof, comprising a step of administering a composition comprising an early apoptotic cell population to said subject. In some embodiments, the method further comprises administering an additional immune therapy, a chemotherapeutic agent, or an immune modulator to said subject, or any combination thereof. In some embodiments, the additional immune therapy, a chemotherapeutic agent, or an immune modulator is administered prior to, concurrent with, or following administration of said early apoptotic cells.

In some embodiments, disclosed herein is a method of increasing survival of a subject suffering from a cancer or a tumor, comprising a step of administering an early apoptotic cell population to said subject, wherein said method increases survival of said subject. In some embodiments, the method further comprises administering an additional immune therapy, a chemotherapeutic agent, or an immune modulator to said subject, or any combination thereof. In some embodiments, the additional immune therapy, a chemotherapeutic agent, or an immune modulator is administered prior to, concurrent with, or following administration of said early apoptotic cells.

In some embodiments, disclosed herein is a method of reducing the size or reducing the growth rate of a cancer or a tumor, or a combination thereof, in a subject, comprising a step of administering an early apoptotic cell population to said subject, wherein said method reduces the size or reduces the growth rate. In some embodiments, the method further comprises administering an additional immune therapy, a chemotherapeutic agent, or an immune modulator to said subject, or any combination thereof. In some embodiments, the additional immune therapy, a chemotherapeutic agent, or an immune modulator is administered prior to, concurrent with, or following administration of said early apoptotic cells.

In some embodiments, administration of a composition comprising apoptotic cells does not affect the efficacy of CAR T-cells to treat, prevent, inhibit, reduce the incidence of, ameliorating, reduce the tumor load, or alleviating a cancer or a tumor. In another embodiment, administration of a composition comprising apoptotic cells does not reduce the efficacy of the CAR T-cells to treat, prevent, inhibit, reduce the incidence of, ameliorating, reduce the tumor load, or alleviating a cancer or a tumor by more than about 5%. In another embodiment, administration of a composition comprising apoptotic cells does not reduce the efficacy of the CAR T-cells to treat, prevent, inhibit, reduce the incidence of, ameliorating, reduce the tumor load, or alleviating a cancer or a tumor by more than about 10%. In another embodiment, administration of a composition comprising apoptotic cells does not reduce the efficacy of the CAR T-cells to treat, prevent, inhibit, reduce the incidence of, ameliorating, reduce the tumor load, or alleviating a cancer or a tumor by more than about 15%. In another embodiment, administration of a composition comprising apoptotic cells does not reduce the efficacy of the CAR T-cells to treat, prevent, inhibit, reduce the incidence of, ameliorating, reduce the tumor load, or alleviating a cancer or a tumor by more than about 20%.

In some embodiments, administration of apoptotic cells increases the efficacy of CAR T-cells. In some embodiments, administration of apoptotic cells increases the efficacy of CAR T-cells by at least 5, by at least 10%, by at least 15%, by at least 20%, by at least 25, by at least 30%, by at least 35%, by at least 40%, by at least 45, or by at least 50%.

In another embodiment, administration of a composition comprising an apoptotic cell supernatant does not reduce the efficacy of the CAR T-cells to treat, prevent, inhibit, reduce the incidence of, ameliorating, or alleviating said cancer or said tumor by more than about 5%. In another embodiment, administration of a composition comprising an apoptotic cell supernatant does not reduce the efficacy of the CAR T-cells to treat, prevent, inhibit, reduce the incidence of, ameliorating, or alleviating said cancer or said tumor by more than about 10%. In another embodiment, administration of a composition comprising an apoptotic cell supernatant does not reduce the efficacy of the CAR T-cells to treat, prevent, inhibit, reduce the incidence of, ameliorating, or alleviating said cancer or said tumor by more than about 15%. In another embodiment, administration of a composition comprising an apoptotic cell supernatant does not reduce the efficacy of the CAR T-cells to treat, prevent, inhibit, reduce the incidence of, ameliorating, or alleviating said cancer or said tumor by more than about 20%. In another embodiment, administration of a composition comprising the apoptotic cell supernatant does not affect the efficacy of the CAR T-cells to treat, prevent, inhibit, reduce the incidence of, ameliorating, or alleviating said cancer or said tumor. In another embodiment, administration of a composition comprising the apoptotic cell supernatant does not reduce the efficacy of the CAR T-cells to treat, prevent, inhibit, reduce the incidence of, ameliorating, or alleviating said cancer or said tumor.

In some embodiments, disclosed herein are methods of inhibiting or reducing the incidence of cytokine release syndrome (CRS) or cytokine storm in a subject undergoing CAR T-cell cancer therapy. In another embodiment, methods disclosed herein decrease or prevent cytokine production in a subject undergoing CAR T-cell cancer therapy thereby inhibiting or reducing the incidence of cytokine release syndrome (CRS) or cytokine storm in a subject. In another embodiment, the methods disclosed herein of inhibiting or reducing the incidence of cytokine release syndrome (CRS) or cytokine storm in a subject undergoing CAR T-cell cancer therapy comprise the step of administering a composition comprising apoptotic cells to the subject undergoing the cancer therapy. In yet another embodiment, methods disclosed herein for decreasing or inhibiting cytokine production in a subject undergoing CAR T-cell cancer therapy comprise the step of administering a composition comprising apoptotic cells to the subject undergoing the cancer therapy. In another embodiment, administration of a composition comprising apoptotic cells does not affect the efficacy of the CAR T-cell therapy. In another embodiment, administration of a composition comprising apoptotic cells or an apoptotic supernatant does not reduce the efficacy of the CAR T-cell therapy. In another embodiment, administration of a composition comprising apoptotic cells or an apoptotic cell supernatant does not reduce the efficacy of the CAR T-cells therapy by more than about 5%. In another embodiment, administration of a composition comprising apoptotic cells or an apoptotic cell supernatant does not reduce the efficacy of the CAR T-cells therapy by more than about 10%. In another embodiment, administration of a composition comprising apoptotic cells or an apoptotic cell supernatant does not reduce the efficacy of the CAR T-cells therapy by more than about 15%. In another embodiment, administration of a composition comprising apoptotic cells or an apoptotic cell supernatant does not reduce the efficacy of the CAR T-cells therapy by more than about 20%.

In some embodiments, disclosed herein are methods of decreasing or inhibiting cytokine production in a subject experiencing cytokine release syndrome or cytokine storm or vulnerable to cytokine release syndrome or cytokine storm comprising the step of administering an apoptotic cell supernatant, as disclosed herein, or a composition comprising said apoptotic cell supernatant. In another embodiment, an apoptotic cell supernatant comprises an apoptotic cell-phagocyte supernatant.

In some embodiments, methods disclosed herein for decreasing or inhibiting cytokine production in a subject undergoing CAR T-cell cancer therapy comprise the step of administering a composition comprising an apoptotic cell supernatant to the subject undergoing the cancer therapy. In another embodiment, administration of a composition comprising an apoptotic cell supernatant does not affect the efficacy of the CAR T-cell therapy. In another embodiment, administration of a composition comprising an apoptotic cell supernatant does not reduce the efficacy of the CAR T-cell therapy.

In some embodiments, a method of inhibiting or reducing the incidence of a cytokine release syndrome (CRS) or a cytokine storm in a subject undergoing chimeric antigen receptor-expressing T-cell (CAR T-cell) cancer therapy comprises the step of administering a composition comprising apoptotic cells or an apoptotic supernatant to said subject. In another embodiment, a method of inhibiting or reducing the incidence of a cytokine release syndrome (CRS) or a cytokine storm in a subject undergoing chimeric antigen receptor-expressing T-cell (CAR T-cell) cancer therapy decreases or inhibits production of at least one pro-inflammatory cytokine in the subject.

In another embodiment, this disclosure provides methods of use of a pooled mononuclear apoptotic cell preparation comprising mononuclear cells in an early apoptotic state, as described herein, for treating, preventing, ameliorating, inhibiting, or reducing the incidence of an immune disease, an autoimmune disease, an inflammatory disease, a cytokine release syndrome (CRS), a cytokine storm, or infertility in a subject in need thereof. In another embodiment, disclosed herein is a pooled mononuclear apoptotic cell preparation, wherein use of such a cell preparation in certain embodiments does not require matching donors and recipients, for example by HLA typing.

Genetically Modified Immune Cells

Genetic modification of immune cells is well known as a strategy for immune-cell therapies against cancer. These immune-cell therapies are based on the manipulation and administration of autologous or allogeneic immune cells to a subject in need Immune-cell based therapies include natural killer cells therapies, dendrite cell therapies, and T-cell immunotherapies including those utilizing naïve T-cells, effector T-cells also known as T-helper cells, cytotoxic T-cells, and regulatory T-cells (Tregs).

In one embodiment, disclosed herein are compositions comprising genetically modified immune cells In another embodiment, the genetically modified immune cell is a T-cell. In another embodiment, a T-cell is a naïve T-cell. In another embodiment, a T-cell is a naïve CD4$^+$ T-cell. In another embodiment, a T-cell is a naïve T-cell. In another embodiment, a T-cell is a naïve CD5$^+$ T-cell. In another embodiment, the genetically modified immune cell is a natural killer (NK) cell. In another embodiment, the genetically modified immune cell is a dendritic cell. In still another embodiment, the genetically modified T-cell is a cytotoxic T lymphocyte (CTL cell). In another embodiment, the genetically modified T-cell is a regulatory T-cell (Treg). In another embodiment, the genetically modified T-cell is a chimeric antigen receptor (CAR) T-cell. In another embodiment, the genetically modified T-cell is a genetically modified T-cell receptor (TCR) cell.

In one embodiment, disclosed herein are compositions comprising genetically modified immune cells and an additional agent selected from the group comprising apoptotic cells, an apoptotic cell supernatant, a CTLA-4 blocking agent, an alpha-1 anti-trypsin or fragment thereof or analogue thereof, a tellurium-based compound, or an immune modulating agent, or any combination thereof. In another embodiment, disclosed herein are compositions comprising genetically modified immune cells, apoptotic cells, and an additional agent selected from the group comprising a CTLA-4 blocking agent, an alpha-1 anti-trypsin or fragment thereof or analogue thereof, a tellurium-based compound, or an immune modulating agent, or any combination thereof. In another embodiment, disclosed herein are compositions comprising genetically modified immune cells, an apoptotic cell supernatant, and an additional agent selected from the group comprising a CTLA-4 blocking agent, an alpha-1 anti-trypsin or fragment thereof or analogue thereof, a tellurium-based compound, or an immune modulating agent, or any combination thereof.

In one embodiment, the immune cells are cytotoxic. In another embodiment, cytotoxic cells for genetic modification can be obtained from bone marrow of the subject (autologous) or a donor (allogeneic). In other cases, the cells are obtained from a stem cell. For example, cytotoxic cells can be derived from human pluripotent stem cells such as human embryonic stem cells or human induced pluripotent T-cells. In the case of induced pluripotent stem cells (IP-SCs), such pluripotent T-cells can be obtained using a somatic cell from the subject to which genetically modified cytotoxic cells will be provided. In one embodiment, immune cells may be obtained from a subject or donor by harvesting cells by venipuncture, by apheresis methods, by white cell mobilization followed by apheresis or venipuncture, or by bone marrow aspiration.

In one embodiment, immune cells, for example T-cell, are generated and expanded by the presence of specific factors in vivo. In another embodiment, T-cell generation and maintenance is affected by cytokines in vivo. In another embodiment, cytokines that affect generation and maintenance to T-helper cells in vivo comprise IL-1, IL-2, IL-4, IL-6, IL-12, IL-21, IL-23, IL-25, IL-33, and TGFβ. In another embodiment, Treg cells are generated from naïve T-cells by cytokine induction in vivo. In still another embodiment, TGF-β and/or IL-2 play a role in differentiating naïve T-cell to become Treg cells.

In another embodiment, the presence of a cytokine selected from the group comprising IL-1, IL-2, IL-4, IL-6, IL-12, IL-21, IL-23, IL-25, IL-33, and TGFβ, maintains or increases the proliferation rate or both, of T-cells in vivo. In another embodiment, the presence of a cytokine IL-2 and/or TGFβ, maintains or increases the proliferation rate or both, of T-cells in vivo. In another embodiment, the presence of a cytokine selected from the group comprising IL-1, IL-2, IL-4, IL-6, IL-12, IL-21, IL-23, IL-25, IL-33, and TGFβ, maintains or increases the proliferation rate or both, of CAR T-cells in vivo. In another embodiment, the presence of a cytokine IL-2 and/or TGFβ, maintains or increases the proliferation rate or both, of CAR T-cells in vivo. In another embodiment, the presence of a cytokine selected from the group comprising IL-1, IL-2, IL-4, IL-6, IL-12, IL-21, IL-23, IL-25, IL-33, and TGFβ, maintains or increases the proliferation rate or both, of TCR T-cells in vivo. In another embodiment, the presence of a cytokine IL-2 and/or TGFβ, maintains or increases the proliferation rate or both, of TCR T-cells in vivo. In another embodiment, the presence of a cytokine selected from the group comprising IL-1, IL-2, IL-4, IL-6, IL-12, IL-21, IL-23, IL-25, IL-33, and TGFβ, maintains or increases the proliferation rate or both, of T-reg cells in vivo. In another embodiment, the presence of a cytokine IL-2 and/or TGFβ, maintains or increases the proliferation rate or both, of T-reg cells in vivo.

In one embodiment T-cells having an altered expression or form of STAT5B encoded protein or BACH2 encoded protein are maintained for an extended time period or have an increased proliferation rate or both. In another embodiment, said altered expression increases expression STAT5B polypeptide. In another embodiment, said altered expression increases expression of BACH2 polypeptide.

In another embodiment, T-cells having an altered expression of a STAT5B encoded protein are maintained for an extended time period or have an increased proliferation rate in vivo. In another embodiment, T-cells having an altered expression of a BACH2 encoded protein are maintained for an extended time period or have an increased proliferation rate in vivo. In another embodiment, T-cells having an altered form of a STAT5B encoded protein are maintained for an extended time period or have an increased proliferation rate in vivo. In another embodiment, T-cells having an altered form of a BACH2 encoded protein are maintained for an extended time period or have an increased proliferation rate in vivo.

In another embodiment, T-cells having an altered expression of a STAT5B encoded protein maintain or increase their proliferation rate in vivo for greater than 1 year. In another embodiment, T-cells having an altered expression of a STAT5B encoded protein maintain or increase their proliferation rate in vivo for greater than 2 years. In another embodiment, T-cells having an altered expression of a STAT5B encoded protein maintain or increase their proliferation rate in vivo for greater than 3 years. In another embodiment, T-cells having an altered expression of a STAT5B encoded protein maintain or increase their proliferation rate in vivo for greater than 4 years. In another embodiment, T-cells having an altered expression of a STAT5B encoded protein maintain or increase their proliferation rate in vivo for greater than 5 years. In another embodiment, T-cells having an altered expression of a STAT5B encoded protein maintain or increase their proliferation rate in vivo for greater than 10 years. In another embodiment, T-cells having an altered expression of a STAT5B encoded protein maintain or increase their proliferation rate in vivo for greater than 20 years.

In another embodiment, T-cells having an altered expression of a BACH2 encoded protein maintain or increase their proliferation rate in vivo for greater than 1 year. In another embodiment, T-cells having an altered expression of a BACH2 encoded protein maintain or increase their proliferation rate in vivo for greater than 2 years. In another embodiment, T-cells having an altered expression of a BACH2 encoded protein maintain or increase their proliferation rate in vivo for greater than 3 years. In another embodiment, T-cells having an altered expression of a BACH2 encoded protein maintain or increase their proliferation rate in vivo for greater than 4 years. In another embodiment, T-cells having an altered expression of a BACH2 encoded protein maintain or increase their proliferation rate in vivo for greater than 5 years. In another embodiment, T-cells having an altered expression of a BACH2 encoded protein maintain or increase their proliferation rate in vivo for greater than 10 years. In another embodiment, T-cells having an altered expression of a BACH2 encoded protein maintain or increase their proliferation rate in vivo for greater than 20 years.

In another embodiment, T-cells having an altered form of a STAT5B encoded protein maintain or increase their proliferation rate in vivo for greater than 1 year. In another embodiment, T-cells having an altered form of a STAT5B encoded protein maintain or increase their proliferation rate in vivo for greater than 2 years. In another embodiment, T-cells having an altered form of a STAT5B encoded protein maintain or increase their proliferation rate in vivo for greater than 3 years. In another embodiment, T-cells having an altered form of a STAT5B encoded protein maintain or increase their proliferation rate in vivo for greater than 4 years. In another embodiment, T-cells having an altered form of a STAT5B encoded protein maintain or increase their proliferation rate in vivo for greater than 5 years. In another embodiment, T-cells having an altered form of a STAT5B encoded protein maintain or increase their proliferation rate in vivo for greater than 10 years. In another embodiment, T-cells having an altered form of a STAT5B encoded protein maintain or increase their proliferation rate in vivo for greater than 20 years.

In another embodiment, T-cells having an altered form of a BACH2 encoded protein maintain or increase their proliferation rate in vivo for greater than 1 year. In another embodiment, T-cells having an altered form of a BACH2 encoded protein maintain or increase their proliferation rate in vivo for greater than 2 years. In another embodiment, T-cells having an altered form of a BACH2 encoded protein maintain or increase their proliferation rate in vivo for greater than 3 years. In another embodiment, T-cells having an altered form of a BACH2 encoded protein maintain or increase their proliferation rate in vivo for greater than 4 years. In another embodiment, T-cells having an altered form of a BACH2 encoded protein maintain or increase their proliferation rate in vivo for greater than 5 years. In another embodiment, T-cells having an altered form of a BACH2 encoded protein maintain or increase their proliferation rate in vivo for greater than 10 years. In another embodiment, T-cells having an altered form of a BACH2 encoded protein maintain or increase their proliferation rate in vivo for greater than 20 years.

In another embodiment, CAR T-cells having an altered expression of a STAT5B encoded protein are maintained for an extended time period or have an increased proliferation rate in vivo. In another embodiment, CAR T-cells having an altered expression of a BACH2 encoded protein are maintained for an extended time period or have an increased proliferation rate in vivo. In another embodiment, CAR T-cells having an altered form of a STAT5B encoded protein are maintained for an extended time period or have an increased proliferation rate in vivo. In another embodiment, CAR T-cells having an altered form of a BACH2 encoded protein are maintained for an extended time period or have an increased proliferation rate in vivo In another embodiment, TCR T-cells having an altered expression of a STAT5B encoded protein are maintained for an extended time period or have an increased proliferation rate in vivo. In another embodiment, TCR T-cells having an altered expression of a BACH2 encoded protein are maintained for an extended time period or have an increased proliferation rate in vivo. In another embodiment, TCR T-cells having an altered form of a STAT5B encoded protein are maintained for an extended time period or have an increased proliferation rate in vivo. In another embodiment, TCR T-cells having an altered form of a BACH2 encoded protein are maintained for an extended time period or have an increased proliferation rate in vivo.

In another embodiment, Treg-cells having an altered expression of a STAT5B encoded protein maintain or increase their proliferation rate in vivo. In another embodiment, Treg-cells having an altered expression of a BACH2 encoded protein maintain or increase their proliferation rate in vivo. In another embodiment, Treg-cells having an altered form of a STAT5B encoded protein maintain or increase their proliferation rate in vivo. In another embodiment, Treg-cells having an altered form of a BACH2 encoded protein maintain or increase their proliferation rate in vivo.

In one embodiment, methods for maintaining or increasing the proliferation rate of a genetically modified immune cell are disclosed herein, wherein the method comprises the step of administering apoptotic cells or an apoptotic supernatant. In another embodiment, methods for increasing the efficacy of a genetically modified immune cell are disclosed herein, wherein the method comprises the step of administering an additional agent comprising apoptotic cells, an apoptotic supernatant, a CTLA-4 blocking agent, an alpha-1 anti-trypsin or fragment thereof or analogue thereof, a tellurium-based compound, or an immune modulating agent, or any combination thereof. In another embodiment, methods for treating, preventing, inhibiting, reducing the incidence of, ameliorating, or alleviating a cancer or a tumor disclosed herein administer a genetically modified immune cell and an additional agent, wherein said additional agent comprises apoptotic cells, an apoptotic supernatant, a CTLA-4 blocking agent, an alpha-1 anti-trypsin or fragment thereof or analogue thereof, a tellurium-based compound, or an immune modulating agent, or any combination thereof.

Chimeric Antigen Receptor-Expressing T-Cells (CAR T-Cells)

In some embodiments, chimeric antigen receptors (CARs) are a type of antigen-targeted receptor composed of intracellular T-cell signaling domains fused to extracellular tumor-binding moieties, most commonly single-chain variable fragments (scFvs) from monoclonal antibodies. CARs directly recognize cell surface antigens, independent of MHC-mediated presentation, permitting the use of a single receptor construct specific for any given antigen in all patients. Initial CARs fused antigen-recognition domains to the CD3 activation chain of the T-cell receptor (TCR) complex. While these first generation CARs induced T-cell effector function in vitro, they were largely limited by poor antitumor efficacy in vivo. Subsequent CAR iterations have included secondary costimulatory signals in tandem with CD3ζ, including intracellular domains from CD28 or a variety of TNF receptor family molecules such as 4-1BB (CD137) and OX40 (CD134). Further, third generation receptors include two costimulatory signals in addition to CD3ζ, most commonly from CD28 and 4-1BB. Second and third generation CARs dramatically improved antitumor efficacy, in some cases inducing complete remissions in patients with advanced cancer.

In some embodiments, a CAR T-cell is an immunoresponsive cell comprising an antigen receptor, which is activated when its receptor binds to its antigen.

In some embodiments, the CAR T-cells used in the compositions and methods as disclosed herein are first generation CAR T-cells. In another embodiment, the CAR T-cells used in the compositions and methods as disclosed herein are second generation CAR T-cells. In another embodiment, the CAR T-cells used in the compositions and methods as disclosed herein are third generation CAR T-cells. In another embodiment, the CAR T-cells used in the compositions and methods as disclosed herein are fourth generation CAR T-cells. In some embodiments, each generation of CAR T-cells is more potent than the CAR T-cells of earlier generations.

In some embodiments, first-generation CARs have one signaling domain, typically the cytoplasmic signaling domain of the CD3 TCRζ chain.

In another embodiment, the CAR T-cells as disclosed herein are second generation CAR T-cells. In another embodiment, CAR T-cells as disclosed herein comprise a tripartite chimeric receptor (TPCR). In some embodiments, CAR T-cells as disclosed herein, comprise one or more signaling moieties that activate naïve T-cells in a co-stimulation independent manner. In another embodiment, the CAR T-cells further encode one or more members of the tumor necrosis factor receptor family, which in some embodiments, is CD27, 4-1BB (CD137), or OX40 (CD134), or a combination thereof.

Third-generation CAR T-cells attempt to harness the signaling potential of 2 costimulatory domains: in some embodiments, the CD28 domain followed by either the 4-1BB or OX-40 signaling domains. In another embodiment, the CAR T-cells used in the compositions and methods as disclosed herein further encode a co-stimulatory signaling domain, which in one embodiment is CD28. In another embodiment, the signaling domain is the CD3ζ-chain, CD97, GDI la-CD18, CD2, ICOS, CD27, CD154, CDS, OX40, 4-1BB, CD28 signaling domain, or combinations thereof.

In some embodiments, telomere length and replicative capacity correlate with the engraftment efficiency and anti-tumor efficacy of adoptively transferred T-cell lines. In some embodiments, CD28 stimulation maintains telomere length in T-cells.

In some embodiments, CAR-modified T-cell potency may be further enhanced through the introduction of additional genes, including those encoding proliferative cytokines (ie, IL-12) or costimulatory ligands (ie, 4-1BBL), thus producing "armored" fourth-generation CAR-modified T-cells. In some embodiments, "armored CAR T-cells," are CAR T-cells which are protected from the inhibitory tumor microenvironment. In another embodiment, the "armored" CAR technology incorporates the local secretion of soluble signaling proteins to amplify the immune response within the tumor microenvironment with the goal of minimizing systemic side effects. In some embodiments, the signaling protein signal is IL-12, which can stimulate T-cell activation and recruitment. In some embodiments, "armored" CAR technology is especially useful in solid tumor indications, in which microenvironment and potent immunosuppressive mechanisms have the potential to make the establishment of a robust anti-tumor response more challenging.

In some embodiments, CAR T-cells are genetically modified to encode molecules involved in the prevention of apoptosis, the remodeling of the tumor microenvironment, induction of homeostatic proliferation, and chemokine receptors that promote directed T-cell homing.

In another embodiment, CAR T-cell therapy used in the compositions and methods as disclosed herein is enhanced using the expression of cytokine transgenes, combination therapy with small molecule inhibitors, or monoclonal antibodies. In another embodiment, other strategies aimed at improving CAR T-cell therapy including using dual CARs and chemokine receptors to more specifically target tumor cells are to be considered part of the CAR T-cells and CAR T-cell therapy as disclosed herein.

In some embodiments, the CAR T-cells of the compositions and methods as disclosed herein comprise a second binding domain that can lead to either an inhibitory or amplifying signal, in order to increase specificity of CAR T-cells for cancer cells versus normal cells. For example, a CAR T-cell can be engineered such that it would be triggered in the presence of one target protein, but if a second protein is present it would be inhibited. Alternatively, it could also be engineered such that two target proteins would be required for maximal activation. These approaches may increase the specificity of the CAR for tumor relative to normal tissue.

In some embodiments, the CAR T-cells used in the compositions and methods as disclosed herein encode antibody-based external receptor structures and cytosolic domains that encode signal transduction modules composed of the immunoreceptor tyrosine-based activation motif.

In some embodiments, the CAR T-cell further encodes a single-chain variable fragment (scFv) that binds a polypeptide that has immunosuppressive activity. In another embodiment, the polypeptide that has immunosuppressive activity is CD47, PD-1, CTLA-4, or a combination thereof.

In some embodiments, the CAR T-cell further encodes a single-chain variable fragment (scFv) that binds a polypeptide that has immunostimulatory activity. In another embodiment, the polypeptide that has immunostimulatory activity is CD28, OX-40, 4-1BB or a combination thereof. In another embodiment, the CAR T-cell further encodes a CD40 ligand (CD40L), which, in some embodiments, enhances the immunostimulatory activity of the antigen.

In some embodiments, the immune cells are cytotoxic. In another embodiment, cytotoxic cells for genetic modification can be obtained from bone marrow of the subject or a donor. In other cases, the cells are obtained from a stem cell. For example, cytotoxic cells can be derived from human pluripotent stem cells such as human embryonic stem cells or human induced pluripotent T-cells. In the case of induced pluripotent stem cells (IPSCs), such pluripotent T-cells can be obtained using a somatic cell from the subject to which genetically modified cytotoxic cells will be provided. In some embodiments, immune cells may be obtained from a subject or donor by harvesting cells by venipuncture, by apheresis methods, by white cell mobilization followed by apheresis or venipuncture, or by bone marrow aspiration.

Figure 1B:
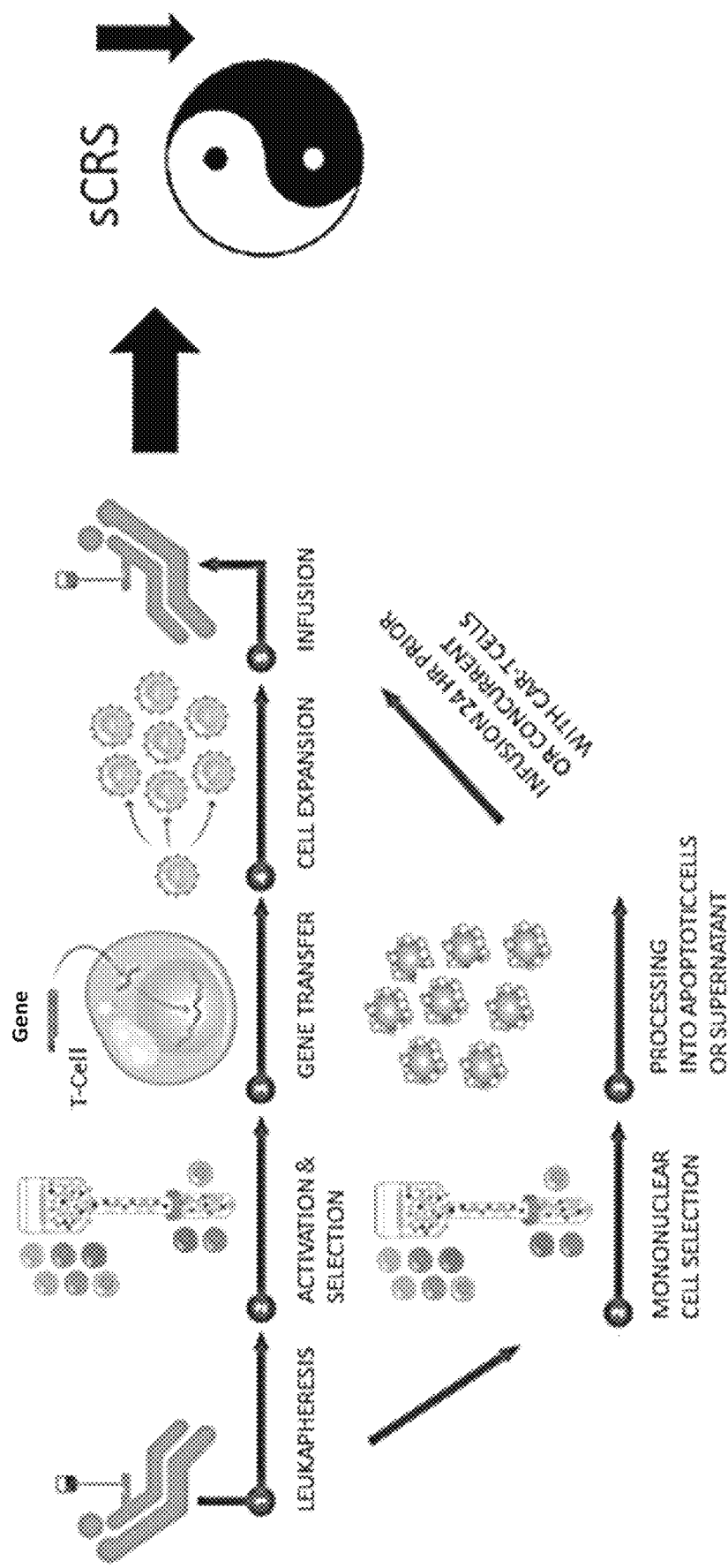
Figure 2:
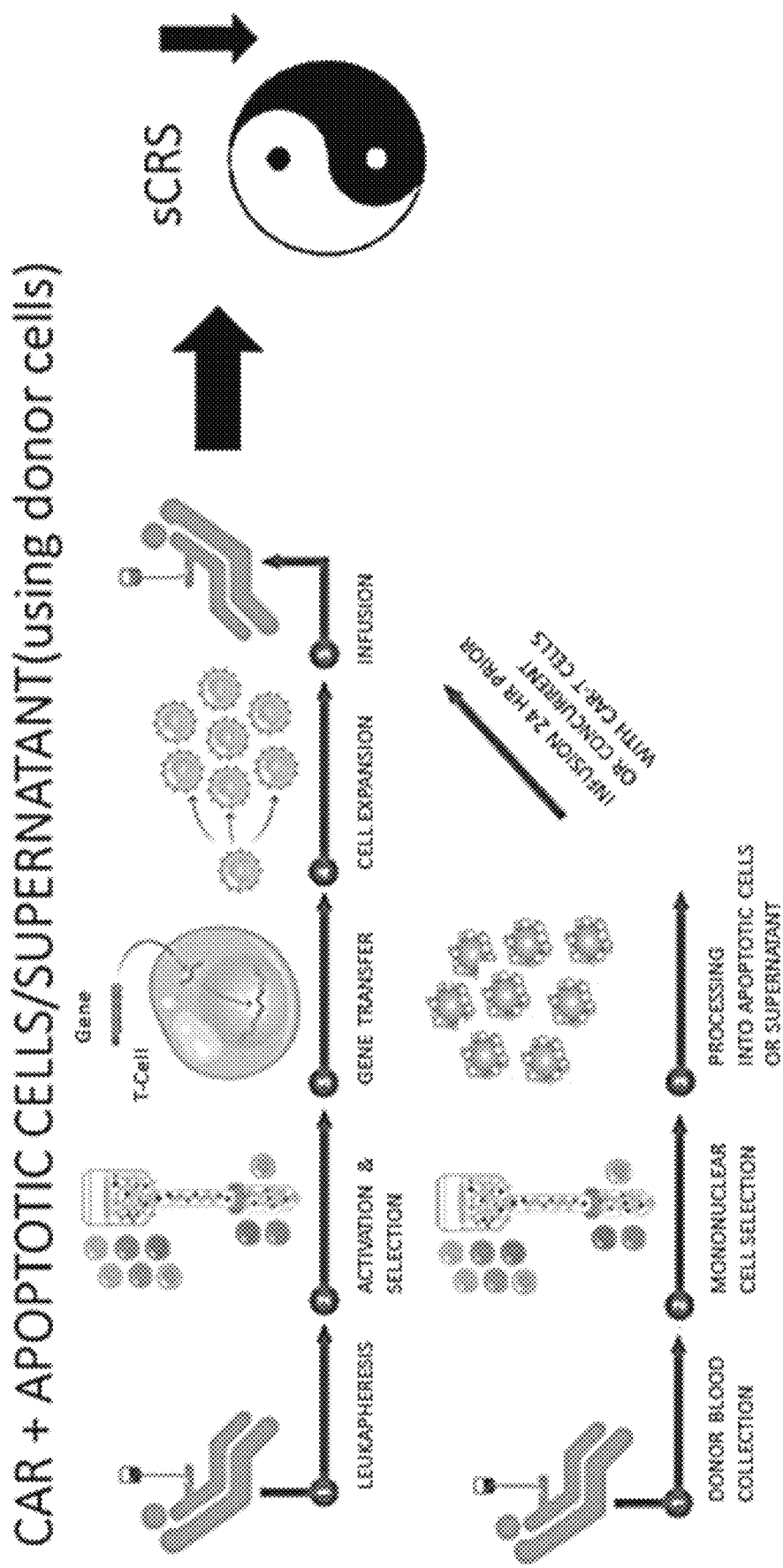
FIG. 2. Schematic showing embodiments of a method of safe and efficacious CAR T-cell cancer therapy in a patient, using donor cells to produce apoptotic cells or an apoptotic cell supernatant.
Figure 3:
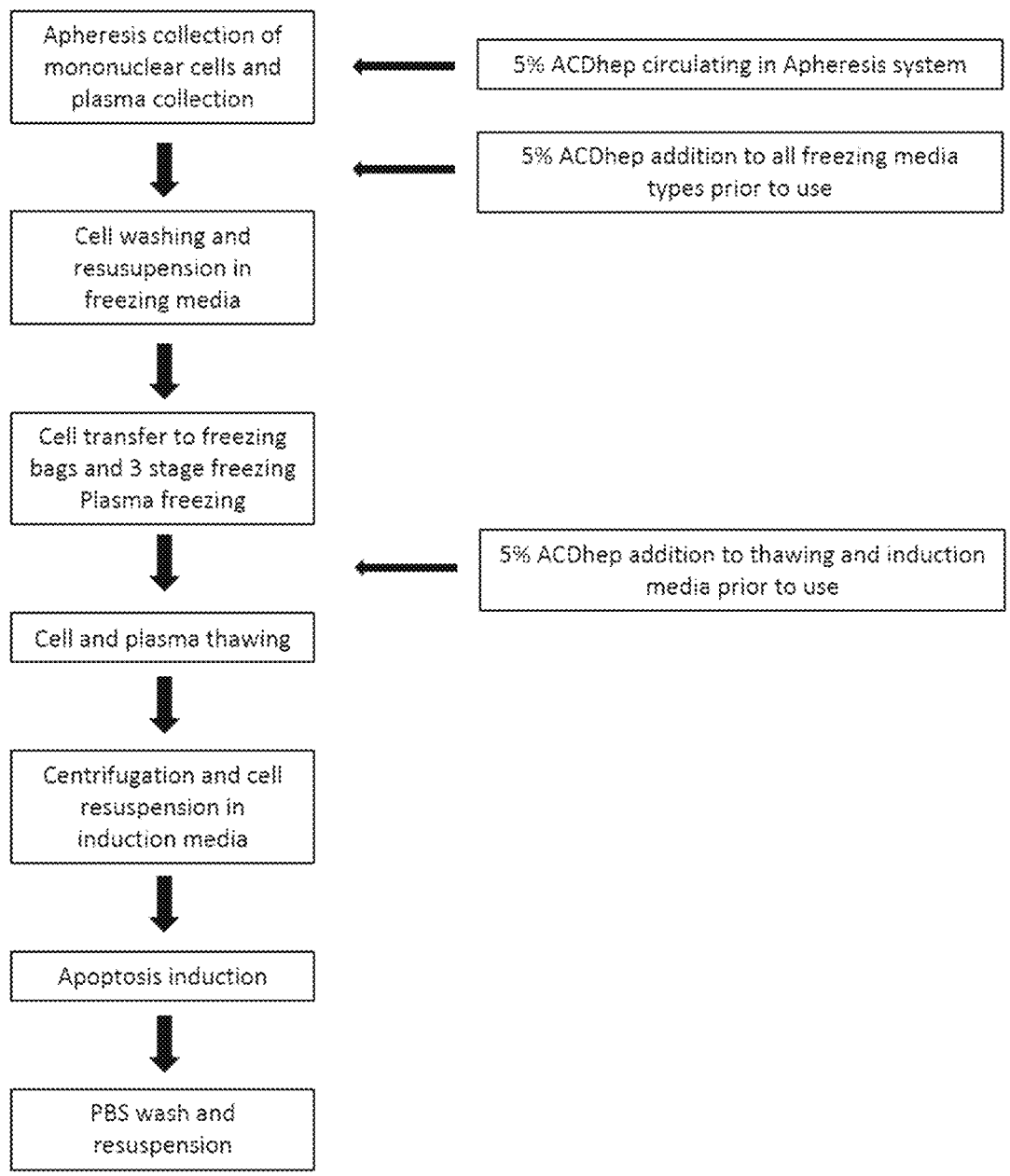
FIG. 3. Flow chart presenting the steps during one embodiment of a manufacturing process of an early apoptotic cell populations, wherein anti-coagulants were included in the process.

In some embodiments, a method as disclosed herein comprises obtaining immune cells from a subject, and genetically modifying the immune cells to express a chimeric antigen receptor. In another embodiment, a method as disclosed herein comprises obtaining immune cells from a subject, genetically modifying the immune cells to express a chimeric antigen receptor and combining with apoptotic cell population resulting in reduced cytokine production in a subject but substantially unaffected cytotoxicity relative to immune cells expressing a CAR not administered with an apoptotic cell population (FIGS. 1A-1B and 2). In another embodiment, a method as disclosed herein comprises obtaining immune cells from a subject, genetically modifying the immune cells to express a chimeric antigen receptor and combining with an apoptotic cell supernatant or a composition comprising the supernatant, resulting in reduced cytokine production in a subject but substantially unaffected cytotoxicity relative to immune cells expressing a CAR not administered with an apoptotic cell supernatant. In another embodiment, administration of an apoptotic cell population or a supernatant from apoptotic cells does not reduce the efficacy of the immune cells expressing the chimeric antigen receptor.

In one embodiment, disclosed herein are immune cells, in some embodiments, CAR T-cells in which the T-cell is autologous to the subject. In another embodiment, the CAR T-cells are heterologous to the subject. In some embodiments, the CAR T-cells are allogeneic. In some embodiments, the CAR T-cells are universal allogeneic CAR T-cells. In another embodiment, the T-cells may be autologous, allogeneic, or derived in vitro from engineered progenitor or stem cells.

In another embodiment, the CAR T-cells and apoptotic cells described herein, are both derived from the same source. In a further embodiment, the CAR T-cells and apoptotic cells described herein, are both derived from the subject (FIG. 1). In an alternative embodiment, the CAR T-cells and apoptotic cells described herein, are derived from different sources. In yet another embodiment, the CAR T-cells are autologous and the apoptotic cells described herein, are allogeneic (FIG. 2). A skilled artisan would appreciate that similarly, an apoptotic cell supernatant may be made from cells derived from the same source as the CAR T-cell, which may in one embodiment be autologous cells, or an apoptotic cell supernatant may be made from cells derived from a source different from the source of CAR T-cells.

A skilled artisan would appreciate that the term "heterologous" may encompass a tissue, cell, nucleic acid molecule or polypeptide that is derived from a different organism. In some embodiments, a heterologous protein is a protein that was initially cloned from or derived from a different T-cell type or a different species from the recipient and that is not normally present in a cell or sample obtained from a cell.

Accordingly, one embodiment as disclosed herein relates to cytotoxic immune cells (e.g., NK cells or T-cells) comprising chimeric antigen receptors (CARs) whereby the cells retain their cytotoxic function. In another embodiment, the chimeric antigen receptor is exogenous to the T-cell. In another embodiment, the CAR is recombinantly expressed. In another embodiment, the CAR is expressed from a vector.

In some embodiments, the T-cell utilized to generate CAR T-cells is a naïve CD4$^+$ T-cell. In another embodiment, the T-cell utilized to generate CAR T-cells is a naïve CD8$^+$ T-cell. In another embodiment, the T-cell utilized to generate CAR T-cells is an effector T-cell. In another embodiment, the T-cell utilized to generate CAR T-cells is a regulatory T-cell (Treg). In another embodiment, the T-cell utilized to generate CAR T-cells is a cytotoxic T-cell.

Sources for genetically modified immune cells, for example T cells, have been described extensively in the literature, see for example Themelli et al. (2015) New Cell Sources for T Cell Engineering and Adoptive Immunotherapy. Cell Stem Cell 16: 357-366; Han et al. (2013) Journal of Hematology & Oncology 6:47-53; Wilkie et al. (2010) J Bio Chem 285(33):25538-25544; and van der Stegen et al. (2013) J. Immunol 191: 4589-4598. CAR T-cells are available to order from a commercial source such as Creative Biolabs (NY USA), which provides custom construction and production services for Chimeric Antigen Receptors (CAR) and also provides premade CAR constructs stock, which can induce protective immunity encode by recombinant adenovirus vaccine. Custom made CAR T-cells may also be obtained from Promab Biotechnologies (CA USA), which can provide specifically designed CAR T-cells.

T-Cell Receptors (TCRs) Cells

In one embodiment, compositions and methods as disclosed herein utilize a designer T-cell receptor (TCR) cells in addition to or in place of CAR T-cells. The TCR is a multi-subunit transmembrane complex that mediates the antigen-specific activation of T-cells. The TCR is composed of two different polypeptide chains. The TCR confers antigenic specificity on the T cell, by recognizing an antigen epitope on the target cell, for example a tumor or cancer cell. Following contact with the antigen present on the tumor or cancer cell, T-cells proliferate and acquire the phenotype and function to allow them eliminate the cancer or tumor cells.

In one embodiment, TCR T-cell therapy comprises introducing a T-cell receptor (TCR) that is specific to an epitope of a protein of interest into a T-cell. In another embodiment, the protein of interest is a tumor-associated antigen. In another embodiment, the genetically engineered TCR recognizes a tumor antigen epitope presented by the major histocompatibility complex (MHC) on the tumor cell along with T-cell activating domains. In another embodiment, the T-cell receptors recognize antigens irrespectively of their intracellular or membrane localization. In another embodiment, TCRs recognize tumor cells that intracellularly express a tumor associated antigen. In one embodiment TCRs recognize internal antigens. In another embodiment, TCRs recognize angiogenic factors. In another embodiment, an angiogenic factor is a molecule involved in the formation of new blood vessels. Various genetically modified T-cell receptors and methods of their production are known in the art.

In one embodiment, TCR T-cell therapy is used to treat, prevent, inhibit, ameliorate, reduce the incidence of, or alleviate a cancer or a tumor. In one embodiment, TCR T-cell therapy is used to treat, prevent, inhibit, ameliorate, reduce the incidence of, or alleviate advanced metastatic disease, including those with hematological (lymphoma and leukemia) and solid tumors (refractory melanoma, sarcoma). In one embodiment, the TCR T-cell therapy used in the compositions and methods as disclosed herein treat a malignancy listed in Table 1 of Sadelain et al., (Cancer Discov. 2013 April; 3(4): 388-398).

In another embodiment, the T-cell receptor is genetically modified to bind NY-ESO-1 epitopes, and the TCR-engineered T-cell is anti-NY-ESO-1. In another embodiment, the T-cell receptor is genetically modified to bind HPV-16 E6 epitopes, and the TCR-engineered T-cell is anti-HPV-16 E6. In another embodiment, the T-cell receptor is genetically modified to bind HPV-16 E7 epitopes, and the TCR-engineered T-cell is anti-HPV-16 E7. In another embodiment, the T-cell receptor is genetically modified to bind MAGE A3/A6 epitopes, and the TCR-engineered T-cell is anti-MAGE A3/A6. In another embodiment, the T-cell receptor is genetically modified to bind MAGE A3 epitopes, and the TCR-engineered T-cell is anti-MAGE A3. In another embodiment, the T-cell receptor is genetically modified to bind SSX2 epitopes, and the TCR-engineered T-cell is anti-SSX2. In another embodiment, the T-cell receptor is genetically modified to bind a target antigen disclosed herein. Using the tools well known in the art, a skilled would appreciate that the T-cell receptor may be genetically modified to bind a target antigen present on a cancer or tumor cell, wherein the TCR-engineer T-cell comprises an anti-tumor or anti-cancer cell.

In one embodiment, a method as disclosed herein comprises obtaining immune cells from a subject, and genetically modifying the immune cells to express a recombinant T-cell receptor (TCR). In another embodiment, a method as disclosed herein comprises obtaining immune cells from a subject, genetically modifying the immune cells to express a recombinant TCR and combining with an additional agent, wherein said additional agent comprises an apoptotic cell population, an apoptotic cell supernatant, a CTLA-4 blocking agent, an alpha-1 anti-trypsin or fragment thereof or analogue thereof, a tellurium-based compound, or an immune modulating agent, or any combination thereof.

In one embodiment, the T-cell utilized to generate TCR T-cells is a naïve CD4$^+$ T-cell. In another embodiment, the T-cell utilized to generate TCR T-cells is a naïve CD8$^+$ T-cell. In another embodiment, the T-cell utilized to generate TCR T-cells is an effector T-cell. In another embodiment, the T-cell utilized to generate TCR T-cells is a regulatory T-cell (Treg). In another embodiment, the T-cell utilized to generate TCR T-cells is a cytotoxic T-cell.

TCR T-cells have been described extensively in the literature, see for example Sharpe and Mount (2015) ibid.;

Essand M, Loskog ASI (2013) Genetically engineered T cells for the treatment of cancer (Review). J Intern Med 273: 166-181; and Kershaw et al. (2014) Clinical application of genetically modified T cells in cancer therapy. Clinical & Translational Immunology 3:1-7.

Targeting Antigens

In some embodiments, the CAR binds to an epitope of an antigen via an antibody or an antibody fragment that is directed to the antigen. In another embodiment, the antibody is a monoclonal antibody. In another embodiment, the antibody is a polyclonal antibody. In another embodiment, the antibody fragment is a single-chain variable fragment (scFv).

In one embodiment, the TCR binds to an epitope of an antigen via a genetically modified T-cell receptor.

In another embodiment, the CAR T-cells of the compositions as disclosed herein bind to a tumor associated antigen (TAA). In another embodiment, said tumor associated antigen is: Mucin 1, cell surface associated (MUC1) or polymorphic epithelial mucin (PEM), Arginine-rich, mutated in early stage tumors (Armet), Heat Shock Protein 60 (HSP60), calnexin (CANX), methylenetetrahydrofolate dehydrogenase (NADP+ dependent) 2, methenyltetrahydrofolate cyclohydrolase (MTHFD2), fibroblast activation protein (FAP), matrix metallopeptidase (MMP6), B Melanoma Antigen-1 (BAGE-1), aberrant transcript of N-acetyl glucosaminyl transferase V (GnTV), Q5H943, Carcinoembryonic antigen (CEA), Pmel, Kallikrein-4, Mammaglobin-1, MART-1, GPR143-OA1, prostate specific antigen (PSA), TRP1, Tyrosinase, FGP-5, NEU proto-oncogene, Aft, MMP-2, prostate specific membrane antigen (PSMA), Telomerase-associated protein-2, Prostatic acid phosphatase (PAP), Uroplakin II or Proteinase 3.

In another embodiment, the CAR binds to CD19 or CD20 to target B cells in the case where one would like to destroy B cells as in leukemia. CD19 is a B cell lineage specific surface receptor whose broad expression, from pro-B cells to early plasma cells, makes it an attractive target for the immunotherapy of B cell malignancies. In another embodiment, the CAR binds to ROR1, CD22, or GD2. In another embodiment, the CAR binds to NY-ESO-1. In another embodiment, the CAR binds to MAGE family proteins. In another embodiment, the CAR binds to mesothelin. In another embodiment, the CAR binds to c-erbB2. In another embodiment, the CAR binds to mutational antigens that are tumor specific, such as BRAFV600E mutations and BCR-ABL translocations. In another embodiment, the CAR binds to viral antigens which are tumor-specific, such as EBV in HD, HPV in cervical cancer, and polyomavirus in Merkel cancer. In another embodiment, the CAR T-cell binds to Her2/neu. In another embodiment, the CAR T-cell binds to EGFRvIII.

In some embodiments, the chimeric antigen receptor (CAR) T-cell binds the CD19 antigen. In another embodiment, the CAR binds the CD22 antigen. In another embodiment, the CAR binds to alpha folate receptor. In another embodiment, the CAR binds to CAIX. In another embodiment, the CAR binds to CD20. In another embodiment, the CAR binds to CD23. In another embodiment, the CAR binds to CD24. In another embodiment, the CAR binds to CD30. In another embodiment, the CAR binds to CD33. In another embodiment, the CAR binds to CD38. In another embodiment, the CAR binds to CD44v6. In another embodiment, the CAR binds to CD44v7/8. In another embodiment, the CAR binds to CD123. In another embodiment, the CAR binds to CD171. In another embodiment, the CAR binds to carcinoembryonic antigen (CEA). In another embodiment, the CAR binds to EGFRvIII. In another embodiment, the CAR binds to EGP-2. In another embodiment, the CAR binds to EGP-40. In another embodiment, the CAR binds to EphA2. In another embodiment, the CAR binds to Erb-B2. In another embodiment, the CAR binds to Erb-B 2,3,4. In another embodiment, the CAR binds to Erb-B3/4. In another embodiment, the CAR binds to FBP. In another embodiment, the CAR binds to fetal acetylcholine receptor. In another embodiment, the CAR binds to GD2. In another embodiment, the CAR binds to GD3. In another embodiment, the CAR binds to HER2. In another embodiment, the CAR binds to HMW-MAA. In another embodiment, the CAR binds to IL-11Ralpha. In another embodiment, the CAR binds to IL-13Ralpha1. In another embodiment, the CAR binds to KDR. In another embodiment, the CAR binds to kappa-light chain. In another embodiment, the CAR binds to Lewis Y. In another embodiment, the CAR binds to L1-cell adhesion molecule. In another embodiment, the CAR binds to MAGE-A1. In another embodiment, the CAR binds to mesothelin. In another embodiment, the CAR binds to CMV infected cells. In another embodiment, the CAR binds to MUC1. In another embodiment, the CAR binds to MUC16. In another embodiment, the CAR binds to NKG2D ligands. In another embodiment, the CAR binds to NY-ESO-1 (amino acids 157-165). In another embodiment, the CAR binds to oncofetal antigen (h5T4). In another embodiment, the CAR binds to PSCA. In another embodiment, the CAR binds to PSMA. In another embodiment, the CAR binds to ROR1. In another embodiment, the CAR binds to TAG-72. In another embodiment, the CAR binds to VEGF-R2 or other VEGF receptors. In another embodiment, the CAR binds to B7-H6. In another embodiment, the CAR binds to CA9. In another embodiment, the CAR binds to $\alpha_v\beta_6$ integrin. In another embodiment, the CAR binds to 8H9. In another embodiment, the CAR binds to NCAM. In another embodiment, the CAR binds to fetal acetylcholine receptor.

In another embodiment, the chimeric antigen receptor (CAR) T-cell targets the CD19 antigen, and has a therapeutic effect on subjects with B-cell malignancies, ALL, Follicular lymphoma, CLL, and Lymphoma. In another embodiment, the CAR T-cell targets the CD22 antigen, and has a therapeutic effect on subjects with B-cell malignancies. In another embodiment, the CAR T-cell targets alpha folate receptor or folate receptor alpha, and has a therapeutic effect on subjects with ovarian cancer or epithelial cancer. In another embodiment, the CAR T-cell targets CAIX or G250/CAIX, and has a therapeutic effect on subjects with renal cell carcinoma. In another embodiment, the CAR T-cell targets CD20, and has a therapeutic effect on subjects with Lymphomas, B-cell malignancies, B-cell lymphomas, Mantle cell lymphoma and, indolent B-cell lymphomas. In another embodiment, the CAR T-cell targets CD23, and has a therapeutic effect on subjects with CLL. In another embodiment, the CAR T-cell targets CD24, and has a therapeutic effect on subjects with pancreatic adenocarcinoma. In another embodiment, the CAR T-cell targets CD30, and has a therapeutic effect on subjects with Lymphomas or Hodgkin lymphoma. In another embodiment, the CAR T-cell targets CD33, and has a therapeutic effect on subjects with AML. In another embodiment, the CAR T-cell targets CD38, and has a therapeutic effect on subjects with Non-Hodgkin lymphoma. In another embodiment, the CAR T-cell targets CD44v6, and has a therapeutic effect on subjects with several malignancies. In another embodiment, the CAR T-cell targets CD44v7/8, and has a therapeutic effect on subjects with cervical carcinoma. In another embodiment, the CAR T-cell targets CD123, and has a therapeutic effect on subjects with myeloid malignancies. In another embodiment, the CAR T-cell targets CEA, and has a therapeutic effect on subjects with colorectal cancer. In another embodiment, the CAR T-cell targets EGFRvIII, and has a therapeutic effect on subjects with Glioblastoma. In another embodiment, the CAR T-cell targets EGP-2, and has a therapeutic effect on subjects with multiple malignancies. In another embodiment, the CAR T-cell targets EGP-40, and has a therapeutic effect on subjects with colorectal cancer. In another embodiment, the CAR T-cell targets EphA2, and has a therapeutic effect on subjects with Glioblastoma. In another embodiment, the CAR T-cell targets Erb-B2 or ErbB3/4, and has a therapeutic effect on subjects with Breast cancer and others, prostate cancer, colon cancer, various tumors. In another embodiment, the CAR T-cell targets Erb-B 2,3,4, and has a therapeutic effect on subjects with Breast cancer and others. In another embodiment, the CAR T-cell targets FBP, and has a therapeutic effect on subjects with Ovarian cancer. In another embodiment, the CAR T-cell targets fetal acetylcholine receptor, and has a therapeutic effect on subjects with Rhabdomyosarcoma. In another embodiment, the CAR T-cell targets $G_{D2}$, and has a therapeutic effect on subjects with Neuroblastoma, melanoma, or Ewing's sarcoma. In another embodiment, the CAR T-cell targets $G_{D3}$, and has a therapeutic effect on subjects with Melanoma. In another embodiment, the CAR T-cell targets HER2, and has a therapeutic effect on subjects with medulloblastoma, pancreatic adenocarcinoma, Glioblastoma, Osteosarcoma, or Ovarian cancer. In another embodiment, the CAR T-cell targets HMW-MAA, and has a therapeutic effect on subjects with Melanoma. In another embodiment, the CAR T-cell targets IL-11Ralpha, and has a therapeutic effect on subjects with Osteosarcoma. In another embodiment, the CAR T-cell targets IL-13Ralpha1, and has a therapeutic effect on subjects with Glioma, Glioblastoma, or medulloblastoma. In another embodiment, the CAR T-cell targets IL-13 receptor alpha2, and has a therapeutic effect on subjects with several malignancies. In another embodiment, the CAR T-cell targets KDR, and has a therapeutic effect on subjects with tumors by targeting tumor neovasculature. In another embodiment, the CAR T-cell targets kappa-light chain, and has a therapeutic effect on subjects with B-cell malignancies (B-NHL, CLL). In another embodiment, the CAR T-cell targets Lewis Y, and has a therapeutic effect on subjects with various carcinomas or epithelial-derived tumors. In another embodiment, the CAR T-cell targets L1-cell adhesion molecule, and has a therapeutic effect on subjects with Neuroblastoma. In another embodiment, the CAR T-cell targets MAGE-A1 or HLA-A1 MAGE A1, and has a therapeutic effect on subjects with Melanoma. In another embodiment, the CAR T-cell targets mesothelin, and has a therapeutic effect on subjects with Mesothelioma. In another embodiment, the CAR T-cell targets CMV infected cells, and has a therapeutic effect on subjects with CMV. In another embodiment, the CAR T-cell targets MUC1, and has a therapeutic effect on subjects with breast or ovarian cancer. In another embodiment, the CAR T-cell targets MUC16, and has a therapeutic effect on subjects with ovarian cancer. In another embodiment, the CAR T-cell targets NKG2D ligands, and has a therapeutic effect on subjects with myeloma, ovarian, and other tumors. In another embodiment, the CAR T-cell targets NY-ESO-1 (157-165) or HLA-A2 NY-ESO-1, and has a therapeutic effect on subjects with multiple myeloma. In another embodiment, the CAR T-cell targets oncofetal antigen (h5T4), and has a therapeutic effect on subjects with various tumors. In another embodiment, the CAR T-cell targets PSCA, and has a therapeutic effect on subjects with prostate carcinoma. In another embodiment, the CAR T-cell targets PSMA, and has a therapeutic effect on subjects with prostate cancer/tumor vasculature. In another embodiment, the CAR T-cell targets ROR1, and has a therapeutic effect on subjects with B-CLL and mantle cell lymphoma. In another embodiment, the CAR T-cell targets TAG-72, and has a therapeutic effect on subjects with adenocarcinomas or gastrointestinal cancers. In another embodiment, the CAR T-cell targets VEGF-R2 or other VEGF receptors, and has a therapeutic effect on subjects with tumors by targeting tumor neovasculature. In another embodiment, the CAR T-cell targets CA9, and has a therapeutic effect on subjects with renal cell carcinoma. In another embodiment, the CAR T-cell targets CD171, and has a therapeutic effect on subjects with renal neuroblastoma. In another embodiment, the CAR T-cell targets NCAM, and has a therapeutic effect on subjects with neuroblastoma. In another embodiment, the CAR T-cell targets fetal acetylcholine receptor, and has a therapeutic effect on subjects with rhabdomyosarcoma. In another embodiment, the CAR binds to one of the target antigens listed in Table 1 of Sadelain et al. (Cancer Discov. 2013 April; 3(4): 388-398), which is incorporated by reference herein in its entirety. In another embodiment, CAR T-cells bind to carbohydrate or glycolipid structures.

In one embodiment the CAR T-cells binds to an angiogenic factor, thereby targeting tumor vasculature. In some embodiments, the angiogenic factor is VEGFR2. in another embodiment, the angiogenic factor is endoglin. In another embodiment, an angiogenic factor disclosed herein is Angiogenin; Angiopoietin-1; Del-1; Fibroblast growth factors: acidic (aFGF) and basic (bFGF); Follistatin; Granulocyte colony-stimulating factor (G-CSF); Hepatocyte growth factor (HGF)/scatter factor (SF); Interleukin-8 (IL-8); Leptin; Midkine; Placental growth factor; Platelet-derived endothelial cell growth factor (PD-ECGF); Platelet-derived growth factor-BB (PDGF-BB); Pleiotrophin (PTN); Progranulin; Proliferin; Transforming growth factor-alpha (TGF-alpha); Transforming growth factor-beta (TGF-beta); Tumor necrosis factor-alpha (TNF-alpha); Vascular endothelial growth factor (VEGF)/vascular permeability factor (VPF). In another embodiment, an angiogenic factor is an angiogenic protein. In some embodiments, a growth factor is an angiogenic protein. In some embodiments, an angiogenic protein for use in the compositions and methods disclosed herein is Fibroblast growth factors (FGF); VEGF; VEGFR and Neuropilin 1 (NRP-1); Angiopoietin 1 (Ang1) and Tie2; Platelet-derived growth factor (PDGF; BB-homodimer) and PDGFR; Transforming growth factor-beta (TGF-β), endoglin and TGF-β receptors; monocyte chemotactic protein-1 (MCP-1); Integrins αVβ3, αVβ5 and α5β1; VE-cadherin and CD31; ephrin; plasminogen activators; plasminogen activator inhibitor-1; Nitric oxide synthase (NOS) and COX-2; AC133; or Id1/Id3. In some embodiments, an angiogenic protein for use in the compositions and methods disclosed herein is an angiopoietin, which in some embodiments, is Angiopoietin 1, Angiopoietin 3, Angiopoietin 4 or Angiopoietin 6. In some embodiments, endoglin is also known as CD105; EDG; HHT1; ORW; or ORW1. In some embodiments, endoglin is a TGFbeta co-receptor.

In another embodiment, the CAR T-cells bind to an antigen associated with an infectious agent. In some embodiments, the infectious agent is *Mycobacterium tuberculosis*. In some embodiments, said *Mycobacterium tuberculosis* associated antigen is: Antigen 85B, Lipoprotein IpqH, ATP dependent helicase putative, uncharacterized protein Rv0476/MTO4941 precursor or uncharacterized protein Rv1334/MT1376 precursor.

In another embodiment, the CAR T-cells binds to an antibody. In some embodiments, the CAR T-cell is an "antibody-coupled T-cell receptor" (ACTR). According to this embodiment, the CAR T-cell is a universal CAR T-cell. In another embodiment, the CAR T-cell having an antibody receptor is administered before, after, or at the same time as the antibody is administered and then binds to the antibody, bringing the T-cell in close proximity to the tumor or cancer. In another embodiment, the antibody is directed against a tumor cell antigen. In another embodiment, the antibody is directed against CD20. In another embodiment, the antibody is rituximab.

In another embodiment, the antibody is Trastuzumab (Herceptin; Genentech): humanized IgG1, which is directed against ERBB2. In another embodiment, the antibody is Bevacizumab (Avastin; Genentech/Roche): humanized IgG1, which is directed against VEGF. In another embodiment, the antibody is Cetuximab (Erbitux; Bristol-Myers Squibb): chimeric human—murine IgG1, which is directed against EGFR. In another embodiment, the antibody is Panitumumab (Vectibix; Amgen): human IgG2, which is directed against EGFR. In another embodiment, the antibody is Ipilimumab (Yervoy; Bristol-Myers Squibb): IgG1, which is directed against CTLA4.

In another embodiment, the antibody is Alemtuzumab (Campath; Genzyme): humanized IgG1, which is directed against CD52. In another embodiment, the antibody is Ofatumumab (Arzerra; Genmab): human IgG1, which is directed against CD20. In another embodiment, the antibody is Gemtuzumab ozogamicin (Mylotarg; Wyeth): humanized IgG4, which is directed against CD33. In another embodiment, the antibody is Brentuximab vedotin (Adcetris; Seattle Genetics): chimeric IgG1, which is directed against CD30. In another embodiment, the antibody is 90Y-labelled ibritumomab tiuxetan (Zevalin; IDEC Pharmaceuticals): murine IgG1, which is directed against CD20. In another embodiment, the antibody is 131I-labelled tositumomab (Bexxar; GlaxoSmithKline): murine IgG2, which is directed against CD20.

In another embodiment, the antibody is Ramucirumab, which is directed against vascular endothelial growth factor receptor-2 (VEGFR-2). In another embodiment, the antibody is ramucirumab (Cyramza Injection, Eli Lilly and Company), blinatumomab (BLINCYTO, Amgen Inc.), pembrolizumab (KEYTRUDA, Merck Sharp & Dohme Corp.), obinutuzumab (GAZYVA, Genentech, Inc.; previously known as GA101), pertuzumab injection (PERJETA, Genentech, Inc.), or denosumab (Xgeva, Amgen Inc.). In another embodiment, the antibody is Basiliximab (Simulect; Novartis). In another embodiment, the antibody is Daclizumab (Zenapax; Roche).

In another embodiment, the antibody to which the CAR T-cell is coupled is directed to a tumor or cancer antigen or a fragment thereof, that is described herein and/or that is known in the art. In another embodiment, the antibody to which the CAR T-cell is couples is directed to a tumor-associated antigen. In another embodiment, the antibody to which the CAR T-cell is couples is directed to a tumor-associated antigen or a fragment thereof that is an angiogenic factor.

In another embodiment, the antibody to which the CAR T-cell is coupled is directed to a tumor or cancer antigen or a fragment thereof, that is described herein and/or that is known in the art.

In some embodiments, antibodies described herein may be used in combination with compositions described herein, for example but not limited to a composition comprising CAR-T cells or early apoptotic cells, or any combination thereof.

Cytokine Storm and Cytokine Release Syndrome

In one embodiment, a method as disclosed herein includes providing immune cells, such as NK cells, dendritic cells, TCR T-cells, or T-cells comprising engineered chimeric antigen receptors (CAR T-cells), with at least an additional agent to decrease toxic cytokine release or "cytokine release syndrome" (CRS) or "severe cytokine release syndrome" (sCRS) or "cytokine storm" that may occur in the subject. In another embodiment the CRS, sCRS or cytokine storm occurs as a result of administration of the immune cells. In another embodiment, the CRS, sCRS or cytokine storm is the result of a stimulus, condition, or syndrome separate from the immune cells (see below). In another embodiment, a cytokine storm, cytokine cascade, or hypercytokinemia is a more severe form of cytokine release syndrome.

In one embodiment, the additional agent for decreasing harmful cytokine release comprises apoptotic cells or a composition comprising said apoptotic cells. In another embodiment, the additional agent for decreasing harmful cytokine release comprises an apoptotic cell supernatant or a composition comprising said supernatant. In another embodiment, the additional agent for decreasing harmful cytokine release comprises a CTLA-4 blocking agent. In another embodiment, the additional agent for decreasing harmful cytokine release comprises apoptotic cells or apoptotic cell supernatants or compositions thereof, and a CTLA-4 blocking agent. In another embodiment, the additional agent for decreasing harmful cytokine release comprises an alpha-1 anti-trypsin or fragment thereof or analogue thereof. In another embodiment, the additional agent for decreasing harmful cytokine release comprises apoptotic cells or apoptotic cell supernatants or compositions thereof, and an alpha-1 anti-trypsin or fragment thereof or analogue thereof. In another embodiment, the additional agent for decreasing harmful cytokine release comprises a tellurium-based compound. In another embodiment, the additional agent for decreasing harmful cytokine release comprises apoptotic cells or apoptotic cell supernatants or compositions thereof, and a tellurium-based compound. In another embodiment, the additional agent for decreasing harmful cytokine release comprises an immune modulating agent. In another embodiment, the additional agent for decreasing harmful cytokine release comprises apoptotic cells or apoptotic cell supernatants or compositions thereof, and an immune modulating agent. In another embodiment, the additional agent for decreasing harmful cytokine release comprises Treg cells. In another embodiment, the additional agent for decreasing harmful cytokine release comprises apoptotic cells or apoptotic cell supernatants or compositions thereof, and Treg cells.

A skilled artisan would appreciate that decreasing toxic cytokine release or toxic cytokine levels comprises decreasing or inhibiting production of toxic cytokine levels in a subject, or inhibiting or reducing the incidence of cytokine release syndrome or a cytokine storm in a subject. In another embodiment toxic cytokine levels are reduced during CRS or a cytokine storm. In another embodiment, decreasing or inhibiting the production of toxic cytokine levels comprises treating CRS or a cytokine storm. In another embodiment, decreasing or inhibiting the production of toxic cytokine levels comprises preventing CRS or a cytokine storm. In another embodiment, decreasing or inhibiting the production of toxic cytokine levels comprises alleviating CRS or a cytokine storm. In another embodiment, decreasing or inhibiting the production of toxic cytokine levels comprises ameliorating CRS or a cytokine storm. In another embodiment, the toxic cytokines comprise pro-inflammatory cytokines. In another embodiment, pro-inflammatory cytokines comprise IL-6. In another embodiment, pro-inflammatory cytokines comprise IL-1β. In another embodiment, pro-inflammatory cytokines comprise TNF-α, In another embodiment, pro-inflammatory cytokines comprise IL-6, IL-1β, or TNF-α, or any combination thereof.

In one embodiment, cytokine release syndrome is characterized by elevated levels of several inflammatory cytokines and adverse physical reactions in a subject such as low blood pressure, high fever and shivering. In another embodiment, inflammatory cytokines comprise IL-6, IL-1β, and TNF-α. In another embodiment, CRS is characterized by elevated levels of IL-6, IL-1β, or TNF-α, or any combination thereof. In another embodiment, CRS is characterized by elevated levels of IL-8, or IL-13, or any combination thereof. In another embodiment, a cytokine storm is characterized by increases in TNF-alpha, IFN-gamma, IL-1beta, IL-2, IL-6, IL-8, IL-10, IL-13, GM-CSF, IL-5, fracktalkine, or a combination thereof or a subset thereof. In yet another embodiment, IL-6 comprises a marker of CRS or cytokine storm.

In another embodiment, cytokines increased in CRS or a cytokine storm in humans and mice may comprise any combination of cytokines listed in Tables 1 and 2 below.

TABLE 1

Panel of Cytokines Increased in CRS or Cytokine Storm in Humans and/or Mice

| Cytokine (Analyte) | Human model (clinical trials) | Mouse model (pre-clinical) | | | Cells secreting this cytokine | Notes/ other |
| --- | --- | --- | --- | --- | --- | --- |
| | | CAR-T (H) origin | Mouse origin | Not specified | | |
| Flt-3L | * | | | | DC (?) | |
| Fractalkine | * | | | | APC, Endothelial cells (?) | =CX3CL1, Neurotactin (Mouse) |
| M-CSF | | | | | | =CSF1 |
| GM-CSF | * | | | * (in vitro) | T cell, MØ | |
| IFN-α | * | | | | T cell, MØ, Monocyte | |
| IFN-β | ? | | | ? | T cell, MØ, Monocyte | |
| IFN-γ | * | * | | * (in vitro) | cytotoxic T cells, helper T cells, NK cells, MØ, Monocyte, DC | |
| IL-1 α | * | | | | Monocyte, MØ, Epithel | |
| IL-1 β | * | | | * | Macrophages, DCs, fibroblasts, endothelial cells, hepatocytes | |
| IL-1 Rα | * | | | | | |
| IL-2 | * | * | | * (in vitro) | T cells | |
| IL-2Rα | * | | | | lymphocytes | |
| IL-4 | * | * | | * (in vitro) | Th2 cells | |
| IL-5 | * | * | | * | T cells | |
| IL-6 | * | | * | * | monocytes/macrophages, dendritic cells, T cells, fibroblasts, keratinocytes, endothelial cells, adipocytes, myocytes, mesangial cells, and osteoblasts | |
| IL-7 | * | | | * | In vitro by BM stromal cells | |
| IL-8 | * | | | | Macrophages, monocytes | |
| IL-9 | * | * | | | T cells, T helper | |
| IL-10 | * | * | | * (in vitro) | monocytes/macrophages, mast cells, B cells, regulatory T cells, and helper T cells | |
| IL-12 | * | | | * | MØ, Monocyte, DC, activated lymphocytes, neutrophils | =p70 (p40 + p35) |
| IL-13 | * | * | | | T cells | |

In some embodiments, cytokines Flt-3L, Fractalkine, GM-CSF, IFN-γ, IL-1β, IL-2, IL-2Rα, IL-4, IL-5, IL-6, IL-7, IL-8, IL-9, IL-10, IL-12, and IL-13 of Table 1 are considered to be significant in CRS or cytokine storm. In another embodiment, IFN-α, IFN-β, IL-1, and IL-1Rα of Table 1 appear to be important in CRS or cytokine storm. In another embodiment, M-CSF has unknown importance. In another embodiment, any cytokine listed in Table 1, or combination thereof, may be used as a marker of CRS or cytokine storm.

TABLE 2

Panel of Cytokines Increased in CRS or Cytokine Storm in Humans and/or Mice

| Cytokine (Analyte) | Human model (clinical trials) | Mouse model (pre-clinical) CAR-T (H) origin | Mouse origin | Not specified | Cells secreting this cytokine | Notes/ other |
|---|---|---|---|---|---|---|
| IL- 15 | * | | | * | Fibroblasts, monocytes (?) | 22 |
| IL- 17 | * | | | * | T cells | |
| IL- 18 | | | | | Macrophages | |
| IL- 21 | * | | | | T helper cells, NK cells | |
| IL- 22 | * | | | | activated DC and T cells | |
| IL- 23 | | | | | | |
| IL- 25 | | | | | | Protective? |
| IL- 27 | * | | | | APC | |
| IP-10 | * | | | | Monocytes (?) | |
| MCP-1 | * | | | | Endothel, fibroblast, epithel, monocytes | =CXCL10 |
| MCP-3 | * | | | | PBMCs, MØ (?) | =CCL2 |
| MIP-1α | * | | * (in vitro) | | T cells | =CXCL9 |
| MIP-1β | * | | | | T cells | =CCL3 |
| PAF | ? | | | | platelets, endothelial cells, neutrophils, monocytes, and macrophages, mesangial cells | =CCL4 |
| PGE2 | * | | | * | Gastrointestinal mucosa and other | |
| RANTES | * | | | | Monocytes | |
| TGF-β | * | | | * | MØ, lymphocytes, endothel, platelets . . . | =CCL5 |
| TNF-α | * | * | * | * (in vitro) | Macrophages, NK cells, T cells | |
| TNF-αR1 | * | | | | | |
| HGF | | | | | | |
| MIG | * | | | | T cell chemoattractant, induced by IFN-γ | |

In one embodiment, IL-15, IL-17, IL-18, IL-21, IL-22, IP-10, MCP-1, MIP-1α, MIP-1β, and TNF-α of Table 2 are considered to be significant in CRS or cytokine storm. In another embodiment, IL-27, MCP-3, PGE2, RANTES, TGF-β, TNF-αR1, and MIG of Table 2 appear to be important in CRS or cytokine storm. In another embodiment, IL-23 and IL-25 have unknown importance. In another embodiment, any cytokine listed in Table 2, or combination thereof, may be used as a marker of CRS or cytokine storm. In another embodiment, mouse cytokines IL-10, IL-1β, IL-2, IP-10, IL-4, IL-5, IL-6, IFNα, IL-9, IL-13, IFN-γ, IL-12p70, GM-CSF, TNF-α, MIP-1a, MIP-1β, IL-17A, IL-15/IL-15R and IL-7 appear to be important in CRS or cytokine storm.

A skilled artisan would appreciate that the term "cytokine" may encompass cytokines (e.g., interferon gamma (IFN-γ), granulocyte macrophage colony stimulating factor, tumor necrosis factor alpha), chemokines (e.g., MIP 1 alpha, MIP 1 beta, RANTES), and other soluble mediators of inflammation, such as reactive oxygen species and nitric oxide.

In one embodiment, increased release of a particular cytokine, whether significant, important or having unknown importance, does not a priori mean that the particular cytokine is part of a cytokine storm. In one embodiment, an increase of at least one cytokine is not the result of a cytokine storm or CRS. In another embodiment, CAR T-cells may be the source of increased levels of a particular cytokine or group of cytokines.

In another embodiment, cytokine release syndrome is characterized by any or all of the following symptoms: Fever with or without rigors, malaise, fatigue, anorexia, myalgias, arthalgias, nausea, vomiting, headache Skin Rash, Nausea, vomiting, diarrhea, Tachypnea, hypoxemia Cardiovascular Tachycardia, widened pulse pressure, hypotension, increased cardiac output (early), potentially diminished cardiac output (late), Elevated D-dimer, hypofibrinogenemia with or without bleeding, Azotemia Hepatic Transaminitis, hyperbilirubinemia, Headache, mental status changes, confusion, delirium, word finding difficulty or frank aphasia, hallucinations, tremor, dymetria, altered gait, seizures. In another embodiment, a cytokine storm is characterized by IL-2 release and lymphoproliferation. In another embodiment, a cytokine storm is characterized by increases in cytokines released by CAR T-cells. In another embodiment, a cytokine storm is characterized by increases in cytokines released by cells other than CAR T-cells.

In another embodiment, cytokine storm leads to potentially life-threatening complications including cardiac dysfunction, adult respiratory distress syndrome, neurologic toxicity, renal and/or hepatic failure, and disseminated intravascular coagulation.

A skilled artisan would appreciate that the characteristics of a cytokine release syndrome (CRS) or cytokine storm are estimated to occur a few days to several weeks following the trigger for the CRS or cytokine storm. In one embodiment, CAR T-cells are a trigger for CRS or a cytokine storm. In another embodiment, a trigger for CRS or a cytokine storm is not CAR T-cells.

In one embodiment, measurement of cytokine levels or concentration, as an indicator of cytokine storm, may be expressed as—fold increase, percent (%) increase, net increase or rate of change in cytokine levels or concentration. In another embodiment, absolute cytokine levels or concentrations above a certain level or concentration may be an indication of a subject undergoing or about to experience a cytokine storm. In another embodiment, absolute cytokine levels or concentration at a certain level or concentration, for example a level or concentration normally found in a control subject not undergoing CAR-T cell therapy, may be an indication of a method for inhibiting or reducing the incidence of a cytokine storm in a subject undergoing CAR T-cell.

A skilled artisan would appreciate that the term "cytokine level" may encompass a measure of concentration, a measure of fold change, a measure of percent (%) change, or a measure of rate change. Further, the methods for measuring cytokines in blood, saliva, serum, urine, and plasma are well known in the art.

In one embodiment, despite the recognition that cytokine storm is associated with elevation of several inflammatory cytokines, IL-6 levels may be used as a common measure of cytokine storm and/or as a common measure of the effectiveness of a treatment for cytokine storms. A skilled artisan would appreciate that other cytokines may be used as markers of a cytokine storm, for example TNF-α, IB-1α, IL-8, IL-13, or INF-γ. Further, that assay methods for measuring cytokines are well known in the art. A skilled artisan would appreciate that methods affecting a cytokine storm may similarly affect cytokine release syndrome.

In one embodiment, disclosed herein is a method of decreasing or inhibiting cytokine production in a subject experiencing cytokine release syndrome or a cytokine storm. In another embodiment, disclosed herein is a method of decreasing or inhibiting cytokine production in a subject vulnerable to experiencing cytokine release syndrome or a cytokine storm. In another embodiment, methods disclosed herein decrease or inhibit cytokine production in a subject experiencing cytokine release syndrome or a cytokine storm, wherein production of any cytokine or group of cytokines listed in Tables 1 and/or 2 is decreased or inhibited. In another embodiment, cytokine IL-6 production is decreased or inhibited. In another embodiment, cytokine IL-beta1 production is decreased or inhibited. In another embodiment, cytokine IL-8 production is decreased or inhibited. In another embodiment, cytokine IL-13 production is decreased or inhibited. In another embodiment, cytokine TNF-alpha production is decreased or inhibited. In another embodiment, cytokines IL-6 production, IL-1beta production, or TNF-alpha production, or any combination thereof is decreased or inhibited.

In one embodiment, cytokine release syndrome is graded. In another embodiment, Grade 1 describes cytokine release syndrome in which symptoms are not life threatening and require symptomatic treatment only, e.g., fever, nausea, fatigue, headache, myalgias, malaise. In another embodiment, Grade 2 symptoms require and respond to moderate intervention, such as oxygen, fluids or vasopressor for hypotension. In another embodiment, Grade 3 symptoms require and respond to aggressive intervention. In another embodiment, Grade 4 symptoms are life-threatening symptoms and require ventilator and patients display organ toxicity.

In another embodiment, a cytokine storm is characterized by IL-6 and interferon gamma release. In another embodiment, a cytokine storm is characterized by release of any cytokine or combination thereof, listed in Tables 1 and 2. In another embodiment, a cytokine storm is characterized by release of any cytokine or combination thereof, known in the art.

In one embodiment, symptoms onset begins minutes to hours after the infusion begins. In another embodiment, symptoms coincide with peak cytokine levels.

In one embodiment, a method of inhibiting or reducing the incidence of a cytokine release syndrome (CRS) or a cytokine storm in a subject undergoing CAR T-cell cancer therapy comprises administering an apoptotic cell population or an apoptotic cell supernatant or compositions thereof. In another embodiment, the apoptotic cell population or an apoptotic cell supernatant or compositions thereof may aid the CAR T-cell therapy. In another embodiment, the apoptotic cell population or an apoptotic cell supernatant or compositions thereof may aid in the inhibition or reducing the incidence of the CRS or cytokine storm. In another embodiment, the apoptotic cell population or an apoptotic cell supernatant or compositions thereof may aid in treating the CRS or cytokine storm. In another embodiment, the apoptotic cell population or an apoptotic cell supernatant or compositions thereof may aid in preventing the CRS or cytokine storm. In another embodiment, the apoptotic cell population or an apoptotic cell supernatant or compositions thereof may aid in ameliorating the CRS or cytokine storm. In another embodiment, the apoptotic cell population or an apoptotic cell supernatant or compositions thereof may aid in alleviating the CRS or cytokine storm.

In one embodiment, a method of inhibiting or reducing the incidence of a cytokine release syndrome (CRS) or a cytokine storm in a subject undergoing CAR T-cell cancer therapy, and being administered an apoptotic cell population or an apoptotic cell supernatant or compositions thereof, comprises administering an additional agent. In another embodiment, the additional agent may aid the CAR T-cell therapy. In another embodiment, the additional agent may aid in the inhibition or reducing the incidence of the CRS or cytokine storm. In another embodiment, the additional agent may aid in treating the CRS or cytokine storm. In another embodiment, the additional agent may aid in preventing the CRS or cytokine storm. In another embodiment, the additional agent may aid in ameliorating the CRS or cytokine storm. In another embodiment, the additional agent may aid in alleviating the CRS or cytokine storm.

In one embodiment, a method of inhibiting or reducing the incidence of a cytokine release syndrome (CRS) or a cytokine storm in a subject undergoing CAR T-cell cancer therapy comprises administering an additional agent. In another embodiment, the additional agent may aid the CAR T-cell therapy. In one embodiment, a method of inhibiting or reducing the incidence of a cytokine release syndrome (CRS) or a cytokine storm in a subject undergoing TCR T-cell cancer therapy comprises administering an additional agent. In another embodiment, the additional agent may aid the TCR T-cell therapy. In one embodiment, a method of inhibiting or reducing the incidence of a cytokine release syndrome (CRS) or a cytokine storm in a subject undergoing comprises administering an additional agent. In another embodiment, the additional agent may aid the. In one embodiment, a method of inhibiting or reducing the incidence of a cytokine release syndrome (CRS) or a cytokine storm in a subject undergoing NK cell therapy comprises administering an additional agent. In another embodiment, the additional agent may aid the NK cell therapy.

In another embodiment, the additional agent may aid in the inhibition or reducing the incidence of the CRS or cytokine storm. In another embodiment, the additional agent may aid in treating the CRS or cytokine storm. In another embodiment, the additional agent may aid in preventing the CRS or cytokine storm. In another embodiment, the additional agent may aid in ameliorating the CRS or cytokine storm. In another embodiment, the additional agent may aid in alleviating the CRS or cytokine storm.

In one embodiment, the additional agent for decreasing harmful cytokine release comprises apoptotic cells or a composition comprising said apoptotic cells. In another embodiment, the additional agent for decreasing harmful cytokine release comprises an apoptotic cell supernatant or a composition comprising said supernatant. In another embodiment, the additional agent for decreasing harmful cytokine release comprises a CTLA-4 blocking agent. In another embodiment, the additional agent for decreasing harmful cytokine release comprises apoptotic cells or apoptotic cell supernatants or compositions thereof, and a CTLA-4 blocking agent. In another embodiment, the additional agent for decreasing harmful cytokine release comprises an alpha-1 anti-trypsin or fragment thereof or analogue thereof. In another embodiment, the additional agent for decreasing harmful cytokine release comprises apoptotic cells or apoptotic cell supernatants or compositions thereof, and an alpha-1 anti-trypsin or fragment thereof or analogue thereof. In another embodiment, the additional agent for decreasing harmful cytokine release comprises a tellurium-based compound. In another embodiment, the additional agent for decreasing harmful cytokine release comprises apoptotic cells or apoptotic cell supernatants or compositions thereof, and a tellurium-based compound. In another embodiment, the additional agent for decreasing harmful cytokine release comprises an immune modulating agent. In another embodiment, the additional agent for decreasing harmful cytokine release comprises apoptotic cells or apoptotic cell supernatants or compositions thereof, and an immune modulating agent.

In another embodiment, compositions and methods as disclosed herein utilize combination therapy of CAR T-cells with one or more CTLA-4-blocking agents such as Ipilimumab. In another embodiment, compositions and methods as disclosed herein utilize combined therapy comprising apoptotic cells, CAR T-cells, and one or more CTLA-4-blocking agents. In another embodiment, compositions and methods as disclosed herein utilize combination therapy of TCR T-cells with one or more CTLA-4-blocking agents such as Ipilimumab. In another embodiment, compositions and methods as disclosed herein utilize combined therapy comprising apoptotic cells, TCR T-cells, and one or more CTLA-4-blocking agents. In another embodiment, compositions and methods as disclosed herein utilize combination therapy of dendritic cells with one or more CTLA-4-blocking agents such as Ipilimumab. In another embodiment, compositions and methods as disclosed herein utilize combined therapy comprising apoptotic cells, dendritic cells, and one or more CTLA-4-blocking agents. In another embodiment, compositions and methods as disclosed herein utilize combination therapy of NK cells with one or more CTLA-4-blocking agents such as Ipilimumab. In another embodiment, compositions and methods as disclosed herein utilize combined therapy comprising apoptotic cells, NK cells, and one or more CTLA-4-blocking agents.

In another embodiment, CTLA-4 is a potent inhibitor of T-cell activation that helps to maintain self-tolerance. In another embodiment, administration of an anti-CTLA-4 blocking agent, which in another embodiment, is an antibody, produces a net effect of T-cell activation.

In another embodiment, other toxicities resulting from CAR T-cell, TCR T-cell, dendritic cell, or NK cell administration that may be treated, prevented, inhibited, ameliorated, reduced in incidence or alleviated by the compositions and methods as disclosed herein comprise B cell aplasia or tumor lysis syndrome (TLS).

In one embodiment, a method of inhibiting or reducing the incidence of a cytokine release syndrome (CRS) or a cytokine storm in a subject undergoing CAR T-cell cancer therapy does not affect the efficacy of the CAR T-cell therapy. In another embodiment, a method of inhibiting or reducing the incidence of CRS or a cytokine storm in a subject undergoing CAR T-cell cancer therapy, does reduce the efficacy of the CAR T-cells therapy by more than about 5%. In another embodiment, a method of inhibiting or reducing the incidence of CRS or a cytokine storm in a subject undergoing CAR T-cell cancer therapy, does reduce the efficacy of the CAR T-cells therapy by more than about 10%. In another embodiment, a method of inhibiting or reducing the incidence of CRS or a cytokine storm in a subject undergoing CAR T-cell cancer therapy, does reduce the efficacy of the CAR T-cells therapy by more than about 15%. In another embodiment, a method of inhibiting or reducing the incidence of CRS or a cytokine storm in a subject undergoing CAR T-cell cancer therapy, does reduce the efficacy of the CAR T-cells therapy by more than about 20%. In another embodiment, a method of inhibiting or reducing the incidence of CRS or a cytokine storm in a subject undergoing CAR T-cell cancer therapy, increases the efficacy of the CAR T-cells therapy by more than about 5%. In another embodiment, a method of inhibiting or reducing the incidence of CRS or a cytokine storm in a subject undergoing CAR T-cell cancer therapy, increases the efficacy of the CAR T-cells therapy by more than about 10%. In another embodiment, a method of inhibiting or reducing the incidence of CRS or a cytokine storm in a subject undergoing CAR T-cell cancer therapy, increases the efficacy of the CAR T-cells therapy by more than about 15%. In another embodiment, a method of inhibiting or reducing the incidence of CRS or a cytokine storm in a subject undergoing CAR T-cell cancer therapy, increases the efficacy of the CAR T-cells therapy by more than about 20%.

Any appropriate method of quantifying cytotoxicity can be used to determine whether activity in an immune cell modified to express a CAR remains substantially unchanged. For example, cytotoxicity can be quantified using a cell culture-based assay such as the cytotoxic assays described in the Examples. Cytotoxicity assays can employ dyes that preferentially stain the DNA of dead cells. In other cases, fluorescent and luminescent assays that measure the relative number of live and dead cells in a cell population can be used. For such assays, protease activities serve as markers for cell viability and cell toxicity, and a labeled cell permeable peptide generates fluorescent signals that are proportional to the number of viable cells in the sample. For example a cytotoxicity assay may use 7-AAD in a flow cytometry analysis. Kits for various cytotoxicity assays are commercially available from manufacturers such as Promega, Abcam, and Life Technologies.

In another embodiment, a measure of cytotoxicity may be qualitative. In another embodiment, a measure of cytotoxicity may be quantitative. In a further embodiment a measure of cytotoxicity may be related to the change in expression of a cytotoxic cytokine. In another embodiment, a measure of cytotoxicity may be determined by survival curve and tumor load in bone marrow and liver.

In one embodiment, the methods as disclosed herein comprise an additional step that is useful in overcoming rejection of allogeneic donor cells. In one embodiment, the methods comprise the step of full or partial lymphodepletion prior to administration of the CAR T-cells, which in one embodiment, are allogeneic CAR T-cells. In another embodiment, the lymphodepletion is adjusted so that it delays the host versus graft reaction for a period sufficient to allow said allogeneic T-cells to attack the tumor to which they are directed, but to an extent insufficient to require rescue of the host immune system by bone marrow transplantation. In another embodiment, agents that delay egression of the allogeneic T-cells from lymph nodes, such as 2-amino-2-[2-(4-octylphenyl)ethyl]propane-1,3-diol (FTY720), 5-[4-phenyl-5-(trifluoromethyl)thiophen-2-yl]-3-[3-(trifluoromethyl)pheny-1]1,2,4-oxadiazole (SEW2871), 3-(2-(-hexylphenylamino)-2-oxoethylamino) propanoic acid (W123), 2-ammonio-4-(2-chloro-4-(3-phenoxyphenylthio)phenyl)-2-(hydroxymethyl)but-yl hydrogen phosphate (KRP-203 phosphate) or other agents known in the art, may be used as part of the compositions and methods as disclosed herein to allow the use of allogeneic CAR T-cells having efficacy and lacking initiation of graft vs host disease. In one embodiment, MHC expression by the allogeneic T-cells is silenced to reduce the rejection of the allogeneic cells. In another embodiment, the apoptotic cells prevent rejection of the allogeneic cells.

Cytokine Release Associated with CAR T-Cell Therapy

In one embodiment, cytokine release occurs between a few days to 2 weeks after administration of immune therapy such as CAR T-cell therapy. In one embodiment, hypotension and other symptoms follow the cytokine release, i.e. from few days to few weeks. Therefore, in one embodiment, apoptotic cells or the apoptotic cell supernatant are administered to subjects at the same time as immune therapy as prophylaxis. In another embodiment, apoptotic cells or supernatant are administered to subjects 2-3 days after administration of immune therapy. In another embodiment, apoptotic cells or supernatant are administered to subjects 7 days after administration of immune therapy. In another embodiment, apoptotic cells or supernatant are administered to subjects 10 days after administration of immune therapy. In another embodiment, apoptotic cells or supernatant are administered to subjects 14 days after administration of immune therapy. In another embodiment, apoptotic cells or supernatant are administered to subjects 2-14 days after administration of immune therapy.

In another embodiment, apoptotic cells or apoptotic cell supernatant are administered to subjects 2-3 hours after administration of immune therapy. In another embodiment, apoptotic cells or supernatant are administered to subjects 7 hours after administration of immune therapy. In another embodiment, apoptotic cells or supernatant are administered to subjects 10 hours after administration of immune therapy. In another embodiment, apoptotic cells or supernatant are administered to subjects 14 hours after administration of immune therapy. In another embodiment, apoptotic cells or supernatant are administered to subjects 2-14 hours after administration of immune therapy.

In an alternative embodiment, apoptotic cells or the apoptotic cell supernatant are administered to subjects prior to immune therapy as prophylaxis. In another embodiment, apoptotic cells or supernatant are administered to subjects 1 day before administration of immune therapy. In another embodiment, apoptotic cells or supernatant are administered to subjects 2-3 days before administration of immune therapy. In another embodiment, apoptotic cells or supernatant are administered to subjects 7 days before administration of immune therapy. In another embodiment, apoptotic cells or supernatant are administered to subjects 10 days before administration of immune therapy. In another embodiment, apoptotic cells or supernatant are administered to subjects 14 days before administration of immune therapy. In another embodiment, apoptotic cells or supernatant are administered to subjects 2-14 days before administration of immune therapy.

In another embodiment, apoptotic cells or apoptotic cell supernatant are administered to subjects 2-3 hours before administration of immune therapy. In another embodiment, apoptotic cells or supernatant are administered to subjects 7 hours before administration of immune therapy. In another embodiment, apoptotic cells or supernatant are administered to subjects 10 hours before administration of immune therapy. In another embodiment, apoptotic cells or supernatant are administered to subjects 14 hours before administration of immune therapy. In another embodiment, apoptotic cells or supernatant are administered to subjects 2-14 hours before administration of immune therapy.

In another embodiment, apoptotic cells or apoptotic cell supernatant may be administered therapeutically, once cytokine release syndrome has occurred. In one embodiment, apoptotic cells or supernatant may be administered once cytokine release leading up to or attesting to the beginning of cytokine release syndrome is detected. In one embodiment, apoptotic cells or supernatant can terminate the increased cytokine levels, or the cytokine release syndrome, and avoid its sequelae.

In another embodiment, apoptotic cells or apoptotic cell supernatant may be administered therapeutically, at multiple time points. In another embodiment, administration of apoptotic cells or apoptotic cell supernatant is at least at two time points described herein. In another embodiment, administration of apoptotic cells or apoptotic cell supernatant is at least at three time points described herein. In another embodiment, administration of apoptotic cells or apoptotic cell supernatant is prior to CRS or a cytokine storm, and once cytokine release syndrome has occurred, and any combination thereof.

In one embodiment, the chimeric antigen receptor-expressing T-cell (CAR T-cell) therapy and the apoptotic cell therapy or supernatant are administered together. In another embodiment, the CAR T-cell therapy is administered after the apoptotic cell therapy or supernatant. In another embodiment, the CAR T-cell therapy is administered prior to the apoptotic cell therapy or supernatant. According to this aspect and in one embodiment, apoptotic cell therapy or supernatant is administered approximately 2-3 weeks after the CAR T-cell therapy. In another embodiment, apoptotic cell therapy or supernatant is administered approximately 6-7 weeks after the CAR T-cell therapy. In another embodiment, apoptotic cell therapy or supernatant is administered approximately 9 weeks after the CAR T-cell therapy. In another embodiment, apoptotic cell therapy is administered up to several months after CAR T-cell therapy.

Therefore, in one embodiment, apoptotic cells or the apoptotic cell supernatant are administered to subjects at the same time as immune therapy as prophylaxis. In another embodiment, apoptotic cells or supernatant are administered to subjects 2-3 days after administration of immune therapy. In another embodiment, apoptotic cells or supernatant are administered to subjects 7 days after administration of immune therapy. In another embodiment, apoptotic cells or supernatant are administered to subjects 10 days after administration of immune therapy. In another embodiment, apoptotic cells or supernatant are administered to subjects 14 days after administration of immune therapy. In another embodiment, apoptotic cells or supernatant are administered to subjects 2-14 days after administration of immune therapy.

In another embodiment, apoptotic cells or apoptotic cell supernatant are administered to subjects 2-3 hours after administration of immune therapy. In another embodiment, apoptotic cells or supernatant are administered to subjects 7 hours after administration of immune therapy. In another embodiment, apoptotic cells or supernatant are administered to subjects 10 hours after administration of immune therapy. In another embodiment, apoptotic cells or supernatant are administered to subjects 14 hours after administration of immune therapy. In another embodiment, apoptotic cells or supernatant are administered to subjects 2-14 hours after administration of immune therapy.

In an alternative embodiment, apoptotic cells or the apoptotic cell supernatant are administered to subjects prior to immune therapy as prophylaxis. In another embodiment, apoptotic cells or supernatant are administered to subjects 1 day before administration of immune therapy. In another embodiment, apoptotic cells or supernatant are administered to subjects 2-3 days before administration of immune therapy. In another embodiment, apoptotic cells or supernatant are administered to subjects 7 days before administration of immune therapy. In another embodiment, apoptotic cells or supernatant are administered to subjects 10 days before administration of immune therapy. In another embodiment, apoptotic cells or supernatant are administered to subjects 14 days before administration of immune therapy. In another embodiment, apoptotic cells or supernatant are administered to subjects 2-14 days before administration of immune therapy.

In another embodiment, apoptotic cells or apoptotic cell supernatant are administered to subjects 2-3 hours before administration of immune therapy. In another embodiment, apoptotic cells or supernatant are administered to subjects 7 hours before administration of immune therapy. In another embodiment, apoptotic cells or supernatant are administered to subjects 10 hours before administration of immune therapy. In another embodiment, apoptotic cells or supernatant are administered to subjects 14 hours before administration of immune therapy. In another embodiment, apoptotic cells or supernatant are administered to subjects 2-14 hours before administration of immune therapy.

In another embodiment, apoptotic cells or apoptotic cell supernatant may be administered therapeutically, once cytokine release syndrome has occurred. In one embodiment, apoptotic cells or supernatant may be administered once cytokine release leading up to or attesting to the beginning of cytokine release syndrome is detected. In one embodiment, apoptotic cells or supernatant can terminate the increased cytokine levels, or the cytokine release syndrome, and avoid its sequelae.

In another embodiment, apoptotic cells or apoptotic cell supernatant may be administered therapeutically, at multiple time points. In another embodiment, administration of apoptotic cells or apoptotic cell supernatant is at least at two time points described herein. In another embodiment, administration of apoptotic cells or apoptotic cell supernatant is at least at three time points described herein. In another embodiment, administration of apoptotic cells or apoptotic cell supernatant is prior to CRS or a cytokine storm, and once cytokine release syndrome has occurred, and any combination thereof.

In one embodiment, the chimeric antigen receptor-expressing T-cell (CAR T-cell) therapy and the apoptotic cell therapy or supernatant are administered together. In another embodiment, the CAR T-cell therapy is administered after the apoptotic cell therapy or supernatant. In another embodiment, the CAR T-cell therapy is administered prior to the apoptotic cell therapy or supernatant. According to this aspect and in one embodiment, apoptotic cell therapy or supernatant is administered approximately 2-3 weeks after the CAR T-cell therapy. In another embodiment, apoptotic cell therapy or supernatant is administered approximately 6-7 weeks after the CAR T-cell therapy. In another embodiment, apoptotic cell therapy or supernatant is administered approximately 9 weeks after the CAR T-cell therapy. In another embodiment, apoptotic cell therapy is administered up to several months after CAR T-cell therapy.

In other embodiments, an additional agent is administered to subjects at the same time as immune therapy as prophylaxis. In one embodiment the additional agent comprises apoptotic cells, an apoptotic supernatant, a CTLA-4 blocking agent, an alpha-1 anti-trypsin or fragment thereof or analogue thereof, of a tellurium-based compound, or an immune-modulating compounds, or any combination thereof. In another embodiment, the additional agent is administered to subjects 2-3 days after administration of immune therapy. In another embodiment, the additional agent is administered to subjects 7 days after administration of immune therapy. In another embodiment, the additional agent is administered to subjects 10 days after administration of immune therapy. In another embodiment, the additional agent is administered to subjects 14 days after administration of immune therapy. In another embodiment, the additional agent is administered to subjects 2-14 days after administration of immune therapy.

In another embodiment, the additional agent is administered to subjects 2-3 hours after administration of immune therapy. In another embodiment, the additional agent is administered to subjects 7 hours after administration of immune therapy. In another embodiment the additional agent is administered to subjects 10 hours after administration of immune therapy. In another embodiment, the additional agent is administered to subjects 14 hours after administration of immune therapy. In another embodiment, the additional agent is administered to subjects 2-14 hours after administration of immune therapy.

In an alternative embodiment, the additional agent is administered to subjects prior to immune therapy as prophylaxis. In another embodiment, the additional agent is administered to subjects 1 day before administration of immune therapy. In another embodiment, the additional agent is administered to subjects 2-3 days before administration of immune therapy. In another embodiment, the additional agent is administered to subjects 7 days before administration of immune therapy. In another embodiment, the additional agent is administered to subjects 10 days before administration of immune therapy. In another embodiment, the additional agent is administered to subjects 14 days before administration of immune therapy. In another embodiment, the additional agent is administered to subjects 2-14 days before administration of immune therapy.

In another embodiment, the additional agent is administered to subjects 2-3 hours before administration of immune therapy. In another embodiment, the additional agent is administered to subjects 7 hours before administration of immune therapy. In another embodiment, the additional agent is administered to subjects 10 hours before administration of immune therapy. In another embodiment, the additional agent is administered to subjects 14 hours before administration of immune therapy. In another embodiment, the additional agent is administered to subjects 2-14 hours before administration of immune therapy.

In another embodiment, the additional agent is administered therapeutically, once cytokine release syndrome has occurred. In one embodiment, the additional agent is administered once cytokine release leading up to or attesting to the beginning of cytokine release syndrome is detected. In one embodiment, the additional agent can terminate the increased cytokine levels, or the cytokine release syndrome, and avoid its sequelae.

In another embodiment, the additional agent is administered therapeutically, at multiple time points. In another embodiment, administration of the additional agent is at least at two time points described herein. In another embodiment, administration of the additional agent is at least at three time points described herein. In another embodiment, administration of the additional agent is prior to CRS or a cytokine storm, and once cytokine release syndrome has occurred, and any combination thereof.

In one embodiment, the chimeric antigen receptor-expressing T-cell (CAR T-cell) therapy and the additional agent is administered together. In another embodiment, the CAR T-cell therapy is administered the additional agent. In another embodiment, the CAR T-cell therapy is administered prior to the additional agent. According to this aspect and in one embodiment, the additional agent is administered approximately 2-3 weeks after the CAR T-cell therapy. In another embodiment, the additional agent is administered approximately 6-7 weeks after the CAR T-cell therapy. In another embodiment, the additional agent is administered approximately 9 weeks after the CAR T-cell therapy. In another embodiment, the additional agent is administered up to several months after CAR T-cell therapy.

In one embodiment, CAR T-cells are heterologous to the subject. In one embodiment, CAR T-cells are derived from one or more donors. In one embodiment, CAR T-cells are derived from one or more bone marrow donors. In another embodiment, CAR T-cells are derived from one or more blood bank donations. In one embodiment, the donors are matched donors. In one embodiment, CAR T-cells are universal allogeneic CAR T-cells. In another embodiment, CAR T-cells are syngeneic CAR T-cells. In another embodiment, CAR T-cells are from unmatched third party donors. In another embodiment, CAR T-cells are from pooled third party donor T-cells. In one embodiment, the donor is a bone marrow donor. In another embodiment, the donor is a blood bank donor. In one embodiment, CAR T-cells of the compositions and methods as disclosed herein comprise one or more MHC unrestricted tumor-directed chimeric receptors. In one embodiment, non-autologous T-cells may be engineered or administered according to protocols known in the art to prevent or minimize autoimmune reactions, such as described in U.S. Patent Application No. 20130156794, which is incorporated herein by references in its entirety.

In another embodiment, CAR T-cells are autologous to the subject. In one embodiment, the patient's own cells are used. In this embodiment, if the patient's own cells are used, then the CAR T-cell therapy is administered after the apoptotic cell therapy.

In one embodiment, apoptotic cells are heterologous to the subject. In one embodiment, apoptotic cells are derived from one or more donors. In one embodiment, apoptotic cells are derived from one or more bone marrow donors. In another embodiment, apoptotic cells are derived from one or more blood bank donations. In one embodiment, the donors are matched donors. In one embodiment, apoptotic cells are from unmatched third party donors. In one embodiment, apoptotic cells are universal allogeneic apoptotic cells. In another embodiment, apoptotic cells are from a syngeneic donor. In another embodiment, apoptotic cells are from pooled third party donor cells. In one embodiment, the donor is a bone marrow donor. In another embodiment, the donor is a blood bank donor. In another embodiment, apoptotic cells are autologous to the subject. In this embodiment, the patient's own cells are used.

According to some embodiments, the therapeutic mononuclear-enriched cell preparation disclosed herein or the apoptotic cell supernatant is administered to the subject systemically. In another embodiment, administration is via the intravenous route. Alternately, the therapeutic mononuclear enriched cell or supernatant may be administered to the subject according to various other routes, including, but not limited to, the parenteral, intraperitoneal, intra-articular, intramuscular and subcutaneous routes.

According to some embodiments, the therapeutic mononuclear-enriched cell preparation disclosed herein or the additional agent is administered to the subject systemically. In another embodiment, administration is via the intravenous route. Alternately, the therapeutic mononuclear enriched cell or the additional agent may be administered to the subject according to various other routes, including, but not limited to, the parenteral, intraperitoneal, intra-articular, intramuscular and subcutaneous routes.

In one embodiment, the preparation is administered in a local rather than systemic manner, for example, via injection of the preparation directly into a specific region of a patient's body. In another embodiment, a specific region comprises a tumor or cancer.

In another embodiment, the therapeutic mononuclear enriched cells or supernatant are administered to the subject suspended in a suitable physiological buffer, such as, but not limited to, saline solution, PBS, HBSS, and the like. In addition the suspension medium may further comprise supplements conducive to maintaining the viability of the cells. In another embodiment, the additional agent is administered to the subject suspended in a suitable physiological buffer, such as, but not limited to, saline solution, PBS, HBSS, and the like.

According to some embodiments the pharmaceutical composition is administered intravenously. According to another embodiment, the pharmaceutical composition is administered in a single dose. According to alternative embodiments the pharmaceutical composition is administered in multiple doses. According to another embodiment, the pharmaceutical composition is administered in two doses. According to another embodiment, the pharmaceutical composition is administered in three doses. According to another embodiment, the pharmaceutical composition is administered in four doses. According to another embodiment, the pharmaceutical composition is administered in five or more doses. According to some embodiments, the pharmaceutical composition is formulated for intravenous injection.

In one embodiment, any appropriate method of providing modified CAR-expressing immune cells to a subject can be used for methods described herein. In one embodiment, methods for providing cells to a subject comprise hematopoietic cell transplantation (HCT), infusion of donor-derived NK cells into cancer patients or a combination thereof.

In another embodiment, disclosed herein is a method of inhibiting or reducing the incidence of cytokine release syndrome or cytokine storm in a subject undergoing chimeric antigen receptor-expressing T-cell (CAR T-cell) therapy, comprising the step of administering a composition comprising apoptotic cells to said subject.

In another embodiment, disclosed herein is a method of inhibiting or reducing the incidence of cytokine release syndrome or cytokine storm in a subject undergoing chimeric antigen receptor-expressing T-cell (CAR T-cell) therapy, comprising the step of administering an apoptotic cell supernatant, such as an apoptotic cell-phagocyte supernatant, to said subject.

In another embodiment, disclosed herein is a method of inhibiting or reducing the incidence of cytokine release syndrome or cytokine storm in a subject undergoing chimeric antigen receptor-expressing T-cell (CAR T-cell) therapy, comprising the step of administering an at least one additional agent to said subject.

In certain embodiments, a CAR T-cell therapy comprises administering a composition disclosed herein comprising CAR T-cells and either apoptotic cells or an apoptotic cell supernatant, or another or combination of additional agents as disclosed herein. In alternative embodiments, a CAR T-cell therapy comprises administering a composition disclosed herein comprising CAR T-cells and a composition comprising either apoptotic cells or an apoptotic cell supernatant, or an additional agent or combination thereof as disclosed herein.

Cytokine Release Associated with Non CAR T-Cell Applications

In one embodiment, disclosed herein is a method of decreasing or inhibiting cytokine production in a subject experiencing cytokine release syndrome or cytokine storm or vulnerable to cytokine release syndrome or cytokine storm, comprising the step of administering a composition comprising apoptotic cells or an apoptotic supernatant to said subject, wherein said administering decreases or inhibits cytokine production in said subject. In another embodiment, decrease or inhibition of cytokine production is compared with a subject experiencing cytokine release syndrome or cytokine storm or vulnerable to cytokine release syndrome or cytokine storm and not administered apoptotic cells or an apoptotic supernatant. In another embodiment, methods for decreasing or inhibiting cytokine production decrease or inhibit pro-inflammatory cytokine production. In another embodiment, methods for decreasing or inhibiting cytokine production decrease or inhibit production of at least one pro-inflammatory cytokine. In another embodiment, methods for decreasing or inhibiting cytokine production decrease or inhibit production of at least cytokine IL-6. In another embodiment, methods for decreasing or inhibiting cytokine production decrease or inhibit production of at least cytokine IL-1beta. In another embodiment, methods for decreasing or inhibiting cytokine production decrease or inhibit production of at least cytokine TNF-alpha. In another embodiment, methods disclosed herein for decreasing or inhibiting cytokine production, result in reduction or inhibition of production of cytokines IL-6, IL-1β, or TNF-α, or any combination in said subject compared with a subject experiencing cytokine release syndrome or cytokine storm or vulnerable to cytokine release syndrome or cytokine storm and not administered apoptotic cells or an apoptotic supernatant.

Cancers or tumors may also affect the absolute level of cytokines including pro-inflammatory cytokines. The level of tumor burden in a subject may affect cytokine levels, particularly proinflammatory cytokines. A skilled artisan would appreciate that the phrase "decrease or inhibit" or grammatical variants thereof may encompass fold decrease or inhibition of cytokine production, or a net decrease or inhibition of cytokine production, or percent (%) decrease or inhibition, or may encompass a rate of change of decrease or inhibition of a cytokine production.

In another embodiment, disclosed herein is a method of decreasing or inhibiting cytokine production in a subject experiencing cytokine release syndrome or cytokine storm or vulnerable to cytokine release syndrome or cytokine storm comprising the step of administering apoptotic cells or a composition comprising apoptotic cells to said subject.

In another embodiment, disclosed herein is a method of decreasing or inhibiting cytokine production in a subject experiencing cytokine release syndrome or cytokine storm or vulnerable to cytokine release syndrome or cytokine storm comprising the step of administering an apoptotic cell supernatant, such as an apoptotic cell-phagocyte supernatant, or a composition comprising said supernatant to said subject.

In another embodiment, disclosed herein is a method of decreasing or inhibiting cytokine production in a subject experiencing cytokine release syndrome or cytokine storm or vulnerable to cytokine release syndrome or cytokine storm comprising the step of administering an apoptotic cell supernatant, such as an additional agent selected from the group comprising apoptotic cells, an apoptotic supernatant, a CTLA-4 blocking agent, an alpha-1 anti-trypsin or fragment thereof or analogue thereof, a tellurium-based compound, or an immune modulating agent, or any combination thereof, or a composition comprising said supernatant to said subject.

In one embodiment, an infection causes the cytokine release syndrome or cytokine storm in the subject. In one embodiment, the infection is an influenza infection. In one embodiment, the influenza infection is H1N1. In another embodiment, the influenza infection is an H5N1 bird flu. In another embodiment, the infection is severe acute respiratory syndrome (SARS). In another embodiment, the subject has Epstein-Barr virus-associated hemophagocytic lymphohistiocytosis (HLH). In another embodiment, the infection is sepsis. In one embodiment, the sepsis is gram-negative. In another embodiment, the infection is malaria. In another embodiment, the infection is an Ebola virus infection. In another embodiment, the infection is variola virus. In another embodiment, the infection is a systemic Gram-negative bacterial infection. In another embodiment, the infection is Jarisch-Herxheimer syndrome.

In one embodiment, the cause of the cytokine release syndrome or cytokine storm in a subject is hemophagocytic lymphohistiocytosis (HLH). In another embodiment, HLH is sporadic HLH. In another embodiment, HLH is macrophage activation syndrome (MAS). In another embodiment, the cause of the cytokine release syndrome or cytokine storm in a subject is MAS.

In one embodiment, the cause of the cytokine release syndrome or cytokine storm in a subject is chronic arthritis. In another embodiment, the cause of the cytokine release syndrome or cytokine storm in a subject is systemic Juvenile Idiopathic Arthritis (sJIA), also known as Still's Disease.

In one embodiment, the cause of the cytokine release syndrome or cytokine storm in a subject is Cryopyrin-associated Periodic Syndrome (CAPS). In another embodiment, CAPS comprises Familial Cold Auto-inflammatory Syndrome (FCAS), also known as Familial Cold Urticaria (FCU).

In another embodiment, CAPS comprises Muckle-Well Syndrome (MWS). In another embodiment, CAPS comprises Chronic Infantile Neurological Cutaneous and Articular (CINCA) Syndrome. In yet another embodiment, CAPS comprises FCAS, FCU, MWS, or CINCA Syndrome, or any combination thereof. In another embodiment, the cause of the cytokine release syndrome or cytokine storm in a subject is FCAS. In another embodiment, the cause of the cytokine release syndrome or cytokine storm in a subject is FCU. In another embodiment, the cause of the cytokine release syndrome or cytokine storm in a subject is MWS. In another embodiment, the cause of the cytokine release syndrome or cytokine storm in a subject is CINCA Syndrome. In still another embodiment, the cause of the cytokine release syndrome or cytokine storm in a subject is FCAS, FCU, MWS, or CINCA Syndrome, or any combination thereof.

In another embodiment, the cause of the cytokine release syndrome or cytokine storm in a subject is a cryopyrinopathy comprising inherited or de novo gain of function mutations in the NLRP3 gene, also known as the CIAS1 gene.

In one embodiment, the cause of the cytokine release syndrome or cytokine storm in a subject is a hereditary auto-inflammatory disorder.

In one embodiment, the trigger for the release of inflammatory cytokines is a lipopolysaccharide (LPS), Gram-positive toxins, fungal toxins, glycosylphosphatidylinositol (GPI) or modulation of RIG-1 gene expression.

In another embodiment, the subject experiencing cytokine release syndrome or cytokine storm does not have an infectious disease. In one embodiment, the subject has acute pancreatitis. In another embodiment, the subject has tissue injury, which in on embodiment, is severe burns or trauma. In another embodiment, the subject has acute respiratory distress syndrome. In another embodiment, the subject has cytokine release syndrome or cytokine storm secondary to drug use. In another embodiment, the subject has cytokine release syndrome or cytokine storm secondary to toxin inhalation.

In another embodiment, the subject has cytokine release syndrome or cytokine storm secondary to receipt of immunotherapy, which in one embodiment is immunotherapy with superagonistic CD28-specific monoclonal antibodies (CD28SA). In one embodiment, the CD28SA is TGN1412. In another embodiment, the immunotherapy is CAR T-cell therapy.

In another embodiment, apoptotic cells or supernatant or a CTLA-4 blocking agent, an alpha-1 anti-trypsin or fragment thereof or analogue thereof, a tellurium-based compound, or an immune modulating agent, or any combination thereof, may be used to control cytokine release syndrome or cytokine storm that results from administration of a pharmaceutical composition. In one embodiment, the pharmaceutical composition is oxaliplatin, cytarabine, lenalidomide, or a combination thereof.

In another embodiment, apoptotic cells or the supernatant or a CTLA-4 blocking agent, an alpha-1 anti-trypsin or fragment thereof or analogue thereof, a tellurium-based compound, or an immune modulating agent, or any combination thereof, may be used to control cytokine release syndrome or cytokine storm that results from administration of an antibody. In one embodiment, the antibody is monoclonal. In another embodiment, the antibody is polyclonal. In one embodiment, the antibody is rituximab. In another embodiment, the antibody is Orthoclone OKT3 (muromonab-CD3). In another embodiment, the antibody is alemtuzumab, tosituzumab, CP-870,893, LO-CD2a/BTI-322 or TGN1412.

In another embodiment, examples of diseases for which control of inflammatory cytokine production can be beneficial include cancers, allergies, any type of infection, toxic shock syndrome, sepsis, any type of autoimmune disease, arthritis, Crohn's disease, lupus, psoriasis, or any other disease for which the hallmark feature is toxic cytokine release that causes deleterious effects in a subject.

Alpha-1-Antitrypsin (AAT)

Alpha-1-antitrypsin (AAT) is a circulating 52-kDa glycoprotein that is produced mainly by the liver. AAT is primarily known as a serine protease inhibitor and is encoded by the gene SERPINA1. AAT inhibits neutrophil elastase, and inherited deficiency in circulating AAT results in lung-tissue deterioration and liver disease. Serum AAT concentrations in healthy individuals increase twofold during inflammation.

There is a negative association between AAT levels and the severity of several inflammatory diseases. For example, reduced levels or activity of AAT have been described in patients with HIV infection, diabetes mellitus, hepatitis C infection-induced chronic liver disease, and several types of vasculitis.

Increasing evidence demonstrates that human serum derived alpha-1-anti-trypsin (AAT) reduces production of pro-inflammatory cytokines, induces anti-inflammatory cytokines, and interferes with maturation of dendritic cells.

Indeed, the addition of AAT to human peripheral blood mononuclear cells (PBMC) inhibits LPS induced release of TNF-α and IL-1β but increases IL-1 receptor antagonist (IL-1Ra) and IL-10 production.

AAT reduces in vitro IL-1β-mediated pancreatic islet toxicity, and AAT monotherapy prolongs islet allograft survival, promotes antigen-specific immune tolerance in mice, and delays the development of diabetes in non-obese diabetic (NOD) mice. AAT was shown to inhibit LPS-induced acute lung injury in experimental models. Recently, AAT was shown to reduce the size of infarct and the severity of heart failure in a mouse model of acute myocardial ischemia-reperfusion injury.

Monotherapy with clinical-grade human AAT (hAAT) reduced circulating pro-inflammatory cytokines, diminished Graft vs Host Disease (GvHD) severity, and prolonged animal survival after experimental allogeneic bone marrow transfer (Tawara et al., Proc Natl Acad Sci USA. 2012 Jan. 10; 109(2):564-9), incorporated herein by reference. AAT treatment reduced the expansion of alloreactive T effector cells but enhanced the recovery of T regulatory T-cells, (Tregs) thus altering the ratio of donor T effector to T regulatory cells in favor of reducing the pathological process. In vitro, AAT suppressed LPS-induced in vitro secretion of proinflammatory cytokines such as TNF-α and IL-1β, enhanced the production of the anti-inflammatory cytokine IL-10, and impaired NF-κB translocation in the host dendritic cells. Marcondes, Blood. 2014 (October 30; 124(18):2881-91) incorporated herein by reference show that treatment with AAT not only ameliorated GvHD but also preserved and perhaps even enhanced the graft vs leukemia (GVL) effect.

In one embodiment, disclosed herein are compositions comprising chimeric antigen receptor-expressing T-cells (CAR T-cells) and Alpha-1-antitrypsin (AAT). In another embodiment, CAR T-cells and Alpha-1-antitrypsin (AAT) are in separate compositions. In another embodiment, AAT comprises a full length AAT or a functional fragment thereof. In another embodiment, AA comprises an analogue of a full length AAT or a functional fragment thereof. In another embodiment, a composition comprising AAT further comprises apoptotic cells or an apoptotic cell supernatant.

In another embodiment, disclosed herein is a method of treating, preventing, inhibiting, reducing the incidence of, ameliorating, or alleviating a cancer or a tumor in a subject comprising the step of administering chimeric antigen receptor-expressing T-cells (CAR T-cells) and a composition comprising Alpha-1-antitrypsin (AAT) to said subject. In another embodiment, the method further comprises apoptotic cells or an apoptotic cell supernatant.

In another embodiment, disclosed herein is a method of inhibiting or reducing the incidence of cytokine release syndrome or cytokine storm in a subject undergoing chimeric antigen receptor-expressing T-cell (CAR T-cell) therapy, comprising the step of administering a composition comprising Alpha-1-antitrypsin (AAT) to said subject. In another embodiment, a method of treating cytokine release syndrome or a cytokine storm in a subject undergoing chimeric antigen receptor-expressing T-cell (CAR T-cell) therapy, comprises the step of administering a composition comprising Alpha-1-antitrypsin (AAT) to said subject. In another embodiment, a method of preventing cytokine release syndrome or a cytokine storm in a subject undergoing chimeric antigen receptor-expressing T-cell (CAR T-cell) therapy, comprises the step of administering a composition comprising Alpha-1-antitrypsin (AAT) to said subject. In another embodiment, a method of ameliorating cytokine release syndrome or a cytokine storm in a subject undergoing chimeric antigen receptor-expressing T-cell (CAR T-cell) therapy, comprises the step of administering a composition comprising Alpha-1-antitrypsin (AAT) to said subject. In another embodiment, a method of alleviating cytokine release syndrome or a cytokine storm in a subject undergoing chimeric antigen receptor-expressing T-cell (CAR T-cell) therapy, comprises the step of administering a composition comprising Alpha-1-antitrypsin (AAT) to said subject.

In another embodiment, disclosed herein is a method of decreasing or inhibiting cytokine production in a subject experiencing cytokine release syndrome or cytokine storm or vulnerable to cytokine release syndrome or cytokine storm, comprising the step of administering a composition comprising Alpha-1-antitrypsin (AAT) to said subject.

In one embodiment, AAT is administered alone to control cytokine release. In another embodiment, both AAT and apoptotic cells or a composition thereof, or apoptotic cell supernatants or a composition thereof, are administered to control cytokine release.

Immuno-Modulatory Agents

A skilled artisan would appreciate that immune-modulating agents may encompass extracellular mediators, receptors, mediators of intracellular signaling pathways, regulators of translation and transcription, as well as immune cells. In one embodiment, an additional agent disclosed herein is an immune-modulatory agent known in the art. In another embodiment, use in the methods disclosed here of an immune-modulatory agent reduces the level of at least one cytokine. In another embodiment, use in the methods disclosed here of an immune-modulatory agent reduces or inhibits CRS or a cytokine storm. In some embodiments, use in the methods disclosed herein of an immune-modulatory agent is for treating, preventing, inhibiting the growth, delaying disease progression, reducing the tumor load, or reducing the incidence of a tumor or a cancer, or any combination thereof. In some embodiments, use of an immune-modulatory agent is in combination with another composition disclosed herein, for example but not limited to a composition comprising early apoptotic cells or comprising CAR T-cells.

In one embodiment, an immune-modulatory agent comprises compounds that block, inhibit or reduce the release of cytokines or chemokines. In another embodiment, an immune-modulatory agent comprises compounds that block, inhibit or reduce the release of IL-21 or IL-23, or a combination thereof. In another embodiment, an immune-modulatory agent comprises an antiretroviral drug in the chemokine receptor-5 (CCR5) receptor antagonist class, for example maraviroc. In another embodiment, an immune-modulatory agent comprises an anti-DNAM-1 antibody. In another embodiment, an immune-modulatory agent comprises damage/pathogen-associated molecules (DAMPs/PAMPs) selected from the group comprising heparin sulfate, ATP, and uric acid, or any combination thereof. In another embodiment, an immune-modulatory agent comprises a sialic acid binding Ig-like lectin (Siglecs). In another embodiment, an immune-modulatory agent comprises a cellular mediator of tolerance, for example regulatory $CD4^+$ $CD25^+$ T cells (Tregs) or invariant natural killer T cells (iNK T-cells). In another embodiment, an immune-modulatory agent comprises dendritic cells. In another embodiment, an immune-modulatory agent comprises monocytes. In another embodiment, an immune-modulatory agent comprises macrophages. In another embodiment, an immune-modulatory agent comprises JAK2 or JAK3 inhibitors selected from the group comprising ruxolitinib and tofacitinib. In another embodiment, an immune-modulatory agent comprises an inhibitor of spleen tyrosine kinase (Syk), for example fostamatinib. In another embodiment, an immune-modulatory agent comprises histone deacetylase inhibitor vorinostat acetylated STAT3. In another embodiment, an immune-modulatory agent comprises neddylation inhibitors, for example MLN4924. In another embodiment, an immune-modulatory agent comprises an miR-142 antagonist. In another embodiment, an immune-modulatory agent comprises a chemical analogue of cytidine, for example Azacitidine. In another embodiment, an immune-modulatory agent comprises an inhibitor of histone deacetylase, for example Vorinostat. In another embodiment, an immune-modulatory agent comprises an inhibitor of histone methylation. In another embodiment, an immune-modulatory agent comprises an antibody. In another embodiment, the antibody is rituximab (RtX)

Tellurium-Based Compounds

Tellurium is a trace element found in the human body. Various tellurium compounds, have immune-modulating properties, and have been shown to have beneficial effects in diverse preclinical and clinical studies. A particularly effective family of tellurium-containing compounds is disclosed for example, in U.S. Pat. Nos. 4,752,614; 4,761,490; 4,764, 461 and 4,929,739. The immune-modulating properties of this family of tellurium-containing compounds is described, for example, in U.S. Pat. Nos. 4,962,207, 5,093,135, 5,102, 908 and 5,213,899, which are all incorporated by reference as if fully set forth herein.

One promising compound is ammonium trichloro(dioxyethylene-O,O')tellurate, which is also referred to herein and in the art as AS101. AS101, as a representative example of the family of tellurium-containing compound discussed hereinabove, exhibits antiviral (Nat. Immun Cell Growth Regul. 7(3):163-8, 1988; AIDS Res Hum Retroviruses. 8(5):613-23, 1992), and tumoricidal activity (Nature 330 (6144):173-6, 1987; J. Clin. Oncol. 13(9):2342-53, 1995; J. Immunol. 161(7):3536-42, 1998). Further, AS101 is characterized by low toxicity.

In one embodiment, a composition comprising tellurium-containing immune-modulator compounds may be used in methods disclosed herein, where the tellurium-based compound stimulates the innate and acquired arm of the immune response. For example, it has been shown that AS101 is a potent activator of interferon (IFN) in mice (J. Natl. Cancer Inst. 88(18):1276-84, 1996) and humans (Nat. Immun Cell Growth Regul. 9(3):182-90, 1990; Immunology 70(4):473-7, 1990; J. Natl. Cancer Inst. 88(18):1276-84, 1996.)

In another embodiment, tellurium-based compounds induce the secretion of a spectrum of cytokines, such as IL-1α, IL-6 and TNF-α.

In another embodiment, a tellurium-based compound comprises a tellurium-based compound known in the art to have immune-modulating properties. In another embodiment, a tellurium-based compound comprises ammonium trichloro(dioxyethylene-O,O')tellurate.

In one embodiment, a tellurium-based compound inhibits the secretion of at least one cytokine. In another embodiment, a tellurium-based compound reduces the secretion of at least one cytokine. In another embodiment, a tellurium-based compound inhibits or reduces a cytokine release syndrome (CRS) of a cytokine storm.

In one embodiment, disclosed herein are compositions comprising chimeric antigen receptor-expressing T-cells (CAR T-cells) and a tellurium-based compound. In another embodiment, CAR T-cells and Tellurium-based compound are in separate compositions. In another embodiment, AAT comprises a full length AAT or a functional fragment thereof. In another embodiment, AA comprises an analogue of a full length AAT or a functional fragment thereof In another embodiment, disclosed herein is a method of treating, preventing, inhibiting, reducing the incidence of, ameliorating, or alleviating a cancer or a tumor in a subject comprising the step of administering chimeric antigen receptor-expressing T-cells (CAR T-cells) and a composition comprising a Tellurium-based compound to said subject.

In another embodiment, disclosed herein is a method of inhibiting or reducing the incidence of cytokine release syndrome or cytokine storm in a subject undergoing chimeric antigen receptor-expressing T-cell (CAR T-cell) therapy, comprising the step of administering a composition comprising a Tellurium-based compound to said subject. In another embodiment, a method of treating cytokine release syndrome or a cytokine storm in a subject undergoing chimeric antigen receptor-expressing T-cell (CAR T-cell) therapy, comprises the step of administering a composition comprising a Tellurium-based compound to said subject. In another embodiment, a method of preventing cytokine release syndrome or a cytokine storm in a subject undergoing chimeric antigen receptor-expressing T-cell (CAR T-cell) therapy, comprises the step of administering a composition comprising a Tellurium-based compound to said subject. In another embodiment, a method of ameliorating cytokine release syndrome or a cytokine storm in a subject undergoing chimeric antigen receptor-expressing T-cell (CAR T-cell) therapy, comprises the step of administering a composition comprising a Tellurium-based compound to said subject. In another embodiment, a method of alleviating cytokine release syndrome or a cytokine storm in a subject undergoing chimeric antigen receptor-expressing T-cell (CAR T-cell) therapy, comprises the step of administering a composition comprising a Tellurium-based compound to said subject.

In another embodiment, disclosed herein is a method of decreasing or inhibiting cytokine production in a subject experiencing cytokine release syndrome or cytokine storm or vulnerable to cytokine release syndrome or cytokine storm, comprising the step of administering a composition comprising a Tellurium-based compound to said subject.

In one embodiment, a tellurium-based compound is administered alone to control cytokine release. In another embodiment, both a tellurium-based compound and apoptotic cells or a composition thereof, or apoptotic cell supernatants or a composition thereof, are administered to control cytokine release.

Dendritic Cells

In one embodiment, dendritic cells (DCs) are antigen-producing and presenting cells of the mammalian immune system that process antigen material and present it on the cell surface to the T-cells of the immune system and are thereby capable of sensitizing T-cells to both new and recall antigens. In another embodiment, DCs are the most potent antigen-producing cells, acting as messengers between the innate and the adaptive immune systems. DC cells may be used, in one embodiment, to prime specific antitumor immunity through the generation of effector cells that attack and lyse tumors.

Dendritic cells are present in those tissues that are in contact with the external environment, such as the skin (where there is a specialized dendritic cell type called the Langerhans cell) and the inner lining of the nose, lungs, stomach and intestines. They can also be found in an immature state in the blood. Once activated, they migrate to the lymph nodes where they interact with T-cells and B cells to initiate and shape the adaptive immune response. At certain development stages, they grow branched projections, the dendrites that give the cell its name Dendritic cells may be engineered to express particular tumor antigens.

The three signals that are required for T-cell activation are: (i) presentation of cognate antigen in self MHC molecules; (ii) costimulation by membrane-bound receptor-ligand pairs; and (iii) soluble factors to direct polarization of the ensuing immune response. Dendritic cells (DCs) are able to provide all of the three signals required for T-cell activation making them an excellent cancer vaccine platform.

Therefore, in one embodiment, disclosed herein are a composition comprising dendritic cells and an additional agent, wherein said additional agent comprises apoptotic cells, apoptotic supernatants, a CTLA-4 blocking agent, an alpha-1 anti-trypsin or fragment thereof or analogue thereof, a tellurium-based compound, or an immune modulating agent, or any combination thereof.

In another embodiment, disclosed herein is a method of treating, preventing, inhibiting, reducing the incidence of, ameliorating, or alleviating a cancer or a tumor in a subject comprising the step of administering dendritic cells and a composition comprising an additional agent, wherein said agent comprises apoptotic cells, apoptotic supernatants, a CTLA-4 blocking agent, an alpha-1 anti-trypsin or fragment thereof or analogue thereof, a tellurium-based compound, or an immune modulating agent, or any combination thereof, to said subject.

Genetic Modification

In some embodiments, genetic modification of T-cells, dendritic cells, and/or apoptotic cells may be accomplished using RNA, DNA, recombinant viruses, or a combination thereof. In some embodiments, vectors derived from gamma retroviruses or lentiviruses are used in the compositions and methods as disclosed herein. In another embodiment, these vectors can integrate into the host genome, with potentially permanent expression of the transgene and have low intrinsic immunogenicity. In another embodiment, another vector that integrates into the host genome and/or has low intrinsic immunogenicity may be used in the compositions and methods as disclosed herein. In another embodiment, the non-viral-vector-mediated sleeping beauty transposon system is used to insert the CAR and other genes into the T-cell. In another embodiment, "suicide genes" are integrated into the T-cells, in which expression of a pro-apoptotic gene is under the control of an inducible promoter responsive to a systemically delivered drug.

In some embodiments, genetic modification may be transient. In another embodiment, genetic modification may utilize messenger RNA (mRNA). In another embodiment, large numbers of cells may be infused on multiple occasions in transiently engineered T-cells, such as mRNA-transfected T-cells. In another embodiment, RNA-based electroporation of lymphocytes using in vitro—transcribed mRNA mediates transient expression of proteins for approximately one week and obviates the risk of integrating viral vectors. In another embodiment, mRNA-transduced dendritic cells or mRNA-electroporated T and NK lymphocytes.

It has been demonstrated that genetically modified T-cells can persist after adoptive transfer for more than a decade without adverse effects, indicating that genetically modifying human T-cells is fundamentally safe.

In another embodiment, the genetic modification of the compositions and in the methods as disclosed herein may be any method that is known in the art.

Apoptotic Cells

Production of apoptotic cells ("ApoCells") for use in compositions and methods as disclosed herein, has been described in WO 2014/087408, which is incorporated by reference herein in its entirety, and is described in brief in Example 1 below. In another embodiment, apoptotic cells for use in compositions and methods as disclosed herein are produced in any way that is known in the art. In another embodiment, apoptotic cells for use in compositions and methods disclosed herein are autologous with a subject undergoing therapy. In another embodiment, apoptotic cells for use in compositions and methods disclosed herein are allogeneic with a subject undergoing therapy. In another embodiment, a composition comprising apoptotic cells comprises apoptotic cells as disclosed herein or as is known in art.

A skilled artisan would appreciate that the term "autologous" may encompass a tissue, cell, nucleic acid molecule or polypeptide in which the donor and recipient is the same person.

A skilled artisan would appreciate that the term "allogeneic" may encompass a tissue, cell, nucleic acid molecule or polypeptide that is derived from separate individuals of the same species. In some embodiments, allogeneic donor cells are genetically distinct from the recipient.

In some embodiments, obtaining a mononuclear-enriched cell composition according to the production method disclosed herein is effected by leukapheresis. A skilled artisan would appreciate that the term "leukapheresis" may encompass an apheresis procedure in which leukocytes are separated from the blood of a donor. In some embodiments, the blood of a donor undergoes leukapheresis and thus a mononuclear-enriched cell composition is obtained according to the production method disclosed herein. It is to be noted, that the use of at least one anticoagulant during leukapheresis is required, as is known in the art, in order to prevent clotting of the collected cells.

In some embodiments, the leukapheresis procedure is configured to allow collection of mononuclear-enriched cell composition according to the production method disclosed herein. In some embodiments, cell collections obtained by leukapheresis comprise at least 65%. In other embodiments, at least 70%, or at least 80% mononuclear cells. as disclosed herein. In some embodiments, blood plasma from the cell-donor is collected in parallel to obtaining of the mononuclear-enriched cell composition. In the production method disclosed herein. In some embodiments, about 300-600 ml of blood plasma from the cell-donor are collected in parallel to obtaining the mononuclear-enriched cell composition according to the production method disclosed herein. In some embodiments, blood plasma collected in parallel to obtaining the mononuclear-enriched cell composition according to the production method disclosed herein is used as part of the freezing and/or incubation medium. Additional detailed methods of obtaining an enriched population of apoptotic cells for use in the compositions and methods as disclosed herein may be found in WO 2014/087408, which is incorporated herein by reference in its entirety.

In some embodiments, the early apoptotic cells for use in the methods disclosed herein comprise at least 85% mononuclear cells. In further embodiments, the early apoptotic cells for use in the methods disclosed herein contains at least 85% mononuclear cells, 90% mononuclear cells or alternatively over 90% mononuclear cells. In some embodiments, the early apoptotic cells for use in the methods disclosed herein comprise at least 90% mononuclear cells. In some embodiments, the early apoptotic cells for use in the methods disclosed herein comprise at least 95% mononuclear cells.

It is to be noted that, in some embodiments, while the mononuclear-enriched cell preparation at cell collection comprises at least 65%, preferably at least 70%, most preferably at least 80% mononuclear cells, the final pharmaceutical population, following the production method of the early apoptotic cells for use in the methods disclosed herein, comprises at least 85%, preferably at least 90%, most preferably at least 95% mononuclear cells.

In certain embodiments, the mononuclear-enriched cell preparation used for production of the composition of the early apoptotic cells for use in the methods disclosed herein comprises at least 50% mononuclear cells at cell collection. In certain embodiments, disclosed herein is a method for producing the pharmaceutical population wherein the method comprises obtaining a mononuclear-enriched cell preparation from the peripheral blood of a donor, the mononuclear-enriched cell preparation comprising at least 50% mononuclear cells. In certain embodiments, disclosed herein is a method for producing the pharmaceutical population wherein the method comprises freezing a mononuclear-enriched cell preparation comprising at least 50% mononuclear cells.

In some embodiments, the cell preparation comprises at least 85% mononuclear cells, wherein at least 40% of the cells in the preparation are in an early-apoptotic state, wherein at least 85% of the cells in the preparation are viable cells. In some embodiments, the apoptotic cell preparation comprises no more than 15% $CD15^{high}$ expressing cells.

A skilled artisan would appreciate that the term "early-apoptotic state" may encompass cells that show early signs of apoptosis without late signs of apoptosis. Examples of early signs of apoptosis in cells include exposure of phosphatidylserine (PS) and the loss of mitochondrial membrane potential. Examples of late events include propidium iodide (PI) admission into the cell and the final DNA cutting. In order to document that cells are in an "early apoptotic" state, in some embodiments, PS exposure detection by Annexin-V and PI staining are used, and cells that are stained with Annexin V but not with PI are considered to be "early apoptotic cells". In another embodiment, cells that are stained by both Annexin-V FITC and PI are considered to be "late apoptotic cells". In another embodiment, cells that do not stain for either Annexin-V or PI are considered non-apoptotic viable cells.

A skilled artisan would appreciate that in some embodiments the terms "apoptotic cell", "Allocetra", Autocetra", "ALC", and "ApoCell", and grammatical variants thereof, may be used interchangeably to represent a population of "early apoptotic cells", wherein said cell population is enriched for mononuclear cells and has unique characteristics (See for example, Example 1). The skilled artisan would appreciate that the compositions and methods described herein, in some embodiments comprise early apoptotic cells.

In some embodiments, Allocetra comprise a population of early apoptotic cells obtained from a single allogeneic donor. In some embodiments, Allocetra comprise a population of early apoptotic cells obtained from multiple allogeneic donors. In some embodiments, Allocetra comprise pooled populations of early apoptotic cells obtained from multiple allogeneic donors or from cells obtained from a blood bank. In some embodiments, Allocetra comprise pooled population of early apoptotic cells obtained from the same allogeneic donor. In some embodiments, Allocetra comprise an irradiated population of early apoptotic cells. In some embodiments, the term "Allocetra" may be used interchangeably with the term "Allocetra-OTS". In some embodiments, the terms "Allocetra" and "Allocetra-OTS" encompass mononuclear early apoptotic cells, prepared as described in Example 1, independent of the source of said cells.

In some embodiments, apoptotic cells comprise cells in an early apoptotic state. In another embodiment, apoptotic cells comprise cells wherein at least 90% of said cells are in an early apoptotic state. In another embodiment, apoptotic cells comprise cells wherein at least 80% of said cells are in an early apoptotic state. In another embodiment, apoptotic cells comprise cells wherein at least 70% of said cells are in an early apoptotic state. In another embodiment, apoptotic cells comprise cells wherein at least 60% of said cells are in an early apoptotic state. In another embodiment, apoptotic cells comprise cells wherein at least 50% of said cells are in an early apoptotic state.

In some embodiments, the composition comprising apoptotic cells further comprises an anti-coagulant.

In some embodiments, early apoptotic cells are stable. A skilled artisan would appreciate that in some embodiments stability encompasses maintaining early apoptotic cell characteristics over time, for example, maintaining early apoptotic cell characteristics upon storage at about 2-8° C. In some embodiments, stability comprises maintaining early apoptotic cell characteristic upon storage at freezing temperatures, for example temperatures at or below 0° C.

In some embodiments, the mononuclear-enriched cell population obtained according to the production method of the early apoptotic cells for use in the methods disclosed herein undergoes freezing in a freezing medium. In some embodiments, the freezing is gradual. In some embodiments, following collection the cells are maintained at room temperature until frozen. In some embodiments, the cell-preparation undergoes at least one washing step in washing medium following cell-collection and prior to freezing.

As used herein, the terms "obtaining cells" and "cell collection" may be used interchangeably. In some embodiments, the cells of the cell preparation are frozen within 3-6 hours of collection. In some embodiments, the cell preparation is frozen within up to 6 hours of cell collection. In some embodiments, the cells of the cell preparations are frozen within 1, 2, 3, 4, 5, 6, 7, 8 hours of collection. In other embodiments, the cells of the cell preparations are frozen up to 8, 12, 24, 48, 72 hours of collection. In other embodiments, following collection the cells are maintained at 2-8° C. until frozen.

In some embodiments, freezing according to the production of an early apoptotic cell population comprises: freezing the cell preparation at about −18° C. to −25° C. followed by freezing the cell preparation at about −80° C. and finally freezing the cell preparation in liquid nitrogen until thawing. In some embodiments, the freezing according to the production of an early apoptotic cell population comprises: freezing the cell preparation at about −18° C. to −25° C. for at least 2 hours, freezing the cell preparation at about −80° C. for at least 2 hours and finally freezing the cell preparation in liquid nitrogen until thawing. In some embodiments, the cells are kept in liquid nitrogen for at least 8, 10 or 12 hours prior to thawing. In some embodiments, the cells of the cell preparation are kept in liquid nitrogen until thawing and incubation with apoptosis-inducing incubation medium. In some embodiments, the cells of the cell preparation are kept in liquid nitrogen until the day of hematopoietic stem cell transplantation. In non-limiting examples, the time from cell collection and freezing to preparation of the final population may be between 1-50 days, alternatively between 6-30 days. In alternative embodiments, the cell preparation may be kept in liquid nitrogen for longer time periods, such as at least several months.

In some embodiments, the freezing according to the production of an early apoptotic cell population comprises freezing the cell preparation at about −18° C. to −25° C. for at least 0.5, 1, 2, 4 hours. In some embodiments, the freezing according to the production of an early apoptotic cell population comprises freezing the cell preparation at about −18° C. to −25° C. for about 2 hours. In some embodiments, the freezing. In the production of an early apoptotic cell population comprises freezing the cell preparation at about −80° C. for at least 0.5, 1, 2, 4, 12 hours.

In some embodiments, the mononuclear-enriched cell composition may remain frozen at least 1, 2, 3, 4, 5, 6, 7, 8, 9, 10, 11, 12, 20 months. In some embodiments, the mononuclear-enriched cell composition may remain frozen at least 0.5, 1, 2, 3, 4, 5 years. In certain embodiments, the mononuclear-enriched cell composition may remain frozen for at least 20 months.

In some embodiments, the mononuclear-enriched cell composition is frozen for at least 8, 10, 12, 18, 24 hours. In certain embodiments, freezing the mononuclear-enriched cell composition is for a period of at least 8 hours. In some embodiments, the mononuclear-enriched cell composition is frozen for at least about 10 hours. In some embodiments, the mononuclear-enriched cell composition is frozen for at least about 12 hours. In some embodiments, the mononuclear-enriched cell composition is frozen for about 12 hours. In some embodiments, the total freezing time of the mononuclear-enriched cell composition (at about −18° C. to −25° C., at about −80° C. and in liquid nitrogen) is at least 8, 10, 12, 18, 24 hours.

In some embodiments, the freezing at least partly induces the early-apoptotic state in the cells of the mononuclear-enriched cell composition. In some embodiments, the freezing medium comprises RPMI 1640 medium comprising L-glutamine, Hepes, Hes, dimethyl sulfoxide (DMSO) and plasma. In some embodiments, the plasma in the freezing medium is an autologous plasma of the donor which donated the mononuclear-enriched cells of the population. In some embodiments, the freezing medium comprises RPMI 1640 medium comprising 2 mM L-glutamine, 10 mM Hepes, 5% Hes, 10% dimethyl sulfoxide and 20% v/v plasma.

In some embodiments, the freezing medium comprises an anti-coagulant. In certain embodiments, at least some of the media used during the production of an early apoptotic cell population, including the freezing medium, the incubation medium and the washing media comprise an anti-coagulant. In certain embodiments, all media used during the production of an early apoptotic cell population which comprise an anti-coagulant comprise the same concentration of anti-coagulant. In some embodiments, anti-coagulant is not added to the final suspension medium of the cell population.

In some embodiments, addition of an anti-coagulant at least to the freezing medium improves the yield of the cell-preparation. In other embodiments, addition of an anti-coagulant to the freezing medium improves the yield of the cell-preparation in the presence of a high triglyceride level. As used herein, improvement in the yield of the cell-preparation relates to improvement in at least one of: the percentage of viable cells out of cells frozen, the percentage of early-state apoptotic cells out of viable cells and a combination thereof.

In some embodiments, early apoptotic cells are stable for at least 24 hours. In another embodiment, early apoptotic cells are stable for 24 hours. In another embodiment, early apoptotic cells are stable for more than 24 hours. In another embodiment, early apoptotic cells are stable for at least 36 hours. In another embodiment, early apoptotic cells are stable for 48 hours. In another embodiment, early apoptotic cells are stable for at least 36 hours. In another embodiment, early apoptotic cells are stable for more than 36 hours. In another embodiment, early apoptotic cells are stable for at least 48 hours. In another embodiment, early apoptotic cells are stable for 48 hours. In another embodiment, early apoptotic cells are stable for at least 48 hours. In another embodiment, early apoptotic cells are stable for more than 48 hours. In another embodiment, early apoptotic cells are stable for at least 72 hours. In another embodiment, early apoptotic cells are stable for 72 hours. In another embodiment, early apoptotic cells are stable for more than 72 hours.

A skilled artisan would appreciate that the term "stable" encompasses apoptotic cells that remain PS-positive (Phosphatidylserine-positive) with only a very small percent of PI-positive (Propidium iodide-positive). PI-positive cells provide an indication of membrane stability wherein a PI-positive cells permits admission into the cells, showing that the membrane is less stable. In some embodiments, stable early apoptotic cells remain in early apoptosis for at least 24 hours, for at least 36 hours, for at least 48 hours, or for at least 72 hours. In another embodiment, stable early apoptotic cells remain in early apoptosis for 24 hours, for 36 hours, for 48 hours, or for 72 hours. In another embodiment, stable early apoptotic cells remain in early apoptosis for more than 24 hours, for more than 36 hours, for more than 48 hours, or for more than 72 hours. In another embodiment, stable early apoptotic cells maintain their state for an extended time period.

In some embodiments, an apoptotic cell population is devoid of cell aggregates. In some embodiments, an apoptotic cell population is devoid of large cell aggregates. In some embodiments, an apoptotic cell population has a reduced number of cell aggregates compared to an apoptotic cell population prepared without adding an anticoagulant in a step other than cell collection (leukapheresis) from the donor. In some embodiments, an apoptotic cell population or a composition thereof, comprises an anticoagulant.

In some embodiments, apoptotic cells are devoid of cell aggregates, wherein said apoptotic cells were obtained from a subject with high blood triglycerides. In some embodiments, blood triglycerides levels of the subject are above 150 mg/dL. In some embodiments, an apoptotic cell population is devoid of cell aggregates, wherein said apoptotic cell population is prepared from cells obtained from a subject with normal blood triglycerides. In some embodiments, blood triglycerides levels of the subject are equal to or below 150 mg/dL. In some embodiments, cell aggregates produce cell loss during apoptotic cell production methods.

A skilled artisan would appreciate that the terms "aggregates" or "cell aggregates" may encompass the reversible clumping of blood cells under low shear forces or at stasis. Cell aggregates can be visually observed during the incubation steps of the production of the apoptotic cells. Cell aggregation can be measured by any method known in the art, for example by visually imaging samples under a light microscope or using flow cytometry.

In some embodiments, the anti-coagulant is selected from the group comprising: heparin, acid citrate dextrose (ACD) Formula A and a combination thereof. In some embodiments, the anti-coagulant is selected from the group consisting of: heparin, acid citrate dextrose (ACD) Formula A and a combination thereof.

In some embodiments of methods of preparing an early apoptotic cell population and compositions thereof, an anti-coagulant is added to at least one medium used during preparation of the population. In some embodiments, the at least one medium used during preparation of the population is selected from the group consisting of: the freezing medium, the washing medium, the apoptosis inducing incubation medium, and any combinations thereof.

In some embodiments, the anti-coagulant is selected from the group consisting of: Heparin, ACD Formula A and a combination thereof. It is to be noted that other anti-coagulants known in the art may be used, such as, but not limited to Fondaparinaux, Bivalirudin and Argatroban.

In some embodiments, at least one medium used during preparation of the population contains 5% of ACD formula A solution comprising 10 U/ml heparin. In some embodiments, anti-coagulant is not added to the final suspension medium of the cell population. As used herein, the terms "final suspension medium" and "administration medium" are used interchangeably having all the same qualities and meanings.

In some embodiments, at least one medium used during preparation of the population comprises heparin at a concentration of between 0.1-2.5 U/ml. In some embodiments, at least one medium used during preparation of the population comprises ACD Formula A at a concentration of between 1%-15% v/v. In some embodiments, the freezing medium comprises an anti-coagulant. In some embodiments, the incubation medium comprises an anti-coagulant. In some embodiments, both the freezing medium and incubation medium comprise an anti-coagulant. In some embodiments the anti-coagulant is selected from the group consisting of: heparin, ACD Formula A and a combination thereof.

In some embodiments, the heparin in the freezing medium is at a concentration of between 0.1-2.5 U/ml. In some embodiments, the ACD Formula A in the freezing medium is at a concentration of between 1%-15% v/v. In some embodiments, the heparin in the incubation medium is at a concentration of between 0.1-2.5 U/ml. In some embodiments, the ACD Formula A in the incubation medium is at a concentration of between 1%-15% v/v. In some embodiments, the anticoagulant is a solution of acid-citrate-dextrose (ACD) formula A. In some embodiments, the anticoagulant added to at least one medium used during preparation of the population is ACD Formula A containing heparin at a concentration of 10 U/ml.

In some embodiments, the apoptosis inducing incubation medium used in the production of an early apoptotic cell population comprises an anti-coagulant. In some embodiments, both the freezing medium and apoptosis inducing incubation medium used in the production of an early apoptotic cell population comprise an anti-coagulant. Without wishing to be bound by any theory or mechanism, in order to maintain a high and stable cell yield in different cell compositions, regardless of the cell collection protocol, in some embodiments addition of anti-coagulants comprising adding the anticoagulant to both the freezing medium and the apoptosis inducing incubation medium during production of the apoptotic cell population. In some embodiments, a high and stable cell yield within the composition comprises a cell yield of at least 30%, preferably at least 40%, typically at least 50% cells of the initial population of cells used for induction of apoptosis.

In some embodiments, both the freezing medium and the incubation medium comprise an anti-coagulant. In some embodiments, addition of an anti-coagulant both to the incubation medium and freezing medium results in a high and stable cell-yield between different preparations of the population regardless of cell-collection conditions, such as, but not limited to, the timing and/or type of anti-coagulant added during cell collection. In some embodiments, addition of an anti-coagulant both to the incubation medium and freezing medium results in a high and stable yield of the cell-preparation regardless of the timing and/or type of anti-coagulant added during leukapheresis. In some embodiments, production of the cell-preparation in the presence of a high triglyceride level results in a low and/or unstable cell-yield between different preparations. In some embodiments, producing the cell-preparation from the blood of a donor having high triglyceride level results in a low and/or unstable cell-yield of the cell preparation. In some embodiments, the term "high triglyceride level" refers to a triglyceride level which is above the normal level of a healthy subject of the same sex and age. In some embodiments, the term "high triglyceride level" refers to a triglyceride level above about 1.7 milimole/liter. As used herein, a high and stable yield refers to a cell yield in the population which is high enough to enable preparation of a dose which will demonstrate therapeutic efficiency when administered to a subject. In some embodiments, therapeutic efficiency refers to the ability to treat, prevent or ameliorate an immune disease, an autoimmune disease or an inflammatory disease in a subject. In some embodiments, a high and stable cell yield is a cell yield of at least 30%, possibly at least 40%, typically at least 50% of cells in the population out of cells initially frozen.

In some embodiments, in case the cell-preparation is obtained from a donor having a high triglyceride level, the donor will take at least one measure selected from the group consisting of: taking triglyceride-lowering medication prior to donation, such as, but not limited to: statins and/or bezafibrate, fasting for a period of at least 8, 10, 12 hours prior to donation, eating an appropriate diet to reduce blood triglyceride level at least 24, 48, 72 hours prior to donating and any combination thereof.

In some embodiments, cell yield in the population relates to cell number in the composition out of the initial number of cells subjected to apoptosis induction. As used herein, the terms "induction of early apoptotic state" and "induction of apoptosis" may be used interchangeably.

In some embodiments, the mononuclear-enriched cell composition is incubated in incubation medium following freezing and thawing. In some embodiments, there is at least one washing step between thawing and incubation. As used herein, the terms "incubation medium" and "apoptosis inducing incubation medium" are used interchangeably. In some embodiments, the incubation medium comprises RPMI 1640 medium supplemented with L-glutamine, Hepes methylprednisolone and plasma. In some embodiments, the washing medium comprises 2 mM L-glutamine, 10 mM Hepes and 10% v/v blood plasma. In some embodiments, the blood plasma in in the incubation medium is derived from the same donor from whom the cells of the cell preparations are derived. In some embodiments, the blood plasma is added to the incubation medium on the day of incubation. In some embodiments, incubation is performed at 37° C. and 5% CO2.

In some embodiments, the incubation medium comprises methylprednisolone. In some embodiments, the methylprednisolone within the incubation medium further induces the cells in the mononuclear-enriched cell composition to enter an early-apoptotic state. In some embodiments, the cells in the mononuclear-enriched cell composition are induced to enter an early-apoptotic state both by freezing and incubating in the presence of methylprednisolone. In some embodiments, the production of an early apoptotic cell population advantageously allows induction of an early-apoptosis state substantially without induction of necrosis, wherein the cells remain stable at said early-apoptotic state for about 24 hours following preparation.

In some embodiments, the incubation medium comprises methylprednisolone at a concentration of about 10-100 µg/ml. In some embodiments, the incubation medium comprises methylprednisolone at a concentration of about 40-60 µg/ml, alternatively about 45-55 µg/ml. In some embodiments, the incubation medium comprises methylprednisolone at a concentration of 50 µg/ml.

In some embodiments, the incubation is for about 2-12 hours, possibly 4-8 hours, typically for about 5-7 hours. In some embodiments, the incubation is for about 6 hours. In some embodiments, the incubation is for at least 6 hours. In a preferred embodiment, the incubation is for 6 hours.

In some embodiments, the incubation medium comprises an anti-coagulant. In some embodiments, addition of an anti-coagulant to the incubation medium improves the yield of the cell-preparation. In some embodiments, the anti-coagulant in the incubation medium is of the same concentration as within the freezing medium. In some embodiments, the incubation medium comprises an anti-coagulant selected from the group consisting of: heparin, ACD Formula A and a combination thereof. In some embodiments, the anti-coagulant used in the incubation medium is ACD Formula A containing heparin at a concentration of 10 U/ml.

In some embodiments, the incubation medium comprises heparin. In some embodiments, the heparin in the incubation medium is at a concentration of between 0.1-2.5 U/ml. In some embodiments, the heparin in the incubation medium is at a concentration of between 0.1-2.5 U/ml, possibly between 0.3-0.7 U/ml, typically about 0.5 U/ml. In certain embodiments, the heparin in the incubation medium is at a concentration of about 0.5 U/ml.

In some embodiments, the incubation medium comprises ACD Formula A. In some embodiments, the ACD Formula A in the incubation medium is at a concentration of between 1%-15% v/v. In some embodiments, the ACD Formula A in the incubation medium is at a concentration of between 1%-15% v/v, possibly between 4%-7% v/v, typically about 5% v/v. In some embodiments, the ACD Formula A in the incubation medium is at a concentration of about 5% v/v.

In some embodiments, improvement in the yield of the cell-preparation comprises improvement in the number of the early-apoptotic viable cells of the preparation out of the number of frozen cells from which the preparation was produced.

In some embodiments, addition of an anti-coagulant to the freezing medium contributes to a high and stable yield between different preparations of the pharmaceutical population. In preferable embodiments, addition of an anti-coagulant at least to the freezing medium and incubation medium results in a high and stable yield between different preparations of the pharmaceutical composition, regardless to the cell collection protocol used.

In some embodiments, the freezing medium comprises an anti-coagulant selected from the group consisting of: heparin, ACD Formula A and a combination thereof. In some embodiments, the anti-coagulant used in the freezing medium is ACD Formula A containing heparin at a concentration of 10 U/ml. In some embodiments, the freezing medium comprises 5% v/v of ACD Formula A solution comprising heparin at a concentration of 10 U/ml.

In some embodiments, the freezing medium comprises heparin. In some embodiments, the heparin in the freezing medium is at a concentration of between 0.1-2.5 U/ml. In some embodiments, the heparin in the freezing medium is at a concentration of between 0.1-2.5 U/ml, possibly between 0.3-0.7 U/ml, typically about 0.5 U/ml. In certain embodiments, the heparin in the freezing medium is at a concentration of about 0.5 U/ml.

In some embodiments, the freezing medium comprises ACD Formula A. In some embodiments, the ACD Formula A in the freezing medium is at a concentration of between 1%-15% v/v. In some embodiments, the ACD Formula A in the freezing medium is at a concentration of between 1%-15% v/v, possibly between 4%-7% v/v, typically about 5% v/v. In some embodiments, the ACD Formula A in the freezing medium is at a concentration of about 5% v/v.

In some embodiments, addition of an anti-coagulant to the incubation medium and/or freezing medium results in a high and stable cell yield within the population regardless of the triglyceride level in the blood of the donor. In some embodiments, addition of an anti-coagulant to the incubation medium and/or freezing medium results in a high and stable cell yield within the composition the invention when obtained from the blood of a donor having normal or high triglyceride level. In some embodiments, addition of an anti-coagulant at least to the incubation medium, results in a high and stable cell yield within the composition regardless of the triglyceride level in the blood of the donor. In some embodiments, addition of an anti-coagulant to the freezing medium and incubation medium results in a high and stable cell yield within the composition regardless of the triglyceride level in the blood of the donor.

In some embodiments, the freezing medium and/or incubation medium and/or washing medium comprise heparin at a concentration of at least 0.1 U/ml, possibly at least 0.3 U/ml, typically at least 0.5 U/ml. In some embodiments, the freezing medium and/or incubation medium and/or washing medium comprise ACD Formula A at a concentration of at least 1% v/v, possibly at least 3% v/v, typically at least 5% v/v.

In some embodiments, the mononuclear-enriched cell composition undergoes at least one washing step following cell collection and prior to being re-suspended in the freezing medium and frozen. In some embodiments, the mononuclear-enriched cell composition undergoes at least one washing step following freezing and thawing. In some embodiments, washing steps comprise centrifugation of the mononuclear-enriched cell composition followed by supernatant extraction and re-suspension in washing medium.

In some embodiments, the mononuclear-enriched cell composition undergoes at least one washing step between each stage of the production of an early apoptotic cell population. In some embodiments, anti-coagulant is added to washing media during washing steps throughout the production of an early apoptotic cell population. In some embodiments, the mononuclear-enriched cell composition undergoes at least one washing step following incubation. In some embodiments, the mononuclear-enriched cell composition undergoes at least one washing step following incubation using PBS. In some embodiments, anti-coagulant is not added to the final washing step prior to re-suspension of the cell-preparation in the administration medium. In some embodiments, anti-coagulant is not added to the PBS used in the final washing step prior to re-suspension of the cell-preparation in the administration medium. In certain embodiments, anti-coagulant is not added to the administration medium.

In some embodiments, the cell concentration during incubating is about $5 \times 10^6$ cells/ml.

In some embodiments, the mononuclear-enriched cell composition is suspended in an administration medium following freezing, thawing and incubating, thereby resulting in the pharmaceutical population. In some embodiments, the administration medium comprises a suitable physiological buffer. Non-limiting examples of a suitable physiological buffer are: saline solution, Phoshpate Buffered Saline (PBS), Hank's Balanced Salt Solution (HBSS), and the like. In some embodiments, the administration medium comprises PBS. In some embodiments, the administration medium comprises supplements conducive to maintaining the viability of the cells. In some embodiments, the mononuclear-enriched cell composition is filtered prior to administration. In some embodiments, the mononuclear-enriched cell composition is filtered prior to administration using a filter of at least 200 μm.

In some embodiments, the mononuclear-enriched cell population is re-suspended in an administration medium such that the final volume of the resulting cell-preparation is between 100-1000 ml, possibly between 200-800 ml, typically between 300-600 ml.

In some embodiments, cell collection refers to obtaining a mononuclear-enriched cell composition. In some embodiments, washing steps performed during the production of an early apoptotic cell population are performed in a washing medium. In certain embodiments, washing steps performed up until the incubation step of the production of an early apoptotic cell population are performed in a washing medium. In some embodiments, the washing medium comprises RPMI 1640 medium supplemented with L-glutamine and Hepes. In some embodiments, the washing medium comprises RPMI 1640 medium supplemented with 2 mM L-glutamine and 10 mM Hepes.

In some embodiments, the washing medium comprises an anti-coagulant. In some embodiments, the washing medium comprises an anti-coagulant selected from the group consisting of: heparin, ACD Formula A and a combination thereof. In some embodiments, the concentration of the anti-coagulant in the washing medium is the same concentration as in the freezing medium. In some embodiments, the concentration of the anti-coagulant in the washing medium is the same concentration as in the incubation medium. In some embodiments, the anti-coagulant used in the washing medium is ACD Formula A containing heparin at a concentration of 10 U/ml.

In some embodiments, the washing medium comprises heparin. In some embodiments, the heparin in the washing medium is at a concentration of between 0.1-2.5 U/ml. In some embodiments, the heparin in the washing medium is at a concentration of between 0.1-2.5 U/ml, possibly between 0.3-0.7 U/ml, typically about 0.5 U/ml. In certain embodiments, the heparin in the washing medium is at a concentration of about 0.5 U/ml.

In some embodiments, the washing medium comprises ACD Formula A. In some embodiments, the ACD Formula A in the washing medium is at a concentration of between 1%-15% v/v. In some embodiments, the ACD Formula A in the washing medium is at a concentration of between 1%-15% v/v, possibly between 4%-7% v/v, typically about 5% v/v. In some embodiments, the ACD Formula A in the washing medium is at a concentration of about 5% v/v.

In some embodiments, the mononuclear-enriched cell composition is thawed several hours prior to the intended administration of the population to a subject. In some embodiments, the mononuclear-enriched cell composition is thawed at about 33° C.-39° C. In some embodiments, the mononuclear-enriched cell composition is thawed for about 30-240 seconds, preferably 40-180 seconds, most preferably 50-120 seconds.

In some embodiments, the mononuclear-enriched cell composition is thawed at least 10 hours prior to the intended administration of the population, alternatively at least 20, 30, 40 or 50 hours prior to the intended administration of the population. In some embodiments, the mononuclear-enriched cell composition is thawed at least 15-24 hours prior to the intended administration of the population. In some embodiments, the mononuclear-enriched cell composition is thawed at least about 24 hours prior to the intended administration of the population. In some embodiments, the mononuclear-enriched cell composition is thawed at least 20 hours prior to the intended administration of the population. In some embodiments, the mononuclear-enriched cell composition is thawed 30 hours prior to the intended administration of the population. In some embodiments, the mononuclear-enriched cell composition is thawed at least 24 hours prior to the intended administration of the population. In some embodiments, the mononuclear-enriched cell composition undergoes at least one step of washing in the washing medium before and/or after thawing.

In some embodiments, the composition further comprises methylprednisolone. At some embodiments, the concentration of methylprednisolone does not exceed 30 μg/ml.

In some embodiments, the apoptotic cells are used at a high dose. In some embodiments, the apoptotic cells are used at a high concentration. In some embodiments, human apoptotic polymorphonuclear neutrophils (PMNs) are used. In some embodiments, a group of cells, of which 50% are apoptotic cells, are used. In some embodiments, apoptotic cells are verified by May-Giemsa-stained cytopreps. In some embodiments, viability of cells are assessed by trypan blue exclusion. In some embodiments, the apoptotic and necrotic status of the cells are confirmed by annexin V/propidium iodide staining with detection by FACS.

In some embodiments, apoptotic cells disclosed herein comprise no necrotic cells. In some embodiments, apoptotic cells disclosed herein comprise less than 1% necrotic cells. In some embodiments, apoptotic cells disclosed herein comprise less than 2% necrotic cells. In some embodiments, apoptotic cells disclosed herein comprise less than 3% necrotic cells. In some embodiments, apoptotic cells disclosed herein comprise less than 4% necrotic cells. In some embodiments, apoptotic cells disclosed herein comprise less than 5% necrotic cells.

In some embodiments, a dose of about $140 \times 10^6$-$210 \times 10^6$ apoptotic cells are administered. In some embodiments, a dose of about $10$-$100 \times 10^6$ apoptotic cells is administered. In some embodiments, a dose of about $20 \times 10^6$ apoptotic cells is administered. In some embodiments, a dose of about $30 \times 10^6$ apoptotic cells is administered. In some embodiments, a dose of about $40 \times 10^6$ apoptotic cells is administered. In some embodiments, a dose of about $50 \times 10^6$ apoptotic cells is administered. In some embodiments, $60 \times 10^6$ apoptotic cells is administered. In some embodiments, a dose of about $60 \times 10^6$ apoptotic cells is administered. In some embodiments, a dose of about $70 \times 10^6$ apoptotic cells is administered. In some embodiments, a dose of about $80 \times 10^6$ apoptotic cells is administered. In some embodiments, a dose of about $90 \times 10^6$ apoptotic cells is administered. In some embodiments, a dose of about $1$-$15 \times 10^7$ apoptotic cells is administered. In some embodiments, a dose of about $10 \times 10^7$ apoptotic cells is administered. In some embodiments, a dose of about $15 \times 10^7$ apoptotic cells is administered.

In some embodiments, a dose of $10 \times 10^6$ apoptotic cells is administered. In another embodiment, a dose of $10 \times 10^7$ apoptotic cells is administered. In another embodiment, a dose of $10 \times 10^8$ apoptotic cells is administered. In another embodiment, a dose of $10 \times 10^9$ apoptotic cells is administered. In another embodiment, a dose of $10 \times 10^{10}$ apoptotic cells is administered. In another embodiment, a dose of $10 \times 10^{11}$ apoptotic cells is administered. In another embodiment, a dose of $10 \times 10^{12}$ apoptotic cells is administered. In another embodiment, a dose of $10 \times 10^5$ apoptotic cells is administered. In another embodiment, a dose of $10 \times 10^4$ apoptotic cells is administered. In another embodiment, a dose of $10 \times 10^3$ apoptotic cells is administered. In another embodiment, a dose of $10 \times 10^2$ apoptotic cells is administered.

In some embodiments, a high dose of apoptotic cells is administered. In some embodiments, a dose of $35 \times 10^6$ apoptotic cells is administered. In another embodiment, a dose of $210 \times 10^6$ apoptotic cells is administered. In another embodiment, a dose of $70 \times 10^6$ apoptotic cells is administered. In another embodiment, a dose of $140 \times 10^6$ apoptotic cells is administered. In another embodiment, a dose of $35$-$210 \times 10^6$ apoptotic cells is administered.

In some embodiments, a single dose of apoptotic cells is administered. In some embodiments, multiple doses of apoptotic cells are administered. In some embodiments, 2 doses of apoptotic cells are administered. In some embodiments, 3 doses of apoptotic cells are administered. In some embodiments, 4 doses of apoptotic cells are administered. In some embodiments, 5 doses of apoptotic cells are administered. In some embodiments, 6 doses of apoptotic cells are administered. In some embodiments, 7 doses of apoptotic cells are administered. In some embodiments, 8 doses of apoptotic cells are administered. In some embodiments, 9 doses of apoptotic cells are administered. In some embodiments, more than 9 doses of apoptotic cells are administered. In some embodiments, multiple doses of apoptotic cells are administered.

In some embodiments, the apoptotic cells may be administered by any method known in the art including, but not limited to, intravenous, subcutaneous, intranodal, intratumoral, intrathecal, intrapleural, intraperitoneal and directly to the thymus.

In some embodiments, the apoptotic cells are prepared from cells obtained from a subject other than the subject that will receive said apoptotic cells. In some embodiments, the methods as disclosed herein comprise an additional step that is useful in overcoming rejection of allogeneic donor cells, including one or more steps described in U.S. Patent Application 20130156794, which is incorporated herein by reference in its entirety. In some embodiments, the methods comprise the step of full or partial lymphodepletion prior to administration of the apoptotic cells, which in some embodiments, are allogeneic apoptotic cells. In some embodiments, the lymphodepletion is adjusted so that it delays the host versus graft reaction for a period sufficient to allow the allogeneic apoptotic cells to control cytokine release. In some embodiments, the methods comprise the step of administering agents that delay egression of the allogeneic apoptotic T-cells from lymph nodes, such as 2-amino-2-[2-(4-octylphenyl)ethyl]propane-1,3-diol (FTY720), 5-[4-phenyl-5-(trifluoromethyl)thiophen-2-yl]-3-[3-(trifluoromethyl)pheny-1]1,2,4-oxadiazole (SEW2871), 3-(2-(-hexylphenylamino)-2-oxoethylamino)propanoic acid (W123), 2-ammonio-4-(2-chloro-4-(3-phenoxyphenylthio)phenyl)-2-(hydroxymethyl)but-yl hydrogen phosphate (KRP-203 phosphate) or other agents known in the art, may be used as part of the compositions and methods as disclosed herein to allow the use of allogeneic apoptotic cells having efficacy and lacking initiation of graft vs host disease. In another embodiment, MHC expression by the allogeneic apoptotic T-cells is silenced to reduce the rejection of the allogeneic cells.

In some embodiments, methods comprise producing a population of mononuclear apoptotic cell comprising a decreased percent of non-quiescent non-apoptotic viable cells; a suppressed cellular activation of any living non-apoptotic cells; or a reduced proliferation of any living non-apoptotic cells; or any combination thereof, said method comprising the following steps, obtaining a mononuclear-enriched cell population of peripheral blood; freezing said mononuclear-enriched cell population in a freezing medium comprising an anticoagulant; thawing said mononuclear-enriched cell population; incubating said mononuclear-enriched cell population in an apoptosis inducing incubation medium comprising methylprednisolone at a final concentration of about 10-100 µg/mL and an anticoagulant; resuspending said apoptotic cell population in an administration medium; and inactivating said mononuclear-enriched population, wherein said inactivation occurs following apoptotic induction, wherein said method produces a population of mononuclear apoptotic cell comprising a decreased percent of non-quiescent non-apoptotic cells; a suppressed cellular activation of any living non-apoptotic cells; or a reduced proliferation of any living non-apoptotic cells; or any combination thereof.

In some embodiments, the methods comprise the step of irradiating a population of apoptotic cells derived from a subject prior to administration of the population of apoptotic cells to the same subject (autologous ApoCells). In some embodiments, the methods comprise the step of irradiating apoptotic cells derived from a subject prior to administration of the population of apoptotic cells to a recipient (allogeneic ApoCells).

In some embodiments, cells are irradiated in a way that will decrease proliferation and/or activation of residual viable cells within the apoptotic cell population. In some embodiments, cells are irradiated in a way that reduces the percent of viable non-apoptotic cells in a population. In some embodiments, the percent of viable non-apoptotic cells in an inactivated early apoptotic cell population is reduced to less than 50% of the population. In some embodiments, the percent of viable non-apoptotic cells in an inactivated early apoptotic cell population is reduced to less than 40% of the population. In some embodiments, the percent of viable non-apoptotic cells in an inactivated early apoptotic cell population is reduced to less than 30% of the population. In some embodiments, the percent of viable non-apoptotic cells in an inactivated early apoptotic cell population is reduced to less than 20% of the population. In some embodiments, the percent of viable non-apoptotic cells in an inactivated early apoptotic cell population is reduced to less than 10% of the population. In some embodiments, the percent of viable non-apoptotic cells in an inactivated early apoptotic cell population is reduced to 0% of the population.

In another embodiment, the irradiated apoptotic cells preserve all their early apoptotic-, immune modulation-, stability-properties. In another embodiment, the irradiation step uses UV radiation. In another embodiment, the radiation step uses gamma radiation. In another embodiment, the apoptotic cells comprise a decreased percent of living non-apoptotic cells, comprise a preparation having a suppressed cellular activation of any living non-apoptotic cells present within the apoptotic cell preparation, or comprise a preparation having reduced proliferation of any living non-apoptotic cells present within the apoptotic cell preparation, or any combination thereof.

In some embodiments, irradiation of apoptotic cells does not increase the population of dead cells (PI+) compared with apoptotic cells not irradiated. In some embodiments, irradiation of apoptotic cells does not increase the population of dead cells (PI+) by more than about 1% compared with apoptotic cells not irradiated. In some embodiments, irradiation of apoptotic cells does not increase the population of dead cells (PI+) by more than about 2% compared with apoptotic cells not irradiated. In some embodiments, irradiation of apoptotic cells does not increase the population of dead cells (PI+) by more than about 3% compared with apoptotic cells not irradiated. In some embodiments, irradiation of apoptotic cells does not increase the population of dead cells (PI+) by more than about 4% compared with apoptotic cells not irradiated. In some embodiments, irradiation of apoptotic cells does not increase the population of dead cells (PI+) by more than about 5% compared with apoptotic cells not irradiated. In some embodiments, irradiation of apoptotic cells does not increase the population of dead cells (PI+) by more than about 6% compared with apoptotic cells not irradiated. In some embodiments, irradiation of apoptotic cells does not increase the population of dead cells (PI+) by more than about 7% compared with apoptotic cells not irradiated. In some embodiments, irradiation of apoptotic cells does not increase the population of dead cells (PI+) by more than about 8% compared with apoptotic cells not irradiated. In some embodiments, irradiation of apoptotic cells does not increase the population of dead cells (PI+) by more than about 9% compared with apoptotic cells not irradiated. In some embodiments, irradiation of apoptotic cells does not increase the population of dead cells (PI+) by more than about 10% compared with apoptotic cells not irradiated. In some embodiments, irradiation of apoptotic cells does not increase the population of dead cells (PI+) by more than about 15% compared with apoptotic cells not irradiated. In some embodiments, irradiation of apoptotic cells does not increase the population of dead cells (PI+) by more than about 20%, 25%, 30%, 35%, 40%, 45%, or 50% compared with apoptotic cells not irradiated.

In some embodiments, a cell population comprising a reduced or non-existent fraction of living non-apoptotic cells may in one embodiment provide a mononuclear early apoptotic cell population that does not have any living/viable cells. In some embodiments, a cell population comprising a reduced or non-existent fraction of living non-apoptotic cells may in one embodiment provide a mononuclear apoptotic cell population that does not elicit GVHD in a recipient.

In some embodiments, use of irradiated ApoCells removes the possible graft versus leukemia effect use of an apoptotic population (that includes a minor portion of viable cells) may cause, demonstrating that the effects shown here in the Examples (See Example 8) result from the apoptotic cells and not from a viable proliferating population of cells with cellular activity, present within the apoptotic cell population.

In another embodiment, the methods comprise the step of irradiating apoptotic cells derived from WBCs from a donor prior to administration to a recipient. In some embodiments, cells are irradiated in a way that will avoid proliferation and/or activation of residual viable cells within the apoptotic cell population. In another embodiment, the irradiated apoptotic cells preserve all their early apoptotic-, immune modulation-, stability-properties. In another embodiment, the irradiation step uses UV radiation. In another embodiment, the radiation step uses gamma radiation. In another embodiment, the apoptotic cells comprise a decreased percent of living non-apoptotic cells, comprise a preparation having a suppressed cellular activation of any living non-apoptotic cells present within the apoptotic cell preparation, or comprise a preparation having reduced proliferation of any living non-apoptotic cells present within the apoptotic cell preparation, or any combination thereof.

In some embodiments, apoptotic cells comprise a pooled mononuclear apoptotic cell preparation. In some embodiments, a pooled mononuclear apoptotic cell preparation comprises mononuclear cells in an early apoptotic state, wherein said pooled mononuclear apoptotic cells comprise a decreased percent of living non-apoptotic cells, a preparation having a suppressed cellular activation of any living non-apoptotic cells, or a preparation having reduced proliferation of any living non-apoptotic cells, or any combination thereof. In another embodiment, the pooled mononuclear apoptotic cells have been irradiated. In another embodiment, disclosed herein is a pooled mononuclear apoptotic cell preparation that in some embodiments, originates from the white blood cell fraction (WBC) obtained from donated blood.

In some embodiments, the apoptotic cell preparation is irradiated. In another embodiment, said irradiation comprises gamma irradiation or UV irradiation. In yet another embodiment, the irradiated preparation has a reduced number of non-apoptotic cells compared with a non-irradiated apoptotic cell preparation. In another embodiment, the irradiated preparation has a reduced number of proliferating cells compared with a non-irradiated apoptotic cell preparation. In another embodiment, the irradiated preparation has a reduced number of potentially immunologically active cells compared with a non-irradiated apoptotic cell population.

In some embodiments, pooled blood comprises 3rd party blood not matched between donor and recipient.

A skilled artisan would appreciate that the term "pooled" may encompass blood collected from multiple donors, prepared and possibly stored for later use. This combined pool of blood may then be processed to produce a pooled mononuclear apoptotic cell preparation. In another embodiment, a pooled mononuclear apoptotic cell preparation ensures that a readily available supply of mononuclear apoptotic cells is available. In another embodiment, cells are pooled just prior to the incubation step wherein apoptosis is induced. In another embodiment, cells are pooled following the incubation step at the step of resuspension. In another embodiment, cells are pooled just prior to an irradiation step. In another embodiment, cells are pooled following an irradiation step. In another embodiment, cells are pooled at any step in the methods of preparation.

In some embodiments, a pooled apoptotic cell preparation is derived from cells present in between about 2 and 25 units of blood. In another embodiment, said pooled apoptotic cell preparation is comprised of cells present in between about 2-5, 2-10, 2-15, 2-20, 5-10, 5-15, 5-20, 5-25, 10-15, 10-20, 10-25, 6-13, or 6-25 units of blood. In another embodiment, said pooled apoptotic cell preparation is comprised of cells present in about 2, 3, 4, 5, 6, 7, 8, 9, 10, 11, 12, 13, 14, 15, 16, 17, 18, 19, 20, 21, 22, 23, 24 or 25 units of blood. The number of units of blood needed is also dependent upon the efficiency of WBC recovery from blood. For example, low efficiency WBC recovery would lead to the need for additional units, while high efficiency WBC recovery would lead to fewer units needed. In some embodiments, each unit is a bag of blood. In another embodiment, a pooled apoptotic cell preparation is comprised of cells present in at least 25 units of blood, at least 50 units of blood, or at least 100 units of blood.

In some embodiments, the units of blood comprise white blood cell (WBC) fractions from blood donations. In another embodiment, the donations may be from a blood center or blood bank. In another embodiment, the donations may be from donors in a hospital gathered at the time of preparation of the pooled apoptotic cell preparation. In another embodiment, units of blood comprising WBCs from multiple donors are saved and maintained in an independent blood bank created for the purpose of compositions and methods thereof as disclosed herein. In another embodiment, a blood bank developed for the purpose of compositions and methods thereof as disclosed herein, is able to supply units of blood comprising WBC from multiple donors and comprises a leukapheresis unit.

In some embodiments, the units of pooled WBCs are not restricted by HLA matching. Therefore, the resultant pooled apoptotic cell preparation comprises cell populations not restricted by HLA matching. Accordingly, in certain embodiments a pooled mononuclear apoptotic cell preparation comprises allogeneic cells.

An advantage of a pooled mononuclear apoptotic cell preparation that is derived from pooled WBCs not restricted by HLA matching, is a readily available source of WBCs and reduced costs of obtaining WBCs.

In some embodiments, pooled blood comprises blood from multiple donors independent of HLA matching. In another embodiment, pooled blood comprises blood from multiple donors wherein HLA matching with the recipient has been taken into consideration. For example, wherein 1 HLA allele, 2 HLA alleles, 3 HLA alleles, 4 HLA alleles, 5 HLA alleles, 6 HLA alleles, or 7 HLA alleles have been matched between donors and recipient. In another embodiment, multiple donors are partially matched, for example some of the donors have been HLA matched wherein 1 HLA allele, 2 HLA alleles, 3 HLA alleles, 4 HLA alleles, 5 HLA alleles, 6 HLA alleles, or 7 HLA alleles have been matched between some of the donors and recipient. Each possibility comprises an embodiment as disclosed herein.

In certain embodiments, some viable non-apoptotic cells (apoptosis resistant) may remain following the induction of apoptosis step described below (Example 1). The presence of these viable non-apoptotic cells is, in some embodiments, is observed prior to an irradiation step. These viable non-apoptotic cells may be able to proliferate or be activated. In some embodiments, the pooled mononuclear apoptotic cell preparation derived from multiple donors may be activated against the host, activated against one another, or both.

In some embodiments, an irradiated cell preparation as disclosed herein has suppressed cellular activation and reduced proliferation compared with a non-irradiated cell preparation. In another embodiment, the irradiation comprises gamma irradiation or UV irradiation. In another embodiment, an irradiated cell preparation has a reduced number of non-apoptotic cells compared with a non-irradiated cell preparation. In another embodiment, the irradiation comprises about 15 Grey units (Gy). In another embodiment, the irradiation comprises about 20 Grey units (Gy). In another embodiment, the irradiation comprises about 25 Grey units (Gy). In another embodiment, the irradiation comprises about 30 Grey units (Gy). In another embodiment, the irradiation comprises about 35 Grey units (Gy). In another embodiment, the irradiation comprises about 40 Grey units (Gy). In another embodiment, the irradiation comprises about 45 Grey units (Gy). In another embodiment, the irradiation comprises about 50 Grey units (Gy). In another embodiment, the irradiation comprises about 55 Grey units (Gy). In another embodiment, the irradiation comprises about 60 Grey units (Gy).

In another embodiment, the irradiation comprises about 65 Grey units (Gy). In another embodiment, the irradiation comprises up to 2500 Gy. In another embodiment, an irradiated pooled apoptotic cell preparation maintains the same or a similar apoptotic profile, stability and efficacy as a non-irradiated pooled apoptotic cell preparation.

In some embodiments, a pooled mononuclear apoptotic cell preparation as disclosed herein is stable for up to 24 hours. In another embodiment, a pooled mononuclear apoptotic cell preparation is stable for at least 24 hours. In another embodiment, a pooled mononuclear apoptotic cell preparation is stable for more than 24 hours. In yet another embodiment, a pooled mononuclear apoptotic cell preparation as disclosed herein is stable for up to 36 hours. In still another embodiment, a pooled mononuclear apoptotic cell preparation is stable for at least 36 hours. In a further embodiment, a pooled mononuclear apoptotic cell preparation is stable for more than 36 hours. In another embodiment, a pooled mononuclear apoptotic cell preparation as disclosed herein is stable for up to 48 hours. In another embodiment, a pooled mononuclear apoptotic cell preparation is stable for at least 48 hours. In another embodiment, a pooled mononuclear apoptotic cell preparation is stable for more than 48 hours.

In some embodiments, methods of producing the pooled cell preparation comprising an irradiation step preserves the early apoptotic, immune modulation, and stability properties observed in an apoptotic preparation derived from a single match donor wherein the cell preparation may not include an irradiation step. In another embodiment, a pooled mononuclear apoptotic cell preparation as disclosed herein does not elicit a graft versus host disease (GVHD) response.

Irradiation of the cell preparation is considered safe in the art. Irradiation procedures are currently performed on a routine basis to donated blood to prevent reactions to WBC.

In another embodiment, the percent of apoptotic cells in a pooled mononuclear apoptotic cell preparation as disclosed herein is close to 100%, thereby reducing the fraction of living non-apoptotic cells in the cell preparation. In some embodiments, the percent of apoptotic cells is at least 40%. In another embodiment, the percent of apoptotic cells is at least 50%. In yet another embodiment, the percent of apoptotic cells is at least 60%. In still another embodiment, the percent of apoptotic cells is at least 70%. In a further embodiment, the percent of apoptotic cells is at least 80%. In another embodiment, the percent of apoptotic cells is at least 90%. In yet another embodiment, the percent of apoptotic cells is at least 99%. Accordingly, a cell preparation comprising a reduced or non-existent fraction of living non-apoptotic cells may in one embodiment provide a pooled mononuclear apoptotic cell preparation that does not elicit GVHD in a recipient. Each possibility represents an embodiment as disclosed herein.

Alternatively, in another embodiment, the percentage of living non-apoptotic WBC is reduced by specifically removing the living cell population, for example by targeted precipitation. In another embodiment, the percent of living non-apoptotic cells may be reduced using magnetic beads that bind to phosphatidylserine. In another embodiment, the percent of living non-apoptotic cells may be reduced using magnetic beads that bind a marker on the cell surface of non-apoptotic cells but not apoptotic cells. In another embodiment, the apoptotic cells may be selected for further preparation using magnetic beads that bind to a marker on the cell surface of apoptotic cells but not non-apoptotic cells. In yet another embodiment, the percentage of living non-apoptotic WBC is reduced by the use of ultrasound.

In one embodiment the apoptotic cells are from pooled third party donors.

In some embodiments, a pooled cell preparation comprises at least one cell type selected from the group consisting of: lymphocytes, monocytes and natural killer cells. In another embodiment, a pooled cell preparation comprises an enriched population of mononuclear cells. In some embodiments, a pooled mononuclear is a mononuclear enriched cell preparation comprises cell types selected from the group consisting of: lymphocytes, monocytes and natural killer cells. In another embodiment, the mononuclear enriched cell preparation comprises no more than 15%, alternatively no more than 10%, typically no more than 5% polymorphonuclear leukocytes, also known as granulocytes (i.e., neutrophils, basophils and eosinophils). In another embodiment, a pooled mononuclear cell preparation is devoid of granulocytes.

In another embodiment, the pooled mononuclear enriched cell preparation comprises no more than 15%, alternatively no more than 10%, typically no more than 5% $CD15^{high}$ expressing cells. In some embodiments, a pooled apoptotic cell preparation comprises less than 15% CD15 high expressing cells.

In some embodiments, the pooled mononuclear enriched cell preparation disclosed herein comprises at least 80% mononuclear cells, at least 85% mononuclear cells, alternatively at least 90% mononuclear cells, or at least 95% mononuclear cells, wherein each possibility is a separate embodiment disclosed herein. According to some embodiments, the pooled mononuclear enriched cell preparation disclosed herein comprises at least 85% mononuclear cells.

In another embodiment, any pooled cell preparation that has a final pooled percent of mononuclear cells of at least 80% is considered a pooled mononuclear enriched cell preparation as disclosed herein. Thus, pooling cell preparations having increased polymorphonuclear cells (PMN) with cell preparations having high mononuclear cells with a resultant "pool" of at least 80% mononuclear cells comprises a preparation as disclosed herein. According to some embodiments, mononuclear cells comprise lymphocytes and monocytes.

A skilled artisan would appreciate that the term "mononuclear cells" may encompass leukocytes having a one lobed nucleus. In another embodiment, a pooled apoptotic cell preparation as disclosed herein comprises less than 5% polymorphonuclear leukocytes.

In some embodiments, the apoptotic cells are T-cells. In another embodiment, the apoptotic cells are derived from the same pooled third party donor T-cells as the CAR T-cells. In another embodiment, the apoptotic cells are derived from the CAR T-cell population.

Surprisingly, the apoptotic cells reduce production of cytokines associated with the cytokine storm including but not limited to IL-6, and interferon-gamma (IFN-γ), alone or in combination, while the effectiveness of CAR T-cell therapy was maintained (Example 2). In one embodiment, the apoptotic cells affect cytokine expression levels in macrophages. In another embodiment, the apoptotic cells reduce cytokine expression levels in macrophages. In one embodiment, the apoptotic cells suppress cytokine expression levels in macrophages. In one embodiment, the apoptotic cells inhibit cytokine expression levels in macrophages. In one embodiment, the apoptotic cells maintain IFN-γ levels to match or nearly match levels present prior to CAR-T cell administration. In another embodiment, apoptotic cells affect cytokine expression levels in macrophages but do not affect cytokine expression levels in the CAR T-cells. In another embodiment, the apoptotic cells affect cytokine expression levels in DCs, but do not affect cytokine expression levels in the CAR T-cells. It was therefore unexpected that apoptotic cells would be useful in maintaining the effectiveness CAR T-cell therapy.

In another embodiment, the effect of apoptotic cells on cytokine expression levels in macrophages, DCs, or a combination thereof, results in reduction of CRS. In another embodiment, the effect of apoptotic cells on cytokine expression levels in macrophages, DCs, or a combination thereof, results in reduction of severe CRS. In another embodiment, the effect of apoptotic cells on cytokine expression levels in macrophages, DCs, or a combination thereof, results in suppression of CRS. In another embodiment, the effect of apoptotic cells on cytokine expression levels in macrophages, DCs, or a combination thereof, results in suppression of severe CRS. In another embodiment, the effect of apoptotic cells on cytokine expression levels in macrophages, DCs, or a combination thereof, results in inhibition of CRS. In another embodiment, the effect of apoptotic cells on cytokine expression levels in macrophages, DCs, or a combination thereof, results in inhibition of severe CRS. In another embodiment, the effect of apoptotic cells on cytokine expression levels in macrophages, DCs, or a combination thereof, results in prevention of CRS. In another embodiment, the effect of apoptotic cells on cytokine expression levels in macrophages, DCs, or a combination thereof, results in prevention of severe CRS.

In another embodiment, the apoptotic cells trigger death of T-cells, but not via changes in cytokine expression levels.

In another embodiment, apoptotic cells antagonize the priming of macrophages and dendritic cells to secrete cytokines that would otherwise amplify the cytokine storm. In another embodiment, apoptotic cells increase Tregs which suppress the inflammatory response and/or prevent excess release of cytokines.

In some embodiments, apoptotic cells stabilize the presence of resident macrophages in the area of the tumor. In some embodiments, methods of treating a cancer by combining CAR-T cell therapy with administration of early apoptotic cells, results in a stabilization of resident macrophages in the area of the tumor.

In some embodiments, administration of apoptotic cells inhibits one or more pro-inflammatory cytokines. In some embodiments, the pro-inflammatory cytokine comprises IL-1beta, IL-6, TNF-alpha, or IFN-gamma, or any combination thereof. In another embodiment, administration of apoptotic cells promotes the secretion of one or more anti-inflammatory cytokines. In some embodiments, the anti-inflammatory cytokine comprises TGF-beta, IL10, or PGE2, or any combination thereof.

In another embodiment, administration of apoptotic cells inhibits dendritic cell maturation following exposure to TLR ligands. In another embodiment, administration of apoptotic cells creates potentially tolerogenic dendritic cells, which in some embodiments, are capable of migration, and in some embodiments, the migration is due to CCR7. In another embodiment, administration of apoptotic cells elicits various signaling events which in one embodiment is TAM receptor signaling (Tyro3, Axl and Mer) which in some embodiments, inhibits inflammation in antigen-presenting cells. In some embodiments, Tyro-3, Axl, and Mer constitute the TAM family of receptor tyrosine kinases (RTKs) characterized by a conserved sequence within the kinase domain and adhesion molecule-like extracellular domains. In another embodiment, administration of apoptotic cells activates signaling through MerTK. In another embodiment, administration of apoptotic cells activates the phosphatidylinositol 3-kinase (PI3K)/AKT pathway, which in some embodiments, negatively regulates NF-κB. In another embodiment, administration of apoptotic cells negatively regulates the inflammasome which in one embodiment leads to inhibition of pro-inflammatory cytokine secretion, DC maturation, or a combination thereof. In another embodiment, administration of apoptotic cells upregulates expression of anti-inflammatory genes such as Nr4a, Thbs1, or a combination thereof. In another embodiment, administration of apoptotic cells induces a high level of AMP which in some embodiments, is accumulated in a Pannexin1-dependent manner. In another embodiment, administration of apoptotic cells suppresses inflammation.

In some embodiments, methods of use of early apoptotic cells, as described herein, includes use of the early apoptotic cells or a composition thereof, in combination with an antibody. In some embodiments, the antibody is directed against a tumor cell antigen. In another embodiment, the antibody is directed against CD20. In another embodiment, the antibody is rituximab (Rtx).

In some embodiments, early apoptotic cells and an antibody are comprised in the same composition. In some embodiments, early apoptotic cells and an antibody are comprised in different compositions. In some embodiments, administration of a combination of early apoptotic cells and an antibody, or composition(s) thereof are concurrent. In some embodiments, administration of a combination of early apoptotic cells and an antibody, or composition(s) thereof comprises administration of apoptotic cells or a composition thereof, prior to the antibody. In some embodiments, administration of a combination of early apoptotic cells and an antibody, or composition(s) thereof comprises administration of apoptotic cells or a composition thereof, following administration of the antibody.

In another embodiment, the antibody is Trastuzumab (Herceptin; Genentech): humanized IgG1, which is directed against ERBB2. In another embodiment, the antibody is Bevacizumab (Avastin; Genentech/Roche): humanized IgG1, which is directed against VEGF. In another embodiment, the antibody is Cetuximab (Erbitux; Bristol-Myers Squibb): chimeric human-murine IgG1, which is directed against EGFR. In another embodiment, the antibody is Panitumumab (Vectibix; Amgen): human IgG2, which is directed against EGFR. In another embodiment, the antibody is Ipilimumab (Yervoy; Bristol-Myers Squibb): IgG1, which is directed against CTLA4.

In another embodiment, the antibody is Alemtuzumab (Campath; Genzyme): humanized IgG1, which is directed against CD52. In another embodiment, the antibody is Ofatumumab (Arzerra; Genmab): human IgG1, which is directed against CD20. In another embodiment, the antibody is Gemtuzumab ozogamicin (Mylotarg; Wyeth): humanized IgG4, which is directed against CD33. In another embodiment, the antibody is Brentuximab vedotin (Adcetris; Seattle Genetics): chimeric IgG1, which is directed against CD30. In another embodiment, the antibody is 90Y-labelled ibritumomab tiuxetan (Zevalin; IDEC Pharmaceuticals): murine IgG1, which is directed against CD20. In another embodiment, the antibody is 131I-labelled tositumomab (Bexxar; GlaxoSmithKline): murine IgG2, which is directed against CD20.

In another embodiment, the antibody is Ramucirumab, which is directed against vascular endothelial growth factor receptor-2 (VEGFR-2). In another embodiment, the antibody is ramucirumab (Cyramza Injection, Eli Lilly and Company), blinatumomab (BLINCYTO, Amgen Inc.), pembrolizumab (KEYTRUDA, Merck Sharp & Dohme Corp.), obinutuzumab (GAZYVA, Genentech, Inc.; previously known as GA101), pertuzumab injection (PERJETA, Genentech, Inc.), or denosumab (Xgeva, Amgen Inc.). In another embodiment, the antibody is Basiliximab (Simulect; Novartis). In another embodiment, the antibody is Daclizumab (Zenapax; Roche).

In another embodiment, the antibody administered in combination with apoptotic cells is directed to a tumor or cancer antigen or a fragment thereof, that is described herein and/or that is known in the art. In another embodiment, the antibody is directed to a tumor-associated antigen. In another embodiment, the antibody is directed to a tumor-associated antigen or a fragment thereof that is an angiogenic factor.

In some embodiments, antibodies described herein may be used in combination with compositions described herein, for example but not limited to a composition comprising early apoptotic cells.

Apoptotic Cell Supernatants (ApoSup and ApoSup Mon)

In some embodiments, compositions for use in the methods and treatments as disclosed herein include an apoptotic cell supernatant as disclosed herein.

In some embodiments, the apoptotic cell supernatant is obtained by a method comprising the steps of a) providing apoptotic cells, b) culturing the apoptotic cells of step a), and c) separating the supernatant from the cells.

In some embodiments, apoptotic cells for use making an apoptotic cell supernatant as disclosed herein are autologous with a subject undergoing therapy. In another embodiment, apoptotic cells for use in making an apoptotic cell supernatant disclosed herein are allogeneic with a subject undergoing therapy.

The "apoptotic cells" from which the apoptotic cell supernatant is obtained may be cells chosen from any cell type of a subject, or any commercially available cell line, subjected to a method of inducing apoptosis known to the person skilled in the art. The method of inducing apoptosis may be hypoxia, ozone, heat, radiation, chemicals, osmotic pressure, pH shift, X-ray irradiation, gamma-ray irradiation, UV irradiation, serum deprivation, corticoids or combinations thereof, or any other method described herein or known in the art. In another embodiment, the method of inducing apoptosis produces apoptotic cells in an early apoptotic state.

In some embodiments, the apoptotic cells are leukocytes.

In an embodiment, said apoptotic leukocytes are derived from peripheral blood mononuclear cells (PBMC). In another embodiment, said leukocytes are from pooled third party donors. In another embodiment, said leukocytes are allogeneic.

According to some embodiments, the apoptotic cells are provided by selecting non-adherent leukocytes and submitting them to apoptosis induction, followed by a cell culture step in culture medium. "Leukocytes" used to make the apoptotic cell-phagocyte supernatant may be derived from any lineage, or sub-lineage, of nucleated cells of the immune system and/or hematopoietic system, including but not limited to dendritic cells, macrophages, masT-cells, basophils, hematopoietic stem cells, bone marrow cells, natural killer cells, and the like. The leukocytes may be derived or obtained in any of various suitable ways, from any of various suitable anatomical compartments, according to any of various commonly practiced methods, depending on the application and purpose, desired leukocyte lineage, etc. In some embodiments, the source leukocytes are primary leukocytes. In another embodiment, the source leukocytes are primary peripheral blood leukocytes.

Primary lymphocytes and monocytes may be conveniently derived from peripheral blood. Peripheral blood leukocytes include 70-95 percent lymphocytes, and 5-25 percent monocytes.

Methods for obtaining specific types of source leukocytes from blood are routinely practiced. Obtaining source lymphocytes and/or monocytes can be achieved, for example, by harvesting blood in the presence of an anticoagulant, such as heparin or citrate. The harvested blood is then centrifuged over a Ficoll cushion to isolate lymphocytes and monocytes at the gradient interface, and neutrophils and erythrocytes in the pellet.

Leukocytes may be separated from each other via standard immunomagnetic selection or immunofluorescent flow cytometry techniques according to their specific surface markers, or via centrifugal elutriation. For example, monocytes can be selected as the CD14+ fraction, T-lymphocytes can be selected as CD3+ fraction, B-lymphocytes can be selected as the CD19+ fraction, macrophages as the CD206+ fraction.

Lymphocytes and monocytes may be isolated from each other by subjecting these cells to substrate-adherent conditions, such as by static culture in a tissue culture-treated culturing recipient, which results in selective adherence of the monocytes, but not of the lymphocytes, to the cell-adherent substrate.

Leukocytes may also be obtained from peripheral blood mononuclear cells (PBMCs), which may be isolated as described herein.

One of ordinary skill in the art will possess the necessary expertise to suitably culture primary leukocytes so as to generate desired quantities of cultured source leukocytes as disclosed herein, and ample guidance for practicing such culturing methods is available in the literature of the art.

One of ordinary skill in the art will further possess the necessary expertise to establish, purchase, or otherwise obtain suitable established leukocyte cell lines from which to derive the apoptotic leukocytes. Suitable leukocyte cell lines may be obtained from commercial suppliers, such as the American Tissue Type Collection (ATCC). It will be evident to the person skilled in the art that source leukocytes should not be obtained via a technique which will significantly interfere with their capacity to produce the apoptotic leukocytes.

In another embodiment, the apoptotic cells may be apoptotic lymphocytes. Apoptosis of lymphocytes, such as primary lymphocytes, may be induced by treating the primary lymphocytes with serum deprivation, a corticosteroid, or irradiation. In another embodiment, inducing apoptosis of primary lymphocytes via treatment with a corticosteroid is effected by treating the primary lymphocytes with dexamethasone. In another embodiment, with dexamethasone at a concentration of about 1 micromolar. In another embodiment, inducing apoptosis of primary lymphocytes via irradiation is effected by treating the primary lymphocytes with gamma-irradiation. In another embodiment, with a dosage of about 66 rad. Such treatment results in the generation of apoptotic lymphocytes suitable for the co-culture step with phagocytes.

In a further embodiment, apoptotic cells may be apoptotic monocytes, such as primary monocytes. To generate apoptotic monocytes the monocytes are subjected to in vitro conditions of substrate/surface-adherence under conditions of serum deprivation. Such treatment results in the generation of non-pro-inflammatory apoptotic monocytes suitable for the co-culture step with phagocytes.

In other embodiments, the apoptotic cells may be any apoptotic cells described herein, including allogeneic apoptotic cells, third party apoptotic cells, and pools of apoptotic cells.

In other embodiments, the apoptotic cell supernatant may be obtained through the co-culture of apoptotic cells with other cells.

Thus, in some embodiments, the apoptotic cell supernatant is an apoptotic cell supernatant obtained by a method comprising the steps of a) providing apoptotic cells, b) providing other cells, c) optionally washing the cells from step a) and b), d) co-culturing the cells of step a) and b), and optionally e) separating the supernatant from the cells.

In some embodiments, the other cells co-cultured with the apoptotic cells are white blood cells.

Thus, in some embodiments, the apoptotic cell supernatant is an apoptotic cell-white blood cell supernatant obtained by a method comprising the steps of a) providing apoptotic cells, b) providing white blood cells, c) optionally washing the cells from step a) and b), d) co-culturing the cells of step a) and b), and optionally e) separating the supernatant from the cells.

In some embodiments, the white blood cells may be phagocytes, such as macrophages, monocytes or dendritic cells.

In some embodiments, the white blood cells may be B cells, T-cells, or natural killer (NK cells).

Thus, in some embodiments, compositions for use in the methods and treatments as disclosed herein include apoptotic cell-phagocyte supernatants as described in WO 2014/106666, which is incorporated by reference herein in its entirety. In another embodiment, apoptotic cell-phagocyte supernatants for use in compositions and methods as disclosed herein are produced in any way that is known in the art.

In some embodiments, the apoptotic cell-phagocyte supernatant is obtained from a co-culture of phagocytes with apoptotic cells, In some embodiments, the apoptotic cell-phagocyte supernatant is obtained by a method comprising the steps of a) providing phagocytes, b) providing apoptotic cells, c) optionally washing the cells from step a) and b), d) co-culturing the cells of step a) and b), and optionally e) separating the supernatant from the cells.

The term "phagocytes" denotes cells that protect the body by ingesting (phagocytosing) harmful foreign particles, bacteria, and dead or dying cells. Phagocytes include for example cells called neutrophils, monocytes, macrophages, dendritic cells, and mast T-cells, preferentially dendritic cells and monocytes/macrophages. The phagocytes may be dendritic cells (CD4+ HLA-DR+ Lineage-BDCA1/BDCA3+), macrophages (CD14+CD206+ HLA-DR+), or derived from monocytes (CD14+). Techniques to distinguish these different phagocytes are known to the person skilled in the art.

In an embodiment, monocytes are obtained by a plastic adherence step. Said monocytes can be distinguished from B and T-cells with the marker CD14+, whereas unwanted B cells express CD19+ and T-cells CD3+. After Macrophage Colony Stimulating Factor (M-CSF) induced maturation the obtained macrophages are in some embodiments, positive for the markers CD14+, CD206+, HLA-DR+.

In an embodiment, said phagocytes are derived from peripheral blood mononuclear cells (PBMC).

Phagocytes may be provided by any method known in the art for obtaining phagocytes. In some embodiments, phagocytes such as macrophages or dendritic cells can be directly isolated from a subject or be derived from precursor cells by a maturation step.

In some embodiments, macrophages may be directly isolated from the peritoneum cavity of a subject and cultured in complete RRPMI medium. Macrophages can also be isolated from the spleen.

Phagocytes are also obtainable from peripheral blood monocytes. In said example, monocytes when cultured differentiate into monocyte-derived macrophages upon addition of, without limitation to, macrophage colony stimulating factor (M-CSF) to the cell culture media.

For example, phagocytes may be derived from peripheral blood mononuclear cells (PBMC). For example, PBMC may be isolated from cytapheresis bag from an individual through Ficoll gradient centrifugation, plated in a cell-adherence step for 90 min in complete RPMI culture medium (10% FBS, 1% Penicillin/Streptomycin). Non-adherent T-cells are removed by a plastic adherence step, and adherent T-cells cultured in complete RPMI milieu supplemented with recombinant human M-CSF. After the culture period, monocyte-derived macrophages are obtained.

Phagocytes can be selected by a cell-adherence step. Said "cell adherence step" means that phagocytes or cells which can mature into phagocytes are selected via culturing conditions allowing the adhesion of the cultured cells to a surface, a cell adherent surface (e.g. a tissue culture dish, a matrix, a sac or bag with the appropriate type of nylon or plastic). A skilled artisan would appreciate that the term "Cell adherent surfaces" may encompass hydrophilic and negatively charged, and may be obtained in any of various ways known in the art, In another embodiment by modifying a polystyrene surface using, for example, corona discharge, or gas-plasma. These processes generate highly energetic oxygen ions which graft onto the surface polystyrene chains so that the surface becomes hydrophilic and negatively charged. Culture recipients designed for facilitating cell-adherence thereto are available from various commercial suppliers (e.g. Corning, Perkin-Elmer, Fisher Scientific, Evergreen Scientific, Nunc, etc.).

B cells, T-cells and NK cells may be provided by any method known in the art for obtaining such cells. In some embodiments, B cells, T-cells or NK cells can be directly isolated from a subject or be derived from precursor cells by a maturation step. In another embodiment, the B, T or NK cells can be from a B, T or NK cell line. One of ordinary skill in the art will possess the necessary expertise to establish, purchase, or otherwise obtain suitable established B cells, T-cells and NK cell lines. Suitable cell lines may be obtained from commercial suppliers, such as the American Tissue Type Collection (ATCC).

In an embodiment, said apoptotic cells and said white blood cells, such as the phagocytes, B, T or NK cells, are cultured individually prior to the co-culture step d).

The cell maturation of phagocytes takes place during cell culture, for example due to addition of maturation factors to the media. In one embodiment said maturation factor is M-CSF, which may be used for example to obtain monocyte-derived macrophages.

The culture step used for maturation or selection of phagocytes might take several hours to several days. In another embodiment said pre-mature phagocytes are cultured for 2, 4, 6, 8, 10, 12, 14, 16, 18, 20, 22, 24, 26, 28, 30, 32, 34, 36, 38, 40, 42, 44, 46, 48, 50, 52, 54, 56, 58 hours in an appropriate culture medium.

The culture medium for phagocytes is known to the person skilled in the art and can be for example, without limitation, RPMI, DMEM, X-vivo and Ultraculture milieus.

In an embodiment, co-culture of apoptotic cells and phagocytes takes place in a physiological solution.

Prior to this "co-culture", the cells may be submitted to a washing step. In some embodiments, the white blood cells (e.g. the phagocytes) and the apoptotic cells are washed before the co-culture step. In another embodiment, the cells are washed with PBS.

During said co-culture the white blood cells (e.g. the phagocytes such as macrophages, monocytes, or phagocytes, or the B, T or NK cells) and the apoptotic cells may be mixed in a ratio of 10:1, 9:1; 8:1, 7:1, 6:1, 5:1, 4:1, 3:1, 2:1, or 1:1, or in a ratio of (white blood cells: apoptotic cells) 1:2, 1:3, 1:4, 1:5, 1:6, 1:7, 1:8, 1:9, or 1:10. In one example, the ratio of white blood cells to apoptotic cells is 1:5.

The co-culture of the cells might be for several hours to several days. In some embodiments, said apoptotic cells are cultured for 2, 4, 6, 8, 10, 12, 14, 16, 18, 20, 22, 24, 26, 28, 30, 32, 34, 36, 38, 40, 42, 44, 46, 48, 50, 52 hours. A person skilled in the art can evaluate the optimal time for co-culture by measuring the presence of anti-inflammatory compounds, the viable amount of white blood cells and the amount of apoptotic cells which have not been eliminated so far. elimination of apoptotic cells by phagocytes is observable with light microscopy due to the disappearance of apoptotic cells.

In some embodiments, the culture of apoptotic cells, such as the co-culture with culture with white blood cells (e.g. phagocytes such as macrophages, monocytes, or phagocytes, or the B, T or NK cells), takes place in culture medium and/or in a physiological solution compatible with administration e.g. injection to a subject.

A skilled artisan would appreciate that a "physiological solution" may encompass a solution which does not lead to the death of white blood cells within the culture time. In some embodiments, the physiological solution does not lead to death over 2, 4, 6, 8, 10, 12, 14, 16, 18, 20, 22, 24, 26, 28, 30, 32, 34, 36, 38, 40, 42, 44, 46, 48, 50, 52 hours. In other embodiment, 48 hours, or 30 hours.

In some embodiments, the white blood cells (e.g. phagocytes such as macrophages, monocytes, or phagocytes, or the B, T or NK cells) and the apoptotic cells are incubated in the physiological solution for at least 30 min. This time of culture allows phagocytosis initiation and secretion of cytokines and other beneficial substances.

In an embodiment, such a physiological solution does not inhibit apoptotic leukocyte elimination by leukocyte-derived macrophages.

At the end of the culture or the co-culture step, the supernatant is optionally separated from the cultured apoptotic cells or the co-cultured cells. Techniques to separate the supernatant from the cells are known in the art. For example, the supernatant can be collected and/or filtered and/or centrifuged to eliminate cells and debris. For example, said supernatant may be centrifuged at 3000 rpm for 15 minutes at room temperature to separate it from the cells.

The supernatant may be "inactivated" prior to use, for example by irradiation. Therefore, the method for preparing the apoptotic cell supernatant may comprise an optional additional irradiation step f). Said "irradiation" step can be considered as a disinfection method that uses X-ray irradiation (25-45 Gy) at sufficiently rate to kill microorganisms, as routinely performed to inactivate blood products.

Irradiation of the supernatant is considered safe in the art. Irradiation procedures are currently performed on a routine basis to donated blood to prevent reactions to WBC.

In an embodiment, the apoptotic cell supernatant is formulated into a pharmaceutical composition suitable for administration to a subject, as described in detail herein.

In some embodiments, the final product is stored at +4° C. In another embodiment, the final product is for use in the next 48 hours.

In some embodiments, the apoptotic cell supernatant, such as an apoptotic cell-phagocyte supernatant, or pharmaceutical composition comprising the supernatant, may be lyophilized, for example for storage at −80° C.

In one specific embodiment, as described in Example 1 of WO 2014/106666, an apoptotic cell-phagocyte supernatant may be made using thymic cells as apoptotic cells. After isolation, thymic cells are irradiated (e.g. with a 35 X-Gray irradiation) and cultured in complete DMEM culture medium for, for example, 6 hours to allow apoptosis to occur. In parallel, macrophages are isolated from the peritoneum cavity, washed and cultured in complete RPMI (10% FBS, Peni-Strepto, EAA, Hepes, NaP and 2-MercaptoEthanol). Macrophages and apoptotic cells are then washed and co-cultured for another 48 hour period in phenol-free X-vivo medium at a 1/5 macrophage/apoptotic cell ratio. Then, supernatant is collected, centrifuged to eliminate debris and may be frozen or lyophilized for conservation. Macrophage enrichment may be confirmed using positive staining for F4/80 by FACS. Apoptosis may be confirmed by FACS using positive staining for Annexin-V and 7AAD exclusion.

In an embodiment, the apoptotic cell supernatant is enriched in TGF-β levels both in active and latent forms of TGF-β, compared to supernatants obtained from either macrophages or apoptotic cells cultured separately. In an embodiment, IL-10 levels are also increased compared to macrophages cultured alone and dramatically increased compared to apoptotic cells cultured alone. In another embodiment, inflammatory cytokines such as IL-6 are not detectable and IL-1 β and TNF are undetectable or at very low levels.

In an embodiment, the apoptotic cell supernatant, when compared to supernatants from macrophages cultured alone or from apoptotic cells cultured alone, has increased levels of IL-1ra, TIMP-1, CXCL1/KC and CCL2/JE/MCP1, which might be implicated in a tolerogenic role of the supernatant to control inflammation, in addition to TGF-β and IL-10.

In another specific embodiment, as described in Example 3 of WO 2014/106666, human apoptotic cell-phagocyte supernatant may be made from the co-culture of macrophages derived from peripheral blood mononuclear cells (PBMC) cultured with apoptotic PBMC. Thus, PBMC are isolated from cytapheresis bag from a healthy volunteer through, for example, Ficoll gradient centrifugation. Then PBMC are plated for 90 min in complete RPMI culture medium (10% FBS, 1% Penicillin/Streptomycin). Then, non-adherenT-cells are removed and rendered apoptotic using, for example, a 35 Gy dose of X-ray irradiation and cultured in complete RPMI milieu for 4 days (including cell wash after the first 48 hrs of culture), in order to allow apoptosis to occur. In parallel, adherent T-cells are cultured in complete RPMI milieu supplemented with 50 µg/mL of recombinant human M-CSF for 4 days including cell wash after the first 48 hrs. At the end of the 4-day culture period, monocyte-derived macrophages and apoptotic cells are washed and cultured together in X-vivo medium for again 48 hours at a one macrophage to 5 apoptotic cell ratio. Then supernatant from the latter culture is collected, centrifuged to eliminate cells and debris, and may be frozen or lyophilized for conservation and subsequent use.

In an embodiment, as described in WO 2014/106666, human apoptotic cell-phagocyte supernatant may be obtained in 6 days from peripheral blood mononuclear cells (PBMC). Four days to obtain PBMC-derived macrophages using M-CSF addition in the culture, and 2 more days for the co-culture of PBMC-derived macrophages with apoptotic cells, corresponding to the non-adherent PBMC isolated at day 0.

In an embodiment, as described in WO 2014/106666, a standardized human apoptotic cell-phagocyte supernatant may be obtained independently of the donor or the source of PBMC (cytapheresis or buffy coat). The plastic-adherence step is sufficient to obtain a significant starting population of enriched monocytes (20 to 93% of CD14+ cells after adherence on plastic culture dish). In addition, such adherent T-cells demonstrate a very low presence of B and T-cells (1.0% of CD19+B cells and 12.8% of CD3+ T-cells). After 4 days of culture of adherent T-cells in the presence of M-CSF, the proportion of monocytes derived-macrophages is significantly increased from 0.1% to 77.7% of CD14+ CD206+HLA-DR+ macrophages. At that time, monocyte-derived macrophages may be co-cultured with apoptotic non-adherent PBMC (47.6% apoptotic as shown by annexin V staining and 7AAD exclusion) to produce the apoptotic cell-phagocyte supernatant during 48 hours.

In an embodiment, the collected apoptotic cell-phagocyte supernatant, contains significantly more latent TGF than in the culture supernatant of monocyte-derived macrophages alone or monocyte-derived macrophages treated in inflammatory conditions (+LPS), and only contains trace or low level of inflammatory cytokines such as IL-1β or TNF.

In some embodiments, the composition comprising the apoptotic cell supernatant further comprises an anti-coagulant. In some embodiments, the anti-coagulant is selected from the group consisting of: heparin, acid citrate dextrose (ACD) Formula A and a combination thereof.

In another embodiment, an anti-coagulant is added during the process of manufacturing apoptotic cells. In another embodiment, the anti-coagulant added is selected from the group comprising ACD and heparin, or any combination thereof. In another embodiment, ACD is at a concentration of 1%. In another embodiment, ACD is at a concentration of 2%. In another embodiment, ACD is at a concentration of 3%. In another embodiment, ACD is at a concentration of 4%. In another embodiment, ACD is at a concentration of 5%. In another embodiment, ACD is at a concentration of 6%. In another embodiment, ACD is at a concentration of 7%. In another embodiment, ACD is at a concentration of 8%. In another embodiment, ACD is at a concentration of 9%. In another embodiment, ACD is at a concentration of 10%. In another embodiment, ACD is at a concentration of between about 1-10%. In another embodiment, ACD is at a concentration of between about 2-8%. In another embodiment, ACD is at a concentration of between about 3-7%. In another embodiment, ACD is at a concentration of between about 1-5%. In another embodiment, ACD is at a concentration of between about 5-10%. In another embodiment, heparin is at a final concentration of 0.5 U/ml. In another embodiment, heparin is at a final concentration of about 0.1 U/ml-1.0 U/ml. In another embodiment, heparin is at a final concentration of about 0.2 U/ml-0.9 U/ml. In another embodiment, heparin is at a final concentration of about 0.3 U/ml-0.7 U/ml. In another embodiment, heparin is at a final concentration of about 0.1 U/ml-0.5 U/ml. In another embodiment, heparin is at a final concentration of about 0.5 U/ml-1.0 U/ml. In another embodiment, heparin is at a final concentration of about 0.01 U/ml-1.0 U/ml. In another embodiment, heparin is at a final concentration of 0.1 U/ml. In another embodiment, heparin is at a final concentration of 0.2 U/ml. In another embodiment, heparin is at a final concentration of 0.3 U/ml. In another embodiment, heparin is at a final concentration of 0.4 U/ml. In another embodiment, heparin is at a final concentration of 0.5 U/ml. In another embodiment, heparin is at a final concentration of 0.6 U/ml. In another embodiment, heparin is at a final concentration of 0.7 U/ml. In another embodiment, heparin is at a final concentration of 0.8 U/ml. In another embodiment, heparin is at a final concentration of 0.9 U/ml. In another embodiment, heparin is at a final concentration of 1.0 U/ml. In another embodiment, ACD is at a concentration of 5% and heparin is at a final concentration of 0.5 U/ml.

In some embodiments, the composition comprising the apoptotic cell supernatant further comprises methylprednisolone. At some embodiments, the concentration of methylprednisolone does not exceed 30 µg/ml.

In some embodiments, the composition may be used at a total dose or aliquot of apoptotic cell supernatant derived from the co-culture of about $14 \times 10^9$ of CD45+ cells obtained by cytapheresis equivalent to about 200 million of cells per kilogram of body weight (for a 70 kg subject). In an embodiment, such a total dose is administered as unit doses of supernatant derived from about 100 million cells per kilogram body weight, and/or is administered as unit doses at weekly intervals, In another embodiment both of which. Suitable total doses according to this embodiment include total doses of supernatant derived from about 10 million to about 4 billion cells per kilogram body weight. In another embodiment, the supernatant is derived from about 40 million to about 1 billion cells per kilogram body weight. In yet another embodiment the supernatant is derived from about 80 million to about 500 million cells per kilogram body weight. In still another embodiment, the supernatant is derived from about 160 million to about 250 million cells per kilogram body weight. Suitable unit doses according to this embodiment include unit doses of supernatant derived from about 4 million to about 400 million cells per kilogram body weight. In another embodiment, the supernatant is derived from about 8 million to about 200 million cells per kilogram body weight. In another embodiment, the supernatant is derived from about 16 million to about 100 million cells per kilogram body weight. In yet another embodiment, the supernatant is derived from about 32 million to about 50 million cells per kilogram body weight.

In another embodiment, a dose of apoptotic cell supernatant derived from the co-culture of about $10 \times 10^6$ apoptotic cells is administered. In another embodiment, a dose derived from $10 \times 10^7$ apoptotic cells is administered. In another embodiment, a dose derived from $10 \times 10^8$ apoptotic cells is administered. In another embodiment, a dose derived from $10 \times 10^9$ apoptotic cells is administered. In another embodiment, a dose derived from $10 \times 10^{10}$ apoptotic cells is administered. In another embodiment, a dose derived from $10 \times 10^{11}$ apoptotic cells is administered. In another embodiment, a dose derived from $10 \times 10^{12}$ apoptotic cells is administered. In another embodiment, a dose derived from $10 \times 10^5$ apoptotic cells is administered. In another embodiment, a dose derived from $10 \times 10^4$ apoptotic cells is administered. In another embodiment, a dose derived from $10 \times 10^3$ apoptotic cells is administered. In another embodiment, a dose derived from $10 \times 10^2$ apoptotic cells is administered.

In some embodiments, a dose of apoptotic cell supernatant derived from $35 \times 10^6$ apoptotic cells is administered. In another embodiment, a dose derived from $210 \times 10^6$ apoptotic cells is administered. In another embodiment, a dose derived from $70 \times 10^6$ apoptotic cells is administered. In another embodiment, a dose derived from $140 \times 10^6$ apoptotic cells is administered. In another embodiment, a dose derived from $35\text{-}210 \times 10^6$ apoptotic cells is administered.

In some embodiments, the apoptotic cell supernatant, or composition comprising said apoptotic cell supernatant, may be administered by any method known in the art including, but not limited to, intravenous, subcutaneous, intranodal, intratumoral, intrathecal, intrapleural, intraperitoneal and directly to the thymus, as discussed in detail herein.

Surprisingly, the apoptotic cell supernatants, such as apoptotic cell-phagocyte supernatants, reduces production of cytokines associated with the cytokine storm such as IL-6. Another cytokine, IL-2, is not involved in cytokine release syndrome although is secreted by DCs and macrophages in small quantities. It is, however, required for the survival and proliferation of CAR-T-cells and is mostly produced by these T-cells. Unexpectedly, the apoptotic cell supernatants, such as apoptotic cell-phagocyte supernatants, do not reduce IL-2 levels sufficiently to negatively affect the survival of CAR T-cells.

In some embodiments, the apoptotic cell supernatants, such as apoptotic cell-phagocyte supernatants, affect cytokine expression levels in macrophages and DCs, but do not affect cytokine expression levels in the T-cells themselves. It was therefore unexpected that apoptotic cell supernatants would be useful in enhancing CAR T-cell therapy or dendritic cell therapy.

In another embodiment, the apoptotic cell supernatants trigger death of T-cells, but not via changes in cytokine expression levels.

In another embodiment, apoptotic cell supernatants, such as apoptotic cell-phagocyte supernatants antagonize the priming of macrophages and dendritic cells to secrete cytokines that would otherwise amplify the cytokine storm. In another embodiment, apoptotic cell supernatants increase Tregs which suppress the inflammatory response and/or prevent excess release of cytokines.

In some embodiments, administration of apoptotic cell supernatants, such as apoptotic cell-phagocyte supernatants, inhibits one or more pro-inflammatory cytokines. In some embodiments, the pro-inflammatory cytokine comprises IL-1beta, IL-6, TNF-alpha, or IFN-gamma, or any combination thereof. In another embodiment, administration of apoptotic cell supernatants promotes the secretion of one or more anti-inflammatory cytokines. In some embodiments, the anti-inflammatory cytokine comprises TGF-beta, IL10, or PGE2, or any combination thereof.

In another embodiment, administration of apoptotic cell supernatants, such as apoptotic cell-phagocyte supernatants, inhibits dendritic cell maturation following exposure to TLR ligands. In another embodiment, administration of apoptotic cell supernatants creates potentially tolerogenic dendritic cells, which in some embodiments, are capable of migration, and in some embodiments, the migration is due to CCR7. In another embodiment, administration of apoptotic cell supernatants elicits various signaling events which in one embodiment is TAM receptor signaling (Tyro3, Axl and Mer) which in some embodiments, inhibits inflammation in antigen-presenting cells. In some embodiments, Tyro-3, Axl, and Mer constitute the TAM family of receptor tyrosine kinases (RTKs) characterized by a conserved sequence within the kinase domain and adhesion molecule-like extracellular domains. In another embodiment, administration of apoptotic cell supernatants activates signaling through MerTK. In another embodiment, administration of apoptotic cell supernatants activates the phosphatidylinositol 3-kinase (PI3K)/AKT pathway, which in some embodiments, negatively regulates NF-κB. In another embodiment, administration of apoptotic cell supernatants negatively regulates the inflammasome which in one embodiment leads to inhibition of pro-inflammatory cytokine secretion, DC maturation, or a combination thereof. In another embodiment, administration of apoptotic cell supernatants upregulates expression of anti-inflammatory genes such as Nr4a, Thbs1, or a combination thereof. In another embodiment, administration of apoptotic cell supernatants induces a high level of AMP which in some embodiments, is accumulated in a Pannexin1-dependent manner. In another embodiment, administration of apoptotic cell supernatants suppresses inflammation.

Compositions

As used herein, the terms "composition" and pharmaceutical composition" may in some embodiments, be used interchangeably having all the same qualities and meanings. In some embodiments, disclosed herein is a pharmaceutical composition for the treatment of a condition or disease as described herein.

In another embodiment, pharmaceutical compositions disclosed here are for maintaining or increasing the proliferation rate of a genetically modified immune cells. In a further embodiment, methods for maintaining or increasing the proliferation rate of genetically modified immune cells further comprise reducing or inhibiting the incidence of cytokine release syndrome (CRS) or cytokine storm. In another embodiment, disclosed herein are pharmaceutical compositions for increasing the efficacy of a genetically modified immune cell therapy. In another embodiment, compositions used in the methods for increasing the efficacy of an immune cell therapy further comprise reducing or inhibiting the incidence of CRS or a cytokine storm. In another embodiment, disclosed herein are compositions for methods treating, preventing, inhibiting, reducing the incidence of, ameliorating, or alleviating a cancer of a tumor in a subject. In another embodiment, compositions used in the methods for treating, preventing, reducing the incidence of, ameliorating, or alleviating a cancer or a tumor in a subject, further comprise reducing or inhibiting the incidence of CRS or a cytokine storm.

In another embodiment, a pharmaceutical composition comprises a genetically modified immune cell or a genetically modified receptor thereof. In another embodiment, a genetically modified immune cell comprises a T-cell. In another embodiment, a genetically modified immune cell comprises a chimeric antigen receptor CAR T-cell. In another embodiment, a genetically modified immune cell comprises a chimeric antigen receptor TCR T-cell. In another embodiment, a genetically modified immune cell comprises a cytotoxic T lymphocyte. In another embodiment, a genetically modified immune cell comprises a dendritic cell. In another embodiment, a genetically modified immune cell comprises a natural killer cell. In another embodiment, a genetically modified receptor comprises a genetically modified T-cell receptor.

In another embodiment, a pharmaceutical composition comprises an early apoptotic cell population. In another embodiment, a pharmaceutical composition comprises an apoptotic supernatant.

In still another embodiment, a pharmaceutical composition for the treatment of a condition or a disease as described herein comprises an effective amount of a genetically modified immune cell or a genetically modified receptor thereof, as described herein in a pharmaceutically acceptable excipient. In another embodiment, a pharmaceutical composition for the treatment of a condition or a disease as described herein comprises an effective amount of a CAR T-cell as described herein in, and a pharmaceutically acceptable excipient. In another embodiment, a pharmaceutical composition for the treatment of a condition or a disease as described herein comprises an effective amount of a TCR T-cell as described herein in, and a pharmaceutically acceptable excipient. In another embodiment, a pharmaceutical composition for the treatment of a condition or a disease as described herein comprises an effective amount of a cytotoxic T-cell, as described herein, and a pharmaceutically acceptable excipient. In another embodiment, a pharmaceutical composition for the treatment of a condition or a disease as described herein comprises an effective amount of a genetically modified dendritic cell, as described herein, and a pharmaceutically acceptable excipient. In another embodiment, a pharmaceutical composition for the treatment of a condition or a disease as described herein comprises an effective amount of a genetically modified natural killer cell, as described herein, and a pharmaceutically acceptable excipient. In another embodiment, a pharmaceutical composition for the treatment of a condition or a disease as described herein comprises an effective amount of a genetically modified T-cell receptor, as described herein, and a pharmaceutically acceptable excipient. In still another embodiment, a pharmaceutical composition for the treatment of a condition or a disease as described herein comprises an effective amount of an early apoptotic cell population, as described herein in a pharmaceutically acceptable excipient. In still another embodiment, a pharmaceutical composition for the treatment of a condition or a disease as described herein comprises an effective amount of an apoptotic supernatant, as described herein in a pharmaceutically acceptable excipient.

In another embodiment, the condition or disease as described herein is a tumor or cancer. In another embodiment, disclosed herein is a composition comprising the genetically modified immune cell or receptor thereof, for example a CAR T-cell, that binds to a protein or peptide of interest as described herein. In another embodiment, disclosed herein is a composition comprising the genetically modified immune cell or receptor thereof, for example a TCR T-cell, that recognizes and binds a protein or peptide of interest as described herein. In another embodiment, the protein or peptide of interest comprises a tumor antigen or a fragment thereof.

In another embodiment, a composition disclosed herein and used in methods disclosed herein comprises apoptotic cells or an apoptotic cell supernatant, and a pharmaceutically acceptable excipient. In some embodiments, a composition comprising apoptotic cells or an apoptotic cell supernatant is used in methods disclosed herein for example for treating, preventing, inhibiting the growth of, delaying disease progression, reducing the tumor load, or reducing the incidence of a cancer or a tumor in a subject, or any combination thereof.

In yet another embodiment, a composition comprising an effective amount of a genetically modified immune cell or a genetically modified receptor thereof may be the same composition as comprises an apoptotic cell population or an apoptotic cell supernatant. In another embodiment, a composition comprising an effective amount of a CAR T-cell, or a TCR T-cell, or a cytotoxic T-cell, or a genetically modified dendritic cell, or a genetically modified natural killer cell may be the same composition as comprises an apoptotic cell population or an apoptotic cell supernatant. In yet another embodiment, a composition comprising an effective amount of genetically modified T-cell receptor may be the same composition as comprises an apoptotic cell population or an apoptotic cell supernatant. In still another embodiment, a composition comprising an effective amount of a genetically modified immune cell selected from the group comprising a CAR T-cell, a TCR T-cell, a cytotoxic T-cell, a natural killer cell, or a dendritic cell, is not the same composition as comprises an apoptotic cell population or an apoptotic cell supernatant. In another embodiment, a composition comprises a chimeric antigen receptor-expressing T-cell (CAR T-cell) and either apoptotic cells or an apoptotic cell supernatant, and a pharmaceutically acceptable excipient. In another embodiment, a composition comprises a genetically modified T-cell receptor expressing T-cell (TCR T-cell) and either apoptotic cells or an apoptotic cell supernatant, and a pharmaceutically acceptable excipient. In another embodiment, a composition comprising an effective amount of a genetically modified T-cell receptor is not the same composition as comprises an apoptotic cell population or an apoptotic cell supernatant.

In another embodiment, apoptotic cells comprised in a composition comprise apoptotic cells in an early apoptotic state. In another embodiment, apoptotic cells comprised in a composition are pooled third party donor cells. In another embodiment, an apoptotic cell supernatant comprised in a composition disclosed herein is collected from early apoptotic cells. In another embodiment, an apoptotic cell supernatant comprised in a composition disclosed herein, is collected pooled third party donor cells.

In one embodiment, a composition comprising a genetically modified immune cells, for example a CAR T-cell, further comprises an additional pharmaceutical composition for preventing, suppressing, or modulating cytokine release in a patient with cytokine release syndrome or experiencing a cytokine storm. In another embodiment, a composition comprising a genetically modified immune cells, for example a CAR T-cell, and apoptotic cells further comprises an additional pharmaceutical composition for preventing, suppressing, or modulating cytokine release in a patient with cytokine release syndrome or experiencing a cytokine storm. In another embodiment, a composition comprising a genetically modified immune cells, for example a CAR T-cell, and an apoptotic cell supernatant, further comprises an additional pharmaceutical composition for preventing, suppressing, or modulating cytokine release in a patient with cytokine release syndrome or experiencing a cytokine storm.

In one embodiment, a composition comprising a genetically modified immune cells, for example a TCR T-cell, further comprises an additional pharmaceutical composition for preventing, suppressing, or modulating cytokine release in a patient with cytokine release syndrome or experiencing a cytokine storm. In another embodiment, a composition comprising a genetically modified immune cells, for example a TCR T-cell, and apoptotic cells further comprises an additional pharmaceutical composition for preventing, suppressing, or modulating cytokine release in a patient with cytokine release syndrome or experiencing a cytokine storm. In another embodiment, a composition comprising a genetically modified immune cells, for example a TCR T-cell, and an apoptotic cell supernatant, further comprises an additional pharmaceutical composition for preventing, suppressing, or modulating cytokine release in a patient with cytokine release syndrome or experiencing a cytokine storm.

In one embodiment, a composition comprising a genetically modified immune cells, for example a dendritic cell, further comprises an additional pharmaceutical composition for preventing, suppressing, or modulating cytokine release in a patient with cytokine release syndrome or experiencing a cytokine storm. In another embodiment, a composition comprising a genetically modified immune cells, for example a dendritic, and apoptotic cells further comprises an additional pharmaceutical composition for preventing, suppressing, or modulating cytokine release in a patient with cytokine release syndrome or experiencing a cytokine storm. In another embodiment, a composition comprising a genetically modified immune cells, for example a dendritic, and an apoptotic cell supernatant, further comprises an additional pharmaceutical composition for preventing, suppressing, or modulating cytokine release in a patient with cytokine release syndrome or experiencing a cytokine storm.

In one embodiment, a composition comprising a genetically modified immune cells, for example a NK cell, further comprises an additional pharmaceutical composition for preventing, suppressing, or modulating cytokine release in a patient with cytokine release syndrome or experiencing a cytokine storm. In another embodiment, a composition comprising a genetically modified immune cells, for example a NK cell, and apoptotic cells further comprises an additional pharmaceutical composition for preventing, suppressing, or modulating cytokine release in a patient with cytokine release syndrome or experiencing a cytokine storm. In another embodiment, a composition comprising a genetically modified immune cells, for example a NK cell, and an apoptotic cell supernatant, further comprises an additional pharmaceutical composition for preventing, suppressing, or modulating cytokine release in a patient with cytokine release syndrome or experiencing a cytokine storm.

In one embodiment, the additional pharmaceutical composition comprises a CTLA-4 blocking agent, which in one embodiment is Ipilimumab. In another embodiment, the additional pharmaceutical composition comprises a alpha-1 anti-trypsin, as disclosed herein, or a fragment thereof, or an analogue thereof. In another embodiment, the additional pharmaceutical composition comprises a tellurium-based compound, a disclosed herein. In another embodiment, the additional pharmaceutical composition comprises an immune modulating agent, as disclosed herein. In another embodiment, the additional pharmaceutical composition comprises a CTLA-4 blocking agent, an alpha-1 anti-trypsin or fragment thereof or analogue thereof, a tellurium-based compound, or an immune modulating compound, or any combination thereof.

In one embodiment, the composition comprising the genetically modified immune cell, for example a CAR T-cell and the pharmaceutical composition comprising any one of a CTLA-4 blocking agent, an alpha-1 anti-trypsin or fragment thereof or analogue thereof, apoptotic cells, or an apoptotic cell supernatant, a tellurium-based compound, or an immune modulating agent comprises a single composition. In another embodiment, the composition comprising the genetically modified immune cell, for example CAR T-cells and the pharmaceutical composition comprising any one of a CTLA-4 blocking agent, an alpha-1 anti-trypsin or fragment thereof or analogue thereof, apoptotic cells, or an apoptotic cell supernatant, a tellurium-based compound, or an immune modulating agent, or any combination thereof, comprises multiple compositions, wherein each of the genetically modified immune cell, which in one embodiment is CAR T-cells, the CTLA-4 blocking agent, the alpha-1 anti-trypsin or fragment thereof or analogue thereof, the apoptotic cells, the apoptotic cell supernatant, the tellurium-based compound, or the immune modulating agent, or any combination thereof, are comprised in a separate composition. In yet another embodiment, the composition comprising the genetically modified immune cell, which in one embodiment is CAR T-cells and the pharmaceutical composition comprising any one of a CTLA-4 blocking agent, an alpha-1 anti-trypsin or fragment thereof or analogue thereof, apoptotic cells, an apoptotic cell supernatant, a tellurium-based compound, or an immune modulating agent, or any combination thereof, comprises multiple compositions, wherein the genetically modified immune cells, which in one embodiment are CAR T-cells, the CTLA-4 blocking agent, or the alpha-1 anti-trypsin or fragment thereof or analogue thereof, the tellurium-based compound, or the immune modulating agent, or any combination thereof, or any combination thereof are present in the genetically modified immune cell, for example a CAR T-cell, composition, and the apoptotic cells, or the apoptotic cell supernatant, are comprised in a separate composition.

In one embodiment, the composition comprising the genetically modified immune cell, for example a TCR T-cell and the pharmaceutical composition comprising any one of a CTLA-4 blocking agent, an alpha-1 anti-trypsin or fragment thereof or analogue thereof, apoptotic cells, or an apoptotic cell supernatant, a tellurium-based compound, or an immune modulating agent comprises a single composition. In another embodiment, the composition comprising the genetically modified immune cell, for example TCR T-cells and the pharmaceutical composition comprising any one of a CTLA-4 blocking agent, an alpha-1 anti-trypsin or fragment thereof or analogue thereof, apoptotic cells, or an apoptotic cell supernatant, a tellurium-based compound, or an immune modulating agent, or any combination thereof, comprises multiple compositions, wherein each of the genetically modified immune cell, which in one embodiment is TCR T-cells, the CTLA-4 blocking agent, the alpha-1 anti-trypsin or fragment thereof or analogue thereof, the apoptotic cells, the apoptotic cell supernatant, the tellurium-based compound, or the immune modulating agent, or any combination thereof, are comprised in a separate composition. In yet another embodiment, the composition comprising the genetically modified immune cell, which in one embodiment is TCR T-cells and the pharmaceutical composition comprising any one of a CTLA-4 blocking agent, an alpha-1 anti-trypsin or fragment thereof or analogue thereof, apoptotic cells, an apoptotic cell supernatant, a tellurium-based compound, or an immune modulating agent, or any combination thereof, comprises multiple compositions, wherein the genetically modified immune cells, which in one embodiment are TCR T-cells, the CTLA-4 blocking agent, or the alpha-1 anti-trypsin or fragment thereof or analogue thereof, the tellurium-based compound, or the immune modulating agent, or any combination thereof, or any combination thereof are present in the genetically modified immune cell, for example a TCR T-cell, composition, and the apoptotic cells, or the apoptotic cell supernatant, are comprised in a separate composition.

In one embodiment, the composition comprising the genetically modified immune cell, for example a dendritic cell and the pharmaceutical composition comprising any one of a CTLA-4 blocking agent, an alpha-1 anti-trypsin or fragment thereof or analogue thereof, apoptotic cells, or an apoptotic cell supernatant, a tellurium-based compound, or an immune modulating agent comprises a single composition. In another embodiment, the composition comprising the genetically modified immune cell, for example dendritic cells and the pharmaceutical composition comprising any one of a CTLA-4 blocking agent, an alpha-1 anti-trypsin or fragment thereof or analogue thereof, apoptotic cells, or an apoptotic cell supernatant, a tellurium-based compound, or an immune modulating agent, or any combination thereof, comprises multiple compositions, wherein each of the genetically modified immune cell, which in one embodiment is dendritic cells, the CTLA-4 blocking agent, the alpha-1 anti-trypsin or fragment thereof or analogue thereof, the apoptotic cells, the apoptotic cell supernatant, the tellurium-based compound, or the immune modulating agent, or any combination thereof, are comprised in a separate composition. In yet another embodiment, the composition comprising the genetically modified immune cell, which in one embodiment is dendritic cells and the pharmaceutical composition comprising any one of a CTLA-4 blocking agent, an alpha-1 anti-trypsin or fragment thereof or analogue thereof, apoptotic cells, an apoptotic cell supernatant, a tellurium-based compound, or an immune modulating agent, or any combination thereof, comprises multiple compositions, wherein the genetically modified immune cells, which in one embodiment are dendritic cells, the CTLA-4 blocking agent, or the alpha-1 anti-trypsin or fragment thereof or analogue thereof, the tellurium-based compound, or the immune modulating agent, or any combination thereof, or any combination thereof are present in the genetically modified immune cell, for example a dendritic cell, composition, and the apoptotic cells, or the apoptotic cell supernatant, are comprised in a separate composition.

In one embodiment, the composition comprising the genetically modified immune cell, for example a NK cell and the pharmaceutical composition comprising any one of a CTLA-4 blocking agent, an alpha-1 anti-trypsin or fragment thereof or analogue thereof, apoptotic cells, or an apoptotic cell supernatant, a tellurium-based compound, or an immune modulating agent comprises a single composition. In another embodiment, the composition comprising the genetically modified immune cell, for example NK cells and the pharmaceutical composition comprising any one of a CTLA-4 blocking agent, an alpha-1 anti-trypsin or fragment thereof or analogue thereof, apoptotic cells, or an apoptotic cell supernatant, a tellurium-based compound, or an immune modulating agent, or any combination thereof, comprises multiple compositions, wherein each of the genetically modified immune cell, which in one embodiment is NK cells, the CTLA-4 blocking agent, the alpha-1 anti-trypsin or fragment thereof or analogue thereof, the apoptotic cells, the apoptotic cell supernatant, the tellurium-based compound, or the immune modulating agent, or any combination thereof, are comprised in a separate composition. In yet another embodiment, the composition comprising the genetically modified immune cell, which in one embodiment is NK cells and the pharmaceutical composition comprising any one of a CTLA-4 blocking agent, an alpha-1 anti-trypsin or fragment thereof or analogue thereof, apoptotic cells, an apoptotic cell supernatant, a tellurium-based compound, or an immune modulating agent, or any combination thereof, comprises multiple compositions, wherein the genetically modified immune cells, which in one embodiment are NK cells, the CTLA-4 blocking agent, or the alpha-1 anti-trypsin or fragment thereof or analogue thereof, the tellurium-based compound, or the immune modulating agent, or any combination thereof, or any combination thereof are present in the genetically modified immune cell, for example a NK cell, composition, and the apoptotic cells, or the apoptotic cell supernatant, are comprised in a separate composition.

In some embodiments, a composition comprises apoptotic cells and an additional agent. In some embodiments, a composition comprises apoptotic cells and an antibody or a functional fragment thereof. In some embodiments, a composition comprises apoptotic cells and a RtX antibody or a functional fragment thereof. In some embodiments, apoptotic cells and an antibody or a functional fragment thereof may be comprised in separate compositions. In some embodiments, apoptotic cells and an antibody or a functional fragment thereof may be comprised in the same composition.

A skilled artisan would appreciate that a "pharmaceutical composition" may encompass a preparation of one or more of the active ingredients described herein with other chemical components such as physiologically suitable carriers and excipients. The purpose of a pharmaceutical composition is to facilitate administration of a compound to an organism.

In some embodiments, disclosed herein is a pharmaceutical composition for treating, preventing, inhibiting the growth of, or reducing the incidence of a cancer or a tumor. In some embodiments, disclosed herein is a pharmaceutical composition for increasing the survival of a subject suffering from a cancer or a tumor. In some embodiments, disclosed herein is a pharmaceutical composition for reducing the size or reducing the growth rate of a tumor or a cancer. In some embodiments, disclosed herein is a pharmaceutical comprising for reducing tumor load in a subject suffering from a cancer or a tumor. In some embodiments, disclosed herein is a pharmaceutical comprising for delaying disease progression in a subject suffering from a cancer or a tumor. In some embodiments, disclosed herein is a pharmaceutical comprising for reducing the incidence of cancer or a tumor in a subject suffering from a cancer or a tumor. In some embodiments, disclosed herein is a pharmaceutical comprising for reducing the size and or growth rate of a cancer or tumor in a subject suffering from a cancer or a tumor.

In some embodiments, a pharmaceutical composition comprises an early apoptotic cell population as described herein. In some embodiments, a pharmaceutical composition comprises an early apoptotic cell population as described herein, and a pharmaceutically acceptable excipient.

A skilled artisan would appreciate that the phrases "physiologically acceptable carrier", "pharmaceutically acceptable carrier", "physiologically acceptable excipient", and "pharmaceutically acceptable excipient", may be used interchangeably may encompass a carrier, excipient, or a diluent that does not cause significant irritation to an organism and does not abrogate the biological activity and properties of the administered active ingredient.

A skilled artisan would appreciate that an "excipient" may encompass an inert substance added to a pharmaceutical composition to further facilitate administration of an active ingredient. In some embodiments, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In some embodiments, compositions are administered at the same time. In an alternative embodiment, compositions are administered at different times. In another embodiment, compositions comprising apoptotic cells are administered prior to infusion or genetically modified immune cells or receptors thereof. In another embodiment, compositions comprising apoptotic cells are administered prior to CAR-T-cell infusion. In another embodiment, compositions comprising apoptotic cells are administered prior to cytotoxic T-cell infusion. In another embodiment, compositions comprising apoptotic cells are administered prior to natural killer cell infusion. In another embodiment, compositions comprising apoptotic cells are administered prior to dendritic infusion. In another embodiment, compositions comprising apoptotic cells are administered prior to infusion of a genetically modified T-cell receptor.

In another embodiment, compositions comprising apoptotic cell supernatants are administered prior to infusion or genetically modified immune cells or receptors thereof. In another embodiment, compositions comprising apoptotic cell supernatants are administered prior to CAR-T-cell infusion. In another embodiment, compositions comprising apoptotic cell supernatants are administered prior to cytotoxic T-cell infusion. In another embodiment, compositions comprising apoptotic cell supernatants are administered prior to natural killer cell infusion. In another embodiment, compositions comprising apoptotic cell supernatants are administered prior to dendritic infusion. In another embodiment, compositions comprising apoptotic cell supernatants are administered prior to infusion of a genetically modified T-cell receptor.

In another embodiment, compositions comprising apoptotic cell supernatants are administered prior to infusion of genetically modified immune cells or receptors thereof. In another embodiment, compositions comprising apoptotic cells are administered about 24 hours prior to genetically modified immune cell or receptor thereof infusion. In another embodiment, compositions comprising apoptotic cells are administered about 24 hours prior to CAR T-cell, or cytotoxic T-cells, or natural killer cells, or dendritic cell or genetically modified T-cell receptor infusion. In another embodiment, compositions comprising apoptotic cell supernatants are administered about 24 hours prior to CAR T-cell or cytotoxic T-cells, or natural killer cells, or dendritic cell or genetically modified T-cell receptor infusion.

In some embodiments, compositions are administered at the same time. In an alternative embodiment, compositions are administered at different times. In another embodiment, compositions comprising apoptotic cells are administered prior to administration of an antibody or fragment thereof, or a composition comprising an antibody or fragment thereof.

In another embodiment, compositions comprising apoptotic cells are administered about 2 hours, 4 hours, 6 hours, 8 hours, 10 hours, 12 hours, 14 hours, 16 hours, 18 hours 20 hours, 22 hours, 24 hours, 36 hours, 48 hours, 60 hours, or 72 hours prior to an antibody or fragment thereof, or composition comprising the antibody or fragment thereof. In another embodiment, compositions comprising apoptotic cell supernatants are administered about 2 hours, 4 hours, 6 hours, 8 hours, 10 hours, 12 hours, 14 hours, 16 hours, 18 hours 20 hours, 22 hours, 24 hours, 36 hours, 48 hours, 60 hours, or 72 hours prior to an antibody or fragment thereof, or composition comprising the antibody or fragment thereof.

In another embodiment, compositions comprising apoptotic cells are administered about 1 day, 2 days, 3 days, 4 days, 5 days, 6 days, 7 days, 8 days, 9 days, 10 days, 11 days, 12 days, 13 days 14 days, or 15 days prior to an antibody or fragment thereof, or composition comprising the antibody or functional fragment thereof. In another embodiment, compositions comprising apoptotic cell supernatants are administered about 2 weeks, 3 weeks, 4 weeks, 5 weeks, 6 weeks, 7 weeks, or 8 weeks prior to an antibody or functional fragment thereof, or composition comprising the antibody or functional fragment thereof.

In another embodiment, compositions comprising apoptotic cells are administered after infusion of an antibody or fragment thereof, or composition comprising the antibody or fragment thereof. In another embodiment, composition comprising apoptotic cells are administered after an antibody or fragment thereof, or composition comprising the antibody or fragment thereof. In another embodiment, compositions comprising apoptotic cell supernatants are administered after administration of an antibody or fragment thereof, or composition comprising the antibody or fragment thereof. In another embodiment, compositions comprising apoptotic cell supernatants are administered after administration of an antibody or fragment thereof, or composition comprising the antibody or fragment thereof. In another embodiment, compositions comprising apoptotic cells are administered about 24 hours after an antibody or fragment thereof, or composition comprising the antibody or fragment thereof. In another embodiment, compositions comprising apoptotic cells are administered after administration of an antibody or fragment thereof, or composition comprising the antibody or fragment thereof. In another embodiment, compositions comprising apoptotic cells are administered about 2 hours, 4 hours, 6 hours, 8 hours, 10 hours, 12 hours, 14 hours, 16 hours, 18 hours 20 hours, 22 hours, 24 hours, 36 hours, 48 hours, 60 hours, or 72 hours after administration of an antibody or fragment thereof, or composition comprising the antibody or fragment thereof. In another embodiment, compositions comprising apoptotic cell supernatants are administered about 2 hours, 4 hours, 6 hours, 8 hours, 10 hours, 12 hours, 14 hours, 16 hours, 18 hours 20 hours, 22 hours, 24 hours, 36 hours, 48 hours, 60 hours, or 72 hours after administration of an antibody or fragment thereof, or composition comprising the antibody or fragment thereof.

In another embodiment, compositions comprising apoptotic cells are administered about 1 day, 2 days, 3 days, 4 days, 5 days, 6 days, 7 days, 8 days, 9 days, 10 days, 11 days, 12 days, 13 days 14 days, or 15 days after an antibody or fragment thereof, or composition comprising the antibody or functional fragment thereof. In another embodiment, compositions comprising apoptotic cell supernatants are administered about 2 weeks, 3 weeks, 4 weeks, 5 weeks, 6 weeks, 7 weeks, or 8 weeks after an antibody or functional fragment thereof, or composition comprising the antibody or functional fragment thereof.

In some embodiments, a composition comprising apoptotic cells is administered independent of CAR T-cells. In some embodiments, a composition comprising apoptotic cells is administered in combination with an additional agent. In some embodiments, the additional agent is an antibody.

In some embodiments, the composition as disclosed herein comprises a therapeutic composition. In some embodiments, the composition as disclosed herein comprises a therapeutic efficacy.

In some embodiments, a composition as disclosed herein is administered once. In another embodiment, the composition is administered twice. In another embodiment, the composition is administered three times. In another embodiment, the composition is administered four times. In another embodiment, the composition is administered at least four times. In another embodiment, the composition is administered more than four times.

In some embodiments, CAR T-cells as disclosed herein are administered once. In another embodiment, CAR T-cells are administered twice. In another embodiment, CAR T-cells are administered three times. In another embodiment, CAR T-cells are administered four times. In another embodiment, CAR T-cells are administered at least four times. In another embodiment, the composition is administered more than four times.

In some embodiments, the composition as disclosed herein is a therapeutic composition. In another embodiment, the composition as disclosed herein has therapeutic efficacy.

In some embodiments, disclosed herein are a composition which provides reduced inflammatory cytokine or chemokine release compared to a composition comprising CAR T-cells alone, but with comparable cytotoxicity compared to a composition comprising CAR T-cells alone.

Formulations

Pharmaceutical compositions disclosed herein comprising early apoptotic cell populations, can be conveniently provided as sterile liquid preparations, e.g., isotonic aqueous solutions, suspensions, emulsions, dispersions, or viscous compositions, which may be buffered to a selected pH, Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the early apoptotic cell population described herein and utilized in practicing the methods disclosed herein, in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the disclosure herein, however, any vehicle, diluent, or additive used would have to be compatible with the genetically modified immunoresponsive cells or their progenitors.

The compositions or formulations described herein can be isotonic, i.e., they can have the same osmotic pressure as blood and lacrimal fluid. The desired isotonicity of the compositions as disclosed herein may be accomplished using sodium chloride, or other pharmaceutically acceptable agents such as dextrose, boric acid, sodium tartrate, propylene glycol or other inorganic or organic solutes. Sodium chloride may be preferred particularly for buffers containing sodium ions.

Viscosity of the compositions, if desired, can be maintained at the selected level using a pharmaceutically acceptable thickening agent. Methylcellulose may be preferred because it is readily and economically available and is easy to work with.

Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions or formulations should be selected to be chemically inert and will not affect the viability or efficacy of the early apoptotic cell populations as described herein, for use in the methods disclosed herein. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of genetically modified immunoresponsive cells disclosed herein is the quantity of cells necessary to achieve an optimal effect. The quantity of cells to be administered will vary for the subject being treated. In a some embodiments, between $10^4$ to $10^{10}$, between $10^5$ to $10^9$, or between $10^6$ and $10^8$ genetically modified immunoresponsive cells disclosed herein are administered to a human subject. More effective cells may be administered in even smaller numbers. In some embodiments, at least about $1\times10^8$, $2\times10^8$, $3\times10^8$, $4\times10^8$, and $5\times10^8$ genetically modified immunoresponsive cells disclosed herein are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods disclosed herein. Typically, any additives (in addition to the active cell(s) and/or agent(s)) are present in an amount of 0.001 to 50% (weight) solution in phosphate buffered saline, and the active ingredient is present in the order of micrograms to milligrams, such as about 0.0001 to about 5 wt %. In another embodiment about 0.0001 to about 1 wt %. In still another embodiment, about 0.0001 to about 0.05 wt % or about 0.001 to about 20 wt %. In a further embodiment, about 0.01 to about 10 wt %. In another embodiment, about 0.05 to about 5 wt %. Of course, for any composition to be administered to an animal or human, and for any particular method of administration, it is preferred to determine therefore: toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Nucleic Acid Sequences, Vectors, Cells

In some embodiments, disclosed herein are an isolated nucleic acid sequence encoding a chimeric antigen receptor (CAR) as described herein for uses in the compositions and methods as disclosed herein.

In another embodiment, disclosed herein are a vector comprising the nucleic acid sequence encoding a chimeric antigen receptor (CAR) as described herein.

In some embodiments, disclosed herein are an isolated nucleic acid sequence encoding a genetically modified T-cell receptor (TCR) as described herein for uses in the compositions and methods as disclosed herein. In another embodiment, disclosed herein are a vector comprising the nucleic acid sequence encoding a genetically modified T-cell receptor (TCR) as described herein.

Genetic modification of immunoresponsive cells (e.g., T-cells, CTL cells, NK cells) can be accomplished by transducing a substantially homogeneous cell composition with a recombinant DNA construct. In some embodiments, a retroviral vector (either gamma-retroviral or lentiviral) is employed for the introduction of the DNA construct into the cell. For example, a polynucleotide encoding a receptor that binds an antigen (e.g., a tumor antigen, or a valiant, or a fragment thereof), can be cloned into a retroviral vector and expression can be driven from its endogenous promoter, from the retroviral long terminal repeat, or from a promoter specific for a targeT-cell type of interest. Non-viral vectors may be used as well.

Non-viral approaches can also be employed for the expression of a protein in cell. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al, Am. J. Med. Sci. 298:278, 1989; Staubinger et al, Methods in Enzymology 101:512, 1983), asialoorosomucoid-polylysine conjugation (Wu et al., Journal of Biological Chemistry 263: 14621, 1988; Wu et al., Journal of Biological Chemistry 264:16985, 1989), or by micro-injection under surgical conditions (Wolff et al., Science 247: 1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases). Transient expression may be obtained by RNA electroporation. cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor la enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

In another embodiment, disclosed herein are a cell comprising the vector comprising the nucleic acid sequence encoding a chimeric antigen receptor (CAR) as disclosed herein.

Methods of Use

In one embodiment, disclosed herein are methods for treating, preventing, inhibiting, reducing the incidence of, ameliorating, or alleviating a cancer or a tumor comprising the step of administering a composition as disclosed herein.

In some embodiments, disclosed herein are methods of treating, preventing, inhibiting, reducing the incidence of, ameliorating, or alleviating a cancer or a tumor in a subject comprising the step of administering a composition comprising apoptotic cells. In some embodiments, disclosed herein are methods of treating, preventing, inhibiting the growth of, delaying disease progression, reducing the tumor load, or reducing the incidence of a cancer or a tumor in a subject, or any combination thereof. In some embodiments, methods disclosed herein reduce the size and or growth rate of a tumor or cancer. In some embodiments, methods disclosed herein increase the survival of a subject suffering from a tumor or cancer. In some embodiments, use of apoptotic cells or a composition thereof increases the efficacy of genetically modified immune cell therapy, for example but not limited to CAR T-cell therapy.

In another embodiment, disclosed herein are methods for treating, preventing, inhibiting, reducing the incidence of, ameliorating, or alleviating a cancer or a tumor comprising the step of administering genetically modified immune cells and a composition comprising an additional agent, wherein said additional agent comprises apoptotic cells, a supernatant from apoptotic cells, a CTLA-4 blocking agent, an alpha-1 anti-trypsin or fragment or analog thereof, a tellurium-based compound, or an immune modulating agent, or any combination thereof, wherein said method treats, prevents, inhibits, reduces the incidence of, ameliorates or alleviates a cancer or a tumor in said subject compared with a subject administered said genetically modified immune cells and not administered the additional agent. In another embodiment, said genetically modified immune cells comprise genetically modified T-cell, cytotoxic T-cells, Treg cells, effector T-cells, helper T-cells, NK cells, or dendritic cells.

In another embodiment, disclosed herein are methods for treating, preventing, inhibiting, reducing the incidence of, ameliorating, or alleviating a cancer or a tumor comprising the step of administering chimeric antigen receptor-expressing T-cells (CAR T-cells) and a composition comprising an additional agent, wherein said additional agent comprises apoptotic cells, a supernatant from apoptotic cells, a CTLA-4 blocking agent, an alpha-1 anti-trypsin or fragment or analog thereof, a tellurium-based compound, or an immune modulating agent, or any combination thereof, wherein said method treats, prevents, inhibits, reduces the incidence of, ameliorates or alleviates a cancer or a tumor in said subject compared with a subject administered said genetically modified immune cells and not administered the additional agent.

In another embodiment, disclosed herein are methods for treating, preventing, inhibiting, reducing the incidence of, ameliorating, or alleviating a cancer or a tumor comprising the step of administering genetically modified T-cell receptor cells (TCR T-cells) and a composition comprising an additional agent, wherein said additional agent comprises apoptotic cells, a supernatant from apoptotic cells, a CTLA-4 blocking agent, an alpha-1 anti-trypsin or fragment or analog thereof, a tellurium-based compound, or an immune modulating agent, or any combination thereof, wherein said method treats, prevents, inhibits, reduces the incidence of, ameliorates or alleviates a cancer or a tumor in said subject compared with a subject administered said genetically modified immune cells and not administered the additional agent.

In another embodiment, administration of apoptotic cells or an apoptotic supernatant or compositions thereof does not reduce the efficacy for treating, preventing, inhibiting, reducing the incidence of, ameliorating, or alleviating a cancer or a tumor, of said administering chimeric antigen receptor-expressing T-cells. In another embodiment, administration of an additional agent comprising apoptotic cells, a supernatant from apoptotic cells, a CTLA-4 blocking agent, an alpha-1 anti-trypsin or fragment or analog thereof, a tellurium-based compound, or an immune modulating agent, or any combination thereof, or compositions thereof does not reduce the efficacy for treating, preventing, inhibiting, reducing the incidence of, ameliorating, or alleviating a cancer or a tumor, of said administering chimeric antigen receptor-expressing T-cells.

In another embodiment, administration of apoptotic cells or an apoptotic supernatant or compositions thereof increases the efficacy for treating, preventing, inhibiting, reducing the incidence of, ameliorating, or alleviating a cancer or a tumor, of said administering chimeric antigen receptor-expressing T-cells. In another embodiment, administration of an additional agent comprising apoptotic cells, a supernatant from apoptotic cells, a CTLA-4 blocking agent, an alpha-1 anti-trypsin or fragment or analog thereof, a tellurium-based compound, or an immune modulating agent, or any combination thereof, or compositions thereof increases the efficacy for treating, preventing, inhibiting, reducing the incidence of, ameliorating, or alleviating a cancer or a tumor, of said administering chimeric antigen receptor-expressing T-cells.

In one embodiment, methods increasing the efficacy of a genetically modified immune cell cancer therapy comprise administering said genetically modified immune cells and an additional agent comprising apoptotic cells, a supernatant from apoptotic cells, a CTLA-4 blocking agent, an alpha-1 anti-trypsin or fragment or analog thereof, a tellurium-based compound, or an immune modulating agent, or any combination thereof, or compositions thereof, wherein the efficacy is increased compared with a subject not administered said additional agent. In another embodiment said genetically modified immune cells are T-cells. In another embodiment, a T-cell is a naïve T-cell. In another embodiment, a T-cell is a naïve CD4+ T-cell. In another embodiment, a T-cell is a naïve T-cell. In another embodiment, a T-cell is a naïve CD8+ T-cell. In another embodiment, the genetically modified immune cell is a natural killer (NK) cell. In another embodiment, the genetically modified immune cell is a dendritic cell. In still another embodiment, the genetically modified T-cell is a cytotoxic T lymphocyte (CTL cell). In another embodiment, the genetically modified T-cell is a regulatory T-cell (Treg). In another embodiment, the genetically modified T-cell is a chimeric antigen receptor (CAR) T-cell. In another embodiment, the genetically modified T-cell is a genetically modified T-cell receptor cell (TCR T-cell). In another embodiment, methods increasing the efficacy of a CAR T-cell cancer therapy comprise administering said genetically modified immune cells and an additional agent comprising apoptotic cells, a supernatant from apoptotic cells, a CTLA-4 blocking agent, an alpha-1 anti-trypsin or fragment or analog thereof, a tellurium-based compound, or an immune modulating agent, or any combination thereof, or compositions thereof, wherein the efficacy is increased compared with a subject not administered said additional agent.

In another embodiment, methods herein reduce the level of production of at least one pro-inflammatory cytokine compared with the level of said pro-inflammatory cytokine in a subject receiving an immune cancer therapy and not administered an additional agent. In another embodiment, methods herein inhibit or reduce the incidence of cytokine release syndrome or cytokine storm in a subject undergoing a genetically modified immune cell cancer therapy and not administered an additional agent.

In another embodiment, methods disclosed herein reduce IL-6.

In another embodiment, methods herein increase the production of at least one cytokine compared with the level of said cytokine in a subject receiving an immune cancer therapy and not administered an additional agent. In some embodiments, the additional agent is apoptotic cells, In other embodiment, the additional agent is an apoptotic cell supernatant. In another embodiment, methods disclosed herein increase IL-2.

A skilled artisan would appreciate that the term "production" as used herein in reference to a cytokine, may encompass expression of the cytokine as well as secretion of the cytokine from a cell. In one embodiment, increased production of a cytokine results in increased secretion of the cytokine from the cell. In an alternate embodiment, decreased production of a cytokine results in decreased secretion of the cytokine from the cell. In another embodiment, methods disclosed herein decrease secretion of at least one cytokine. In another embodiment, methods disclosed herein decrease secretion of IL-6. In another embodiment, methods disclosed herein increase secretion of at least one cytokine. In another embodiment, methods disclosed herein increase secretion of IL-2.

In another embodiment, a cell secreting at least one cytokine is a tumor cell. In another embodiment, a cell secreting at least one cytokine is a T-cell. In another embodiment, a cell secreting at least one cytokine is an immune cell. In another embodiment, a cell secreting at least one cytokine is a macrophage. In another embodiment, a cell secreting at least one cytokine is a B cell lymphocyte. In another embodiment, a cell secreting at least one cytokine is a mast cell. In another embodiment, a cell secreting at least one cytokine is an endothelial cell. In another embodiment, a cell secreting at least one cytokine is a fibroblast. In another embodiment, a cell secreting at least one cytokine is a stromal cell. A skilled artisan would recognize that the level of cytokines may be increased or decreased in cytokine secreting cells depending on the environment surrounding the cell.

In yet another embodiment, an additional agent used in the methods disclosed herein increases secretion of at least one cytokine. In yet another embodiment, an additional agent used in the methods disclosed herein maintains secretion of at least one cytokine. In still another embodiment, an additional agent used in the methods disclosed herein does not decrease secretion of at least one cytokine. In another embodiment, an additional agent used in the methods disclosed herein increases secretion of IL-2. In another embodiment, an additional agent used in the methods disclosed herein increases secretion of IL-2R. In another embodiment, an additional agent used in the methods disclosed herein maintains secretion levels of IL-2. In another embodiment, an additional agent used in the methods disclosed herein maintains secretion levels of IL-2R. In another embodiment, an additional agent used in the methods disclosed herein does not decrease secretion levels of IL-2R. In another embodiment, an additional agent used in the methods disclosed herein maintains or increases secretion levels of IL-2. In another embodiment, an additional agent used in the methods disclosed herein maintains or increases secretion levels of IL-2R. In another embodiment, an additional agent used in the methods disclosed herein does not decrease secretion levels of IL-2R.

In still a further embodiment, an additional agent used in the methods disclosed herein decreases secretion of IL-6. In another embodiment, an additional agent used in the methods disclosed herein maintains, increases, or does not decrease secretion levels of IL-2 while decreasing secretion of IL-6. In another embodiment, an additional agent used in the methods disclosed herein maintains, increases, or does not decrease secretion levels of IL-2R while decreasing secretion of IL-6.

In one embodiment, methods of increasing the efficacy of a CAR T-cell cancer therapy disclosed herein comprises decreasing the level of IL-6 in said subject, said method comprising administering CAR T-cells and an additional agent comprising apoptotic cells, a supernatant from apoptotic cells, a CTLA-4 blocking agent, an alpha-1 anti-trypsin or fragment or analog thereof, a tellurium-based compound, or an immune modulating agent, or any combination thereof, or compositions thereof, wherein the efficacy is increased compared with a subject not administered said additional agent. In another embodiment, methods of increasing the efficacy of a CAR T-cell cancer therapy disclosed herein comprises increasing the level of IL-2 in said subject, said method comprising administering CAR T-cells and an additional agent comprising apoptotic cells, a supernatant from apoptotic cells, a CTLA-4 blocking agent, an alpha-1 anti-trypsin or fragment or analog thereof, a tellurium-based compound, or an immune modulating agent, or any combination thereof, or compositions thereof, wherein the efficacy is increased compared with a subject not administered said additional agent. In another embodiment, methods of increasing the efficacy of a CAR T-cell cancer therapy disclosed herein comprises increasing proliferation of said CAR T-cells, said method comprising administering CAR T-cells and an additional agent comprising apoptotic cells, a supernatant from apoptotic cells, a CTLA-4 blocking agent, an alpha-1 anti-trypsin or fragment or analog thereof, a tellurium-based compound, or an immune modulating agent, or any combination thereof, or compositions thereof, wherein the efficacy and proliferation of said CAR T-cells is increased compared with a subject not administered said additional agent.

In one embodiment, methods of increasing the efficacy of CAR T-cell cancer therapy, decrease or inhibit cytokine production in the subject, said methods comprising the step of administering a composition comprising CAR T-cells and a CTLA-4 blocking agent, an alpha-1 anti-trypsin or fragment or analog thereof, a tellurium-based compound, or an immune modulating agent, or any combination thereof, or compositions thereof. In another embodiment, methods of treating, preventing, inhibiting, reducing the incidence of, ameliorating, or alleviating a cancer or tumor also decrease or inhibit cytokine production in the subject, said methods comprising the step of administering a composition comprising CAR T-cells and a CTLA-4 blocking agent, an alpha-1 anti-trypsin or fragment or analog thereof, a tellurium-based compound, or an immune modulating agent, or any combination thereof, or compositions thereof.

In another embodiment, disclosed herein are methods of treating cytokine release syndrome or cytokine storm in a subject undergoing CAR T-cell cancer therapy.

In another embodiment, methods of treating, preventing, inhibiting, reducing the incidence of, ameliorating, or alleviating a cancer or tumor, decrease or inhibit cytokine production in a subject, said methods comprising the step of administering a composition comprising CAR T-cells and a CTLA-4 blocking agent, an alpha-1 anti-trypsin or fragment or analog thereof, a tellurium-based compound, or an immune modulating agent, or any combination thereof, or compositions thereof.

In another embodiment, disclosed herein is a method of treating a cancer or a tumor in a subject, said method comprising the step of administering to said subject any of the compositions as described herein. In another embodiment, disclosed herein is a method of preventing a cancer or a tumor in a subject, said method comprising the step of administering to said subject any of the compositions as described herein. In another embodiment, disclosed herein is a method of inhibiting a cancer or a tumor in a subject, said method comprising the step of administering to said subject any of the compositions as described herein. In another embodiment, disclosed herein is a method of reducing a cancer or a tumor in a subject, said method comprising the step of administering to said subject any of the compositions as described herein. In another embodiment, disclosed herein is a method of ameliorating a cancer or a tumor in a subject, said method comprising the step of administering to said subject any of the compositions as described herein. In another embodiment, disclosed herein is a method of alleviating a cancer or a tumor in a subject, said method comprising the step of administering to said subject any of the compositions as described herein.

In one embodiment, disclosed herein are methods of maintaining or increasing the proliferation rate of a genetically modified immune cell during an immunotherapy, the method comprising the step of administering a composition comprising apoptotic cells or an apoptotic supernatant during the immunotherapy. In another embodiment, said genetically modified immune cells comprise a T-cell, a naïve T-cell, a naïve CD4+ T-cell, a naïve CD8+ T-cell, a natural killer (NK) cell, a dendritic cell, a cytotoxic T lymphocyte (CTL cell),a regulatory T-cell (Treg), a chimeric antigen receptor (CAR) T-cell, or a genetically modified T-cell receptor (TCR) cell. In another embodiment, disclosed herein are methods of maintaining or increasing the proliferation rate of a CAR T-cell during an immunotherapy, the method comprising the step of administering a composition comprising apoptotic cells or an apoptotic supernatant during the immunotherapy.

In another embodiment, methods of maintaining or increasing the proliferation rate of the genetically modified immune cells does not reduce or inhibit the efficacy of the immunotherapy. For example, in another embodiment, methods of maintaining or increasing the proliferation rate of CAR T-cells does not reduce or inhibit the efficacy of the CAR T-cell cancer therapy. In another embodiment, methods of maintaining or increasing the proliferation rate of the genetically modified immune cells, for example CAR T-cells, decrease or inhibit cytokine production in the subject.

In another embodiment, compositions and methods as disclosed herein utilize combination therapy with apoptotic cells or apoptotic supernatants as disclosed herein, and one or more CTLA-4-blocking agents such as Ipilimumab. In one embodiment, CTLA-4 is a potent inhibitor of T-cell activation that helps to maintain self-tolerance. In one embodiment, administration of an anti-CTLA-4 blocking agent, which in another embodiment, is an antibody, produces a net effect of T-cell activation. In another embodiment, compositions and methods as disclosed herein utilize combined therapy comprising apoptotic cells, CAR T-cells, and one or more CTLA-4-blocking agents.

In some cases, a polypeptide of and for use in the methods as disclosed herein comprises at least one conservative amino acid substitution relative to an unmodified amino acid sequence. In other cases, the polypeptide comprises a non-conservative amino acid substitution. In such cases, polypeptides having such modifications exhibit increased stability or a longer half-life relative to a polypeptide lacking such an amino acid substitution.

In some embodiment, "treating" comprises therapeutic treatment and "preventing" comprises prophylactic or preventative measures, wherein the object is to prevent or lessen the targeted pathologic condition or disorder as described hereinabove. Thus, in some embodiments, treating may include directly affecting or curing, suppressing, inhibiting, preventing, reducing the severity of, delaying the onset of, reducing symptoms associated with the disease, disorder or condition, or a combination thereof. Thus, in some embodiments, "treating," "ameliorating," and "alleviating" refer inter alia to delaying progression, expediting remission, inducing remission, augmenting remission, speeding recovery, increasing efficacy of or decreasing resistance to alternative therapeutics, or a combination thereof. In some embodiments, "preventing" refers, inter alia, to delaying the onset of symptoms, preventing relapse to a disease, decreasing the number or frequency of relapse episodes, increasing latency between symptomatic episodes, or a combination thereof. In some embodiments, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

A skilled artisan would appreciate that the term "antigen recognizing receptor" may encompass a receptor that is capable of activating an immune cell (e.g., a T-cell) in response to antigen binding. Exemplary antigen recognizing receptors may be native or endogenous T-cell receptors or chimeric antigen receptors in which a tumor antigen-binding domain is fused to an intracellular signaling domain capable of activating an immune cell (e.g., a T-cell).

In some embodiments, methods described herein increase the survival of a subject suffering from a cancer or a tumor, and comprise administering an early apoptotic cell population to said subject, wherein the method increases the survival of the subject.

A skilled artisan would appreciate that the term "disease" may encompass any condition or disorder that damages or interferes with the normal function of a cell, tissue, or organ. Examples of diseases include neoplasia or pathogen infection of cell.

A skilled artisan would appreciate that the term "effective amount" may encompass an amount sufficient to have a therapeutic effect. In some embodiments, an "effective amount" is an amount sufficient to arrest, ameliorate, or inhibit the continued proliferation, growth, or metastasis (e.g., invasion, or migration) of a neoplasia.

A skilled artisan would appreciate that the term "neoplasia" may encompass a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells).

A skilled artisan would appreciate that the term "pathogen" may encompass a virus, bacteria, fungi, parasite or protozoa capable of causing disease.

A skilled artisan would appreciate that the term "tumor antigen" or "tumor associated antigen" may encompass an antigen (e.g., a polypeptide) that is uniquely or differentially expressed on a tumor cell compared to a normal or non-IS neoplastic cell. With reference to the compositions and methods disclosed herein, a tumor antigen includes any polypeptide expressed by a tumor that is capable of activating or inducing an immune response via an antigen recognizing receptor (e.g., CD 19, MUCI) or capable of suppressing an immune response via receptor-ligand binding (e.g., CD47, PD-L1/L2, B7.1/2).

A skilled artisan would appreciate that the term "virus antigen" may encompass a polypeptide expressed by a virus that is capable of inducing an immune response.

The terms "comprises", "comprising", and are intended to have the broad meaning ascribed to them in U.S. Patent Law and can mean "includes", "including" and the like. Similarly, the term "consists of" and "consists essentially of" have the meanings ascribed to them in U.S. Patent Law. The compositions and methods as disclosed herein are envisioned to either comprise the active ingredient or specified step, consist of the active ingredient or specified step, or consist essentially of the active ingredient or specified step.

A skilled artisan would appreciate that the term "treatment" may encompass clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

A skilled artisan would appreciate that the term "subject" may encompass a vertebrate, in some embodiments, to a mammal, and in some embodiments, to a human. Subject may also refer, in some embodiments, to domesticated such as cows, sheep, horses, cats, dogs and laboratory animals such as mice, rats, gerbils, hamsters, etc.

In some embodiments, disclosed herein are CAR T-cells in which the CAR is directed to a peptide of interest. In some embodiments, the CAR binds to a peptide of interest. In another embodiment, the CAR targets a peptide of interest. In another embodiment, the CAR activates a peptide of interest. In another embodiment, the CAR is a ligand of the peptide of interest. In another embodiment, the peptide of interest is a ligand of the CAR. Each of these embodiments is to be considered part disclosed herein.

In some embodiments, the immune cell as disclosed herein is not a T-cell. In another embodiment, the immune cell as disclosed herein is not an NK cell. In another embodiment, the immune cell as disclosed herein is not a CTL. In another embodiment, the immune cell as disclosed herein is not a regulatory T-cell. In another embodiment, the immune cell is not a human embryonic stem cell. In another embodiment, the immune cell is not a pluripotent stem cell from which lymphoid cells may be differentiated.

One approach to immunotherapy involves engineering a patient's own immune cells to create genetically modified immune cells that will recognize and attack their tumor Immune cells are collected and genetically modified, as described herein, for example to produce chimeric antigen receptors (CAR) on their cell surface that will allow the immune cell, for example a T-cell, to recognize a specific protein antigen on a tumor or cancer cell. An expanded population of genetically modified immune cells, for example CAR T-cells, is then administered to the patient. In some embodiments, the administered cells multiply in the patient's body and recognize and kill cancer and tumor cells that harbor the antigen on their surface. In another embodiment, the administered cells multiply in a patient's body and recognize and kill tumor-associated antigens, which leads to the death of cancer and tumor cells.

In some embodiments, disclosed herein are methods of inhibiting or reducing the incidence of cytokine release syndrome or cytokine storm in a subject undergoing CAR T-cell cancer therapy, and methods of decreasing or inhibiting cytokine production in a subject experiencing cytokine release syndrome or cytokine storm, said methods comprising the step of administering a composition comprising apoptotic cells or a supernatant of apoptotic cells. In another embodiment, disclosed herein are methods of treating cytokine release syndrome or cytokine storm in a subject undergoing CAR T-cell cancer therapy. In another embodiment, disclosed herein are methods of preventing cytokine release syndrome or cytokine storm in a subject undergoing CAR T-cell cancer therapy. In another embodiment, disclosed herein are methods of alleviating cytokine release syndrome or cytokine storm in a subject undergoing CAR T-cell cancer therapy. In another embodiment, disclosed herein are methods of ameliorating cytokine release syndrome or cytokine storm in a subject undergoing CAR T-cell cancer therapy. In another embodiment, administration of apoptotic cells or an apoptotic supernatant or compositions thereof does not reduce the efficacy of the CAR T-cell therapy.

In some embodiments, disclosed herein are methods of inhibiting or reducing the incidence of a cytokine release syndrome (CRS) or a cytokine storm in a subject undergoing chimeric antigen receptor-expressing T-cell (CAR T-cell) cancer therapy, wherein the method comprises the step of administering a composition comprising apoptotic cells or an apoptotic cell supernatant or compositions thereof to said subject. In another embodiment, inhibiting or reducing the incidence of a cytokine release syndrome (CRS) or a cytokine storm is determined by measuring cytokine levels in a subject undergoing chimeric antigen receptor-expressing T-cell cancer therapy and being administered apoptotic cells or an apoptotic supernatant. In another embodiment, measured levels of cytokines are compared with cytokine levels in a subject not undergoing CAR T-cell cancer therapy. In another embodiment, measured cytokine levels are compared with cytokine levels in a subject not administer apoptotic cells or an apoptotic supernatant. In yet another embodiment, measured cytokine levels are compared with a control subject.

In another embodiment, the level of pro-inflammatory cytokines are reduced in the subject compared with a subject undergoing CAR T-cell cancer therapy and not administered said apoptotic cells or said apoptotic cell supernatant or compositions thereof. In another embodiment, methods disclosed herein reduce or inhibit the level of production of at least one pro-inflammatory cytokines compared with a subject undergoing CAR T-cell cancer therapy and not administered said apoptotic cells or said apoptotic cell supernatant or compositions thereof.

In another embodiment, a method disclosed herein may further comprise administration of additional agents. Alternatively, a method disclosed herein may comprise administration of additional agents and not apoptotic cells or an apoptotic cell supernatant. In still a further embodiment, additional agents may be those compounds or compositions that enhance or improve, or any combination thereof, CAR T-cell cancer therapy. In yet a further embodiment, additional agents that enhance or improve CAR T-cell cancer therapy include CTLA-4 blocking agents, an alpha-1antitrypsin or functional fragment thereof, or an analogue thereof, a tellurium-based compound, or an immune-modulating agent, or any combination thereof. In another embodiment, an additional agent includes apoptotic cells or an apoptotic supernatant. In another embodiment, administration of an additional agent, a described herein, is prior to, concurrent with, of following said CAR T-cell cancer therapy.

In some embodiments, an IL-6 receptor antagonist, which in one embodiment is tocilizumab is used with the compositions and methods as disclosed herein.

In some embodiments, adoptively transferred T-cells engraft and expand more efficiently in a lymphopenic host. Thus, in some embodiments, the subject is subjected to lymphodepletion prior to transfer of CAR T-cells or other modified immune cells. In another embodiment, the subject receiving the CAR T-cells is given T-cell-supportive cytokines.

In some embodiments, the T-cells are effector T-cells. In another embodiment, the T-cells are naïve T-cells. In another embodiment, the T-cells are central memory ($T_{CM}$) T-cells. In another embodiment, the T-cells are Th17 cells. In another embodiment, the T-cells are T stem memory cells. In another embodiment, the T-cells have high replicative capacity. In another embodiment, T-cell expansion occurs in the patient. In another embodiment, small numbers of cells may be transferred to a patient. In another embodiment, T-cell expansion occurs in vitro. In another embodiment, large numbers of cells may be transferred to a patient, cells and/or supernatants may be transferred to a patient on multiple occasions, or a combination thereof.

In some embodiments, an advantage of CAR T-cells is that because they are specific for cell-surface molecules, they overcome the constraints of MHC-restricted TCR recognition and avoid tumor escape through impairments in antigen presentation or human leukocyte antigen expression.

In some embodiments, disclosed herein is a method of reducing a tumor burden in a subject, said method comprising the step of administering to said subject any of the compositions as described herein.

In some embodiments, reducing the tumor burden comprises reducing the number of tumor cells in the subject. In another embodiment, reducing the tumor burden comprises reducing tumor size in the subject. In another embodiment, reducing the tumor burden comprises eradicating the tumor in the subject.

In another embodiment, disclosed herein is a method of inducing tumor cell death in a subject, said method comprising the step of administering to said subject any of the compositions as described herein. In another embodiment, a method as disclosed herein for inducing tumor cell death in a subject comprises administering immune cells, such as NK cells or T-cells comprising engineered chimeric antigen receptors with at least an additional agent to decrease toxic cytokine release or "cytokine release syndrome" (CRS) or "severe cytokine release syndrome" (sCRS) or "cytokine storm" in the subject.

In another embodiment, disclosed herein is a method of increasing or lengthening the survival of a subject having neoplasia, comprising the step of administering to said subject any of the compositions as described herein. In another embodiment, a method of increasing or lengthening the survival of a subject comprises administering immune cells, such as NK cells or T-cells comprising engineered chimeric antigen receptors with at least an additional agent to decrease toxic cytokine release or "cytokine release syndrome" (CRS) or "severe cytokine release syndrome" (sCRS) or "cytokine storm" in the subject.

In another embodiment, disclosed herein is a method of increasing or lengthening the survival of a subject having neoplasia, comprising the step of administering to said subject any of the compositions as described herein.

In some embodiments, disclosed herein is a method of delaying cancer progression in a subject, comprising a step of administering to the subject any of the compositions or combinations of compositions described herein. In some embodiments, disclosed herein is a method of delaying progression of a leukemia or lymphoma in a subject, comprising a step of administering to the subject any of the compositions or combinations of compositions described herein. In some embodiments, disclosed herein is a method of increasing, extending, or prolonging the survival of a subject suffering from a cancer or a tumor, comprising a step of administering to the subject any of the compositions or combinations of compositions described herein. In some embodiments, disclosed herein is a method of increasing, extending, or prolonging the survival of a subject suffering from a leukemia or lymphoma, comprising administering to the subject any of the compositions or combinations of compositions described herein. In some embodiments, disclosed herein is a method of reducing the tumor cell burden in a subject, comprising administering to the subject any of the compositions or combinations of compositions described herein. In some embodiments, tumor burden is reduced the liver and bone marrow.

In another embodiment, disclosed herein is a method of preventing neoplasia in a subject, said method comprising the step of administering to the subject any of the compositions or combinations of compositions described herein. In some embodiments, the neoplasia is selected from the group consisting of blood cancer, B cell leukemia, multiple myeloma, lymphoblastic leukemia (ALL), chronic lymphocytic leukemia, non-Hodgkin's lymphoma, ovarian cancer, or a combination thereof.

In another embodiment, disclosed herein is a method of treating blood cancer in a subject in need thereof, comprising the step of administering to said subject any of the compositions as described herein. In some embodiments, the blood cancer is selected from the group consisting of B cell leukemia, multiple myeloma, acute lymphoblastic leukemia (ALL), chronic lymphocytic leukemia, and non-Hodgkin's lymphoma.

In some embodiments, administration comprises administering a composition comprising CAR T-cells. In some embodiments, administration comprises administering a composition comprising early apoptotic cells. In some embodiments, administration comprises administering a composition comprising a supernatant obtained from early apoptotic cells. In some embodiments, administration comprises administering a combination of compositions described herein. In some embodiments, administration comprises administering CAR T-cells and apoptotic cells in the same or different compositions. In some embodiments, administration comprises administering CAR T-cells in combination with an additional agent as described herein. In some embodiments, administration comprises administering apoptotic cells and an antibody or fragment thereof in the same or different compositions.

In some embodiments, combination therapy provides a synergistic effect. In some embodiments, methods of use an early apoptotic cells in combination with CAR T-cells increases CAR T-cell efficacy in comparison to use of CAR T-cells alone. In some embodiments, methods of use an early apoptotic cells in combination with CAR T-cells extends the survival time of a subject suffering from a cancer or tumor in comparison to use of CAR T-cells alone. In some embodiments, methods of use an early apoptotic cells in combination with CAR T-cells extends the survival time of a subject suffering from a lymphoma or leukemia in comparison to use of CAR T-cells alone.

In some embodiments, methods of use an early apoptotic cells in combination with an antibody or fragment thereof delays the onset of cancer or the appearance of a tumor, in comparison to use of either apoptotic cells or the antibody alone. In some embodiments, methods of use an early apoptotic cells in combination with an antibody or fragment thereof delays the progression of a cancer, in comparison to use of either apoptotic cells or the antibody alone. In some embodiments, methods of use an early apoptotic cells in combination with an antibody or fragment thereof delays the growth of a tumor, in comparison to use of either apoptotic cells or the antibody alone. In some embodiments, methods of use an early apoptotic cells in combination with an antibody or fragment thereof extends the survival time of a subject suffering from a cancer or tumor in comparison to use of either apoptotic cells or the antibody alone. In some embodiments, methods of use an early apoptotic cells in combination with an antibody or fragment thereof extends the survival time of a subject suffering from a lymphoma or leukemia in comparison to use of either apoptotic cells or the antibody alone.

In some embodiments, methods of use comprising administration of an early apoptotic cells in combination with an antibody or fragment thereof comprising RtX, delays the onset of cancer or the appearance of a tumor, in comparison to use of either apoptotic cells or the antibody alone. In some embodiments, methods of use an early apoptotic cells in combination with an antibody or fragment thereof comprising RtX, delays the progression of a cancer, in comparison to use of either apoptotic cells or the antibody alone. In some embodiments, methods of use an early apoptotic cells in combination with an antibody or fragment thereof comprising RtX, delays the growth of a tumor, in comparison to use of either apoptotic cells or the antibody alone. In some embodiments, methods of use an early apoptotic cells in combination with an antibody or fragment thereof comprising RtX, extends the survival time of a subject suffering from a cancer or tumor in comparison to use of either apoptotic cells or the antibody alone. In some embodiments, methods of use an early apoptotic cells in combination with an antibody or fragment thereof comprising RtX, extends the survival time of a subject suffering from a lymphoma or leukemia in comparison to use of either apoptotic cells or the antibody alone.

In some embodiments, methods of use described herein reduce tumor load. A skilled artisan would appreciate that the term "tumor load" may refer to the number of cancer cells, the size of a tumor, or the amount of cancer in the body. The term "tumor load" may be used interchangeably with the term "tumor burden" having all the same meanings and qualities. In some embodiments, methods of use comprising administration of an early apoptotic cells reduces the number of cancer cells in a subject, reduces the size of a tumor in a subject, or reduces the amount of cancer in the body of a subject, or any combination thereof compared with a subject not administered apoptotic cells. In some embodiments, methods of use comprising administration of an early apoptotic cells in combination with an antibody or fragment thereof reduces the number of cancer cells in a subject, reduces the size of a tumor in a subject, or reduces the amount of cancer in the body of a subject, or any combination thereof, compared with a subject not administered apoptotic cells or not administer the antibody, or the combination thereof. In some embodiments, methods of use comprising administration of an early apoptotic cells in combination with a RtX antibody or fragment thereof reduces the number of cancer cells in a subject, reduces the size of a tumor in a subject, or reduces the amount of cancer in the body of a subject, or any combination thereof, compared with a subject not administered apoptotic cells, the RtX antibody, or the combination thereof.

In some embodiments, a method of decreasing or inhibiting cytokine production in a subject experiencing cytokine release syndrome or cytokine storm or vulnerable to a cytokine release syndrome or cytokine storm, as disclosed herein, decreases or inhibits cytokine production. In another embodiment, the method decreases or inhibits pro-inflammatory cytokine production. In a further embodiment, the method decreases or inhibits at least one pro-inflammatory cytokine. In another embodiment, wherein the subject is undergoing CAR T-cell cancer therapy, the method does not reduce the efficacy of the CAR T-cell therapy.

The methods provided herein comprise administering a T-cell, NK cell, or CTL cell disclosed herein, in an amount effective to achieve the desired effect, be it palliation of an existing condition or prevention of recurrence. For treatment, the amount administered is an amount effective in producing the desired effect. An effective amount can be provided in one or a series of administrations. An effective amount can be provided in a bolus or by continuous perfusion.

A skilled artisan would recognize that an "effective amount" (or, "therapeutically effective amount") may encompass an amount sufficient to effect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the antigen-binding fragment administered.

In one embodiment, methods disclosed herein comprise administering a composition comprising a genetically modified cell, and the additional agent or combination thereof, comprised in a single composition. In another embodiment, methods comprise administering a composition comprising a CAR T-cell, and the additional agent or combination thereof, comprised in a single composition. In another embodiment, methods comprise administering a composition comprising a TCR T-cell, and the additional agent or combination thereof, comprised in a single composition.

In one embodiment, methods disclosed herein comprise administering a composition comprising a genetically modified cell, and the additional agent or combination thereof, comprised in a at least two compositions. In another embodiment, methods comprise administering a composition comprising a CAR T-cell, and the additional agent or combination thereof, comprised in at least two compositions. In another embodiment, methods comprise administering a composition comprising a TCR T-cell, and the additional agent or combination thereof, comprised in at least two compositions.

For adoptive immunotherapy using antigen-specific T-cells, for example CAR T-cells, cell doses in the range of $10^6$-$10^{10}$ (e.g., $10^9$) are typically infused. Upon administration of the genetically modified cells into the host and subsequent differentiation, T-cells are induced that are specifically directed against the specific antigen. "Induction" of T-cells may include inactivation of antigen-specific T-cells such as by deletion or anergy. Inactivation is particularly useful to establish or reestablish tolerance such as in autoimmune disorders. The modified cells can be administered by any method known in the art including, but not limited to, intravenous, subcutaneous, intranodal, intratumoral, intrathecal, intrapleural, intraperitoneal and directly to the thymus. In some embodiments, the T-cells are not administered intraperitoneally. In some embodiments, the T-cells are administered intratumorallly.

Compositions comprising genetically modified immunoresponsive cells as disclosed herein (e.g., T-cells, N cells, CTL cells, or their progenitors) can be provided systemically or directly to a subject for the treatment of a neoplasia, pathogen infection, or infectious disease. In some embodiments, cells disclosed herein are directly injected into an organ of interest (e.g., an organ affected by a neoplasia). Alternatively, compositions comprising genetically modified immunoresponsive cells are provided indirectly to the organ of interest, for example, by administration into the circulatory system (e.g., the tumor vasculature). Expansion and differentiation agents can be provided prior to, during or after administration of the cells to increase production of T-cells, NK cells, or CTL cells in vitro or in vivo.

As described above in methods disclosed herein, compositions comprising additional agents may be provided prior to, concurrent with, or following administrations of the genetically modified immune cells. In one embodiment, in methods disclosed herein genetically modified immune cells for example CAR T-cells are administered prior to an additional agent as disclosed herein. In another embodiment, in methods disclosed herein genetically modified immune cells for example CAR T-cells are administered concurrent with an additional agent, as disclosed herein. In another embodiment, in methods disclosed herein genetically modified immune cells for example CAR T-cells are administered following administration of an additional agent.

In one embodiment, methods disclosed herein administer compositions comprising apoptotic cells as disclosed herein. In another embodiment, methods disclosed herein administer compositions comprising apoptotic cell supernatants as disclosed herein.

The modified cells can be administered in any physiologically acceptable vehicle, normally intravascularly, although they may also be introduced into bone or other convenient site where the cells may find an appropriate site for regeneration and differentiation (e.g., thymus). Usually, at least $1 \times 10^5$ cells will be administered, eventually reaching $1 \times 10^{10}$ or more. Genetically modified immunoresponsive cells disclosed herein may comprise a purified population of cells. Those skilled in the art can readily determine the percentage of genetically modified immunoresponsive cells in a population using various well-known methods, such as fluorescence activated cell sorting (FACS). In some embodiments, ranges of purity in populations comprising genetically modified immunoresponsive cells are about 50 to about 55%, about 55 to about 60%, and about 65 to about 70%. In other embodiments, the purity is about 70 to about 75%, about 75 to about 80%, about 80 to about 85%. In further embodiments, the purity is about 85 to about 90%, about 90 to about 95%, and about 95 to about 100%. Dosages can be readily adjusted by those skilled in the art (e.g., a decrease in purity may require an increase in dosage). The cells can be introduced by injection, catheter, or the like. If desired, factors can also be included, including, but not limited to, interleukins, e.g. IL-2, IL-3, IL-6, IL-1 1, IL7, IL12, ILIS, IL21, as well as the other interleukins, the colony stimulating factors, such as G-, M- and GM-CSF, interferons, e.g. gamma-interferon and erythropoietin.

Compositions include pharmaceutical compositions comprising genetically modified immunoresponsive cells or their progenitors and a pharmaceutically acceptable carrier. Administration can be autologous or heterologous. For example, immunoresponsive cells, or progenitors can be obtained from one subject, and administered to the same subject or a different, compatible subject. Peripheral blood derived immunoresponsive cells disclosed herein or their progeny (e.g., in vivo, ex vivo or in vitro derived) can be administered via localized injection, including catheter administration, systemic injection, localized injection, intravenous injection, or parenteral administration. When administering a therapeutic composition as disclosed herein (e.g., a pharmaceutical composition containing a genetically modified immunoresponsive cell), it will generally be formulated in a unit dosage injectable form (solution, suspension, emulsion).

In another embodiment, disclosed herein is a method of producing a composition comprising CAR T-cells or other immune cells as disclosed herein and apoptotic cells or an apoptotic cell supernatant, the method comprising introducing into the T-cell or immune cell the nucleic acid sequence encoding the CAR that binds to an antigen of interest. In an alternative embodiment, the compositions comprising CAR T-cells or other immune cells as disclosed herein are separate from the composition comprising apoptotic cells or an apoptotic supernatant.

In one embodiment, disclosed herein is a method of treating, preventing, inhibiting, reducing the incidence of, ameliorating, or alleviating a malignancy comprising the step of administering a composition comprising chimeric antigen receptor-expressing T-cells (CAR T-cells) and apoptotic cells or an apoptotic cell supernatant.

A skilled artisan would appreciate that an anti-tumor immunity response elicited by the genetically modified immune cells, for example CAR-modified T cells, may be an active or a passive immune response. In addition, the CAR mediated immune response may be part of an adoptive immunotherapy approach in which CAR-modified T-cells induce an immune response specific to the antigen binding moiety in the CAR.

A skilled artisan would appreciate that immunotherapeutics may encompass the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In some embodiments, the early apoptotic cells and compositions thereof, as disclosed herein may be used to treat, prevent, inhibit the growth of, or reduce the incidence of, any hematological tumor known in the art. In some embodiments, the early apoptotic cells and compositions thereof, as disclosed herein may be used to treat, prevent, inhibit the growth of, or reduce the incidence of, any diffuse cancer known in the art, for example but not limited to diffuse breast cancer, wherein a solid tumor is not formed in the breast. In some embodiments, the early apoptotic cells and compositions thereof, as disclosed herein may be used to extend the survival time of any hematological tumor known in the art. In some embodiments, the early apoptotic cells and compositions thereof, as disclosed herein may be used to extend the survival time of any diffuse cancer known in the art, for example but not limited to diffuse breast cancer, wherein a solid tumor is not formed in the breast.

In some embodiments, the early apoptotic cells and compositions thereof, as disclosed herein may be used to increase the survival of a subject suffering from any hematological tumor known in the art. In some embodiments, the early apoptotic cells and compositions thereof, as disclosed herein may be used to increase the survival of a subject suffering from any diffuse cancer known in the art, for example but not limited to diffuse breast cancer, wherein a solid tumor is not formed in the breast.

In some embodiments, the early apoptotic cells and compositions thereof, as disclosed herein may be used to reduce the growth rate of any hematological tumor known in the art. In some embodiments, the early apoptotic cells and compositions thereof, as disclosed herein may be used to reduce the growth rate any diffuse cancer known in the art, for example but not limited to diffuse breast cancer, wherein a solid tumor is not formed in the breast.

In some embodiments, the tumor or cancer being treated comprises a metastasis of a tumor or cancer. In some embodiments, methods of use herein prevent or reduce metastasis of a tumor or cancer. In some embodiments, methods of use herein inhibit the growth or reduce the incidence of metastasis.

In some embodiments, the subject is a human subject. In some embodiments, the subject is a child. In some embodiments, the subject is an adult. In some embodiments, the subject is animal mammal.

In some embodiments, a method disclosed herein comprises administering an early apoptotic cell population comprising a mononuclear enriched cell population, as described in detail above. In some embodiments, a method disclosed herein comprises administering an early apoptotic cell population comprising a stable population cell, wherein said cell population is stable for greater than 24 hours. Stable populations of early apoptotic cells have been described in detail above. In some embodiments, a method disclosed herein comprises administering an early apoptotic cell population comprising a population of cells devoid of cell aggregates. Early apoptotic cell populations devoid of aggregates and methods of making them have been described in detail above.

In some embodiments, a method disclosed herein comprises administering an autologous early apoptotic cell population to a subject in need. In some embodiments, a method disclosed herein comprises administering an allogeneic early apoptotic cell population to a subject in need.

In some embodiments, methods of administration of early apoptotic cell populations or compositions thereof comprise administering a single infusion of said apoptotic cell population or composition thereof. In some embodiments, a single infusion may be administered as a prophylactic to a subject predetermined to be at risk for a cancer or tumor. In some embodiments, a single infusion may be administered to a subject having a cancer or tumor on a regular basis as a part of the subject therapeutic treatment. In some embodiments, a single infusion may be administered as a prophylactic to a subject having a cancer or tumor in order to prevent, reduce the risk of, or delay the appearance of metastatic cancer.

In some embodiments, methods of administration of early apoptotic cell populations or compositions thereof comprise administering multiple infusions of said apoptotic cell population or composition thereof. In some embodiments, multiple infusions may be administered as a prophylactic to a subject predetermined to be at risk for a cancer or tumor. In some embodiments, multiple infusions may be administered to a subject having a cancer or tumor on a regular basis as a part of the subject therapeutic treatment. In some embodiments, multiple infusions may be administered as a prophylactic to a subject having a cancer or tumor in order to prevent, reduce the risk of, or delay the appearance of metastatic cancer.

In some embodiments, multiple infusions comprise at least two infusions. In some embodiments, multiple infusions comprise 2 infusions. In some embodiments, multiple infusions comprise more than 2 infusions. In some embodiments, multiple infusions comprise at least 3 infusions. In some embodiments, multiple infusions comprise 3 infusions. In some embodiments, multiple infusions comprise more than 3 infusions. In some embodiments, multiple infusions comprise at least 4 infusions. In some embodiments, multiple infusions comprise 4 infusions. In some embodiments, multiple infusions comprise more than 4 infusions. In some embodiments, multiple infusions comprise at least 5 infusions. In some embodiments, multiple infusions comprise 5 infusions. In some embodiments, multiple infusions comprise more than 5 infusions. In some embodiments, multiple infusions comprise at least six infusions. In some embodiments, multiple infusions comprise 6 infusions. In some embodiments, multiple infusions comprise more than 6 infusions. In some embodiments, multiple infusions comprise at least 7 infusions. In some embodiments, multiple infusions comprise 7 infusions. In some embodiments, multiple infusions comprise more than 7 infusions. In some embodiments, multiple infusions comprise at least 8 infusions. In some embodiments, multiple infusions comprise 8 infusions. In some embodiments, multiple infusions comprise more than 8 infusions. In some embodiments, multiple infusions comprise at least nine infusions. In some embodiments, multiple infusions comprise 9 infusions. In some embodiments, multiple infusions comprise more than 9 infusions. In some embodiments, multiple infusions comprise at least 10 infusions. In some embodiments, multiple infusions comprise 10 infusions. In some embodiments, multiple infusions comprise more than 10 infusions.

In some embodiments, multiple infusions comprise smaller amounts of early apoptotic cell, wherein the total dosage of cells administered is the sum of the infusions.

In some embodiments, multiple infusions are administered over a period of hours. In some embodiments, multiple infusions are administered over a period of days. In some embodiments, multiple infusions are administered over a period of hours, wherein there is at least 12 hours between infusions. In some embodiments, multiple infusions are administered over a period of hours, wherein there is at least 24 hours between infusions. In some embodiments, multiple infusions are administered over a period of hours, wherein there is at least a day between infusions. In some embodiments, multiple infusions are administered over a period of hours, wherein there is at least two days between infusions. In some embodiments, multiple infusions are administered over a period of hours, wherein there is at least three days between infusions. In some embodiments, multiple infusions are administered over a period of hours, wherein there is at least four days between infusions. In some embodiments, multiple infusions are administered over a period of hours, wherein there is at least five days between infusions. In some embodiments, multiple infusions are administered over a period of hours, wherein there is at least six days between infusions. In some embodiments, multiple infusions are administered over a period of hours, wherein there is at least seven days between infusions. In some embodiments, multiple infusions are administered over a period of hours, wherein there is at least a week between infusions. In some embodiments, multiple infusions are administered over a period of hours, wherein there is at least two weeks between infusions.

In some embodiments, the amount of cells in multiple infusions is essentially equivalent one to the other. In some embodiments, the amount of cells in multiple infusions is different one to the other.

In some embodiments, the methods described herein further comprise administering an additional chemotherapeutic agent or an immune modulator to said subject.

In some embodiments, an additional chemotherapeutic agent or immune modulator is administered concurrent or essentially concurrent with the early apoptotic cells. In some embodiments, an additional chemotherapeutic agent or immune modulator is comprised in the same composition as the early apoptotic cells. In some embodiments, an additional chemotherapeutic agent or immune modulator is comprised in a different composition as the early apoptotic cells.

In some embodiments, an additional chemotherapeutic agent or immune modulator is administered prior to the administration of the early apoptotic cells. In some embodiments, an additional chemotherapeutic agent or immune modulator is administered following the administration of the early apoptotic cells.

In some embodiments, the chemotherapeutic agent comprises alkylating agents, nitrogen mustards, nitrosoureas, tetrazines, aziridines, cisplatins and derivatives, non-classical alkylating agents, mechlorethamine, cyclophosphamide, melphalan, chlorambucil, ifosfamide, busulfan, N-Nitroso-N-methylurea (MNU), carmustine (BCNU), lomustine (CCNU), semustine (MeCCNU), fotemustine, streptozotocin, dacarbazine, mitozolomide, temozolomide, thiotepa, mitomycin, diaziquone (AZQ), cisplatin, carboplatin, oxaliplatin, procarbazine, hexamethylmelamine, antimetabolites, anti-folates, methotrexate, pemetrexed, fluoropyrimidines, fluorouracil, capecitabine, deoxynucleoside analogues, cytarabine, gemcitabine, decitabine, azacitidine, fludarabine, nelarabine, cladribine, clofarabine, and pentostatin, thiopurines, thioguanine, mercaptopurine, anti-microtubule agents, vinca alkaloids, taxanes, vincristine, vinblastine, semi-synthetic vinca alkaloids, vinorelbine, vindesine, vinflunine, paclitaxel, docetaxel, podophyllotoxin, etoposide, teniposide, topoisomerase inhibitors, irinotecan, topotecan, camptothecin, etoposide, doxorubicin, mitoxantrone, teniposide, catalytic inhibitors, novobiocin, merbarone, aclarubicin, cytotoxic antibiotics, anthracyclines, bleomycins, mitomycin C, mitoxantrone, actinomycin, doxorubicin, daunorubicin, epirubicin, idarubicin, anthracyclines, pirarubicin, aclarubicin, mitoxantrone, bleomycin, mitomycin, targeted therapies, monoclonal antibodies, naked monoclonal antibodies, conjugated monoclonal antibodies, chemolabeled antibodies, bispecific monoclonal antibodies, or any combination thereof.

In some embodiments, an immune modulator comprises an antibody or a functional fragment thereof. In some embodiments, an antibody or functional fragment thereof comprises a monoclonal antibody, a single chain antibody, an Fab fragment, an F(ab')2 fragment, or an Fv fragment.

In some embodiments, disclosed herein are active fragments of any one of the polypeptides or peptide domains disclosed herein. A skilled artisan would appreciate that the term "a fragment" may encompass at least 5, 10, 13, or 15 amino acids. In other embodiments a fragment is at least 20 contiguous amino acids. Fragments disclosed herein can be generated by methods known to those skilled in the art or may result from normal protein processing (e.g., removal of amino acids from the nascent polypeptide that are not required for biological activity or removal of amino acids by alternative mRNA splicing or alternative protein processing events).

The terms "antibody" and "immunoglobulin" are used interchangeably in the broadest sense and specifically refer to a polyclonal antibody, a monoclonal antibody, or any fragment thereof, which retains the binding activity of the antibody. In certain embodiments, methods disclosed herein comprise use of a chimeric antibody, a humanized antibody, or a human antibody.

In some embodiments, the term "antibody" refers to intact molecules as well as functional fragments thereof, such as Fab, F(ab')2, and Fv that are capable of specifically interacting with a desired target as described herein, for example, binding to phagocytic cells. In some embodiments, the antibody fragments comprise:

(1) Fab, the fragment which contains a monovalent antigen-binding fragment of an antibody molecule, which can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

In some embodiments, the antibody fragments may be prepared by proteolytic hydrolysis of the antibody or by expression in E. coli or mammalian cells (e.g. Chinese hamster ovary cell culture or other protein expression systems) of DNA encoding the fragment.

Antibody fragments can, in some embodiments, be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments.

Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. Fv fragments comprise an association of VH and VL chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

In some embodiments, the antibodies or fragments as described herein may comprise "humanized forms" of antibodies. In some embodiments, the term "humanized forms of antibodies" refers to non-human (e.g. murine) antibodies, which are chimeric molecules of immunoglobulins, immunoglobulin chains or fragments thereof (such as Fv, Fab, Fab', F(ab'). sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e g mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

In some embodiments, the immune modulator comprises an anti-CD20 monoclonal antibody. In some embodiments, the antiCD20 monoclonal antibody is Rituximab. Rituximab is commercially available and sold under the name Rituxan®, marketed jointly by Biogen and Genentech USA, Inc.

In some embodiments, methods disclosed herein comprise a first-line therapy.

A skilled artisan would appreciate that the term "first-line therapy" may encompass the first treatment given for a disease. It is often part of a standard set of treatments, such as surgery followed by chemotherapy and radiation. When used by itself, first-line therapy is the one accepted as the best treatment. If it doesn't cure the disease or it causes severe side effects, other treatment may be added or used instead. Also called induction therapy, primary therapy, and primary treatment.

In some embodiments, methods disclosed herein comprise an adjuvant therapy.

A skilled artisan would appreciate that the term "adjuvant therapy" may encompass a treatment that is given in addition to the primary or initial treatment. In some embodiments, adjuvant therapy may comprise an additional cancer treatment given prior to the primary treatment in preparation of a further treatment. In some embodiments, adjuvant therapy may comprise an additional cancer treatment given after the primary treatment to lower the risk that the cancer will come back. Adjuvant therapy may include chemotherapy, radiation therapy, hormone therapy, targeted therapy, or biological therapy.

In some embodiments, a method disclosed herein, reduces the minimal residual disease, increases remission, increases remission duration, reduces tumor relapse rate, decreases the size of said tumor, decreases growth rate of said tumor or said cancer, prevents metastasis of said tumor or said cancer, or reduces the rate of metastasis of said tumor or said cancer, or any combination thereof.

A skilled artisan would appreciate that the term "minimal residual disease" may encompass small numbers of cancer cells that remain in the patient during treatment or after treatment when the patient has no symptoms or signs of disease.

Additionally, the term "remission" may encompass a decrease or disappearance of signs and symptoms of cancer, though cancer may still be in the body. In some embodiments, remission may comprise partial remission, wherein some, but not all, signs and symptoms of cancer have disappeared. In some embodiments, remission comprises complete remission, wherein all signs and symptoms of cancer have disappeared, although cancer still may be in the body. In some embodiments, methods disclosed herein may be comprise a remission induction therapy, wherein the initial treatment with early apoptotic cells or compositions thereof, decreases the signs or symptoms of cancer or make them disappear.

A skilled artisan would appreciate that the term "relapse" may encompass the return of a disease or the signs and symptoms of a disease after a period of improvement. In some embodiments, methods used herein lead to a relapse-free survival, wherein the relapse-free survival encompasses the length of time after primary treatment for a cancer ends that the patient survives without any signs or symptoms of that cancer.

A skilled artisan would appreciate that the term "metastasis" encompasses the spread of cancer cells from the place where they first formed to another part of the body. In metastasis, cancer cells break away from the original (primary) tumor, travel through the blood or lymph system, and form a new tumor in other organs or tissues of the body. In some embodiments, the new, metastatic tumor is the same type of cancer as the primary tumor. For example, if breast cancer spreads to the lung, the cancer cells in the lung are breast cancer cells, not lung cancer cells.

Malignancies

In some embodiments, CAR T-cells are utilized in methods of treating, preventing, inhibiting, reducing the incidence of, ameliorating, or alleviating a cancer or a tumor wherein the methods comprise the step of administering chimeric antigen receptor-expressing T-cells (CAR T-cells). As disclosed herein, these methods may further comprise administering an additional agent in an effort to inhibit or decrease the incidence of CRS or cytokine storm.

In some embodiments, a method disclosed herein increases the survival of the subject. In some embodiments, disclosed herein is a method of increasing or lengthening the survival of a subject having a diffuse cancer, comprising the step of administering an early apoptotic cell population to said subject, wherein the method increases the survival of the subject.

In some embodiments, a cancer is a B-cell malignancy. In some embodiments, the B-cell malignancy is leukemia. In another embodiment, the B-cell malignancy is acute lymphoblastic leukemia (ALL). In another embodiment, the B-cell malignancy is chronic lymphocytic leukemia.

In some embodiments, the cancer is leukemia. In some embodiments, the cancer is lymphoma. In some embodiments, the lymphoma is large B-cell lymphoma.

In some embodiments, methods described herein reduce the size or reduce the growth rate of a cancer or a tumor, and comprise administering an early apoptotic cell population to said subject, wherein the method reduces the size or the growth rate of a cancer or tumor. In some embodiments, disclosed herein is a method of reducing the growth rate of a diffuse cancer, comprising the step of administering an early apoptotic cell population to said subject, wherein the method reduces the growth rate of the cancer. In some embodiments, disclosed herein is a method of reducing the size or reducing the growth rate of a solid cancer or tumor, comprising the step of administering an early apoptotic cell population to a subject, wherein the method reduces the size or reduces the growth rate of the solid cancer or tumor.

In some embodiments, a cancer may comprise a solid tumor. In some embodiments, a solid tumor comprises an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas. Leukemias (cancers of the blood) generally do not form solid tumors. In some embodiments, a solid tumor comprises a sarcoma or a carcinoma.

In some embodiments, solid tumors are neoplasms (new growth of cells) or lesions (damage of anatomic structures or disturbance of physiological functions) formed by an abnormal growth of body tissue cells other than blood, bone marrow or lymphatic cells. In some embodiments, a solid tumor consists of an abnormal mass of cells which may stem from different tissue types such as liver, colon, breast, or lung, and which initially grows in the organ of its cellular origin. However, such cancers may spread to other organs through metastatic tumor growth in advanced stages of the disease.

In some embodiments, examples of solid tumors comprise sarcomas, carcinomas, and lymphomas. In some embodiments, a solid tumor comprises a sarcoma or a carcinoma. In some embodiments, the solid tumor is an intra-peritoneal tumor.

In some embodiments, a solid tumor comprises, but is not limited to, lung cancer, breast cancer, ovarian cancer, stomach cancer, esophageal cancer, cervical cancer, head and neck cancer, bladder cancer, liver cancer, and skin cancer. In some embodiments, a solid tumor comprises a fibrosarcoma, a myxosarcoma, a liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, an Ewing's tumor, a leiomyosarcoma, a rhabdomyosarcoma, a colon carcinoma, a pancreatic cancer or tumor, a breast cancer or tumor, an ovarian cancer or tumor, a prostate cancer or tumor, a squamous cell carcinoma, a basal cell carcinoma, an adenocarcinoma, a sweat gland carcinoma, a sebaceous gland carcinoma, a papillary carcinoma, a papillary adenocarcinomas, a cystadenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilm's tumor, a cervical cancer or tumor, a uterine cancer or tumor, a testicular cancer or tumor, a lung carcinoma, a small cell lung carcinoma, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodenroglioma, a schwannoma, a meningioma, a melanoma, a neuroblastoma, or a retinoblastoma.

In some embodiments, the solid tumor comprises an Adrenocortical Tumor (Adenoma and Carcinoma), a Carcinoma, a Colorectal Carcinoma, a Desmoid Tumor, a Desmoplastic Small Round Cell Tumor, an Endocrine Tumor, an Ewing Sarcoma, a Germ Cell Tumor, a Hepatoblastoma a Hepatocellular Carcinoma, a Melanoma, a Neuroblastoma, an Osteosarcoma, a Retinoblastoma, a Rhabdomyosarcoma, a Soft Tissue Sarcoma Other Than Rhabdomyosarcoma, and a Wilms Tumor. In some embodiments, the solid tumor is a breast tumor. In another embodiment, the solid tumor is a prostate cancer. In another embodiment, the solid tumor is a colon cancer. In some embodiments, the tumor is a brain tumor. In another embodiment, the tumor is a pancreatic tumor. In another embodiment, the tumor is a colorectal tumor.

In some embodiments, early apoptotic cells or compositions thereof as disclosed herein, have therapeutic and/or prophylactic efficacy against a cancer or a tumor, for example sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

In some embodiments, the early apoptotic cells and compositions thereof as disclosed herein may be used to treat, prevent, inhibit the growth of, or reduce the incidence of, any solid tumor known in the art.

In some embodiments, the early apoptotic cells and compositions thereof as disclosed herein, may be used to increase the survival of a subject suffering from any solid tumor as disclosed herein or known in the art.

In some embodiments, the early apoptotic cells and compositions thereof as disclosed herein, may be used to reduce the size or reduce the growth rate any solid tumor as disclosed herein or known in the art.

In some embodiments, a cancer may be a diffuse cancer, wherein the cancer is widely spread; not localized or confined. In some embodiments, a diffuse cancer may comprise a non-solid tumor. Examples of diffuse cancers include leukemias. Leukemias comprise a cancer that starts in blood-forming tissue, such as the bone marrow, and causes large numbers of abnormal blood cells to be produced and enter the bloodstream.

In some embodiments, a diffuse cancer comprises a B-cell malignancy. In some embodiments, the diffuse cancer comprises leukemia. In some embodiments, the cancer is lymphoma. In some embodiments, the lymphoma is large B-cell lymphoma.

In some embodiments, the diffuse cancer or tumor comprises a hematological tumor. In some embodiments, hematological tumors are cancer types affecting blood, bone marrow, and lymph nodes. Hematological tumors may derive from either of the two major blood cell lineages: myeloid and lymphoid cell lines. The myeloid cell line normally produces granulocytes, erythrocytes, thrombocytes, macrophages, and masT-cells, whereas the lymphoid cell line produces B, T, NK and plasma cells. Lymphomas (e.g. Hodgkin's Lymphoma), lymphocytic leukemias, and myeloma are derived from the lymphoid line, while acute and chronic myelogenous leukemia (AML, CML), myelodysplastic syndromes and myeloproliferative diseases are myeloid in origin.

In some embodiments, a non-solid (diffuse) cancer or tumor comprises a hematopoietic malignancy, a blood cell cancer, a leukemia, a myelodysplastic syndrome, a lymphoma, a multiple myeloma (a plasma cell myeloma), an acute lymphoblastic leukemia, an acute myelogenous leukemia, a chronic myelogenous leukemia, a Hodgkin lymphoma, a non-Hodgkin lymphoma, or plasma cell leukemia.

In another embodiment, early apoptotic cells and compositions thereof, as disclosed herein have therapeutic and/or prophylactic efficacy against diffuse cancers, for example but not limited to leukemias (e.g., acute leukemia, acute lymphocytic leukemia, acute myelocytic leukemia, acute myeloblastic leukemia, acute promyelocyte leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease.

The compositions and methods as disclosed herein may be used to treat, prevent, inhibit, ameliorate, reduce the incidence of, or alleviate any hematological tumor known in the art.

A skilled artisan would appreciate that the use of the term comprising throughout, may in certain embodiments be replace by the use of the term consisting essentially of or consisting of. The skilled artisan would appreciate that the term "comprising" is intended to mean that the system includes the recited elements, but not excluding others which may be optional. For example a composition comprising early apoptotic cells but not limited to this population of cells. Further, the term "consisting essentially of" may encompass a method that includes the recited elements, for example a composition consisting essentially or early apoptotic cells but exclude other elements that may have an essential significant effect on the performance of the method. Thus, such a composition may still include a pharmaceutically acceptable excipient that does not comprise an essential activity in treating cancer. Further, "consisting of" encompasses excluding more than traces of other elements. Thus, such a composition consisting of early apoptotic cells would not include more than traces of other elements as disclosed herein.

In some embodiments, methods as disclosed herein may be represented as uses of the compositions as described herein for various therapeutic and prophylactic purposes as described herein, or alternatively, uses of the compositions as described herein in the preparation of a medicament or a therapeutic composition or a composition for various therapeutic and prophylactic purposes as described herein.

In some embodiments, the compositions and methods as disclosed herein comprise the various components or steps. However, in another embodiment, the compositions and methods as disclosed herein consist essentially of the various components or steps, where other components or steps may be included. In another embodiment, the compositions and methods as disclosed herein consist of the various components or steps.

In some embodiments, the term "comprise" may encompass the inclusion of other components of the composition which affect the efficacy of the composition that may be known in the art. In some embodiments, the term "consisting essentially of" comprises a composition, which has chimeric antigen receptor-expressing T-cells (CAR T-cells), and apoptotic cells or any apoptotic cell supernatant. However, other components may be included that are not involved directly in the utility of the composition. In some embodiments, the term "consisting" encompasses a composition having chimeric antigen receptor-expressing T-cells (CAR T-cells), and apoptotic cells or an apoptotic cell supernatant as disclosed herein, in any form or embodiment as described herein.

A skilled artisan would appreciate that the term "about", may encompass a deviance of between 0.0001-5% from the indicated number or range of numbers. Further, it may encompass a deviance of between 1-10% from the indicated number or range of numbers. In addition, it may encompass a deviance of up to 25% from the indicated number or range of numbers.

A skilled artisan would appreciate that the singular form "a", "an" and "the" include plural references unless the context clearly dictates otherwise. For example, the term "an agent" or "at least an agent" may include a plurality of agents, including mixtures thereof.

Throughout this application, various embodiments disclosed herein may be presented in a range format. It should be understood that the description in range format is merely for convenience and brevity and should not be construed as an inflexible limitation on the scope of the disclosure. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicated number and a second indicated number and "ranging/ranges from" a first indicated number "to" a second indicated number are used herein interchangeably and are meant to include the first and second indicated numbers and all the fractional and integral numerals there between.

The following examples are presented in order to more fully illustrate embodiments disclosed herein. They should in no way be construed, however, as limiting the broad scope of the disclosure.

EXAMPLES

Example 1: Apoptotic Cell Production

Objective:
To produce early-apoptotic cells.
Methods:
Methods of making populations of early-apoptotic cells have been well documented in International Publication No. WO 2014/087408 and United States Application Publication No. US2015/0275175-A1, see for example, the Methods section preceding the Examples at "Early apoptotic cell population Preparation" and "Generation of apoptotic cells" (paragraphs [0223] through [0288]), and Examples 11, 12, 13, and 14, which are incorporated herein in their entirety).

The flow chart presented in FIG. 1 provides an overview of one embodiment of the steps used during the process of producing a population of early apoptotic cells, wherein anticoagulants were included in the thawing and induction of apoptosis steps. As is described in detailed in Example 14 of International Publication No. WO 2014/087408 and United States Application Publication No. US US-2015-0275175-A1, early apoptotic cell populations were prepared wherein anti-coagulants were added at the time of freezing, or at the time of incubation, or at the time of freezing and at the time of incubation. The anticoagulant used was acid-citrate dextrose, NIH Formula A (ACD formula A) was supplemented with 10 U/ml heparin to a final concentration of 5% ACD of the total volume and 0.5 U/ml heparin.

Briefly: The cells were collected and then frozen with addition of 5% anticoagulant citrate dextrose formula A and 10 U/ml heparin (ACDhep) to the freezing media. Thawing, incubation in an apoptosis induction media containing 5% ACDhep, and final product preparation were performed in a closed system.

Apoptosis and viability analysis, potency assay, and cell population characterization were performed in each experiment. In order to establish consistence in production of the early apoptotic cell product, the final product (FP) of initial batches of apoptotic cells were stored at 2-8° C. and examined at t0, t24 h, t48 h and t72 h. At each point apoptosis analysis, short potency assay (Applicants CD14+ frozen cells), trypan blue measurement and cell population characterization were performed. The FP was tested for cell count to assess average cell loss during storage and apoptosis and viability analysis.

The methods sections cited above and Example 11 of International Publication No. WO 2014/087408 and United States Application Publication No. US US-2015-0275175-A1 provide details of preparing other embodiment of apoptotic cell populations in the absence of anti-coagulants, and are incorporated herein in full.

Methods of Preparing Irradiated Apoptotic Cells:

Similar methods were used to prepare an inactivated apoptotic cell population, wherein a mononuclear early apoptotic cell population comprises a decreased percent of non-quiesnce non-apoptoic cells, or a population of cells having a suppressed cellular activation of any living non-apoptotic cells, or a population of cells having a reduced proliferation of any living non-apoptotic cells, or any combination thereof.

Briefly, an enriched mononuclear cell fraction was collected via leukapheresis procedure from healthy, eligible donors. Following apheresis completion, cells were washed and resuspended with freezing media comprising 5% Anti-coagulant Citrate Dextrose Solution-Formula A (ACD-A)

and 0.5 U\ml heparin. Cell were then gradually frozen and transferred to liquid nitrogen for long term storage.

For preparation of irradiated ApoCells, cryopreserved cells were thawed, washed and resuspended with apoptosis induction media comprising 5% ACD-A, 0.5 U\ml heparin sodium and 50 µg/ml methylprednisolone. Cells were then incubated for 6 hours at 37° C. in 5% $CO_2$. At the end of incubation, cells were collected, washed and resuspended in Hartmann's solution using a cell processing system (Fresenius Kabi, Germany). Following manufacturing completion, ApoCell were irradiated at 4000 cGy using g-camera at the radiotherapy unit, Hadassah Ein Kerem. Apoptosis and viability of ApoCell determined using AnnexinV and PI (MBL, MA, USA) staining (≥40% and ≤15%, respectively) via Flow cytometer. Results analyzed using FCS express software.

This irradiated APOcell population is considered to include early apoptotic cells, wherein any viable cells present have suppressed cellular activity and reduced or no proliferation capabilities. In certain cases, the Apocell population has no viable non-apoptotic cells. Results:

The stability of the FP produced with inclusion of anticoagulant at freezing and incubation (apoptotic induction) and then stored at 2-8° C. are shown below in Table 3.

TABLE 3

Cell count* - performed using a MICROS 60 hematology analyzer.

| FP Time point | Cell concentration (×10⁶ cells\ml) | % of cell loss |
|---|---|---|
| t0 | 20.8 | NA |
| t24 h | 20.0 | −3.85 |
| t48 h | 20.0 | −3.85 |
| t72 h | 19.7 | −5.3 |

*Results Representative of 6 (six) experiments.

When manufacturing the cells without including an anticoagulant in the induction medium, cells were stable for 24 hours and less stable thereafter. Use of anticoagulants unexpectedly extended the stability of the apoptotic cell population for at least 72 hours, as shown in Table 3.

TABLE 4

Trypan blue measurement

| FP Time point | trypan blue positive cells (%) |
|---|---|
| t0 | 3.0 |
| t24 h | 5.9 |
| t48 h | 5.2 |
| t72 h | 6.5 |

The results of Table 4 show viability of the FP remained high for at least 72 hours.

TABLE 5

Apoptosis analysis - (AnPI staining) performed using Flow Cytometry

| | 1.5 mM Ca | | |
|---|---|---|---|
| FP Time point | An−PI− (%) | An+PI− (%) | An+PI+ (%) |
| t0 | 44.3 | 50.9 | 4.8 |
| t24 h | 39.0 | 55.9 | 5.1 |
| t48 h | 34.8 | 60.1 | 5.1 |
| t72 h | 33.4 | 60.5 | 6.1 |

The results of Table 5 show that the percent apoptotic cells versus necrotic cells was maintained over at extended time period of at least 72 hours post preparation of the cells, as was the percentage of early apoptotic cells.

Inclusion of anticoagulants both at the time of freezing and during induction of apoptosis resulted in the most consistently high yield of stable early-apoptotic cells (average yield of early apoptotic cells 61.3±2.6% % versus 48.4±5.0%, wherein 100% yield is based on the number of cells at freezing). This high yield was maintained even after 24 hours storage at 2-8° C.

Next a comparison was made between the inclusion of the anticoagulant at freezing or thawing or both, wherein percent (%) recovery was measured as well as stability. Anticoagulant was included in the apoptotic incubation mix for all populations. Table 6 presents the results of these studies.

TABLE 6

Yield and stability comparison of final products (FP) manufactured from cells collected, with ("+") or without ("−") addition of anticoagulant during freezing ("F") and thawing ("Tha")

| Donor ID | # of Collected Cells (×10⁹, 100%) | % Cell Recovery in Final Product of Collected Cells | | | | | | | |
|---|---|---|---|---|---|---|---|---|---|
| | | FP t0 | | | | FP t24 h* | | | |
| | | F−/Tha− | F−/Tha+ | F+/Tha+ | F+/Tha− | F−/Tha− | F−/Tha+ | F+/Tha+ | F+/Tha− |
| 1 | 13.3 | 52.1 | 53.4 | 62.5 | 62 | 52.1 | 48.9 | 62.5 | 62 |
| 2 | 13.6 | 50.5 | 36.7 | 53.5 | 63.5 | 47.6 | 36.7 | 53.1 | 59.7 |
| 3 | 15.0 | 42.7 | 42 | 53.6 | 58.4 | 42.7 | 41.7 | 53.6 | 57.8 |
| Avg | 14.0 | 48.4 ± 5.0 | 44.0 ± 8.5 | 56.5 ± 5.2 | 61.3 ± 2.6 | 47.5 ± 4.7 | 42.4 ± 6.1 | 56.4 ± 5.3 | 59.8 ± 2.1 |

Additional population analysis comparisons of early apoptotic cell populations (batches of cells) prepared with and without anti-coagulant added, show the consistency of these results.

TABLE 7

Cell population analysis comparison between batches prepared with and without anticoagulant

| Test | Specification | At Thawing | | ApoCell Time 0 h | | ApoCell Time 24 h Storage | |
|---|---|---|---|---|---|---|---|
| | | w\o ACDhep | +ACDhep | w\o ACDhep | +ACDhep | w\o ACDhep | +ACDhep |
| Change in Total Cell Count Percent change (min-max) | >35.0% | 85.5 (79.5-92.5) | 82.8 (67.7-96.4) | 49.9 (46.6-52.3) | 66.7 (62.5-71.2) | 49.0 46.6-50.3) | 66.7 (62.5-71.2) |
| Changes in ApoCell Percent change Range (min-max) | 90.0 ± 10.0% | | | 100 | 100 | 98.2 (96.2-100) | 100 |
| Cell viability PI exclusion Percent viable Range (min-max) | >85.0% | 98.0 (97.4-98.4) | 96.0 (91.9-98.1) | 98.5 (97.9-99.2) | 94.6 (93.5-95.5) | 97.7 (96.4-98.6) | 94.5 (93.4-95.1) |
| Identity/ Purity Analysis of cell phenotype Average (%) (maximal calculated range) | CD3 (T cells): 71.9 (50.0-85.0) ApoCell CD3: 71.6 (50.0-85.0) | 75.7 (71.6-81.4) | 66.5 (60.1-70.1) | 73.3 (70.3-78.3) | 62.8 (61.1-65.3) | 71.6 (61.5-79.1) | 64.2 (61.6-68.1) |
| | CD19 (B cells): 9.3 (3.0-15.0) ApoCell CD19: 9.5 (4-15) | 7.5 (4.0-11.1) | 9.8 (8.6-12.0) | 9.0 (7.6-10.2) | 9.9 (9.3-10.2) | 9.5 (8.6-10.3) | 9.7 (9.2-10.4) |
| | CD14 (monocytes): 10.1 (2.5-22.0) ApoCell CD14: 10.6 (2.5-22.0) | 9.8 (6.4-13.0) | 14.0 (8.8-22.1) | 11.6 (10.2-13.3) | 15.4 (8.2-19.3) | 9.3 (4.8-17.2) | 16.1 (9.0-20.4) |
| | $CD15^{high}$ (granulocytes): 0.4 (0-6.0) ApoCell $CD15^{high}$: 0.2 (0-2.0) | 0.2 (0-0.3) | 0.46 (0.18-0.69) | 0.2 (0.1-0.4) | 0.083 (0.08-0.09) | 0.1 (0.1-0.2) | 0.09 (0.07-0.1) |
| | CD 56 (NK): 7.2 (1.5-22.0) ApoCell CD56: 5.2 (1.5-15.0) | 7.4 (2.4-11.0) | 10.1 (6.6-14.2) | 4.7 (2.7-8.0) | 11.2 (7.2-14.2) | 4.9 (2.2-9.2) | 10.0 (6.4-13.0) |

Percentage of Final Product Cells (Yield) in the Presence or Absence of Anticoagulants.

Similar to the results presented above at Table 3, the data presented in Table 6 demonstrates that early apoptotic cells manufactured from cells frozen in the presence of anticoagulant had a beneficial effect on average yield of fresh final product (FP t0) as compared to cells frozen without anticoagulant. The beneficial effect was seen when anticoagulant was used while freezing only (61.3±2.6% versus 48.4±5.0%), or both freezing and thawing (56.5±5.2% versus 48.4±5.0%). The beneficial effect was less significant when anticoagulant was used upon thawing only (44.0±8.5% versus 48.4±5.0%). These were non-high triglyceride samples.

Effect of Anticoagulants on Aggregation.

No cell aggregations were seen in these 3 non-high triglyceride samples, or in 21 additional samples (data not shown). However, in 41 other non-high triglyceride samples manufactured without anticoagulants (data not shown), mild aggregates were seen in 10 (24.4%) and severe aggregates in 5 (12.2%); thus, anticoagulants avoid completely cell aggregates.

Effect of Anticoagulants on Stability.

Fresh FPs manufactured with- or without anticoagulants were stored at 2-8° C. for 24 hours to determine whether addition of ACDhep to the manufacturing procedure impairs the stability of the FP. Cells were sampled following 24 hours of storage and yield was calculated. In cell count. Similar to the results shown in Table 3 for extended time periods (up to 72 hours), Table 6 shows that the beneficial effect was kept and observed when anticoagulant was used while freezing only (59.8±2.1% versus 47.5±4.7%), or both freezing and thawing (56.4±5.3% versus 47.5±4.7%). The beneficial effect was less significant when anticoagulant was added only upon thawing (42.4±6.1% versus 47.5±4.7%). These were all non-high triglyceride samples. These results show minimal cell loss following 24 hours of FP storage in all treatments with significant advantage to cells treated with anticoagulant during both freezing and thawing. Average loss of cells treated with anticoagulant during freezing only was 2.3±3.2% compared to 1.9±3.3% without anticoagulants, upon thawing only was 3.0±4.7 compared to 1.9±3.3% without anticoagulants, and 0.2±0.4% compared to 1.9±3.3% without anticoagulants when cells were both frozen and thawed with ACDhep. In summary, the beneficial effect of anticoagulants on yield was kept for at least 24 hours.

The characteristics of a representative cell population of the FP are shown below in Table 8.

TABLE 8

Characterization of the cell population of fresh (t0) FP manufactured from cells collected with ("+") or without ("−") addition of anticoagulant during freezing ("F") and thawing ("Tha") procedures.*

| | Donor ID FP t0 | | | | | | | | | |
|---|---|---|---|---|---|---|---|---|---|---|
| | F−/Tha− | | | | | F−/Tha+ | | | | |
| | CD3+ (%) | CD19+ (%) | CD56+ (%) | CD14+ (%) | CD15+ (%) | CD3+ (%) | CD19+ (%) | CD56+ (%) | CD14+ (%) | CD15+ (%) |
| 1-3 | 62.2 ± 6.1 | 5.6 ± 0.7 | 9.8 ± 0.9 | 13.5 ± 1.1 | 0 ± 0 | 61 ± 6.1 | 8.6 ± 0.4 | 8.6 ± 0.9 | 14.1 ± 1.1 | 0 ± 0 |

| | Donor ID FP t0 | | | | | | | | | |
|---|---|---|---|---|---|---|---|---|---|---|
| | F+/Tha+ | | | | | F+/Tha− | | | | |
| | CD3+ (%) | CD19+ (%) | CD56+ (%) | CD14+ (%) | CD15+ (%) | CD3+ (%) | CD19+ (%) | CD56+ (%) | CD14+ (%) | CD15+ (%) |
| 1-3 | 63.9 ± 5.8 | 7.4 ± 0.6 | 9.4 ± 0.8 | 13.3 ± 1.9 | 0 ± 0 | 61.9 ± 6.0 | 11.5 ± 1.1 | 10.1 ± 1.0 | 14.3 ± 1.3 | 0 ± 0 |

*Induction of apoptosis was performed using a medium containing anticoagulant for all batches.

The results of Table 8 show the cell characteristics of the final products (FP) manufactured with or without anticoagulant at freezing and thawing. Batches were sampled, stained for mononuclear markers, and analyzed via flow cytometry to determine the cell distribution in each sample and to examine whether the addition of anticoagulant affected the cell population. As presented in Table 7, there were no significant differences detected in cell populations manufactured with or without anticoagulants at freezing or thawing. The average T cell population (CD3+ cells) in fresh FP was 62.3±1.2% between treatments compared to 62.9±1.1% before freezing; the average B cell population (CD19+ cells) was 8.3±2.5% between treatments compared to 3.1±0.8% before freezing; the average natural killer cell population (CD56+ cells) was 9.5±0.7% between treatments compared to 12.9±0.5% before freezing; the average monocyte cell population (CD14+ cells) was 13.8±0.5% between treatments compared to 17.5±0.3% before freezing; and the average granulocyte population (CD15+ cells) was 0.0% in the fresh FP compared to 0.35±0.2% at freezing.

The potency of the early apoptotic population was also examined

TABLE 9

Potency analysis of fresh (t0) FP manufactured from cells with ("+") or without ("−") addition of anticoagulant during freezing ("F") and thawing ("Tha") procedures.

| | Donor ID # FP t0 Treatment | | | | | | | |
|---|---|---|---|---|---|---|---|---|
| Median fluorescence | F−/Tha− | | F−/Tha+ | | F+/Tha+ | | F+/Tha− | |
| | DR | CD86 | DR | CD86 | DR | CD86 | DR | CD86 |
| DCs 1:2 Early apoptotic cell population + LPS | 3% | 28% | 4% up from LPS | 24% | 5% | 24% | 9% | 15% |

TABLE 9-continued

Potency analysis of fresh (t0) FP manufactured from cells with ("+") or without ("−") addition of anticoagulant during freezing ("F") and thawing ("Tha") procedures.

| | Donor ID # FP t0 Treatment | | | | | | | |
|---|---|---|---|---|---|---|---|---|
| | F−/Tha− | | F−/Tha+ | | F+/Tha+ | | F+/Tha− | |
| Median fluorescence | DR | CD86 | DR | CD86 | DR | CD86 | DR | CD86 |
| DCs 1:4 Early apoptotic cell population + LPS | 4% | 38% | 6% | 35% | 6% | 34% | 6% | 24% |
| DCs 1:8 Early apoptotic cell population + LPS | 13% | Not done | 10% | 45% | 15% | 54% | 8% | 48% |

The results presented in Table 9 are from a potency assay performed to determine the ability of each final product to enhance a tolerogenic state in immature dendritic cells (iDCs) following stimulation with (LPS). The tolerogenic effect was determined by assessing downregulation of co-stimulatory molecule HLA-DR and CD86 expression on iDCs following interaction with the early apoptotic cell populations and different treatments leading to LPS upregulation. The analysis was performed on DCsign+ cells. Results represent the percent delay in maturation following interaction with early apoptotic cell population and following addition of LPS versus LPS-induced maturation. The experiment tested the potency of fresh FP (t0) manufactured with- or without anticoagulant. Results presented in Table 9 show that apoptotic cells manufactured with or without anticoagulant enhance the tolerance effect of both co-stimulatory markers in a dose-dependent manner.

The early apoptotic cells produced herein were from non-high triglyceride samples. This consistent high yield of stable early apoptotic cells was produced even in the cases when the donor plasma is high in triglycerides (See for example, Examples 12 and 13 of International Publication No. WO 2014/087408 and United States Application Publication No. US US-2015-0275175-A1). Note that anticoagulants were not added to the PBS media used for formulation of the final early apoptotic cell dose for infusion.

SUMMARY

The objective of this study was to produce a stable, high yield early apoptotic cell population. The rational for use of anticoagulants was that aggregates were seen first in patients with high-triglycerides, but later in a significant portion of other patients. A concern here was the disclosure in U.S. Pat. No. 6,489,311 that the use of anticoagulants prevented cell apoptosis.

In short, with minimal impact on the composition, viability, stability, and the apoptotic nature of the cells, there was a significant improvement of at least 10-20% in the number of collected cells in the final product (Yield) when anticoagulant was added. In this study an up to 13% increase in yield was shown, which represents 26.8% augmentation in yield in controlled conditions but in real GMP conditions it went up to 33% and more augmentations in cell number then can be produced in a single collection. This effect is crucial, since it may avoid the need for a second apheresis from a donor.

This effect was surprising because the anticipated impact was expected to be dissolution of mild aggregates. It had been hypothesize that thawing cells with anticoagulant reduced the amount of aggregates. When formed, these aggregates eventually lead to massive cell loss. Cells collected and frozen without anticoagulant demonstrated aggregate formation at thawing, immediately after wash. Furthermore, a high level of aggregates was also detected in cells that were frozen without anticoagulant and resuspended with media containing anticoagulant. No aggregates were seen in cells that were both frozen and resuspended with media containing anticoagulant. Taken together, it was conclude that the addition of anticoagulants during freezing and apoptosis induction is of high importance, and did not appear to negatively impact the induction of early apoptosis on the cell population.

Recovery of early apoptotic cells was further tested, for example, following 24 hours of storage at 2-8° C., for stability purposes, during which an average cell loss of 3-4.7% was measured, regardless of manufacturing conditions, with favorable results for cells that were both frozen and thawed with media containing anticoagulant (0.2±0.4% cell loss following 24 hours of FP storage), suggesting that addition of anticoagulant is critical during freezing and thawing, but once finally formulated, the early apoptotic cell population is stable. Extended time point studies showed this stability to at least 72 hours.

Apoptosis and viability, as well as cell composition of the FP product were not significantly affected by the addition of anticoagulant at the freezing and/or thawing stage. Values measured from a wide variety of characteristics were similar, indicating the ACDhep did not change the early apoptotic cell characteristics and the final product met the acceptance criteria of ≥40% apoptotic cells.

The assay used to test apoptotic cells potency was based on immature dendritic cells (iDCs), DCs that are characterized by functions such as phagocytosis, antigen presentation, and cytokine production.

The HLA-DR (MHC class II) membrane molecule and co-stimulatory molecule CD86 were selected as markers to detect the tolerogenic effects of antigen-presenting cells (APCs). Using flow cytometry, changes in expression of HLA-DR and CD86 on iDCs were measured following stimulation with LPS, as well as in the presence of the early apoptotic cell population manufactured with- or without anticoagulant and stimulated with LPS. Early apoptotic cell populations were offered to DCs in ascending ratios of 1:2, 1:4, and 1:8 iDCs: early apoptotic cell population. As presented in Table 6, it was shown that early apoptotic cell population enhanced the tolerogenic effect over stimulated DCs in a dose-dependent manner, with slightly better results for early apoptotic cell population manufactured with anticoagulant both at freezing and apoptosis induction.

Taken together, it was concluded that addition of anticoagulant to both freezing and apoptosis media is of high importance to increase cell recovery and avoid massive cell loss due to aggregates, and to avoid in many cases a second round of apheresis from a donor. It was shown that all cells met acceptance criteria for the validated FP, indicating that the addition of anticoagulant does not impair the FP.

Example 2: Effect of Apoptotic Cells on Cytokine Release in an In Vitro Cytokine Storm Model Objective:

Test the effect of apoptotic cells on the level of cytokine storm markers (cytokines IL-6, IL-10, MIP-1α, IL-8, TNF-α, MIP-1β, MCP-1, and IL-9) in a cytokine storm induced in an LPS-Sterile model of macrophage activation syndrome.

Methods:

Cell Lines and Culturing Reagents

The human lymphoma cell line Raji (eCACC, UK, access no. 85011429), the human cervical adenocarcinoma cell line HeLa (ATCC, USA, number: CCL-2) and HeLa-CD19 (ProMab, USA, cat. no. PM-Hela-CD19) were cultured in RPMI 1640 (Gibco, ThermoFisher Scientific, USA, cat. no. 31870-025) supplemented with 10% FBS (Gibco, ThermoFisher Scietific, South America, cat. no. 12657-029), 2 mM GlutaMAX (Gibco, ThermoFisher Scientific, USA, cat. no. 35050-038), and 100 U/ml Penicillin+100 U/ml Streptomycin (Gibco, ThermoFisher Scientific, USA, cat. no. 15140-122), henceforth referred to as "Complete Medium". HeLa-CD19 medium was further supplemented with 1 µg/ml puromycin (Sigma-Aldrich, USA, cat. no. P9620), as the selective antibiotics, during standard culturing.

All cells were kept in sub-confluent conditions. Raji cells were maintained in a concentration range of $0.3\times10^6$-$2\times10^6$ cell/ml. HeLa and HeLa-CD19 cells were passaged when receptacle was filled to 90% confluence.

Primary monocytes were isolated from blood donations buffy coats (Sheba Medical Center, Israel). First, peripheral blood mononuclear cells (PBMCs) were isolated on a Ficoll density gradient (Ficoll-Paque PLUS, GE Healthcare, UK, cat. no. 17-1440-03). Upon centrifugation (800×g, 2-8° C., 20 min. with break 0), the interphase containing the PBMCs were transferred to a fresh test tube and washed with RPMI-1640 (Lonza, Switzerland, cat. no. BE12-918F) supplemented with 2 mM L-glutamine (Lonza, Switzerland, cat. no. BE17-605E) and 10 mM Hepes (Lonza, Switzerland, cat. no. BE17-737B), henceforth "Wash Medium", and centrifuged (650×g, 2-8° C., 10 min) Pelleted cells were re-suspended in "Wash Medium" to a concentration of $15\times10^6$ cell/ml. Cells were seeded as a 0.9 ml drop at the center of a 35-mm plate (Corning, USA, cat. no. 430165). Plates were incubated for 1.5 h in a humidified incubator (37° C., 5% $CO_2$), allowing monocytes to adhere, and then washed three times with pre-warmed PBS (Lonza, Switzerland, cat. no. BE17-516F), removing other cell types. After washing, cells were cultured in 2 ml RPMI 1640 (Gibco, ThermoFisher Scientific, USA, cat. no. 31870-025) supplemented with 10% FBS (Gibco, ThermoFisher Scietific, South America, cat. no. 12657-029), 2 mM GlutaMAX (Gibco, ThermoFisher Scientific, USA, cat. no. 35050-038), and 100 U/ml Penicillin+100 U/ml Streptomycin (Gibco, ThermoFisher Scientific, USA, cat. no. 15140-122), aka "Complete Medium".

All cell lines were cultured in a humidified incubator at 37° C. and containing 5% $CO_2$.

In brief, and following manufacturer's guidelines, target cells (HeLa or HeLa-CD19) were cultured alone or in conjunction with monocytes. After target cells adhered to the plate (6 h-overnight), cultures were exposed to $y\times10^6$ ApoCells cells for 1 h, after which these cells were washed off by 4-5 washes of RPMI. Removal of ApoCells cells was confirmed visually under a light microscope. 10 ng/ml LPS (Sigma-Aldrich, USA, cat. no. L4391) was introduced to the co-culture and incubated for 1 h. After incubation, LPS was removed by 3-5 washing cycles with RPMI. Viable CD19-CAR T cells or naïve T cells were added at the designated E/T ratio(s) and incubated for 4 h. To collect media, plates were centrifuged at 250×g, 2-25° C., 4 min. (Centrifuge 5810 R, Eppendorf, Germany) to sediment cells. 50 µl of supernatant medium from each well was transferred to a fresh flat-bottom 96-well microplate well (Corning, USA, cat. no. 3596) and 50 µl CytoTox 96 Reagent was added to each well. Plates were incubated in the dark at room temperature for 30 min., after which the reaction was terminated by addition of 50 µl Stop Solution per well. Absorbance was read at 492 nm using Infinite F50 (Tecan, Switzerland) and captured using Magellan F50 software. Data analysis and graph generation was performed using Microsoft Excel 2010.

Analysis of cytokine release was performed using Liminex technology following incubation with apoptotic cells or incubation with supernatant from apoptotic cells.

Results:

FIGS. 4A through 4H show that there was a significant reduction in the levels of cytokine storm markers IL-10, IL-6, MIP-1α, IL-8, TNF-α, MIP-1β, MCP-1, and IL-9 which were induced by LPS in an in vitro model of macrophage activation syndrome. While administration of ApoCells to achieve a macrophage:Apocell ratio of 1:8 resulted in significantly decreased levels of both IL-10, IL-6, MIP-1α, IL-8, TNF-α, MIP-1β, MCP-1, and IL-9 released into the medium (FIGS. 4A, 4B, 4C, 4D, 4E, 4F, 4G, 4H), administration of ApoCells to achieve a macrophage: ApoCell ratio of 1:16 actually inhibited or nearly inhibited the release of cytokines IL-10, IL-6, MIP-1α, IL-8, TNF-α, MIP-1β, MCP-1, and IL-9 in this model.

Addition of apoptotic cells resulted in the inhibition of at least 20 pro-inflammatory cytokine and chemokines induced in macrophage activating, a sample of the results are shows in FIGS. 4A-4H. The common mechanism for pro-inflammatory cytokine and chemokine release is NF-κB inhibition.

Figure 4A:
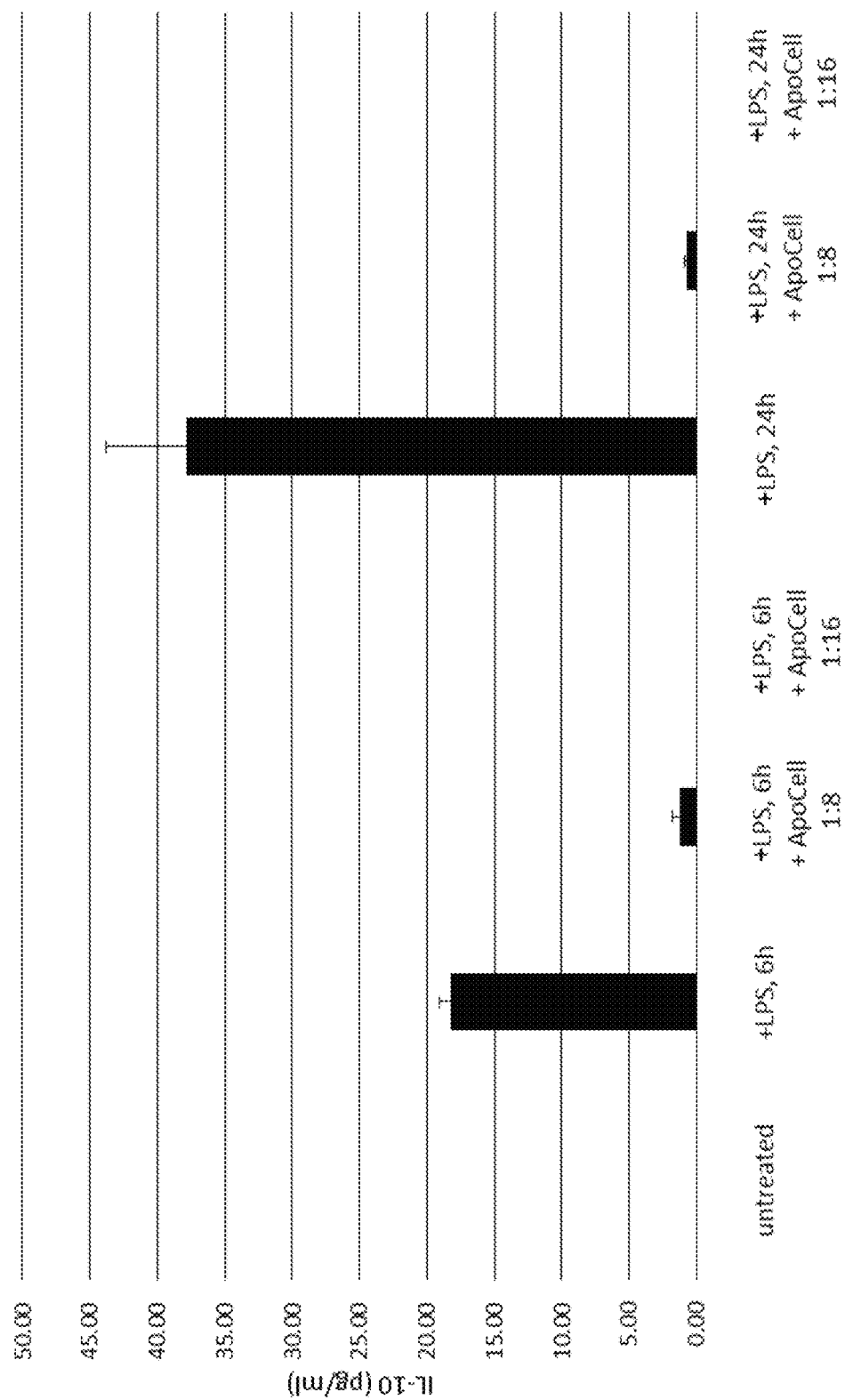
FIGS. 4A-4J. Apoptotic cells prevent cytokine storm in in vitro model of cytokine storm induced in LPS-Sterile model of macrophage activation syndrome in a cancer environment.
Figure 4B:
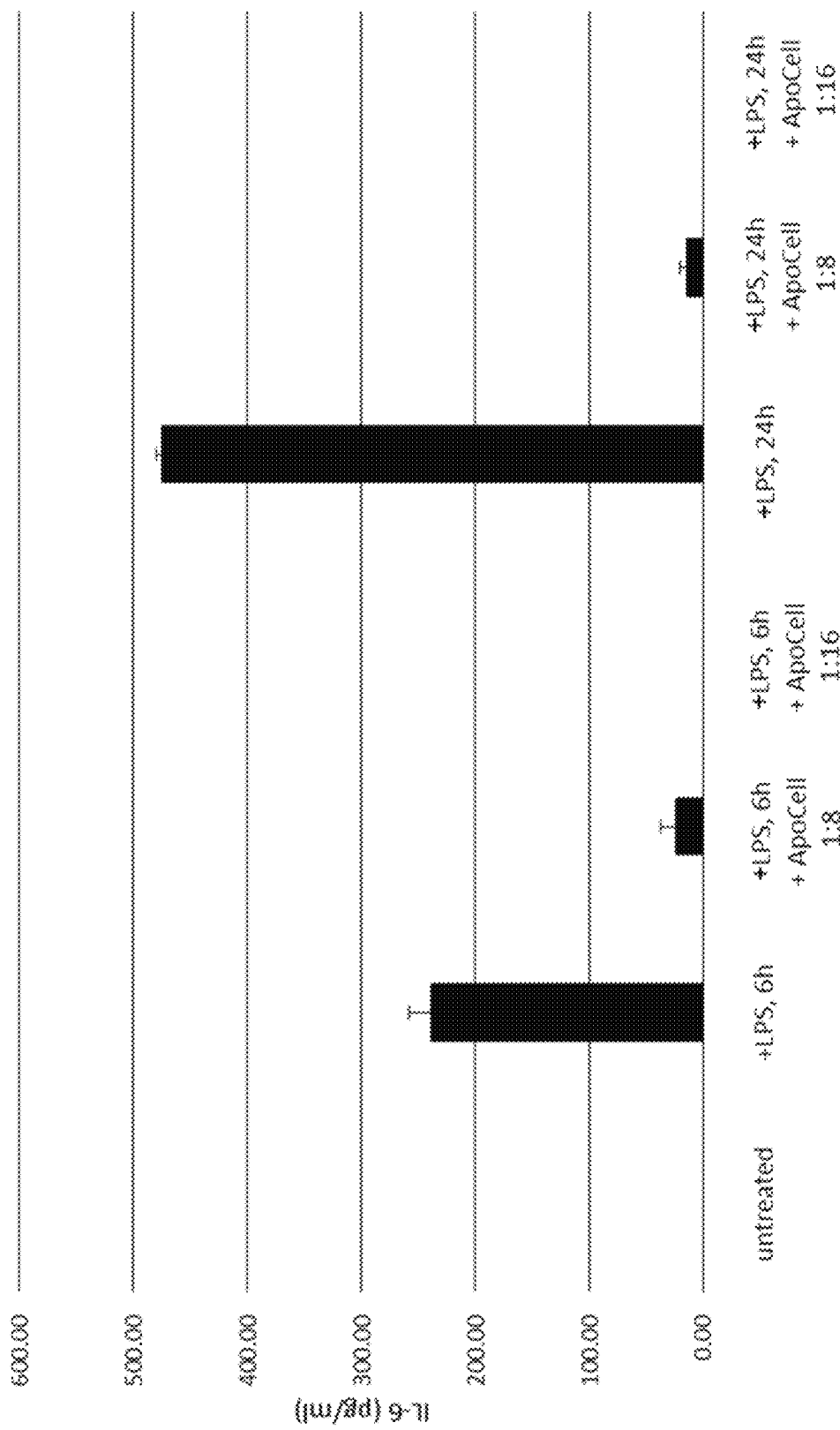
Figure 4C:
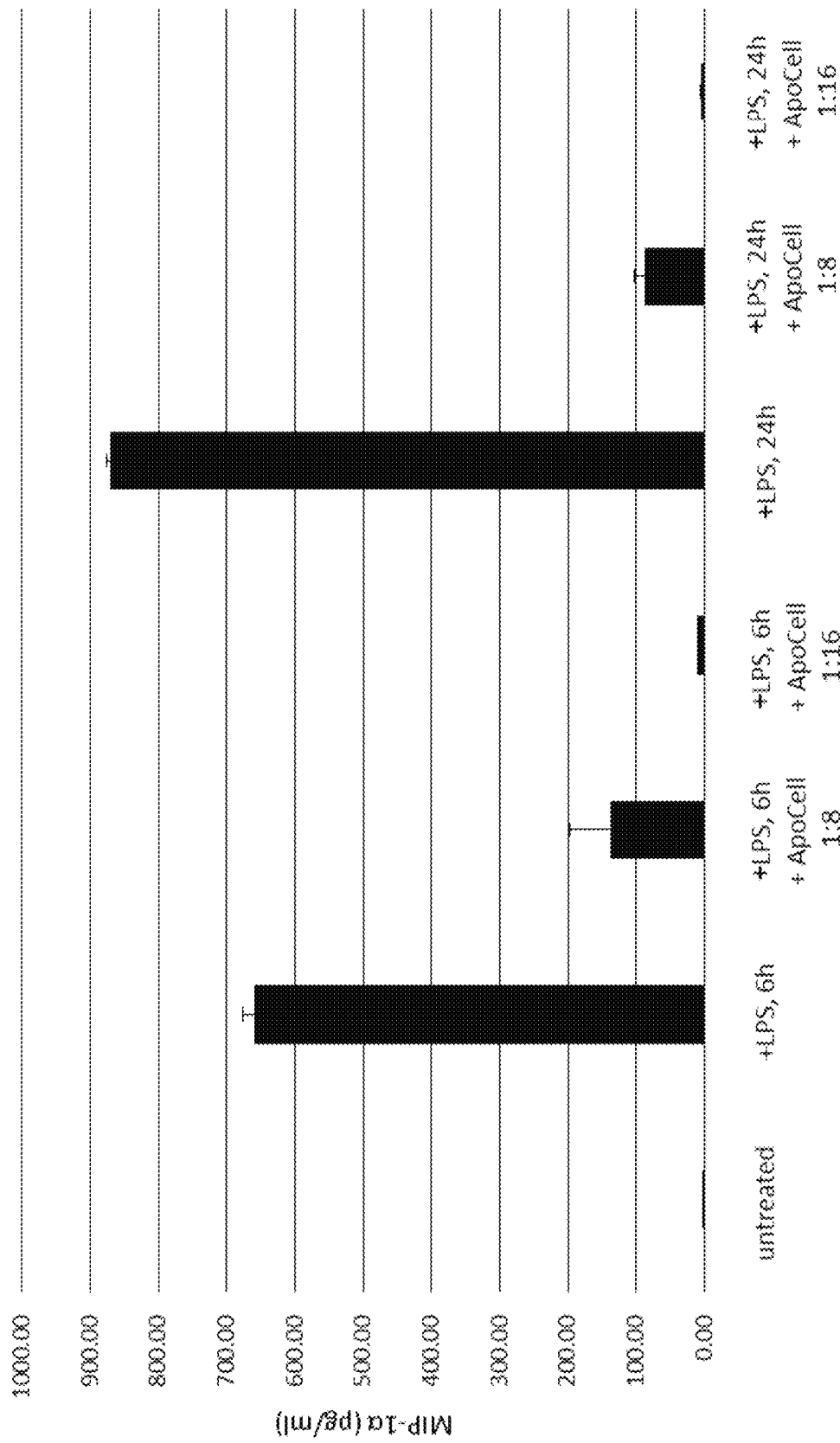
Figure 4D:
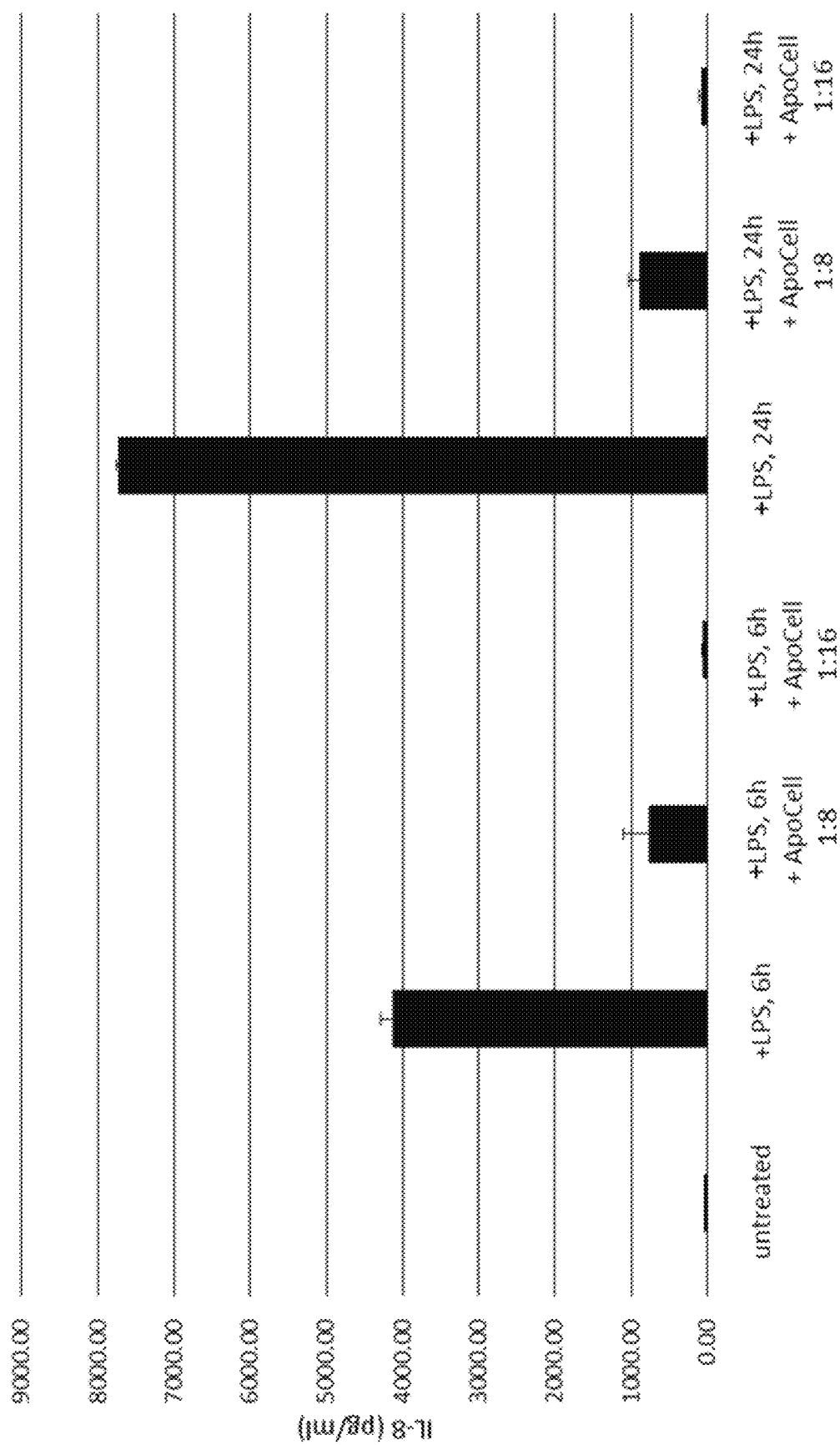
Figure 4E:
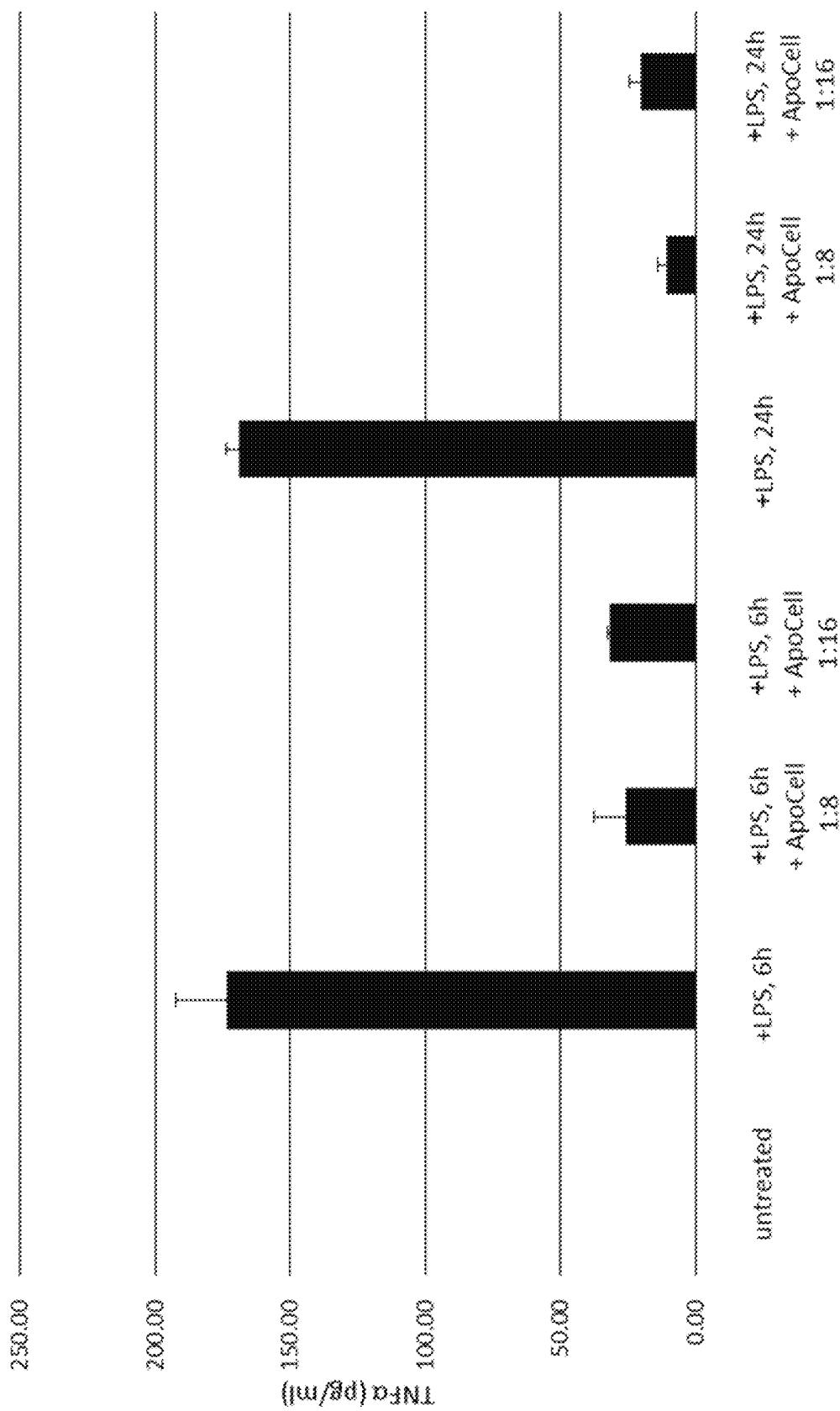
Figure 4F:
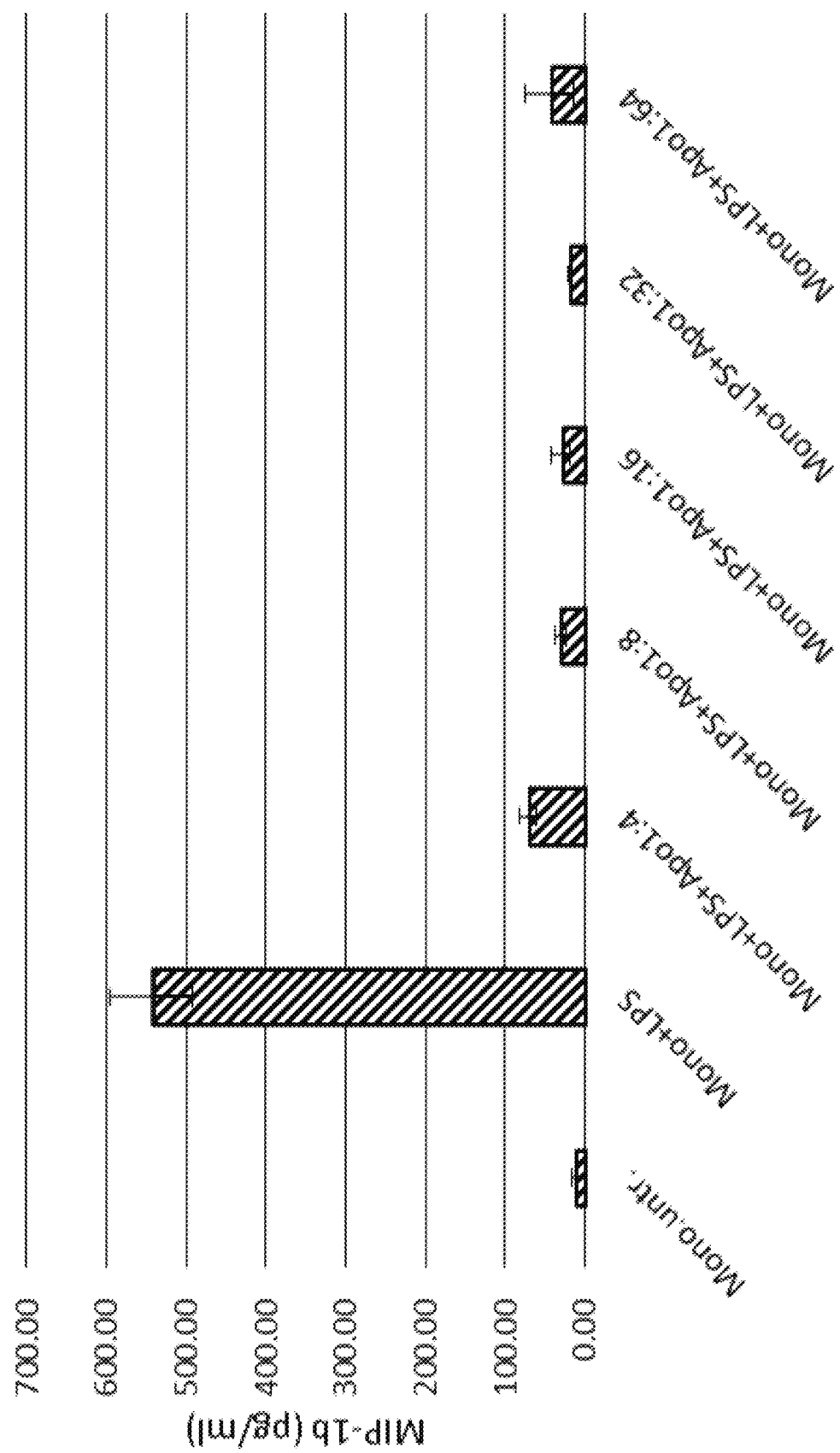
Figure 4G:
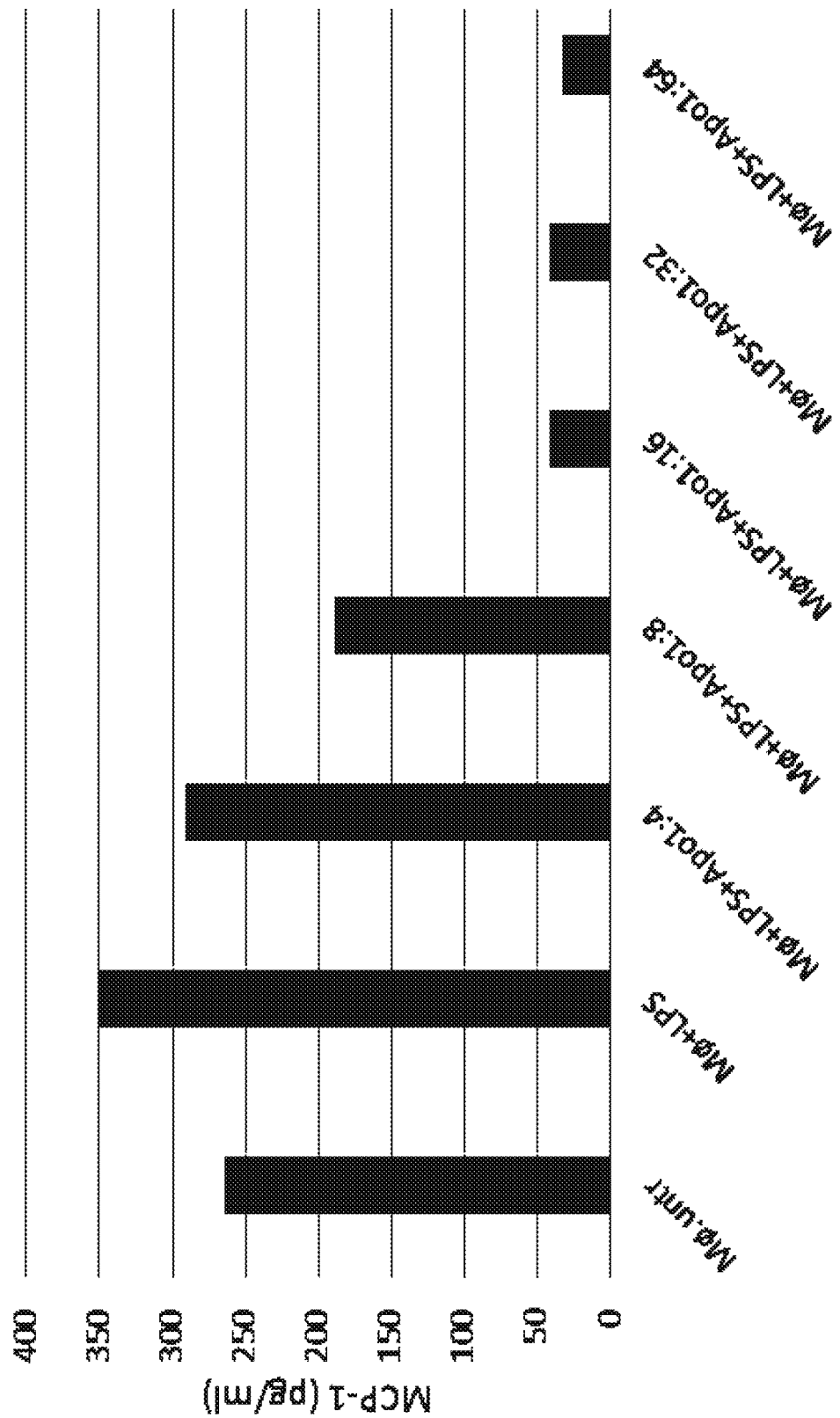
Figure 4H:
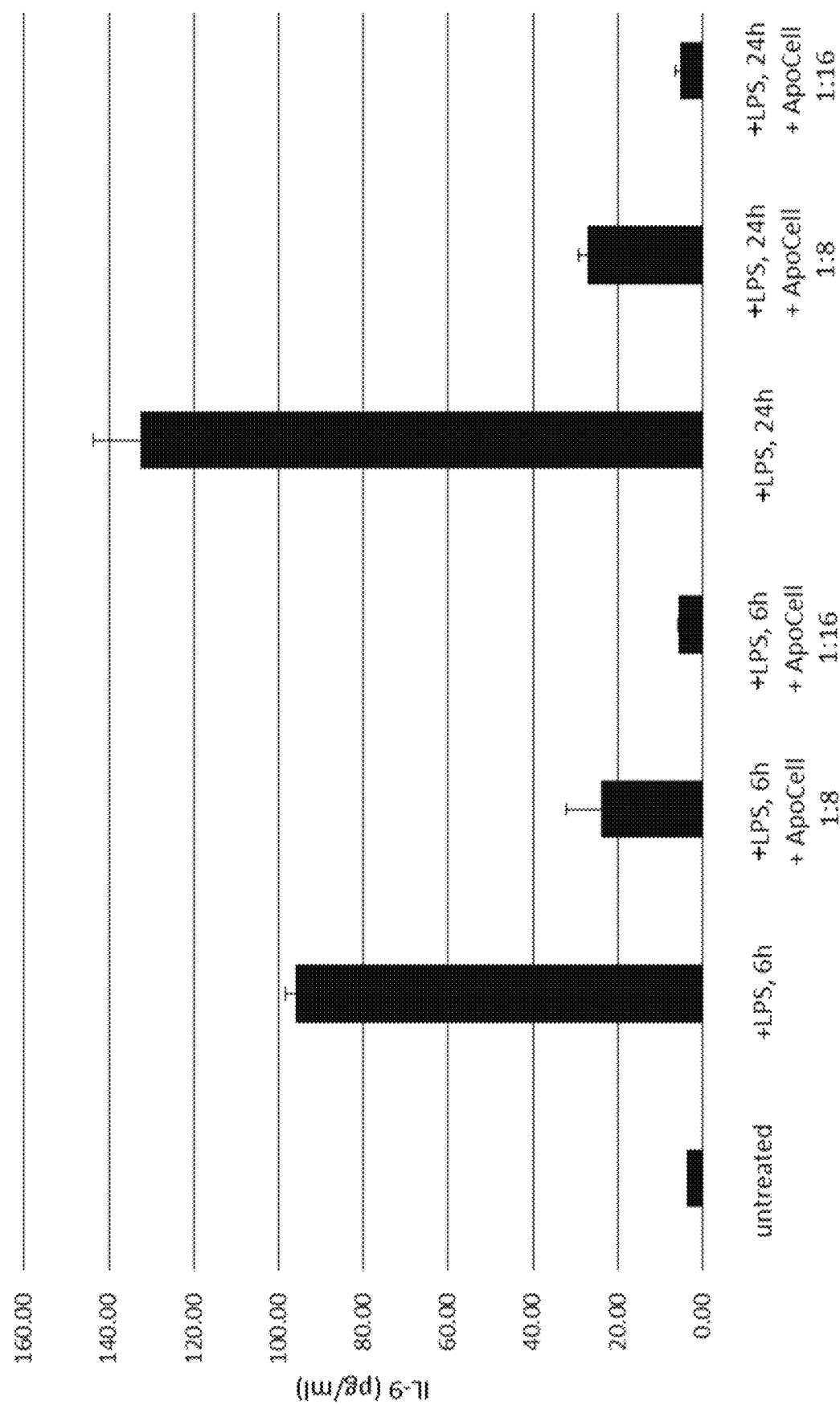
Figure 4I:
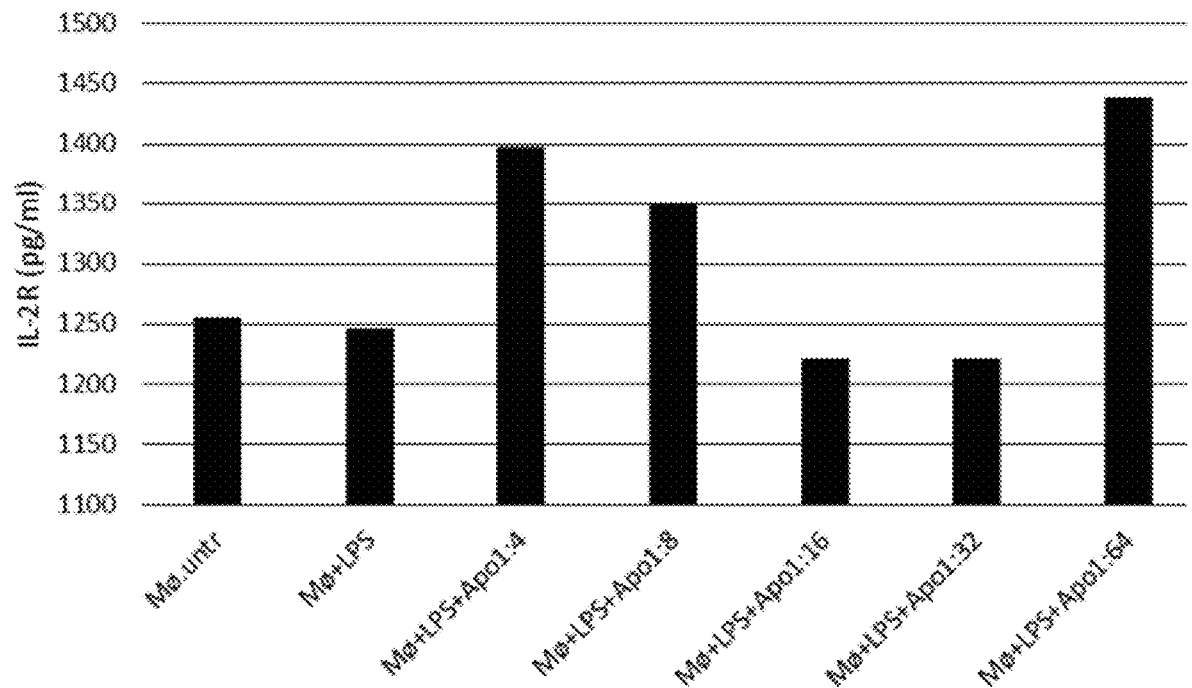
Figure 4J:
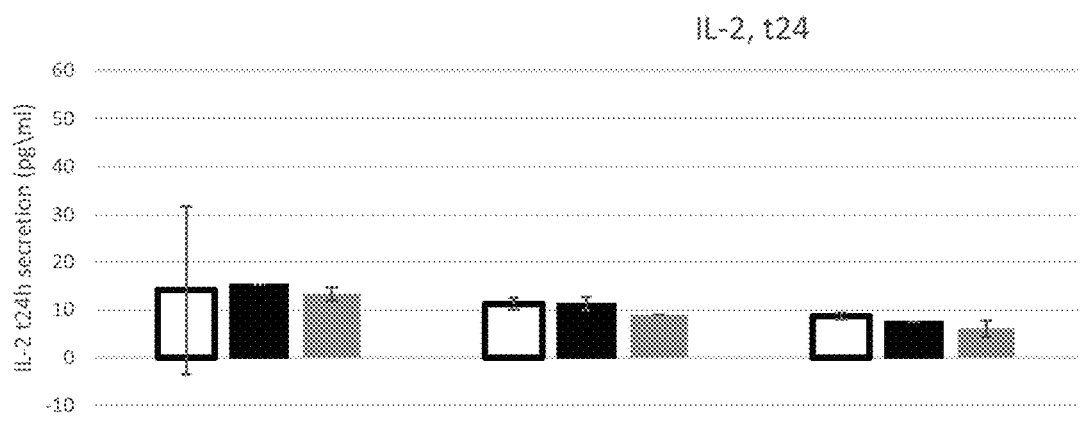

The inhibition of release of pro-inflammatory cytokines and chemokines appears to be specific, as examination of cytokine IL-2R (IL-2 receptor) levels under similar conditions showed that IL-2R levels released was not influenced in the same manner at the pro-inflammatory cytokines. (FIG. 4I). Addition of apoptotic cells increased the release of IL-2R at 1:4 and 1:8 ratios. Further, FIG. 4J shows that apoptotic cells had no influence on release of IL-2 over a 24 hour time period. Activation of the IL-2 receptor is considered to have an essential role in key functions of the immune system including tolerance.

Conclusion:

Addition of early apoptotic cells in a cytokine storm model of macrophage activation syndrome in the presence of cancer and CAR-19, resulted in significant reduction and, surprisingly even prevention of pro-inflammatory cytokines, for example IL-10, IL-6, MIP-1α, IL-8, TNF-α, MIP-1β, MCP-1, and IL-9, while increasing or not affecting cytokine IL-2R levels. Thus, the results here show that while pro-inflammatory cytokines were reduced by incubation with apoptotic cells, IL-2 and IL-2R were not influenced in the same manner with incubation of early apoptotic cells. Thus, the T-cell associated cytokines are not influenced by the CAR T-cell therapy+apoptotic cells, whereas the innate immunity cytokines, for example those released from monocytes, macrophages, and dendritic cells are.

Example 3: Effect of Apoptotic Cells on Cytokine Storm without a Negative Effect on the CAR-T Cell Efficacy Objective:

Test the effect of apoptotic cells or supernatants derived from apoptotic cells on cytokine storm marker cytokines and CAR T-cell efficacy on tumor cells.

Methods:

T4+ CAR T-Cells

Figure 5:
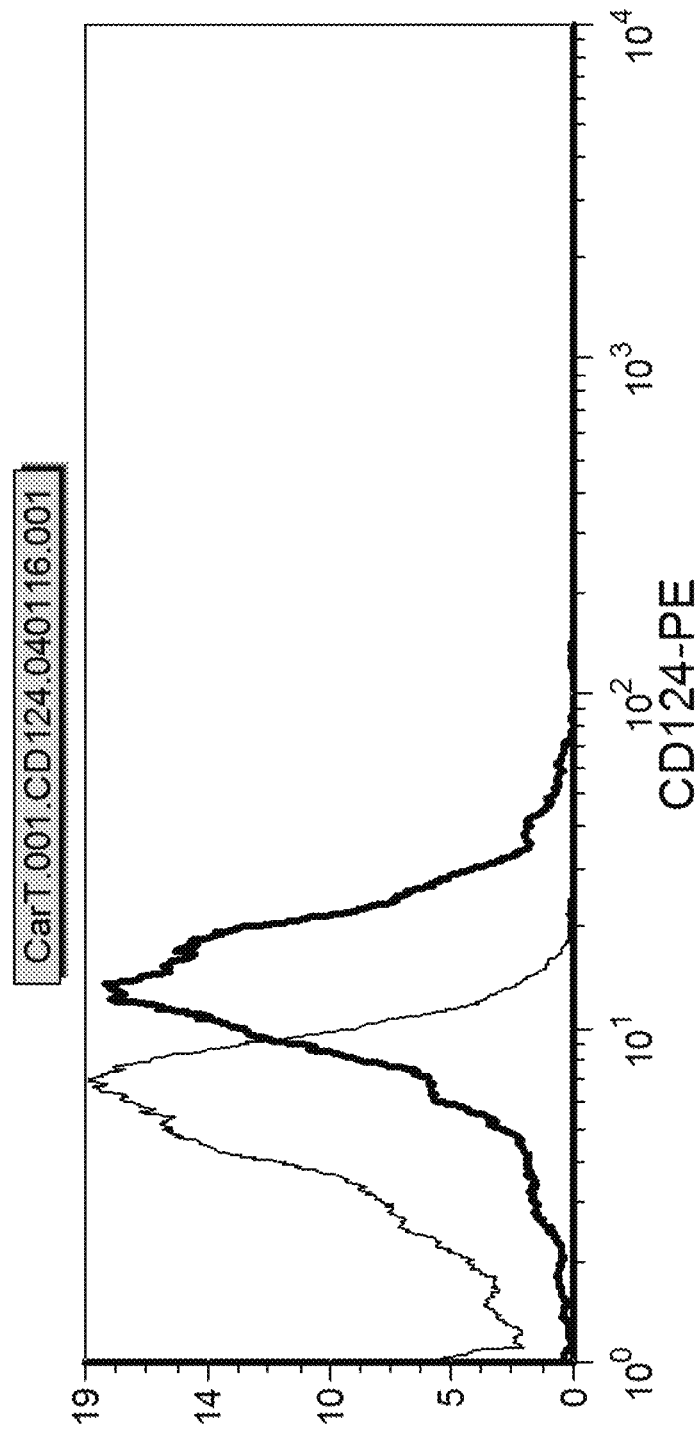
FIG. 5. Verification of Transduction of T-cells showing the flow cytometry results of anti-CD124 analysis of transduced T4$^+$ CAR-T cells.

A solid tumor model (van der Stegen et al., 2013 ibid) reported to induce cytokine storms in mice was utilized. In this model, T cells were engineered with a chimeric antigen receptor (CAR) targeting certain ErbB dimers (T4+ CAR-T cells), which are often highly up-regulated in specific solid tumors such as head and neck tumors and ovarian cancers. T-cells were isolated from PBMC separated from peripheral blood using CD3 micro-beads. Vectors containing the chimeric T4+ receptor were constructed and transducer into the isolated T-cells, resulting in T4+ CAR T-cells. For the experiments performed herein, T4+ CAR T-cells were purchased from Creative Biolabs (NY USA) or Promab Biotechnologies (CA USA). FIG. 5 presents flow cytometry curves verifying the surface expression of $4\alpha\beta$ chimeric receptor on the T4+ CAR T-cells using an anti-CD124 monoclonal antibody (Wilkie et al., ibid). In addition, a PCR procedure was performed and verified the presence of the vector in transduced T cells.

SKOV3-Luc Cells

SKOV3-luc ovarian adenocarcinoma tissue culture cells were purchased from Cell BioLabs (cat. #AKR-232). SKOV3-luc highly express ErbB receptors and are a target for the T4+ CAR-T cells (van der Stegen et al., 2013, ibid). These cells had been further manipulated to constitutively express the firefly luciferase gene, allowing tracking of cell proliferation in vitro and tumor growth and recession in vivo.

Apoptotic Cells

Apoptotic cells were prepared as per Example 1.

Apoptotic Cell Supernatants

Eight (8) million apoptotic cells per seeded per well in a 12-well plate. After 24 hours the cells were centrifuge (290 g, 4 degrees Celsius, 10 minutes). Supernatant was collected and frozen in aliquots at −80 degrees until use. Different numbers of cells are used to make supernatants. Some aliquots contain concentrated supernatants.

Monocyte Isolation

PBMCs were isolated using Ficoll (GE healthcare, United Kingdome) from peripheral blood\ buffy coat obtained from healthy, eligible donors. Cells were brought to a concentration of $15\times10^6$ cells\ml in RPMI1640 (Gibco, Thermo Fisher Scientific, MA, USA) and seeded in a 0.9 ml drop in the middle of 35 mm plates (Corning, N.Y., USA). Plates were then incubated at 37° C. in 5% $CO_2$ for 1 hour. At the end of incubation, cells were washed three times with PBS (Biological industries, Beit Haemek, Israel) and adhesion was determined using a light microscope. Cells were then incubated with complete media (RPMI1640+10% heat inactivated FBS+1% Glutamax+1% PenStrep, all from Gibco).

An alternative method of monocyte isolation was also used wherein human mononuclear cells were isolated from heparinized peripheral blood by density gradient centrifugation. The isolated mononuclear cells then were separated into monocyte, B-cell and T-cell populations by positively selecting monocytes as the CD14+ fraction by magnetic bead separation (Miltenyi Biotec., Auburn, Calif., USA), positively selecting B-cells as the CD22+ fraction, and negatively selecting T-cells as the CD14−CD22− fraction. Purity was greater than 95 percent for monocytes.

For macrophage differentiation, at the end of adhesion, cells were washed three times with PBS then incubated with RPMI1640+1% Glutamax+1% PenStrep and 10% heat inactivated human AB serum (Sigma, MO, USA). Cells were incubated at 37° C. and 5% for 7-9 days, with media exchange at day 3 and day 6. Differentiation was determined by morphology via light microscope.

Supernatant from Apo+ Monocytes

CD14+ monocytes were cultured with apoptotic cells as prepared above at a ratio of 1:16, for 24 h. The number of monocytes was: 0.5 million cells per well in a 12-well plate and the number of apoptotic cells was: 8 million cells per well in a 12-well plate. After incubation for 24 hours the cells were centrifuge (290 g, 4 degrees Celsius, 10 minutes). Supernatant was collected and frozen in aliquots at −80 degrees until use Similar procedures could be performed at different ratios of monocytes:apoptotic cells and/or using other sources of cells, such as macrophages and dendritic cells.

In Vitro Culturing Conditions

Initial experiments were performed by incubating SKOV3-luc cancer cells with apoptotic cells, or apoptotic supernatants, for 1 hour followed by co-culturing with T4+ CAR T-cells (+/− monocytes-macrophages) for 48 hours.

In order to simulate in vivo conditions, $1\times10^5$ THP-1 cells/ml (HTCC USA), or monocytes or macrophages or dendritic cells, will be differentiated with 200 nM (123.4 ng/ml) phorbol myristate acetate (PMA) for 72 hrs and will then be cultured in complete medium without PMA for an additional 24 h. Next, cancer or tumor cells—for example SKOV3-luc cells will be plated in a 24-well plate at $5\times10^5$ SKOV3-luc cells/well on the differentiated THP-1 cells. Following initial culturing of the cancer or tumor cells, $4\times10^5$-$8\times10^5$ apoptotic cells (ApoCell) will be added to the culture for 1-3 h to induce an immunotolerant environment. The ratio of cancer cell to ApoCell will be optimized for each cell type. After washing, the co-culture will be treated with 10 ng/ml LPS after which $1\times10^6$ T4+ CAR T cells (or a quantity to be determined by an effector/target (E/T) ratio graph) will be added. The ratios of tumor cells and T4+ CAR T-cells will be varied in order to generate effector/target (E/T) ratio graphs for each tumor or cancer cell type.

To assay for SKOV3 cancer cell cytotoxicity, lysates were prepared and luciferase activity was determined after the 48 hour incubation period. Additional experiments will be performed assaying for cancer or tumor cell cytotoxicity for the other cancer cell types and at intervals within the 48 h incubation time period. Alternatively, Promega's CytoTox 96 Non-Radioactive Cytotoxicity Assay (Promega, cat #G1780) will be used.

Lysate Preparation

SKOV3-luc cell lysates were prepared by washing the SKOV3-luc monolayer with PBS to remove any residual serum and adding 70 µl CCLR lysis bufferx1/well (for 24-well plates). Detachment was further enhanced by physical scraping of well bottoms. Following vortexing for 15 seconds, lysates were centrifuged at 12,000 g for 2 minutes at 4° C. Supernatants were collected and stored at −80° C.

In Vitro Luciferase Activity

To detect luciferase activity in SKOV3-luc cells in culture, Luciferase Assay System (Promega, cat. #E1501) was used. Calibration of this kit with the luminometer reader (Core Facility, Faculty of Medicine, Ein Kerem, Hebrew University of Jerusalem) was done by using QuantiLum recombinant luciferase (Promega, cat. #E170A). 612 ag-61.2 µg ($10^{-20}$-$10^{-9}$ moles) was used to determine detection range and following manufacturer's guidelines. In brief, each rLuciferase quantity in 20 µl volume was placed in a well of black 96-well plates (Nunc). Each quantity was done in triplicate. 100 µl LAR (luciferin substrate from Luciferase Assay System kit) was added to each well and read immediately with a 10 second exposure.

For luciferase activity reading, lysates were thawed on ice and 20 µl samples were placed in a black 96-well plate (Nunc). Each sample was read in duplicate. 100 µl LAR was added and luminescence was read for 10 second exposure period every 2.5 minutes for 25 minutes and every 40 seconds for the ensuing 10 minutes.

Cytokine Analysis

Initial assays for IL-2, IL-2 receptor (IL-2R), IL-6, IL-1α, IL-4, IL-2, TNF-α were performed. To assay for cytokine release reduction of IL-2, IL-2 receptor (IL-2R), IL-6, IL-1α, IL-4, IL-2, TNF-α as well as other cytokines, supernatants were be collected and examined for selected cytokine using Luminex MagPix reader and ELISA assays.

Results:

SKOV3-Luc Growth

Figure 6:
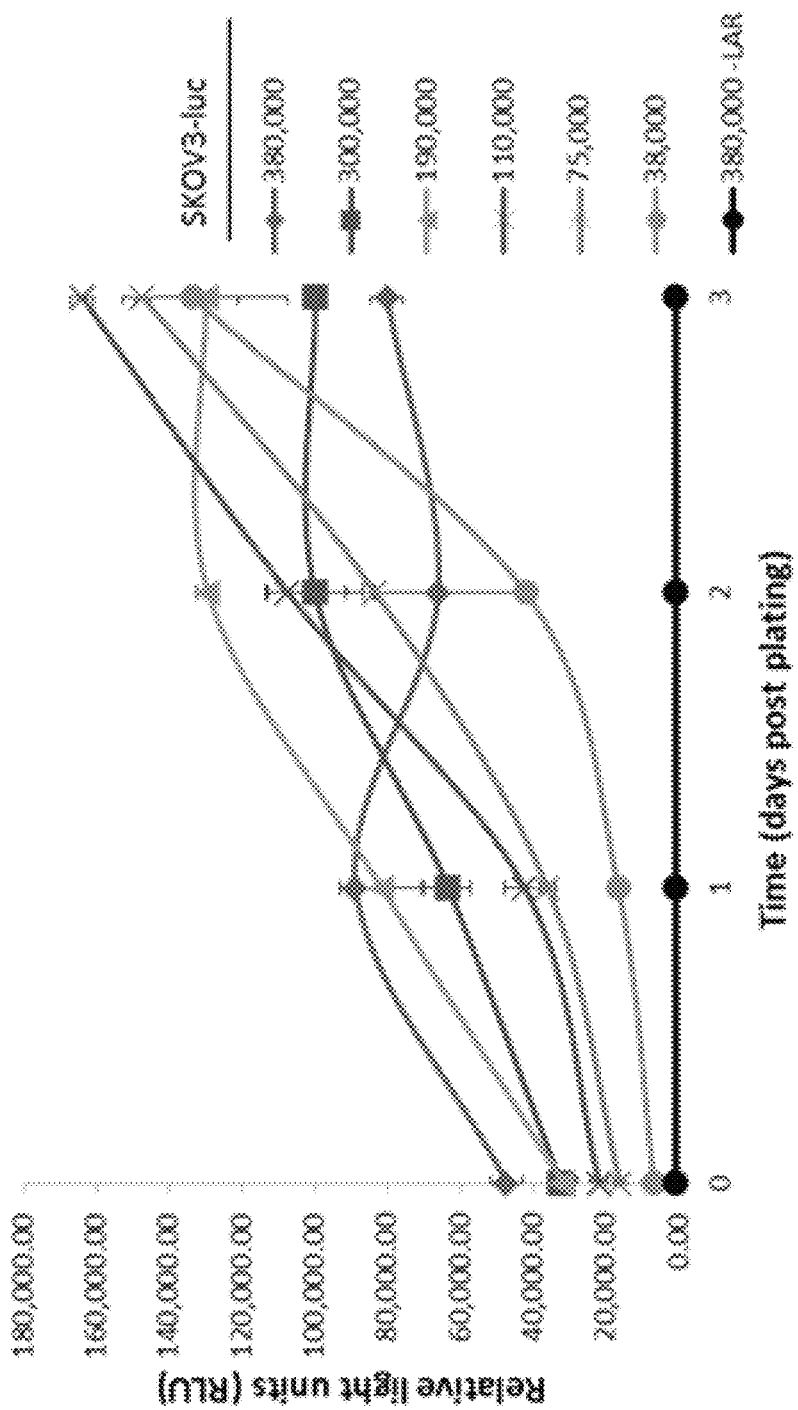
FIG. 6. T4$^+$ CAR T-Cells reduced proliferation of SKOV3-luc ovarian adenocarcinoma cells. The results of the cytotoxicity assay, wherein a monolayer of SKOV3-luc cells were cultured either by non-transduced T cells or by T4+ CAR-T cells, are presented in a bar graph.

SKOV3-luc growth was followed using luciferase activity as an indicator, to determine target SKOV3-luc cell number in future experiments. $3.8\times10^4$-$3.8\times10^5$ SKOV3-luc cells/well were plated in 24-well plates (Corning) and luciferase activity was monitored daily for 3 days. $1.9\times10^5$ cells/well or higher cell number plated reach confluence and present growth saturation indicated by luciferase activity 2 days after plating (FIG. 6). Note that $3.8\times10^4$-$1.1\times10^5$ SKOV3-luc cells/well were still in the linear or exponential growth phase three days after plating (FIG. 6, plots orange, turquoise and purple). Negative control ($3.8\times10^5$ SKOV3-luc cells without LAR substrate) displayed only background-level reading and demonstrates that bioluminescent readings from SKOV3-luc cells result from luciferase activity.

Verification of T4$^+$ CAR-T Cell Activity Against SKOV3-Luc Tumor Cells

Figure 7:
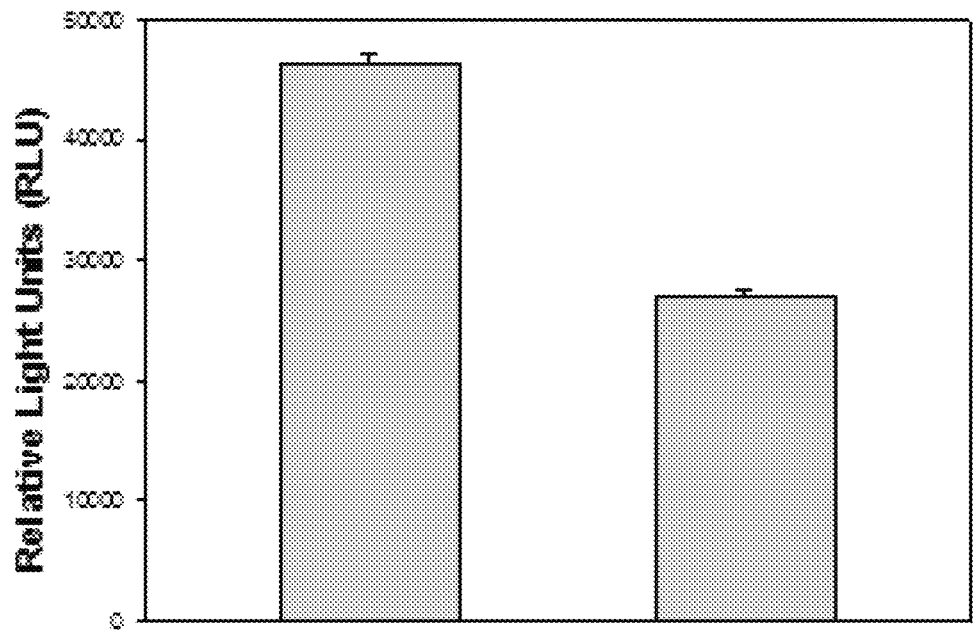
FIG. 7. Apoptotic Cells do not abrogate T4$^+$ CAR-T cells anti-tumor activity. Results are based on a cytotoxicity assay, wherein a monolayer of SKOV3-luc cells were cultured either with non-transduced T cells or with T4$^+$ CAR-T cells in the presence of a vehicle (Hartmann solution), or apoptotic cells (Apocell), or a supernatant of apoptotic cells (ApoSup), or supernatant of co-culture of apoptotic cells and monocytes/macrophages (ApoMon Sup).

To corroborate the T4$^+$ CAR-T cell activity, monolayers of SKOV3-luc were exposed to either 1,000,000 (one million) T4$^+$ CAR-T cells or to 1,000,000 (one million) non-transduced T cells. After 24 h incubation, T4$^+$ CAR-T cells reduced SKOV3-luc proliferation by 30% compared to the non-transduced T cell control (FIG. 7), showing anti-tumor activity of the T4$^+$ CAR-T cells.

Activity of Stand-Alone T4+ CAR-T Cells Against SKOV3-Luc Tumor Cells was Compared to Activity Post Exposure to Apoptotic Cells Apoptotic cells (ApoCell) and apoptotic cell supernatants (ApoSup and ApoMon Sup) were tested to determine if they interfere with T4+ CAR-T cell anti-tumor activity. The SKOV3-luc tumor cells were incubate with Apoptotic Cells for one hour, followed by the addition of T4+ CAR-T cells (500,000, five hundred thousands) or T4+non-transduced T cells (500,000, five hundred thousands) (ratio of 1:2 T4$^+$ CAR-T cells to Apoptotic Cells). The tumor cell/Apoptotic cell/T4$^+$ CAR T-cells were then co-cultured for 48 h. The control SKOV3-luc tumor cells were co-cultured with T4+ CAR-T cells and Hartman solution (the vehicle of Apoptotic Cells), but without Apoptotic Cells, for 48 h.

Figure 8:
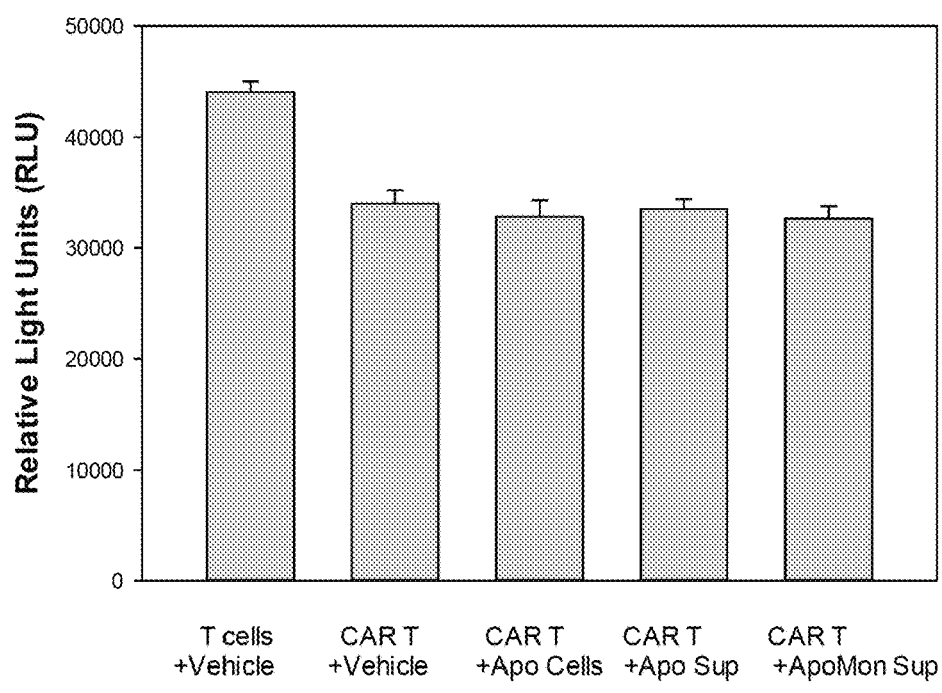
FIG. 8. Il-6, secreted at high levels during cytotoxicity, is down-regulated by apoptotic cells. The results shown here demonstrate the effect of co-culture of SKOV3-luc and human monocytes/macrophages were exposed to apoptotic cells (ApoCell), or ApoCell supernatant (ApoSup), or apoptotic cells and monocyte/macrophage co-culture (ApoMon Sup).

The results showed that after 48 h incubation, T4+ CAR-T cells anti-tumor activity was superior to incubation with non-transduced T cells. Similar incubations were performed with apoptotic cells or apoptotic cell supernatants. Surprisingly, T4+ CAR T-cell anti-tumor activity was comparable with or without exposure to apoptotic cells or apoptotic cell supernatants. (FIG. 8).

Effect of Apoptotic Cells on Amelioration, Reduction or Inhibition of Cytokine Storms Resulting from CAR-T Treatment The effect of apoptotic cells to reduce cytokine storms was examined next. IL-6 is a prototype pro-inflammatory cytokine that is released in cytokine storms (Lee D W et al. (2014) Blood 124(2): 188-195) and is often used as a marker of a cytokine storm response.

Cultures were established to mimic an in vivo CAR T-cell therapy environment. SKOV3-luc tumor cells were cultured in the presence of human monocyte-macrophages and T4+ CAR T-cells. The concentration of 11-6 measured in the culture media was approximately 500-600 pg/ml. This concentration of IL-6 is representative of a cytokine storm.

Figure 9:
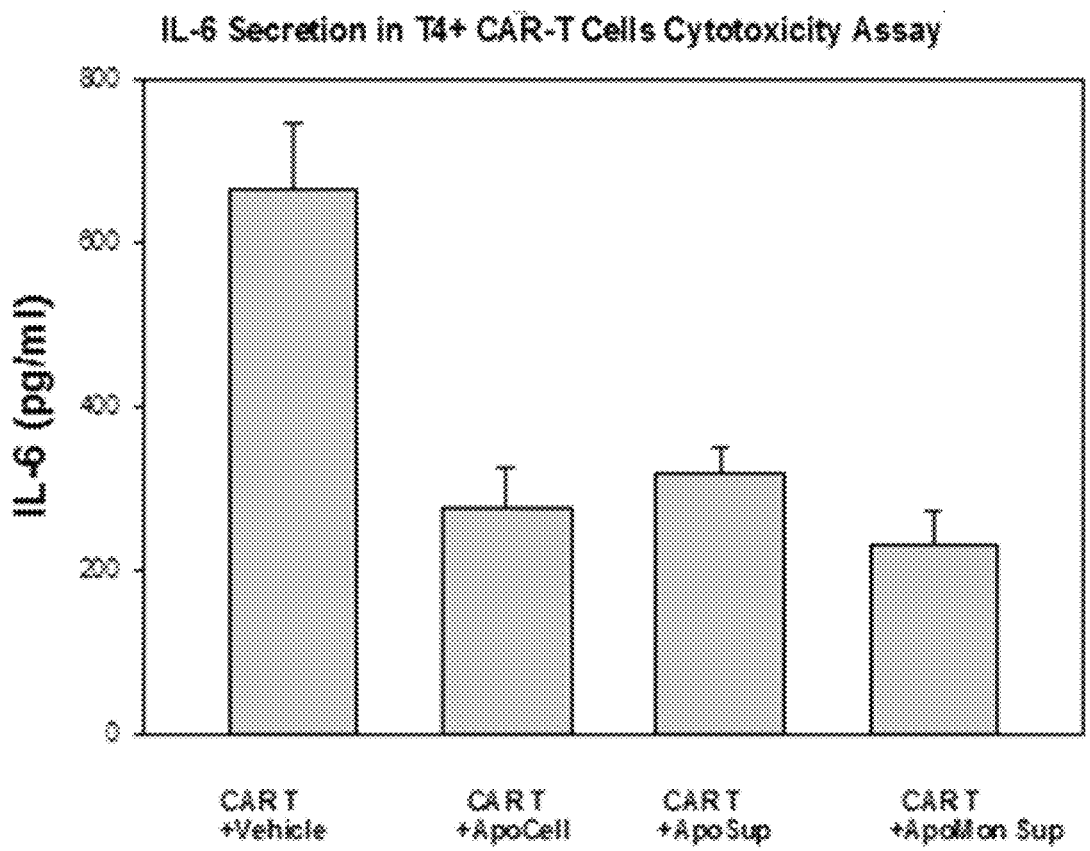
FIG. 9. Effect of Apoptotic Cells or Apoptotic Cell Supernatant or a co-culture of Apoptotic cells and Monocytes following LPS exposure during CAR-T cell therapy. Extremely high secretion of IL-6 was documented when lipopolysaccharides (LPS) were added to the cytotoxic assay. Results show that exposure to Apoptotic cells (Apocell), or supernatant of apoptotic cells (ApoSup) or supernatant of co-culture of apoptotic cells and monocytes/macrophages (ApoMon Sup), down regulated IL-6, wherein IL-6 was reduced to acceptable levels.

Unexpectedly, IL-6 levels measured in the cultured media of SKOV3-luc tumor cells, human monocyte-macrophages, T4+ CAR-T cells, wherein the tumor cells had been previously incubated with apoptotic cells for one hour (ratio of 1:2 T4+ CAR-T cells to Apoptotic Cells) were dramatically reduced. Similarly, IL-6 levels measured in the cultured media of SKOV3-luc tumor cells, human monocyte-macrophages, T4+ CAR-T cells, wherein the tumor cells had been previously incubated with apoptotic cell supernatants for one hour, were also dramatically reduced. This reduction in concentration of IL-6 is representative of a decrease in the cytokine storm (FIG. 9).

It was concluded that unexpectedly, apoptotic cells and apoptotic supernatants do not abrogate the effect of CAR-T cells on tumor cell proliferation while at the same time they down regulating pro-inflammatory cytokines such as IL-6, which was been described as a major cytokine leading to morbidity.

Analysis Using a Wider Range of Cytokines

Figure 10:
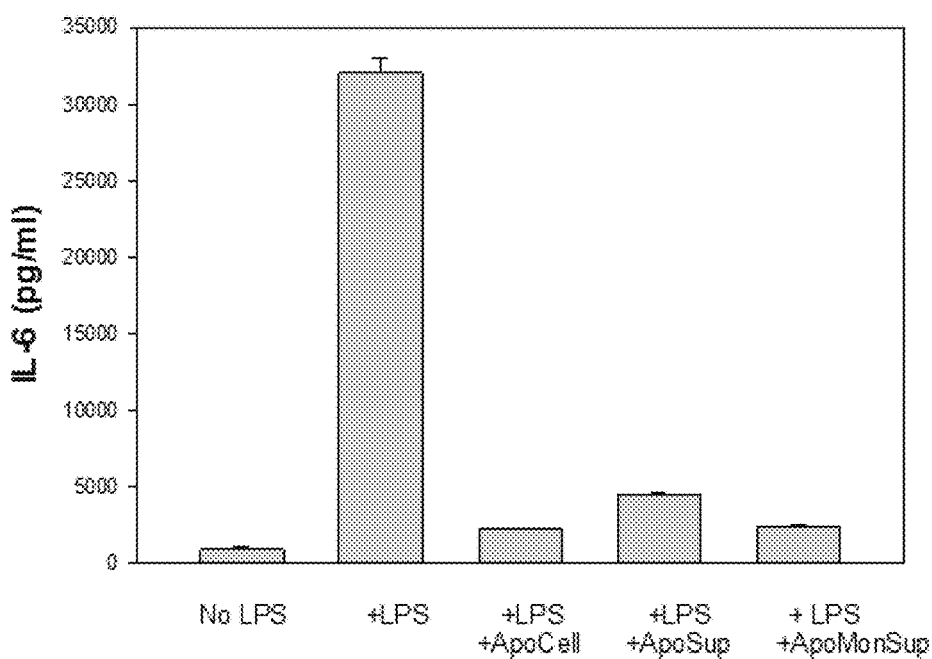
FIG. 10. Effect of Apoptotic Cells or Apoptotic Cell Supernatant or a co-culture of Apoptotic cells and Monocytes following LPS exposure during CAR T-cell treatment mimicking CAR T-cell clinical therapy. Extremely high secretion of IL-6 was documented when lipopolysaccharides (LPS) were added to the cytotoxic assay. Results show that exposure to Apoptotic cells (Apocell), or supernatant of apoptotic cells (ApoSup) or supernatant of co-culture of apoptotic cells and monocytes/macrophages (ApoMon Sup), down regulated IL-6, wherein IL-6 was reduced to acceptable levels.

To further evaluate the effect on a possible wider range and levels of cytokines that are not generated during experimental procedures but do appear in clinical settings during a human cytokine storm, LPS (10 ng/ml) was added to the SKOV3-luc culture conditions outlined above. The addition of LPS is expected to exponentially increase the cytokine storm level. As expected, the addition of LPS increased the cytokine storm effect and as a result IL-6 levels increased to approximately 30,000 pg/ml. Other cytokines known to be expressed in high levels during a cytokine storm showed elevated levels, for example: TNF-α (250-300 pg/ml), IL-10 (200-300 pg/ml), IL1-alpha (40-50 pg/ml) and IL-18 (4-5 pg/ml). As shown in FIG. 10, exposure to apoptotic cells dramatically reduced the levels of IL-6 even during the exponential state of the cytokine storm to almost normal levels that may be seen in clinical settings, and is not always seen in experimental procedures with CAR T-cells. This effect was similar across the other pro-inflammatory cytokines TNF-alpha, IL-10, IL1-alpha, IL-1β, and IL-18, which showed a reduction of between 20-90% Similar results were found when using apoptotic cell supernatants in place of the apoptotic cells.

Effect of Apoptotic Cells on IL-2 and IL-2R

The concentration of IL-2 measured in culture supernatants following incubation of SKOV3-luc cells with T4+ CAR T-cells was 1084 pg/ml. Surprisingly, when SKOC3-luc cells were first incubated with apoptotic cells and then T4+ CAR T-cells the concentration of IL-2 increased to 1190 pg/ml. Similarly, the concentration of IL-2R measured in culture supernatants following incubation of SKOV3-luc cells with T4+ CAR T-cells was 3817 pg/ml. Surprisingly, when SKOC3-luc cells were first incubated with apoptotic cells and then T4+ CAR T-cells the concentration of IL-2R increased to 4580 pg/ml. In SKOV3-luc alone the concentration of Il-2 was 3.2 pg/ml and with the addition of apoptotic cells the concentration was 10.6 pg/ml. In SKOV3-luc alone the concentration of Il-2R was 26.3 pg/ml and with the addition of apoptotic cells the concentration was 24.7 pg/ml.

Conclusion

CAR-T cell therapy has been documented to cause cytokine storms in a significant number of patients. These results demonstrate that apoptotic cells and apoptotic cell supernatants surprisingly decreased cytokine storms cytokine markers without affecting CAR-T cell efficacy against tumor cells. Moreover, it appears that apoptotic cells increase cytokine IL-2, which may increase duration of CAR T-cell therapy by maintaining or increasing CAR T-cell proliferation.

Example 4: Apoptotic Cell Therapy Prevents Cytokine Storms in Mice Administered CAR T-Cell Therapy Objective:

Test the in vivo effect of apoptotic cells or apoptotic cell supernatants in a solid tumor model (SKOV3 ovarian adenocarcinoma), in order to determine T4+ CAR T-cell efficacy and the level of cytokine storm marker cytokines.

Materials and Methods

In Vitro Studies

In vitro methods including methods of making, culturing, and analyzing the results described above and relevant for use of T4+ CAR T-cells that recognize the ErbB target antigen (referred to herein as "T4+ CAR T-cells", SKOV3-luc cells, apoptotic cells, apoptotic supernatants, monocytes, macrophages, and the various assays, have all been described above in Example 1. The same methods were used herein.

In Vivo Studies

Mice 7-8 week old SCID-beige mice and NSGS mice were purchased from Harlan (Israel) and kept in the SPF animal facility in Sharett Institute.

SKOV3-luc tumor cells ($1 \times 10^6$ or $2 \times 10^6$) are inoculated into SCID beige mice or NSGS mice, by either i.p. in PBS or s.c. in 200 ml Matrigel (BD Biosciences). Tumor engraftment is confirmed by bioluminescence imaging (BLI) at about 14-18 days post injection, and mice are sorted into groups with similar signal intensity prior to T-cell administration.

Mice will receive $30 \times 10^6$ apoptotic cells either 24 hours prior to administration of T4+ CAR T-cells or concurrent with administration of T4+ CAR T-cells ($10-30 \times 10^6$ T4+ CAR T-cells). Tumor growth will be followed by bioluminescence imaging (BLI) and circulating cytokine levels will be determined by Luminex.

In Vivo Luciferase Assay

Tumor growth was monitored weekly through firefly luciferase activity. In brief, 3 mg D-luciferin (E1605. Promega, USA)/mouse (100 μl of 30 mg/ml D-luciferin) was injected i.p. into isoflurane-anesthetized mice and ventral images were acquired 10 minutes after injection using IVIS Imaging System and Live Image image capture software (both from Perkin Elmer, USA).

Image acquisition parameters were chosen for each image session by imaging mice that received $0.5 \times 10^6$ SKOV3-luc cells/mouse, 5 minutes post D-luciferin injection the "auto" option. Capture parameters were set for binning 4, F/stop 1.2 and exposure of 2-4 minutes using the 24× lens. Data analysis and quantification was performed with the Live Image software and graphs were generated using Microsoft's Excel program.

In Vivo Cytotoxicity

To assess in vivo toxicity of T-cells, organs are collected from mice, formalin fixed, and subjected to histopathologic analysis.

Cytokine Analysis

Supernatants and sera are analyzed using Luminex MagPix reader and/or ELISA kits, cytometric bead arrays (Th1/Th2/Th17; BD Biosciences) as described by the manufacturers. For example, analysis may be for pro-inflammatory cytokine, which in one case would be IL-6, though, in some embodiments, any of the cytokines listed in Tables 1 and 2 or known in the art may be analyzed herein.

Results

Calibrating SKOV3-Luc Tumors In Vivo $0.5 \times 10^6$, $1 \times 10^6$ or $4.5 \times 10^6$ SKOV3-luc cells were injected i.p. to SCID beige mice and bioluminescence imaging (BLI) was conducted weekly in order to follow tumor growth, as described in the Methods (data not shown).

Clinical Score of Mice

Figure 11A:
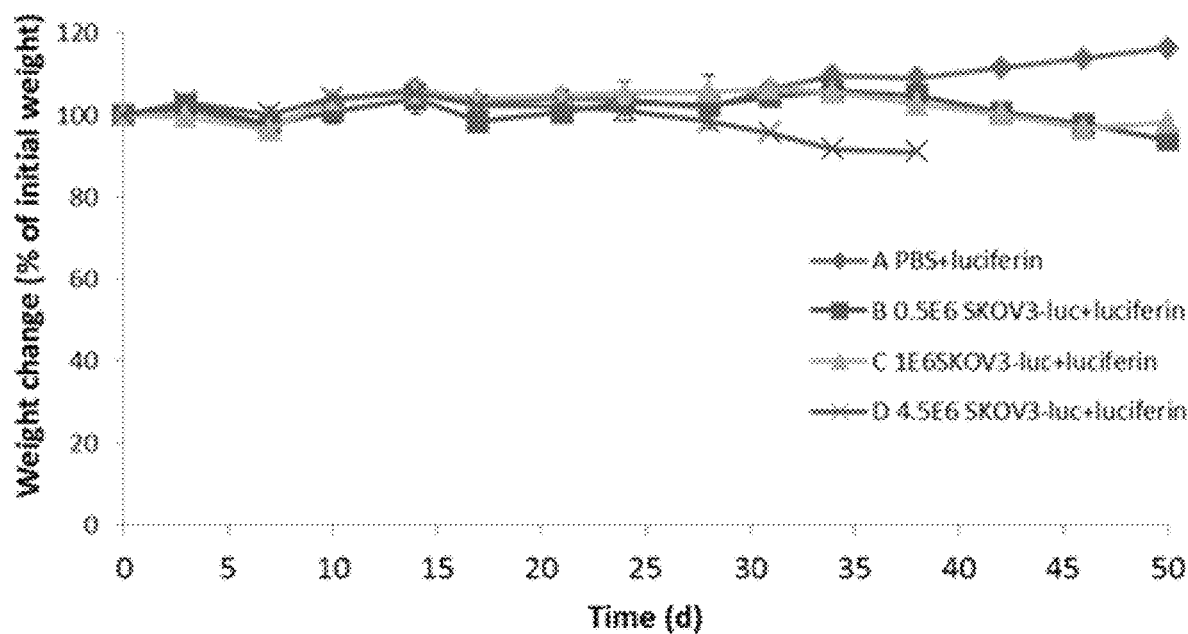
FIGS. 11A-11B. Weight and Tumor Size in Mice at time of Culling.
Figure 11B:

Mice displayed no clinical symptoms for the initial 4 weeks. However, 28 days post SKOV3-luc injection, the mice that received the high dose ($4.5 \times 10^6$; purple line) began to lose weighed steadily (FIG. 11A) and the overall appearance of the mice deteriorated, manifested in lethargy, abnormal pacing and general loss of activity. This group was culled at the day 39, and an abdominal autopsy was performed to expose tumor appearance and size (FIG. 11B). SKOV3-luc tumors were large, solid, vascularized and displayed a whitish shining complexion. One large tumor predominated on the side of the injection (left) either caudal or rostral in the abdominal cavity. This tumor encompassed approximately 25-75% of the cavity and clearly pressed and disturbed the intestines. Smaller foci were also observed at various locations within the abdominal cavity. Tumors were contained within the abdominal cavity and no other tumors were observed in any other part of the body in any mice. Mice receiving low ($0.5 \times 10^6$) or medium ($1 \times 10^6$) dose of SKOV3-luc cease gaining weight 40 days after SKOV3-luc injection and began to steadily lose weighed. Experiment was terminated 50 days after SKOV3-luc injection.

SKOV3-Luc Tumor Kinetics

Figure 12:
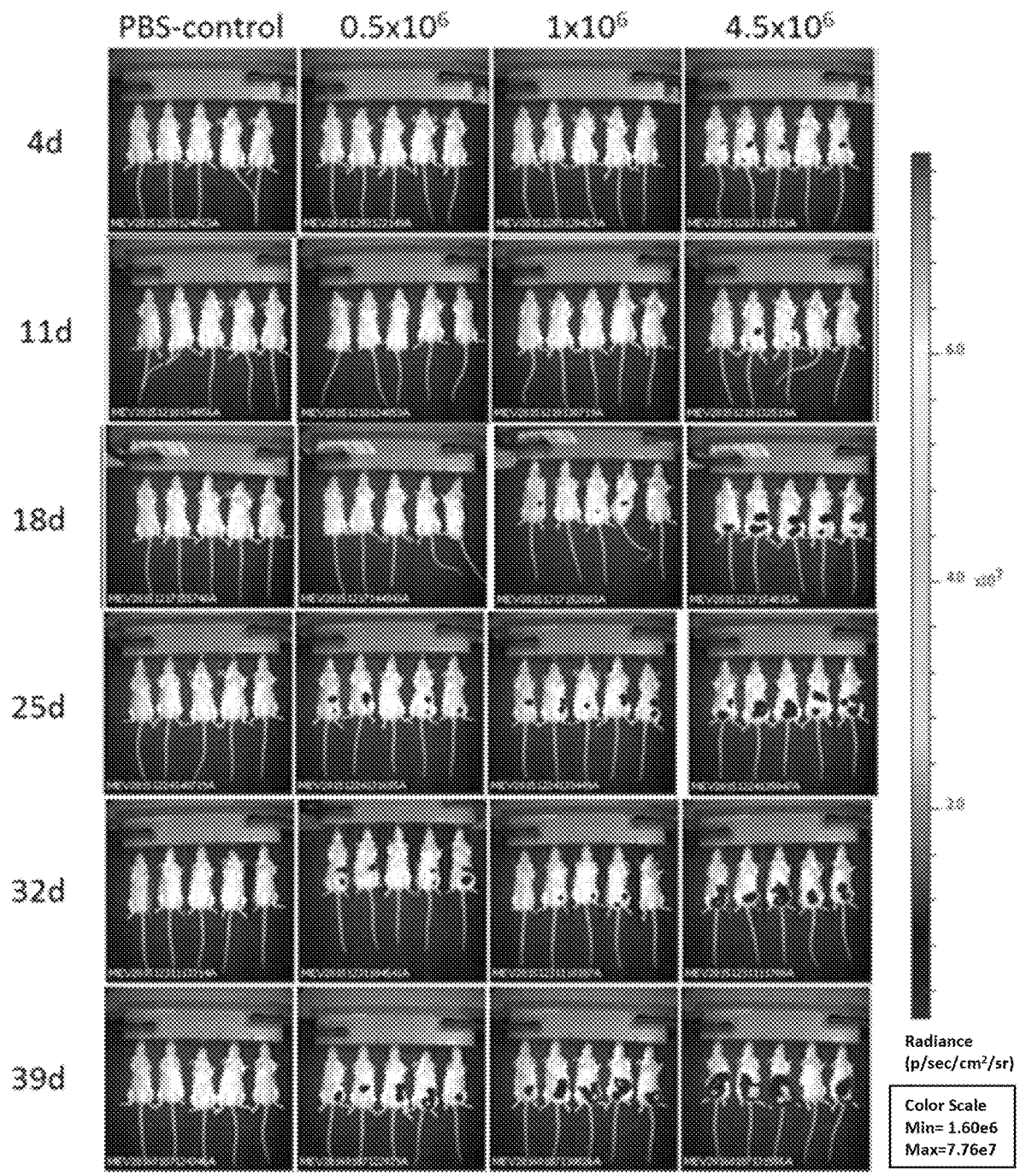
FIG. 12. SKOV3-luc Tumor Growth. Mice bearing SKOV3-luc tumors imaged by Bioluminescent imaging (BLI) are presented showing the differences between control (PBS) and inoculation with $0.5 \times 10^6$, $1 \times 10^6$, and $4.5 \times 10^6$ SKOV3-luc cells.
Figures 13A, 13B:
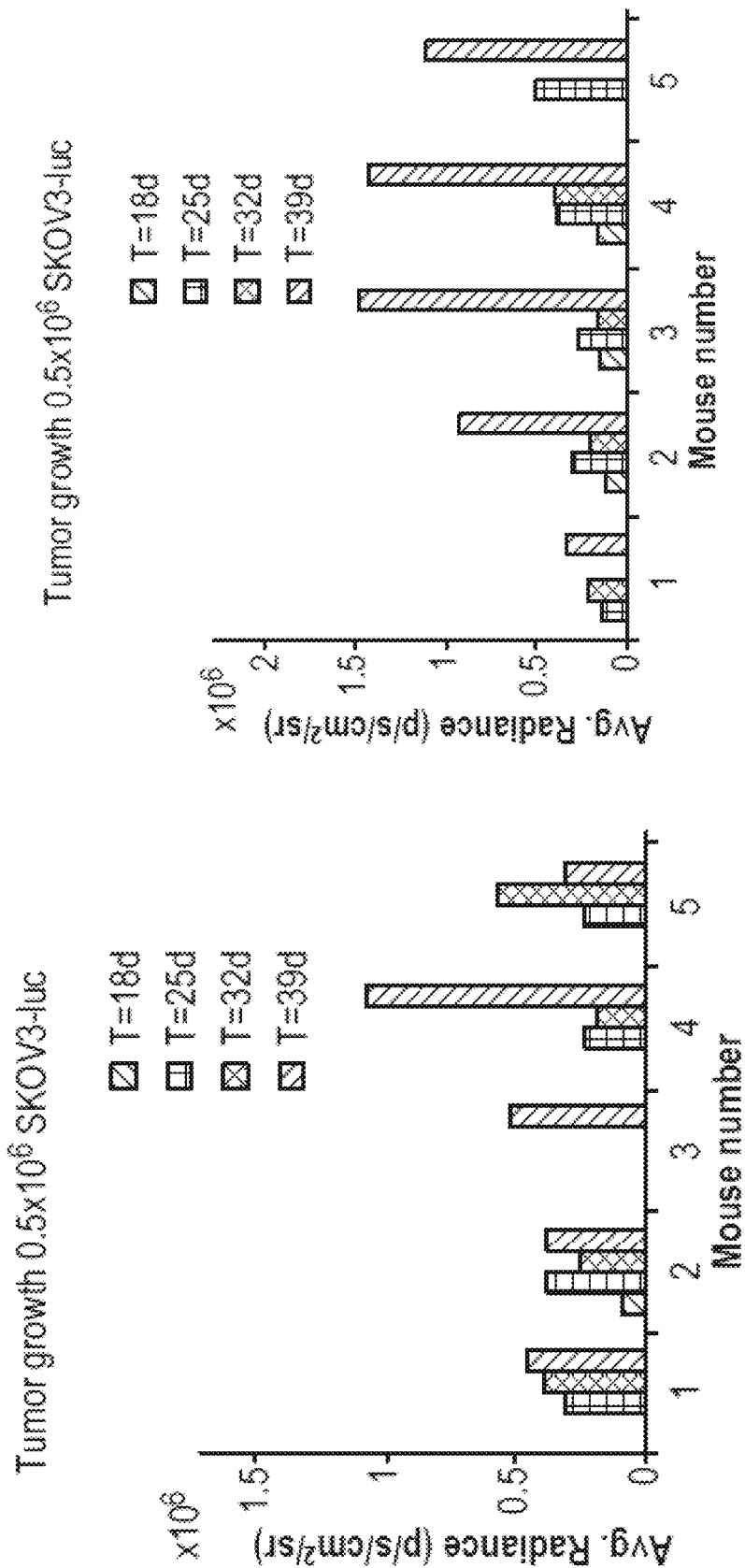
FIGS. 13A-13D. SKOV3-luc Tumor Burden. Quantification of bioluminescence (BLI) of SKOV3-luc tumors in vivo (See FIG. 12). A 600 photon count cut-off was implemented as instructed by the manufacturer.
Figure 13D:
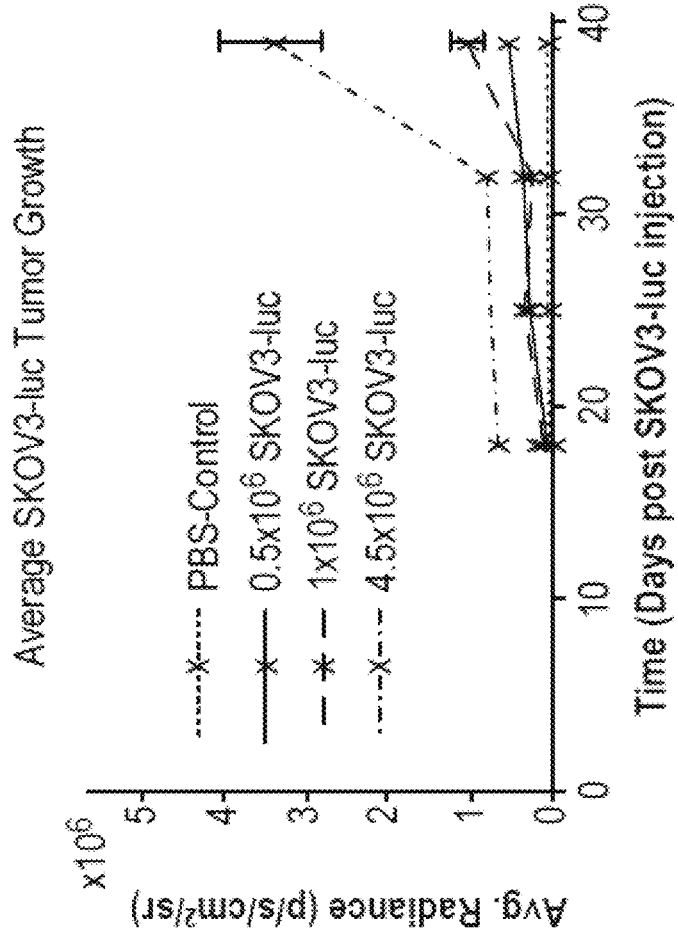
Figure 13C:
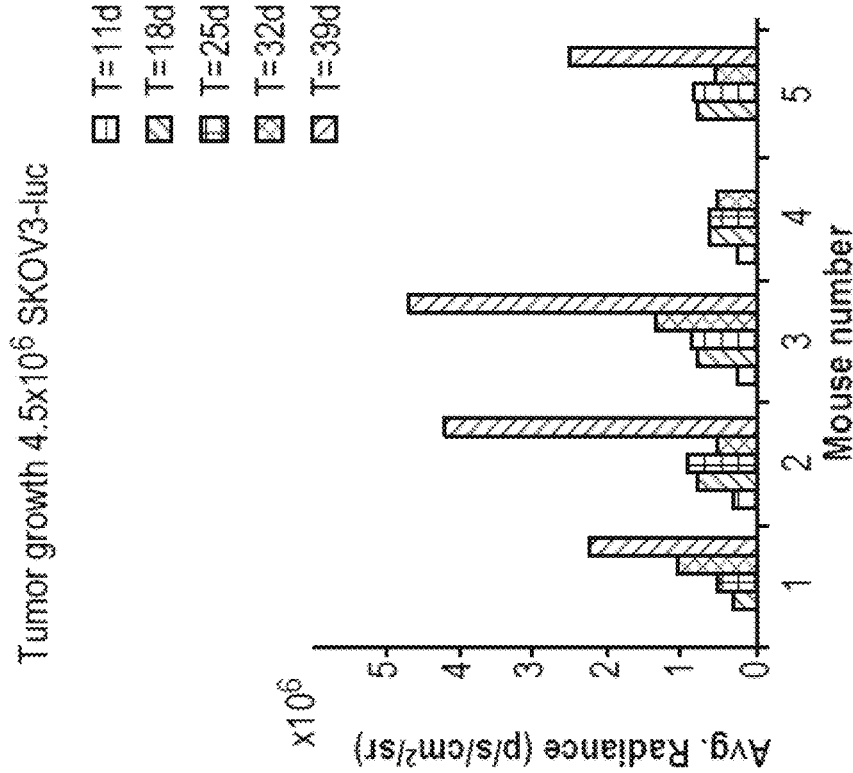

PBS was injected to control for SKOV3-luc cells and these mice did not exhibit any luciferase activity throughout the experiment (FIG. 12, Left panel). Tumor detection and growth was dose-dependent. Lower dose ($0.5 \times 10^6$ SKOV3-luc cells) began to display tumors 25 days post-injection (4/5 animals), medium dose ($1 \times 10^6$) injections showed tumors at 18 days post-injection (4/5 animals), whereas at higher dose ($4.5 \times 10^6$) tumors were detected as early as 11 days post-injection in 3/5 animals and by day 18 all animals displayed well-established tumors (FIG. 12 and FIGS. 13A-13D).

CAR T-Cell Therapy Induces Cytokine Release Syndrome

Three groups of tumor-free mice as well as mice with tumors are administered (i.p. or directly into the tumor) increasing doses of T4+ CAR T-cells ($3 \times 10^6$, $10 \times 10^6$ or $30 \times 10^6$). At the highest dose, tumor-free mice and mice with tumors demonstrate subdued behavior, piloerection, and reduced mobility within 24 h, accompanied by rapid weight loss followed by death within 48 hrs. At least Human interferon-gamma and mouse IL-6 are detectable in blood samples from the mice given the highest dose of CAR T-cells Animals that receive a high dose of CAR T-cells directed to a different tumor antigen do not exhibit weight loss or behavioral alterations.

Administration of Apoptotic Cells Inhibits or Reduces the Incidence of Cytokine Release Syndrome Induced by CAR T-Cell Therapy One group of mice given the highest dose of CAR T-cells is concomitantly administered $2.10 \times 10^8$/kg apoptotic cells, which was previously demonstrated to be a safe and effective dose. Mice receiving human CAR T+apoptotic cells have significantly lowered levels of mouse IL-6, lower weight loss, and reduced mortality.

Example 5: Effect of Combination Immune Therapy on In Vitro Diffuse Tumor Models Objective:

Test the effect of apoptotic cells or supernatants derived from apoptotic cells in a diffuse tumor model where the cancer is widely spread and not localized or confined, in order to determine CAR T-cell efficacy on the cancer cells and the level of cytokine storm marker cytokines.

Methods:

CD19+T4+ CAR T-Cells ("CD19+ CAR T-Cells")

CD19-specific CAR-T cells were purchased from ProMab (Lot #012916). The T cells were 30% positive for CAR (according to manufacturer's FACS data-Fab staining). Briefly, cells were thawed into AimV+5% heat-inactivated FBS, centrifuged (300 g, 5 minutes, room-temperature), and resuspended in AimV. On day 6 of the experiment $20 \times 10^6$ cells were injected IV per mouse (70% AnnexinPI negative, of which 30% CAR positive).

Recombinant HeLa cells expressing CD19 will be used as a control cell-type that also expresses CD19 on their cell surface.

CD123+ CAR T-Cells

T4+ CAR T-cells will also be engineered with a CAR targeting CD123 epitopes (referred to herein as "CD123+ CAR T-cells").

Raji Cells, CD19 Expressing HeLa Cells, and CD123 Expressing Leukemic Cells

Raji cells Raji cells were purchased from ECACC (Cat. #: 85011429), and routinely cultured in complete medium (RPMI-1640 supplemented with 10% H.I. FBS, 1% Glutamax, 1% Penicillin/Streptomycin), and maintained at a concentration of $3 \times 10^5$-$3 \times 10^6$ cells/ml. On day 1 of the experiment $0.1 \times 10^6$ cells were injected IV per mouse.

Similarly, CD19 expressing HeLa cells will be generated in the laboratory and used as a target for CD19+ CAR T-cells. CD123 expressing leukemic cells will be used as targets for CD123+ CAR T-cells. In addition, primary cancer cells will be utilized as a target for CAR T-cells.

HeLa cells expressing CD19 were prepared using methods known in the art. Cells will be cultured as is well known in the art.

CD123 is a membrane biomarker and a therapeutic target in hematologic malignancies. CD123 expressing leukemic cells, for example leukemic blasts and leukemic stem cells will be cultured as is known in the art.

Apoptotic cells, Apoptotic cell supernatants and monocyte isolation, will be prepared as described in Example 1. Early apoptotic cells produced were at least 50% annexin V-positive and less than 5% PI-positive cells.

Macrophages.

Were generated from CD14positive cells by adherence.

Dendritic Cells.

Were CD14 derived grown in the presence of IL4 and GMCSF.

Flow-Cytometry.

The following antibodies were used: hCD19-PE (eBiosciences, Cat. #12-0198-42); mIgG1-PE (eBiosciences, Cat. #12-0198-42); hCD3-FITC (eBiosciences, Cat. #11-0037-42); mIgG2a-FITC (eBiosciences, Cat. #11-4724-82). Acquisition was performed using FACS Calibur, BD.

Naïve T Cells.

Naïve T cells were isolated from Buffy coat using magnetic beads (BD), and cryopreserved in 90% human AB serum and 10% DMSO. Thawing and injection was identical to the CAR-T cells.

In Vitro Culturing Conditions

Cell Lines and Culturing Reagents

The human lymphoma cell line Raji (eCACC, UK, access no. 85011429), the human cervical adenocarcinoma cell line HeLa (ATCC, USA, number: CCL-2) and HeLa-CD19 (ProMab, USA, cat. no. PM-Hela-CD19) were cultured in RPMI 1640 (Gibco, ThermoFisher Scientific, USA, cat. no. 31870-025) supplemented with 10% FBS (Gibco, ThermoFisher Scietific, South America, cat. no. 12657-029), 2 mM GlutaMAX (Gibco, ThermoFisher Scientific, USA, cat. no. 35050-038), and 100 U/ml Penicillin+100 U/ml Streptomycin (Gibco, ThermoFisher Scientific, USA, cat. no. 15140-122), henceforth referred to as "Complete Medium". HeLa-CD19 medium was further supplemented with 1 μg/ml puromycin (Sigma-Aldrich, USA, cat. no. P9620), as the selective antibiotics, during standard culturing.

All cells were kept in sub-confluent conditions. Raji cells were maintained in a concentration range of $0.3 \times 10^6$-$2 \times 10^6$ cell/ml. HeLa and HeLa-CD19 cells were passaged when receptacle was filled to 90% confluence.

Primary monocytes were isolated from blood donations buffy coats (Sheba Medical Center, Israel). First, peripheral blood mononuclear cells (PBMCs) were isolated on a Ficoll density gradient (Ficoll-Paque PLUS, GE Healthcare, UK, cat. no. 17-1440-03). Upon centrifugation (800×g, 2-8° C., 20 min with break 0), the interphase containing the PBMCs were transferred to a fresh test tube and washed with RPMI-1640 (Lonza, Switzerland, cat. no. BE12-918F) supplemented with 2 mM L-glutamine (Lonza, Switzerland, cat. no. BE17-605E) and 10 mM Hepes (Lonza, Switzerland, cat. no. BE17-737B), henceforth "Wash Medium", and centrifuged (650×g, 2-8° C., 10 min) Pelleted cells were re-suspended in "Wash Medium" to a concentration of $15 \times 10^6$ cell/ml. Cells were seeded as a 0.9 ml drop at the center of a 35-mm plate (Corning, USA, cat. no. 430165). Plates were incubated for 1.5 h in a humidified incubator (37° C., 5% $CO_2$), allowing monocytes to adhere, and then washed three times with pre-warmed PBS (Lonza, Switzerland, cat. no. BE17-516F), removing other cell types. After washing, cells were cultured in 2 ml RPMI 1640 (Gibco, ThermoFisher Scientific, USA, cat. no. 31870-025) supplemented with 10% FBS (Gibco, ThermoFisher Scietific, South America, cat. no. 12657-029), 2 mM GlutaMAX (Gibco, ThermoFisher Scientific, USA, cat. no. 35050-038), and 100 U/ml Penicillin+100 U/ml Streptomycin (Gibco, ThermoFisher Scientific, USA, cat. no. 15140-122), aka "Complete Medium".

All cell lines were cultured in a humidified incubator at 37° C. and containing 5% $CO_2$.

CD19-CAR T cells (ProMab, USA, cat. no. FMC63) were delivered either in AIM-V medium or frozen. Cryopreserved CAR T cells for in vitro experiments were thawed on the day of the experiment in a 35-38° C. bath and immediately immersed in pre-warmed AIM V medium (Gibco, ThermoFisher Scientific, USA, cat. no. 12055-091) supplemented with 5% FBS (Gibco, South America, cat. no. 12657-029). DMSO was removed by centrifuging the cells (300×g, room temperature, 5 min) and re-suspending in pre-warmed AIM V medium. Concentration and viability of CD19-CAR+ cell population was determined by anti-FLAG (BioLegend, USA, cat. no. 637310) staining and by Annexin V and PI staining (MEBCYTO Apoptosis kit, MBL, USA, cat. no. 4700) read with FACSCalibur flow cytometer (BD, USA).

For Naïve T cell isolation, PBMCs were extracted either from leukapheresis fractions collected from informed consenting eligible donors at Hadassah Medical Center (Ein Kerem Campus, Jerusalem, Israel) using a Cobe Spectra™ apheresis apparatus (Gambro BCT, USA) according to Leaukapheresis Unit's SOP or from buffy coats (Sheba Medical Center, Israel) loaded on a Ficoll density gradient and centrifuged 800×g, 2-8° C., 20 min T cells were isolated from the positive fraction using MagniSort Human CD3 Positive Selection Kit (eBioscience, USA, cat. no. 8802-6830-74) following manufacturer's guidelines. T cells were cryopreserved in "Complete Medium" (defined above) containing an additional 20% FBS (Gibco, ThermoFisher Scietific, South America, cat. no. 12657-029) and 5% DMSO (CryoSure-DMSO, WAK-Chemie Medical GmbH, Germany, cat. no. WAK-DMSO-70) and thawed on the day of experiment parallel to the CD19-CAR T cells.

A LDH Cytotoxicity Assay

Lactate dehydrogenase (LDH), a stable cytosolic enzyme, is released by cells undergoing lysis in a correlative manner Hence, LDH levels in the medium can be used to quantify cytotoxic activity. CytoTox 96 Non-Radioactive Cytotoxicity Assay (Promega, USA, cat. no. G1780) is a colorimetric assay to quantify LDH levels in the medium. A tetrazolium salt substrate (iodonitro-tetrazolium violet, INT) is introduced to the medium in excess and LDH converts the substrate into a red formazan product. The amount of red color formed is directly proportional to the number of cells lysed.

In brief, and following manufacturer's guidelines, target cells (HeLa or HeLa-CD19) were cultured alone or in conjunction with monocytes. After target cells adhered to the plate (6 h-overnight), cultures were exposed to y×10$^6$ ApoCells cells for 1 h, after which these cells were washed off by 4-5 washes of RPMI. Removal of ApoCells cells was confirmed visually under a light microscope. 10 ng/ml LPS (Sigma-Aldrich, USA, cat. no. L4391) was introduced to the co-culture and incubated for 1 h. After incubation, LPS was removed by 3-5 washing cycles with RPMI. Viable CD19-CAR T cells or naïve T cells were added at the designated E/T ratio(s) and incubated for 4 h. To collect media, plates were centrifuged at 250×g, 2-25° C., 4 min (Centrifuge 5810 R, Eppendorf, Germany) to sediment cells. 50 µl of supernatant medium from each well was transferred to a fresh flat-bottom 96-well microplate well (Corning, USA, cat. no. 3596) and 50 µl CytoTox 96 Reagent was added to each well. Plates were incubated in the dark at room temperature for 30 min., after which the reaction was terminated by addition of 50 µl Stop Solution per well. Absorbance was read at 492 nm using Infinite F50 (Tecan, Switzerland) and captured using Magellan F50 software. Data analysis and graph generation was performed using Microsoft Excel 2010.

Flow Cytometry Cytotoxicity Assay

HeLa-CD19 (target) and HeLa (control) cells were pre-stained with 5 µM carboxyfluorescein succinimidyl ester (CFSE, Life Technologies, USA, cat. no. C1157), mixed together, and plated on either fresh plates or on plates populated with isolated primary monocyte. After target cells adhere to the plate (6 h-overnight), cultures were exposed to y×10$^6$ ApoCells cells for 1 h. Plates were washed with RPMI 3-5 times and visually verified that suspended ApoCells cells were washed off. 10 ng/ml LPS was introduced to the co-culture and incubated for 1 h, after which LPS was removed by 3-5 washing cycles with RPMI. Viable CD19-CAR T cells were then added to the co-cultures as indicated by specific E/T ratio(s) and incubated for 4 h. After incubation, cells were harvested by adding trypsin-EDTA (Biological Industries, Israel, cat. no. 03-052-1B) and incubating for 4 min. at 37° C. To terminate the enzymatic activity, two- to four-fold volume of "complete medium" was added. Cells were collected, centrifuged at 200×g for 5 min at room temperature and re-suspended in 100 µl RPMI (Gibco, ThermoFisher Scientific, USA, cat. no. 15140-122) Staining ensued first against anti-CD19 (eBioscience, USA, cat. no. 12-0198-42), incubated in dark for 30 min at room temperature. After centrifugation (290×g, 1 min., 2-8° C.) and re-suspended in 300 µl RPMI, cells were stained against anti-7AAD (eBioscience, USA, cat. no. 00-6993-50). Analysis was gated on 7ADD-negative cells (live cells), where live target cell (HeLa-CD19) and live control cells (HeLa) was calculated. Percent survival was calculated by dividing percent live target cells by percent live control cells. To correct for variation in starting cell numbers and spontaneous target cell death, percent survival was divided by the ratio of percent target cells to percent control cells cultured without effector cells (CD19-CAR T cells). Finally, percent cytotoxicity was determined by subtracting the corrected survival percentage from 100%[2].

Initial experiments are performed by incubating Raji cancer cells with CD19+ CAR T-cells (+/− monocytes-macrophages) for 48 hours in order to determine optimal ratios of CD19+ CAR T-cells to target Raji cancer cells, beginning with 5×10$^4$ Raji cells/well in a 96-well plate. An effector/target (E/T) ratio plate is constructed based on the results.

Combination immunotherapy experiments are performed by incubating the Raji cancer cells with apoptotic cells, or apoptotic supernatants, for 1 hour followed by co-culturing with CD19+ CAR T-cells (+/− monocytes-macrophages) for 48 hours.

In order to simulate in vivo conditions, 1×10$^5$ THP-1 cells/ml will be differentiated with 200 nM (123.4 ng/ml) phorbol myristate acetate (PMA) for 72 hrs and will then be cultured in complete medium without PMA for an additional 24 h. Next, Raji cancer cells will be plated in a 24-well plate at 5×10$^5$ Raji cells/well on the differentiated THP-1 cells.

Following initial culturing of the Raji cancer cells, 4×10$^5$-8×10$^5$ apoptotic cells (ApoCell) will be added to the culture for 1-3 h to induce an immunotolerant environment. The ratio of cancer cell to ApoCell will be optimized for each cell type. After washing, the co-culture will be treated with a pre-determined number of CD19+ CAR-T cells based on the E/T ratio graph. In certain experiments, 10 ng/ml LPS will be added to the culture media prior to addition of the CD19+ CAR T-cells. In other experiments, interferon γ (IFN-γ) will be added to the culture media prior to addition of the CD19+ CAR T-cells. The addition of LPS or IFN-γ is expected to exponentially increase the cytokine storm level.

To assay for Raji cancer cell cytotoxicity, lysates are prepared and viability is determined after the 48 hour incubation period. Additional experiments will be performed assaying for Raji cell cytotoxicity at intervals within the 48 h incubation time period. Alternatively, Promega's CytoTox 96 Non-Radioactive Cytotoxicity Assay (Promega, cat #G1780) will be used.

Similar experiments are run with CD19 expressing HeLa cells and CD19+ CAR T-cells.

Similar experiments are run with CD123 expressing leukemic cells and CD123+ CAR T-cells.

Cytokine Analysis

Initial cytokine assays examine the levels of MIP1a, IL-4, IL-2, IL-2R, IL-6, IL8, IL-9, IL-10, IL-13, IL-15, INF-γ, GMCSF, TNF-α, in the culture supernatant.

Additional cytokine assays examine the level of cytokines IL-10, IL-1β, IL-2, IP-10, IL-4, IL-5, IL-6, IFNα, IL-9, IL-13, IFN-γ, IL-12p70, GM-CSF, TNF-α, MIP-1α, MIP-1β, IL-17A, IL-15/IL-15R, or IL-7, or any combination thereof.

Cultures were established to mimic an in vivo CAR T-cell therapy environment. Raji Burkett Lymphoma cells were cultured in the presence of human monocyte-macrophages, LPS and CD19+ CAR T-cells without and with the addition of apoptotic cells.

Raji cells were incubated in the presence of monocytes and LPS, followed by addition of Naïve T-cells (Raji+Naïve T), CD19+ CAR T-cells (Raji+CAR T), CD19+ CAR T-cells and apoptotic cells (ApoCell) at a ratio of 1:8 CAR T-cells: ApoCells (Raji+CAR T+ApoCell 1:8), CD19+ CAR T-cells and apoptotic cells (ApoCell) at a ratio of 1:32 CAR T-cells:ApoCells (Raji+CAR T+ApoCell 1:32), and CD19+ CAR T-cells and apoptotic cells (ApoCell) at a ratio of 1:64 CAR T-cells:ApoCells (Raji+CAR T+ApoCell 1:64). Concentration measurements were made following GM-CSF and TNF-α (TNF-α).

To assay for cytokine release reduction of IL-6, IL-8, and IL-13, as well as other cytokines, supernatants will be collected and examined for selected cytokine using Luminex MagPix reader and ELISA assays. Cytokines (mouse or human) may be evaluated by Luminex technology using MAPIX system analyzer (Mereck Millipore)) and MILIPLEX analysis software (Merek Millipore). Mouse IL-6Rα, MIG (CXCL9) and TGF-β1 were evaluated by Quantikine ELISA (R&D systems).

Tissue Analysis

Bone marrow and liver were evaluated using flow cytometry and immunohistochemistry. Upon sacrifice liver and bone marrow were collected for histopathological analysis. Tissues were fixed in 4% formalin for 48 h at room temperature, and then submitted to the animal facility at the Hebrew University for processing. Bones were decalcified prior to processing. Paraffin sections were stained for Hematoxylin and Eosin, and CD19.

IFN-γ Effect

IFN-γ effect is evaluated both by STAT1 phosphorylation and biological products.

Results:

Calibrating Cell Number for Cytotoxicity Assay

Figure 14:
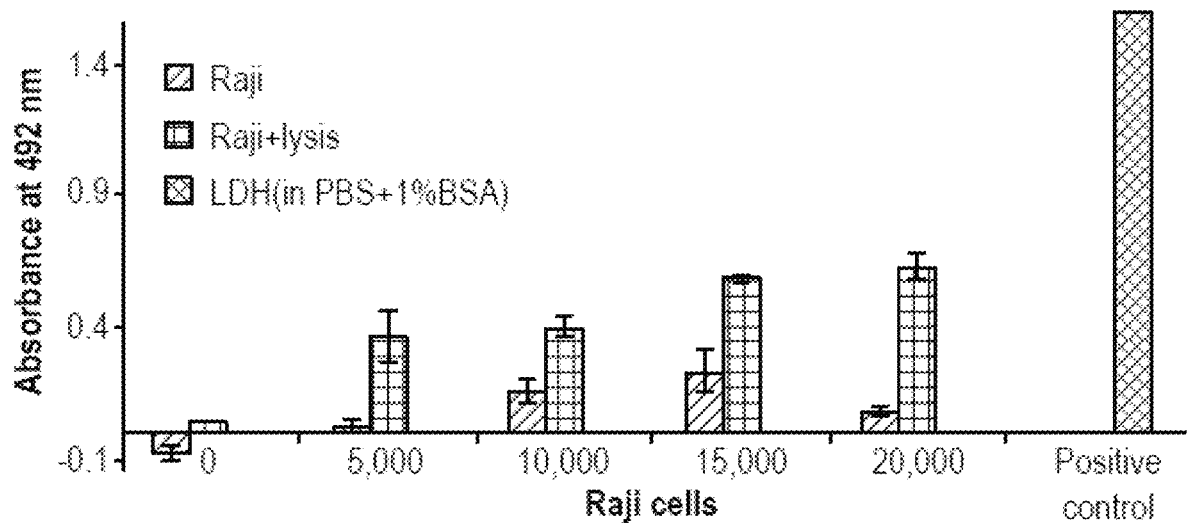
FIG. 14. Cytotoxic Calibration for Raji Burkett Lymphoma Cells. Raji cells were plated at various cell densities, with cell lysis occurring immediately prior to centrifugation. The results show Raji cell number (x-axis) vs. at absorbance at 492 nm (y-axis). All cell numbers exhibited significant readings relative to the unlysed counterpart.

To determine the number of Raji cells to be used in the in vitro model, sensitivity limits of the cytotoxicity assay was assessed. $5 \times 10^4$-$20 \times 10^4$ Raji cells/well were plated in a 96-well plate, in quadruplicate. Lysis was performed on one set of quadruplicate to be compared with cells that are still completely viable. Lysis was momentary, adding the lysis solution immediately prior to centrifugation to simulate partial cell cytotoxicity. Indeed, all cell quantities exhibited readings well above viable cells, with the $5 \times 10^4$ cell number producing the greatest relative reading (FIG. 14; extrapolation of data). Therefore, subsequent experiments will be using this cell number as default, unless otherwise required by experimental deign.

Verification of CD19$^+$ CAR-T Cell Activity Against Raji Burkett Lymphoma Cells To corroborate the CD19$^+$ CAR T-cell activity, monolayers of Raji cancer cells are exposed to either 1,000,000 (one million) CD19$^+$ CAR-T cells or to 1,000,000 (one million) non-transduced T cells. After 24 h incubation, CD19$^+$ CAR-T cells reduce Raji cancer cell proliferation, showing anti-tumor activity of the CD19$^+$ CAR-T cells.

Activity of stand-alone CD19+ CAR-T cells against Raji Burkett Lymphoma cells was compared to activity post exposure to Apoptotic Cells Apoptotic cells (ApoCell) and apoptotic cell supernatants (ApoSup and ApoMon Sup) are tested to determine if they interfere with CD19+ CAR-T cell anti-tumor activity. The Raji Burkett Lymphoma cells are incubate with Apoptotic Cells for one hour, followed by the addition of CD19+ CAR-T cells (500,000, five hundred thousands) or CD19+ non-transduced T cells (500,000, five hundred thousands) (ratio of 1:2 CD19$^+$ CAR-T cells to Apoptotic Cells). The tumor cell/Apoptotic cell/CD19$^+$ CAR T-cells are then co-cultured for 48 h. The control Raji Burkett Lymphoma cells are co-cultured with CD19+ CAR-T cells and Hartman solution (the vehicle of Apoptotic Cells), but without Apoptotic Cells, for 48 h.

The results are showing that after 48 h incubation, CD19+ CAR-T cells anti-tumor activity was superior to incubation with non-transduced T cells. Similar incubations will be performed with apoptotic cell supernatants. Surprisingly, CD19+ CAR T-cell anti-tumor activity is comparable with or without exposure to apoptotic cells or apoptotic cell supernatants No negative effect of apoptotic cells on CAR-modified T cells against CD19 both in vitro was seen with comparable E/T ratio results of CAR T in the presence or absence of apoptotic cells.

Verification of CD19$^+$ CAR-T Cell Activity Against HeLa Leukemia Cells

HeLa cells are specific CD19 expressing cells, which renders them susceptible to CAR CD19+ T-cell activity. In addition, in contrast to Raji cells, which are a non-adherent cell line, HeLa cells are adherent.

To corroborate the CD19$^+$ CAR T-cell activity, monolayers of HeLa cancer cells were exposed to either 1,000,000 (one million) CD19$^+$ CAR-T cells or to 1,000,000 (one million) non-transduced T cells. After 24 h incubation, CD19$^+$ CAR-T cells reduce HeLa cancer cell proliferation, showing anti-tumor activity of the CD19$^+$ CAR-T cells (FIG. 15 CD19$^+$+RPMI and CD19$^+$+CAR T-19 cells).

Activity of Stand-Alone CD19$^+$ CAR-T Cells Against CD19$^+$HeLa Cells was Compared to Activity Post Exposure to Apoptotic Cells Apoptotic cells (ApoCell) were tested to determine if they interfere with CD19$^+$ CAR-T cell anti-tumor activity. The HeLa cells were incubated with Apoptotic Cells for one hour, followed by the addition of CD19+ CAR-T cells (500,000, five hundred thousand) or CD19+non-transduced T cells (Naïve T cells; 500,000, five hundred thousand) (ratio of 1:2 CD19$^+$ CAR-T cells to Apoptotic Cells). The tumor cell/Apoptotic cell/CD19$^+$ CAR T-cells were then co-cultured for 48 h. The control HeLa cells were co-cultured with CD19+ CAR-T cells and RPMI (the vehicle of Apoptotic Cells), but without Apoptotic Cells, for 48 h. The CD19$^+$ CAR-T cell: HeLa cell ratio (E/T ratio) ranged from 5-20 (FIG. 15).

Figure 15:
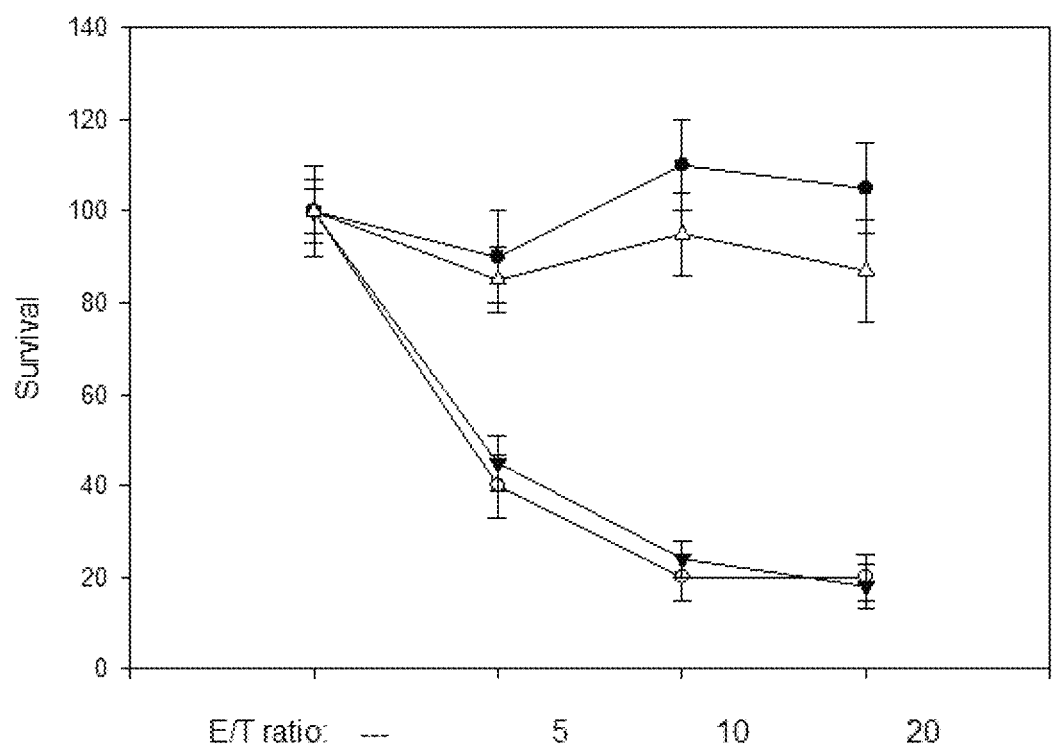
FIG. 15. Addition of early apoptotic cells does not affect CAR T-cell anti-tumor activity. E/T ratio shows the CD19+ CAR T-cell to HeLa cell ratio. Survival is of CD19+ Tumor cells. Filled circle CD19+ Hela; Empty triangle CD19+ Hela+Naïve T cells; Filled triangle CD19+ Hela+CAR T-CD19; Empty circle CD19+ Hela+CAR T-CD19+Apo-Cells.

FIG. 15 shows that after 48 h incubation, CD19+ CAR-T cells anti-tumor activity was superior to incubation with non-transduced T cells (Naïve cells) or buffer alone. Similar incubations were performed with apoptotic cells. Surprisingly, CD19+ CAR T-cell anti-tumor activity was comparable with or without exposure to apoptotic cells. Similar experiments are performed using apoptotic cell supernatants. FIG. 15 shows the same in vitro cytotoxicity effect of CAR T-CD19 therapy with or without the addition of ApoCells.

No negative effect of the apoptotic cells on CAR-modified T cells against CD19+HeLa cells was observed at comparable E/T ratios in the presence or absence of apoptotic cells.

Thus, the same in vitro cytotoxic effect of the CD19+ CAR T-cells was observed with or without the addition of early apoptotic cells.

Effect of Apoptotic Cells on Amelioration, Reduction or Inhibition of Cytokine Storms Resulting from CAR-T Treatment Cytokines IL-8 and IL-13 are measured in the culture media prior to and following addition of CD19+ CAR T-cells and are showing a concentration consistent with a cytokine storm. Addition of apoptotic cells or apoptotic cell supernatant is showing a reduction of IL-8 and IL-13 concentrations in the media.

Analysis Using a Wider Range of Cytokines

Figure 16:
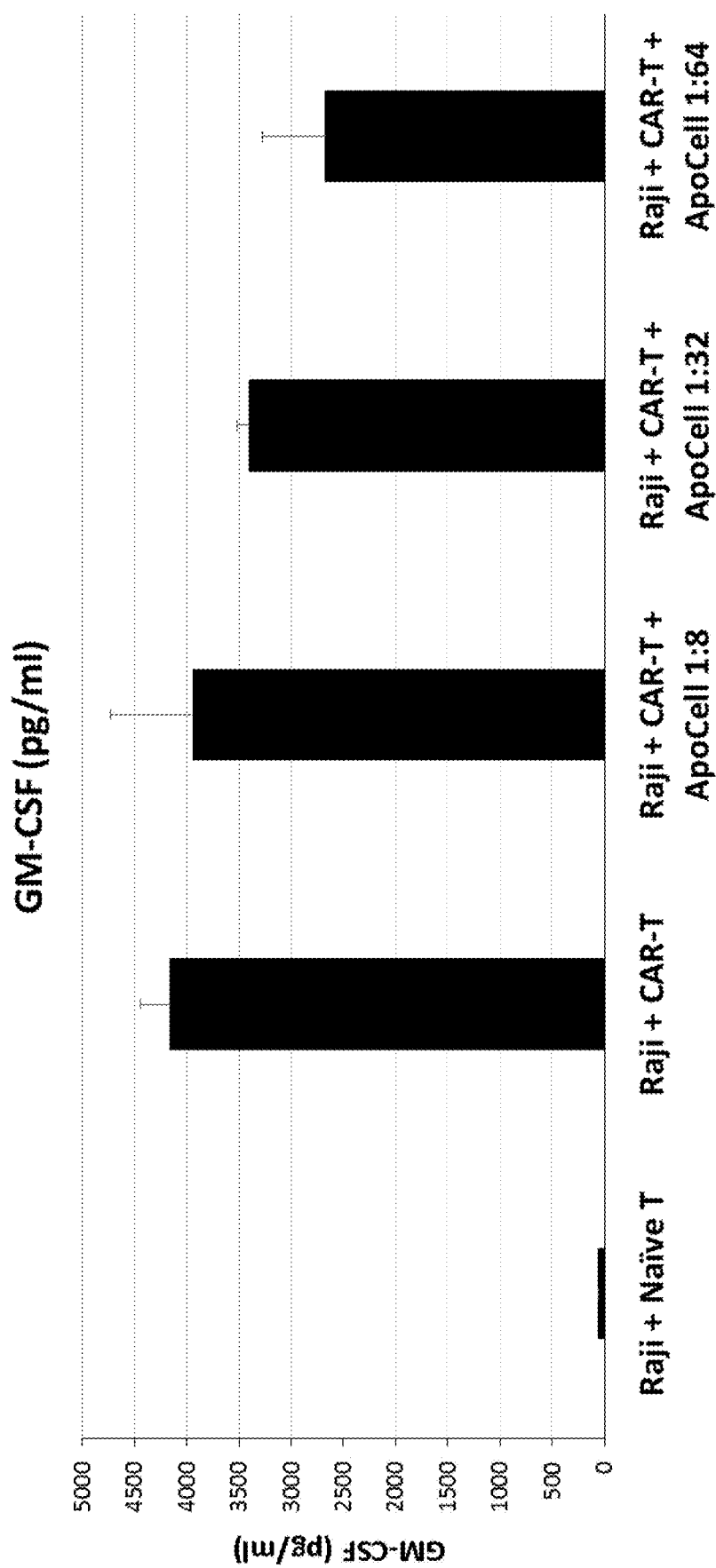
FIG. 16. Cytokine Analysis (GM-CSF) in Raji Burkett Lymphoma Cells in the Presence and Absence of Apoptotic cells. The bar graph presents the concentration measurements of cytokine GM-CSF (pg/ml) found in culture supernatants of Raji cells incubated in the presence of monocytes and LPS, followed by addition of Naïve T-cells (Raji+Naïve T), CD19+ CAR T-cells (Raji+CAR T), CD19+ CAR T-cells and apoptotic cells (ApoCell) at a ratio of 1:8 CAR T-cells:ApoCells (Raji+CAR T+ApoCell 1:8), CD19+ CAR T-cells and apoptotic cells (ApoCell) at a ratio of 1:32 CAR T-cells:ApoCells (Raji+CAR T+ApoCell 1:32), and CD19+ CAR T-cells and apoptotic cells (ApoCell) at a ratio of 1:64 CAR T-cells:ApoCells (Raji+CAR T+ApoCell 1:64).
Figure 17:
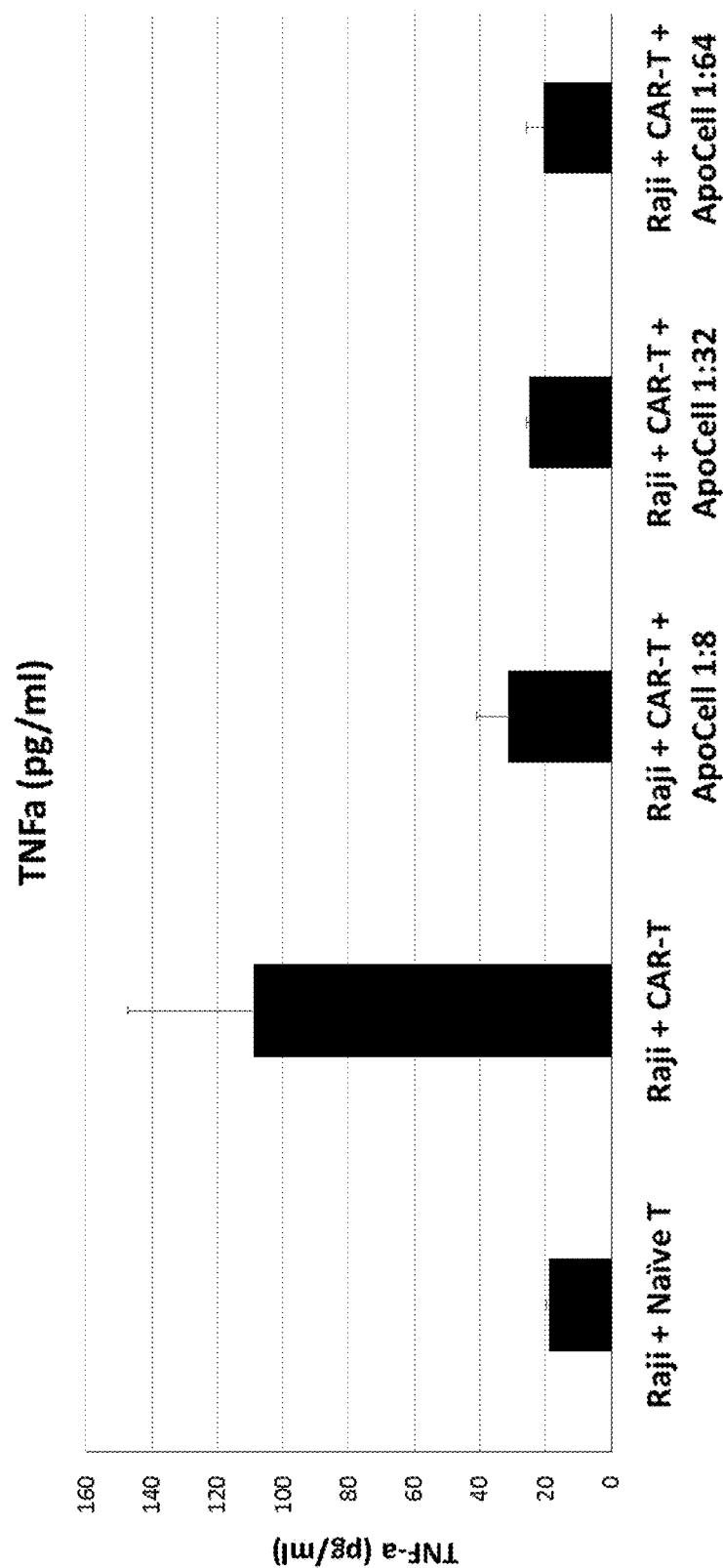
FIG. 17. Cytokine Analysis (TNF-alpha) in Raji Burkett Lymphoma Cells in the Presence and Absence of Apoptotic cells. The bar graph presents the concentration measurements of cytokine TNF-alpha (TNF-a) (pg/ml) found in culture supernatants of Raji cells incubated in the presence of monocytes and LPS, followed by addition of Naïve T-cells (Raji+Naïve T), CD19+ CAR T-cells (Raji+CAR T), CD19+ CAR T-cells and apoptotic cells (ApoCell) at a ratio of 1:8 CAR T-cells:ApoCells (Raji+CAR T+ApoCell 1:8), CD19+ CAR T-cells and apoptotic cells (ApoCell) at a ratio of 1:32 CAR T-cells:ApoCells (Raji+CAR T+ApoCell 1:32), and CD19+ CAR T-cells and apoptotic cells (ApoCell) at a ratio of 1:64 CAR T-cells:ApoCells (Raji+CAR T+ApoCell 1:64).

To further evaluate the effect on a possible wider range and levels of cytokines that are not generated during experimental procedures but do appear in clinical settings during a human cytokine storm, LPS (10 ng/ml) was added to the Raji cell culture conditions outlined above in the presence of cancer and CAR-19. The addition of LPS was expected to exponentially increase the cytokine storm level. Exposure to apoptotic cells is dramatically reduced the levels of cytokines. The results presented in FIG. 16 and FIG. 17 show that while addition of CD19+ CAR T-cell greatly increases cytokine concentration (pg/ml) of GM-CSF and TNF-α in the culture medium, there is a significant decrease of both GM-CSF and TNF-α in the presence of apoptotic cells. The decrease in the cytokine concentration is dose dependent with respect to apoptotic cell ratio of CAR T-cells to apoptotic cells.

Conclusion:

Apoptotic cells were able to down regulate cytokine markers of cytokine storm associated with CAR T-cell clinical procedures. Significantly, the apoptotic cells did not show an effect on the tumor activity of the CAR T-cells. Apoptotic cells decreased pro-inflammatory cytokines that originated from innate immunity and inhibit IFN-γ effect without harming IFN-γ levels and CAR-T cytotoxicity.

Example 6: Apoptotic Cell Therapy Prevents Cytokine Storms in a Diffuse Cancer In Vivo Model Administered Car T-Cell Therapy Objective:

Test the in vivo effect of apoptotic cells or supernatants derived from apoptotic cells in a diffuse tumor model, in order to determine CAR T-cell efficacy on the cancer cells and the level of cytokine storm marker cytokines.

Materials and Methods

In Vitro Studies

See methods described in Example 5 for in vitro studies.

Cells and Cell Culture

Raji Burkitt lymphoma cells (Sigma-Aldrich cat. #85011429) were cultured as per the manufacture's guidelines. CD19+ CAR T-cells, cell cultures, apoptotic cells, apoptotic cell supernatants, monocyte isolation, and in vitro measurements are as above for Examples. Early apoptotic cells produced were least 50% annexin V-positive and less than 5% PI-positive cells.

In Vivo Studies

Mice 7-8 week old SCID beige mice were purchased from Envigo (formerly known as Harlan). Mice were kept in an SPF free animal facility in compliance with institutional IACUC guidelines. During the course of the experiments the mice were monitored daily, and weighted 3 times a week. Mice showing hind limb paralysis were sacrificed. Upon sacrifice bone marrow and liver were collected for FACS analysis and histological processing, and sera were frozen at −80° C. for cytokine profiling. In vivo experiments SCID beige mice (C.B-17/IcrHsd-Prkdc-SCID-Lyst-bg, Harlan, Israel) were housed in SPF conditions at The Authority for Animal Facilities (AAF), The Hebrew University of Jerusalem (Ein Kerem Campus, Israel) and following the Association for Assessment and Accreditation of Laboratory Animal Care (AAALAC). The studies were approved by The Hebrew University Ethics Committee for Animal Experiments, and animal suffering was minimized as possible.

Figure 18A:
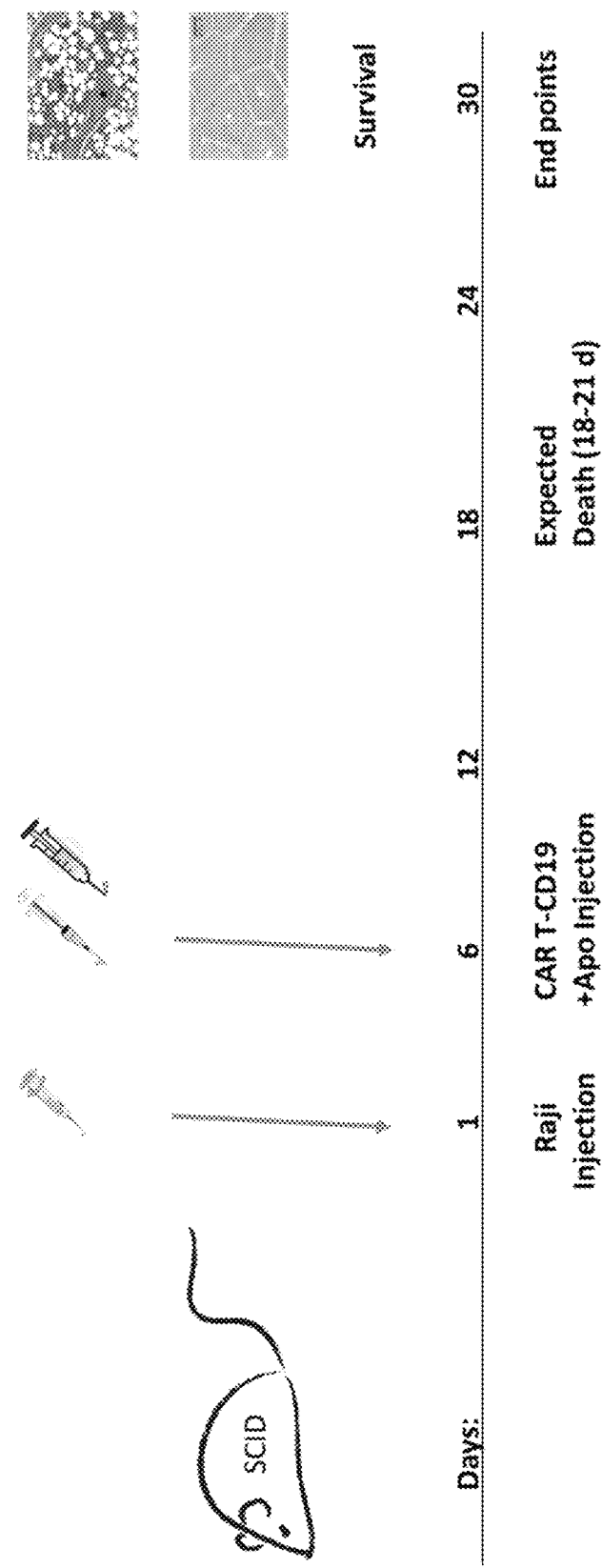
FIGS. 18A and 18B. Experimental Scheme.

(FIG. 18A) For the disseminating tumor model, 7-8 week female SCID beige mice were injected i.v. with $1\times10^5$ Raji cells suspended in 200 µl RPMI (Gibco, ThermoFisher Scientific, USA, cat. no. 15140-122) per mouse (day 1). On day 6, mice of pertinent groups were inoculated i.v. with $30\times10^6$ cells ApoCells in 200 µl Hartmann's solution Lactated Ringer's Injection, Teva Medical, Israel, cat. no. AWN2324) per mouse. On day 6, mice of relevant groups were inoculated i.v. with $10\times10^6$ viable CD19-CAR T cells or naïve T cells in 200 µl AIM V per mouse. Control mice received equal volume of RPMI for each treatment.

Mice were examined for clinical indications and weighed twice a week and were sacrificed upon development of hind limb paralysis. Pathological samples of bone and liver were prepared by the Animal Facility Unit of The Hebrew University of Jerusalem and stained against human CD20 (Cell Marque, USA, clone L26, cat. no. 120M-84), to detect Raji cells, and against human CD3 (Cell Signaling Technology, USA, cat. no. 85061), to detect human T cells.

In certain experiments, LPS will be administered to the animal subject prior to addition of the CD19+ CAR T-cells. In other experiments, interferon-γ (IFN-γ) will be administered prior to addition of the CD19+ CAR T-cells. The addition of LPS or IFN-γ is expected to exponentially increase the cytokine storm level.

Cytokine assays examine the level of cytokines including but not limited to IL-10, IL-1β, IL-2, IP-10, IL-4, IL-5, IL-6, IFNα, IL-9, IL-13, IFN-γ, IL-12p70, GM-CSF, TNF-α, MIP-1α, MIP-1β, IL-17A, IL-15/IL-15R, or IL-7, or any combination thereof. Cytokines (mouse or human) are evaluated by Luminex technology using MAPIX system analyzer (Mereck Millipore)) and MILIPLEX analysis software (Merek Millipore). Mouse IL-6Rα, MIG (CXCL9) and TGF-β1 are evaluated by Quantikine ELISA (R&D systems).

Tissue Analysis

Bone marrow and liver are evaluated using flow cytometry and immunohistochemistry. Upon sacrifice liver and bone marrow were collected for histopathological analysis. Tissues were fixed in 4% formalin for 48 h at room temperature, and then submitted to the animal facility at the Hebrew University for processing. Bones were decalcified prior to processing. Paraffin sections were stained for Hematoxylin and Eosin, and CD19.

IFN-γ Effect

IFN-γ effect is evaluated both by STAT1 phosphorylation and biological products.

Results

CAR T-Cell Therapy Induces Cytokine Release Syndrome

Three groups of tumor-free mice as well as mice with tumors are administered (i.p. or directly into the tumor) increasing doses of CD19+ CAR T-cells ($3 \times 10^6$, $10 \times 10^6$ or $30 \times 10^6$). At the highest dose, tumor-free mice and mice with tumors demonstrate subdued behavior, piloerection, and reduced mobility within 24 h, accompanied by rapid weight loss followed by death within 48 hrs. Human interferon-gamma, and mouse IL-6, IL-8, and IL-13 are detectable in blood samples from the mice given the highest dose of $CD19^+$ CAR T-cells Animals that receive a high dose of CD19+ CAR T-cells directed to a different tumor antigen do not exhibit weight loss or behavioral alterations.

Administration of Apoptotic Cells Inhibits or Reduces the Incidence of Cytokine Release Syndrome Induced by CAR T-Cell Therapy One group of mice given the highest dose of CD19+ CAR T-cells is concomitantly administered $2.10 \times 10^8$/kg apoptotic cells, which was previously demonstrated to be a safe and effective dose. Mice receiving human CD19+ CAR T+apoptotic cells have significantly lowered levels of at least one mouse pro-inflammatory cytokines, lower weight loss, and reduced mortality.

Figure 18B:
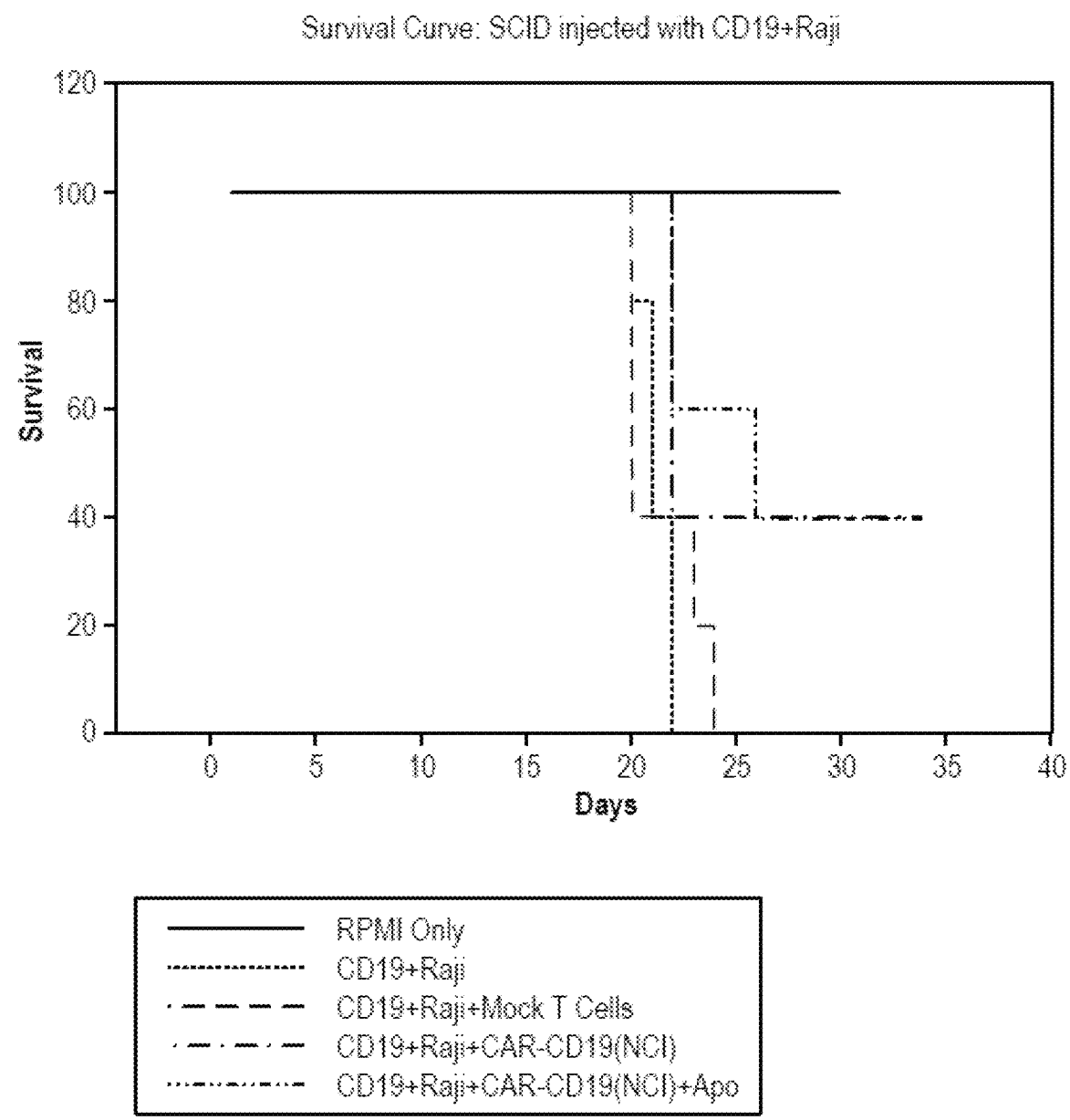

Administration of Apoptotic Cells in Combination with CAR T-Cell Administration Did not Affect CAR T-Cell Anti-Tumor Activity FIG. 18B shows that the expected death of SCID mice injected with $CD19^+$ Raji cells without administration of $CD19^+$ CAR T-cells was 18-21 days. Forty percent (40%) of the mice who received $CD19^+$ CAR T-cells survived to at least day 30 (FIG. 18 dash-dot-dash line and dash-double dot-dash line). The percentage of survivors was independent of the addition of apoptotic cells (FIG. 18). The surviving mice were sacrifice on day 30.

Conclusion: There was comparable survival and no negative effect of apoptotic cells on CAR-modified T cells against CD19 in vivo.

Significant down regulation ($p<0.01$) of pro-inflammatory cytokines including, IL-6, IP-10, TNF-α, MIP-1α, MIP-1β was documented. IFN-γ was not downregulated but its effect on macrophages and dendritic cells was inhibited both at the level of phosphorylated STAT1 and IFN-γ-induced expression of CXCL10 and CXCL9.

Conclusion:

Apoptotic cells decrease pro-inflammatory cytokines that originate from innate immunity and inhibit IFN-γ effect without harming IFN-γ levels and CAR-T cytotoxicity.

Example 7: Apoptotic Cell Therapy Prevents Cytokine Storms in a Solid Tumor Cancer In Vivo Model Administered CAR T-Cell Therapy Objective:

Test the in vivo effect of apoptotic cells or supernatants derived from apoptotic cells in a solid tumor model, in order to determine CAR T-cell efficacy on the cancer cells and the level of cytokine storm marker cytokines.

Materials and Methods

In Vitro Studies

Cells and Cell Culture

CD19+ CAR T-cells, Second generation CAR-T-CD19 cells containing TMCD28 were used, cell cultures, apoptotic cells, apoptotic cell supernatants, monocyte isolation, and in vitro measurements were as above for Examples 2 & 4 & 6. Early apoptotic cells produced were least 50% annexin V-positive and less than 5% PI-positive cells, as described in detail in Example 1.

In Vivo Studies

Mice 7-8 week old SCID-beige mice and NSGS mice were purchased from Harlan (Israel) and kept in the SPF animal facility in Sharett Institute.

SCID beige mice or NSGS mice were inoculated with CD19 expressing Hela cells, that can adhere to the peritoneum, in order to form solid intra-peritoneal tumors. Mice were sorted into groups prior to T-cell administration.

Six days post i.v. inoculation, mice were administered $10 \times 10^6$CD19+ CAR T-cells with and without apoptotic cell (ApoCell) preconditioning on day 5. Mice receiving preconditioning were administered $5 \times 10^6$ or $30 \times 10^6$ ApoCells. Tumors were surveyed weekly and circulating cytokine levels were monitored weekly and determined by the Luminex system. 25 mouse cytokines and 32 human cytokines were evaluated using the Luminex technology. Upon termination of the experiment, mice were culled and organs (bone marrow, liver and spleen) were examined (by FACS and immunohistochemistry) for the presence/size of tumors.

Cytokine assays examined the level of cytokines including but not limited to GM-CSF, IFNγ, IL-1β, IL-10, IL-12p70, IL-13, IL-15, IL-17A, IL-2, IL-4, IL-5, IL-6, IL-7, IL-9, MIP-1α, TNFα, MIP-1β, IFNα, and IP-10. Cytokines (mouse or human) were evaluated by Luminex technology using MAPIX system analyzer (Mereck Millipore)) and MILIPLEX analysis software (Merck Millipore). Mouse IL-6Rα, MIG (CXCL9) and TGF-β1 were evaluated by Quantikine ELISA (R&D systems).

Tissue Analysis

Bone marrow and liver are evaluated using flow cytometry and immunohistochemistry.

IFN-γ Effect

IFN-γ effect was evaluated both by STAT1 phosphorylation and biological products.

Results

CAR T-Cell Therapy Induces Cytokine Release Syndrome

Three groups of tumor-free mice as well as mice with tumors were administered (i.p. or directly into the tumor) increasing doses of CD19+ CAR T-cells ($3 \times 10^6$, $10 \times 10^6$ or $30 \times 10^6$). At the highest dose, tumor-free mice and mice with tumors demonstrate subdued behavior, piloerection, and reduced mobility within 24 h, accompanied by rapid weight loss followed by death within 48 hrs.

Figure 19A:
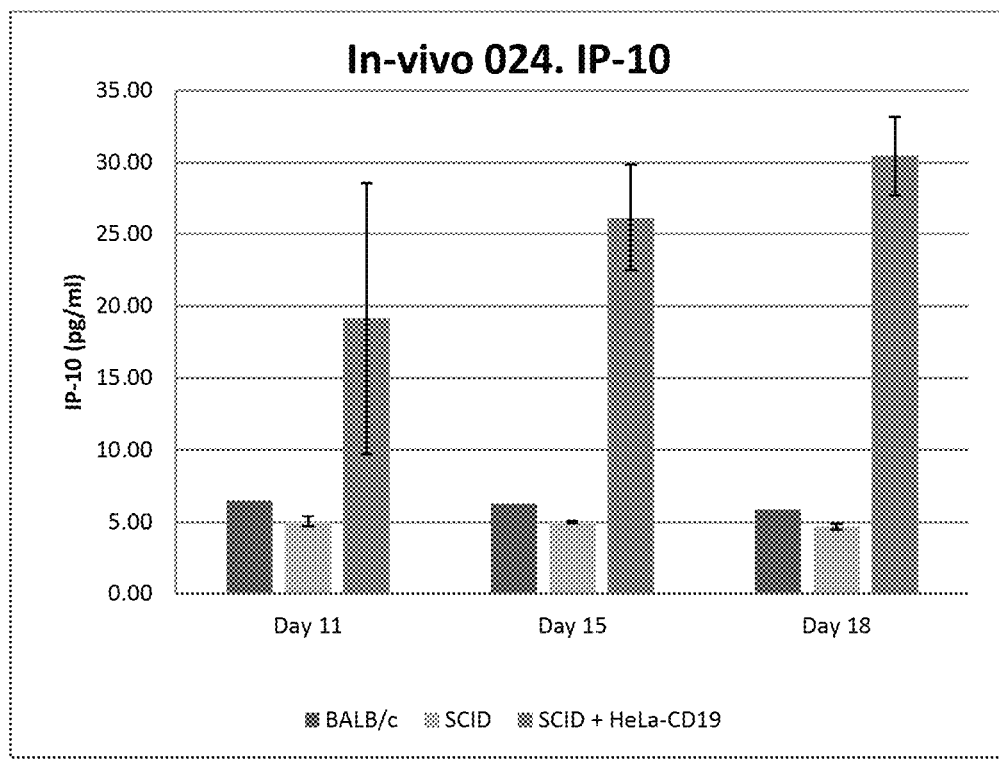
FIGS. 19A, 19B, and 19C. Increased release of pro-inflammatory cytokines from a tumor, in a solid tumor in vivo model.
Figure 19B:
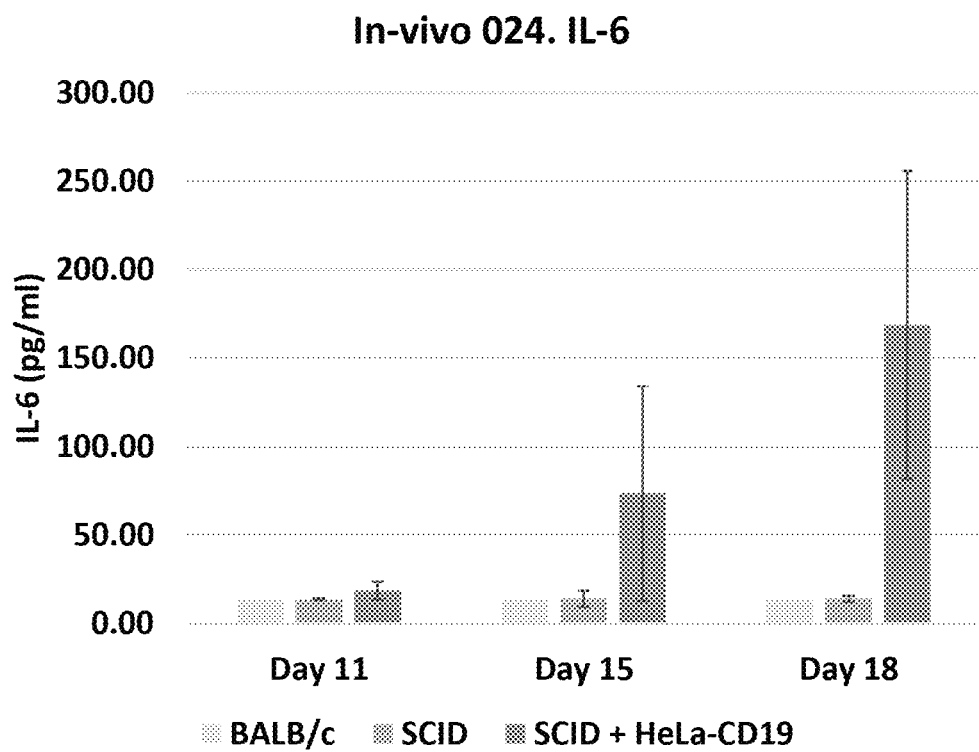
Figure 19C:
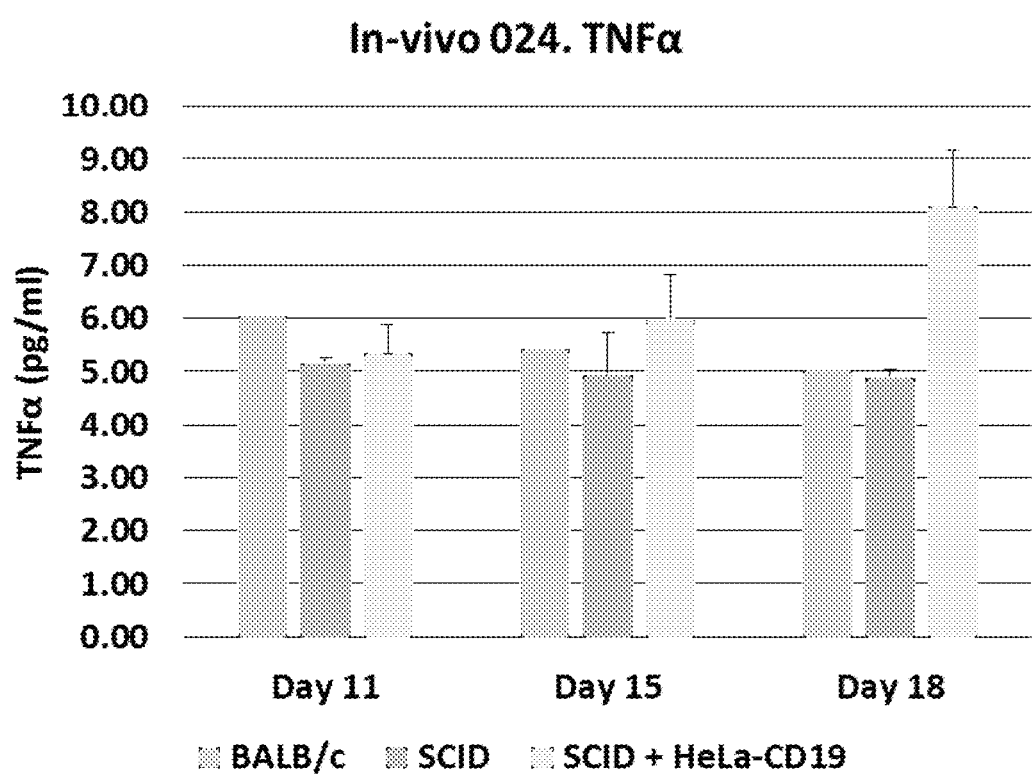

FIGS. 19A-19C graphically show the increased levels of IL-6, IP-10 and surprisingly even TNF-α cytokine release from tumors even before the presence of CAR T-cells. FIGS. 19A-19C show that unexpectedly IL-6, IP-10, and TNF-α were increased by the presence of cancer cells even without CAR T-cell therapy. In the presence of CAR T-Cell therapy (Hela-CAR T-cell CD-19) the release of cytokines was significantly augmented. These results show that the tumor itself releases pro-inflammatory cytokines.

In order to evaluate the benefit of the addition of early apoptotic cells, cytokines GM-CSF, IFNγ, IL-1β, IL-10, IL-12p70, IL-13, IL-15, IL-17A, IL-2, IL-4, IL-5, IL-6, IL-7, IL-9, MIP-1a, TNFα, MIP-1β, IFNα, and IP-10 were measured in three experiments, wherein the results showed that macrophage associated cytokines were down-regulated in the presence of ApoCell administration, while T-cell associated cytokine levels were not significantly changed (Table 10).

TABLE 10

Cytokine levels from an intra-peritoneum in vivo model that contained CD19 expressing Hela cells solid tumor, +/− CAR T-cell CD19 therapy, and +/− ApoCell

| Pg/ml | Before Tumor Car or Apo | After tumor + CAR | After tumor, CAR, +with ApoCell |
|---|---|---|---|
| GM-CSF | 4 ± 2 | 88 ± 10 | 12 ± 4 |
| IFNγ | 4 ± 1 | 5 ± 8 | 5 ± 21 |
| IL-1β | 8 ± 3 | 14 ± 6 | 16 ± 8 |
| IL-10 | 76 ± 13 | 222 ± 44 | 36 ± 22 |
| IL-12p70 | 5 ± 1 | 188 ± 22 | 12 ± 11 |
| IL-13 | 6 ± 2 | 8 ± 1 | 8 ± 4 |
| IL-15 | 4 ± 2 | 6 ± 2 | 8 ± 2 |
| IL-2 | 4 ± 2 | 26 ± 2 | 29 ± 2 |
| IL-4 | 1 ± 2 | 16 ± 4 | 18 ± 6 |
| IL-6 | 24 ± 6 | 820 ± 56 | 74 ± 12 |
| MIP-1α | 8 ± 5 | 99 ± 13 | 18 ± 8 |
| TNFα | 6 ± 2 | 760 ± 33 | 17 ± 15 |
| MIP-1β | 7 ± 1 | 144 ± 21 | 21 ± 10 |
| IFNα | 74 ± 12 | 68 ± 26 | 71 ± 14 |
| IP-10 | 8 ± 4 | 188 ± 33 | 21 ± 16 |

Table 10 shows cytokine measurement twenty-four (24) hours after CAR T-Cell administration+/−ApoCells. Resultant cytotoxicity from CAR T-cell therapy elevated cytokines including GM-CSF, IL-10, IL-12p70, IL-6, MIP-1α, TNFα, MIP-1β, and IP-10, the levels of which were significantly down regulated ($p<0.05$-$0.0001$) in the presence of ApoCells. These cytokines are mainly associated with macrophages. In contrast, the levels of cytokines associated with T-cells such as IL-2, IL-4, IL-13, and IL 15 were not changed significantly.

The results presented in FIGS. 19A-C and Table 10, illustrate that the CRS in the context of cancer and CAR has several ingredients: a tumor that can secrete cytokines; an innate immunity that respond to tumor and to CAR and to other factors; and that CAR T-cells that secrete cytokines causes death that influence innate immunity ApoCells are interacting with innate immunity, mainly macrophages, monocytes and dendritic cells, to down regulate the response of these macrophages, monocytes and dendritic cells without interacting with T cells or CAR T cells.

Animals that received a high dose of CD19+ CAR T-cells directed to a different tumor antigen do not exhibit weight loss or behavioral alterations.

Administration of Apoptotic Cells Inhibits or Reduces the Incidence of Cytokine Release Syndrome Induced by CAR T-Cell Therapy One group of mice given the highest dose of CD19+ CAR T-cells was concomitantly administered $2.10 \times 10^8$/kg apoptotic cells, which was previously demonstrated to be a safe and effective dose. Apoptotic cells had no negative effect in vitro or in vivo on CAR-modified T cells with specificity against CD19. There were comparable E/T ratios for CAR T-cells in the presence/absence of apoptotic cells in vitro, and comparable survival curves in vivo (Data not shown).

Mice receiving human CD19+ CAR T+apoptotic cells had significantly lowered levels of at least one mouse pro-inflammatory cytokines, lower weight loss, and reduced mortality.

No negative effect of apoptotic cells on CAR-modified T cells against CD19 in vivo was seen with comparable E/T ratio results of CAR T in the presence or absence of apoptotic cells, and a comparable survival curve in vivo.

Significant down regulation ($p<0.01$) of pro-inflammatory cytokines including, IL-6, IP-10, TNF-α, MIP-1β was documented (Data not shown). IFN-γ was not downregulated but its effect on macrophages and dendritic cells was inhibited both at the level of phosphorylated STAT1 and IFN-γ-induced expression of CXCL10 and CXCL9 (Data not shown.

Conclusion:

CRS evolves from several factors, including tumor biology, interaction with monocytes/macrophages/dendritic cells, and as a response to the CAR T cell effect and expansion. Apoptotic cells decrease pro-inflammatory cytokines that originate from innate immunity and inhibit the IFN-g effect on monocyte/macrophages/dendritic cells without harming IFN-γ levels or CAR-T cytotoxicity. Thus, apoptotic cells decreased pro-inflammatory cytokines that originate from innate immunity and inhibit IFN-γ effect without harming IFN-γ levels and CAR-T cytotoxicity. These results support the safe use of ApoCells for the prevention of CRS in clinical studies using CAR-T cell therapy.

Example 8: Apoptotic Cells Downregulate Cytokine Release Syndrome (CRS) and Increases CAR-T-Cell Efficacy Objective:

To test the effects of early apoptotic cells on cytokines and CAR T cell cytotoxicity over an extended time period. To demonstrate the in vivo efficacy of CD19-CAR T-cells. To demonstrate the synergistic effect of early apoptotic cells and CD19-CAR T-cells.

Methods:

CD19-expressing HeLa cells (ProMab) were used alone or after co-incubation with human macrophages for in vitro and intraperitoneal experiments in mice. Raji was used in vivo for leukemia induction. LPS and IFN-g were used to trigger additional cytokine release. Second generation, CD28-bearing, CD19-specific CAR-modified cells were used (either ProMab or produced using a retronectin manufacturing protocol or a polybrene manufacturing protocol) for anti-tumor effect against CD19-bearing cells. Cytotoxicity assay was examined in vivo (7-AAD flow cytometry) and in vitro (survival curves; tumor load in bone marrow and liver, flow cytometry and immunohistochemistry). CRS occurred spontaneously or in response to LPS and IFN-g. Mouse IL-10, IL-1ß, IL-2, IP-10, IL-4, IL-5, IL-6, IFN-α, IL-9, IL-13, IFN-g, IL-12p70, GM-CSF, TNF-α, MIP-1a, MIP-1ß, IL-17A, IL-15/IL-15R, IL-7, and 32 human cytokines were evaluated (Luminex technology, MAPIX system; MILLIPLEX Analyst, Merck Millipore). Mouse IL-6Rα, MIG (CXCL9), and TGF-ß1 were evaluated (Quantikine ELISA, R&D systems). IFN-γ effect was evaluated (STAT1 phosphorylation, biological products). Human macrophages and dendritic cells were generated from monocytes. Early apoptotic cells were produced generally as presented in Example 1 above; ≥40% of cells were Annexin V-positive; ≤15% were PI-positive.

Mice:

SCID-Bg mice (female, 7-8 wk) were injected with 2 consecutive doses of $0.25 \times 10^6$ HeLa-CD19 cells, intraperitoneally (i.p) on days 1 and 2 of experiment. On day 9 mice received i.p. dose of $10 \times 10^6$ 4000-rad (cGy) irradiated ApoCell (using a cell processing system) and an i.p. dose of a population of $10 \times 10^6$ CAR-T cells comprising either 0.5×10⁶ CAR-T positive cells or 2.2×10⁶ CAR-T positive cells, on the following day. As control, mice received 10×10⁶ activated mononuclear cells or Mock-T cells. Mice were kept in an SPF animal facility in compliance with institutional IACUC guidelines. Mice were weighted twice a week and monitored daily for clinical signs and peritonitis. End point was defined as severe peritonitis manifested as enlarged and tense abdomen, lethargy, reduced mobility or increased respiratory effort. Survival analysis was performed according to the Kaplan-Meier method.

Results:

Significant downregulation (p<0.01) of pro-inflammatory cytokines, including IL-6, IP-10, TNF-α, MIP-1a, MIP-1ß, was documented (Data not shown). IFN-g was not downregulated, but its effect on macrophages and dendritic cells was inhibited at the level of phosphorylated STAT1 (Data not shown). IFN-γ induced expression of CXCL10 and CXCL9 in macrophages was reduced (Data not shown).

Figure 20A:
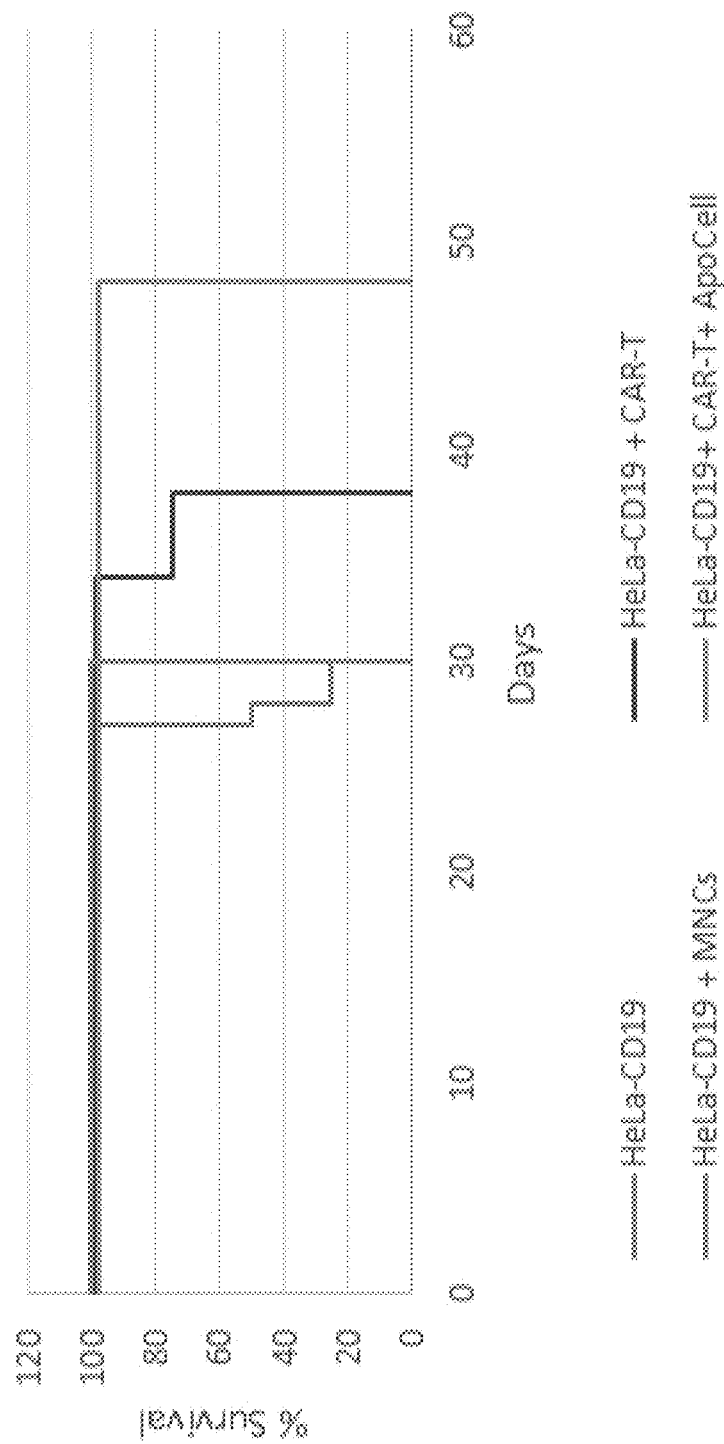
FIGS. 20A and 20B. Testing the efficacy of CD19-CAR-T cells in an IP model of HeLaCD19 (Leukemia), in the presence or absence of ApoCell. HeLa-CD19—Blue; HeLaCD19+Mock—Green; HeLaCD19+CAR-T—Purple; and HeLaCD19+CAR-T+ApoCell—orange.

In the experiment wherein 0.5×10⁶ CAR-T positive cells were used, 2 mice per group were sacrificed on day 17 and 21. HeLa-CD19 treated mice showed peritonitis manifested as blood accumulation in the peritoneum, enlarged spleen and tumor loci (Data not shown). Mice treated with control MNCs had a little bit less blood in peritoneum and less tumor loci. Mice treated with CAR-T or with CAR-T and ApoCell had no signs of peritonitis. This observation correlated to the survival curve presented in FIG. 20A.

Figure 20B:
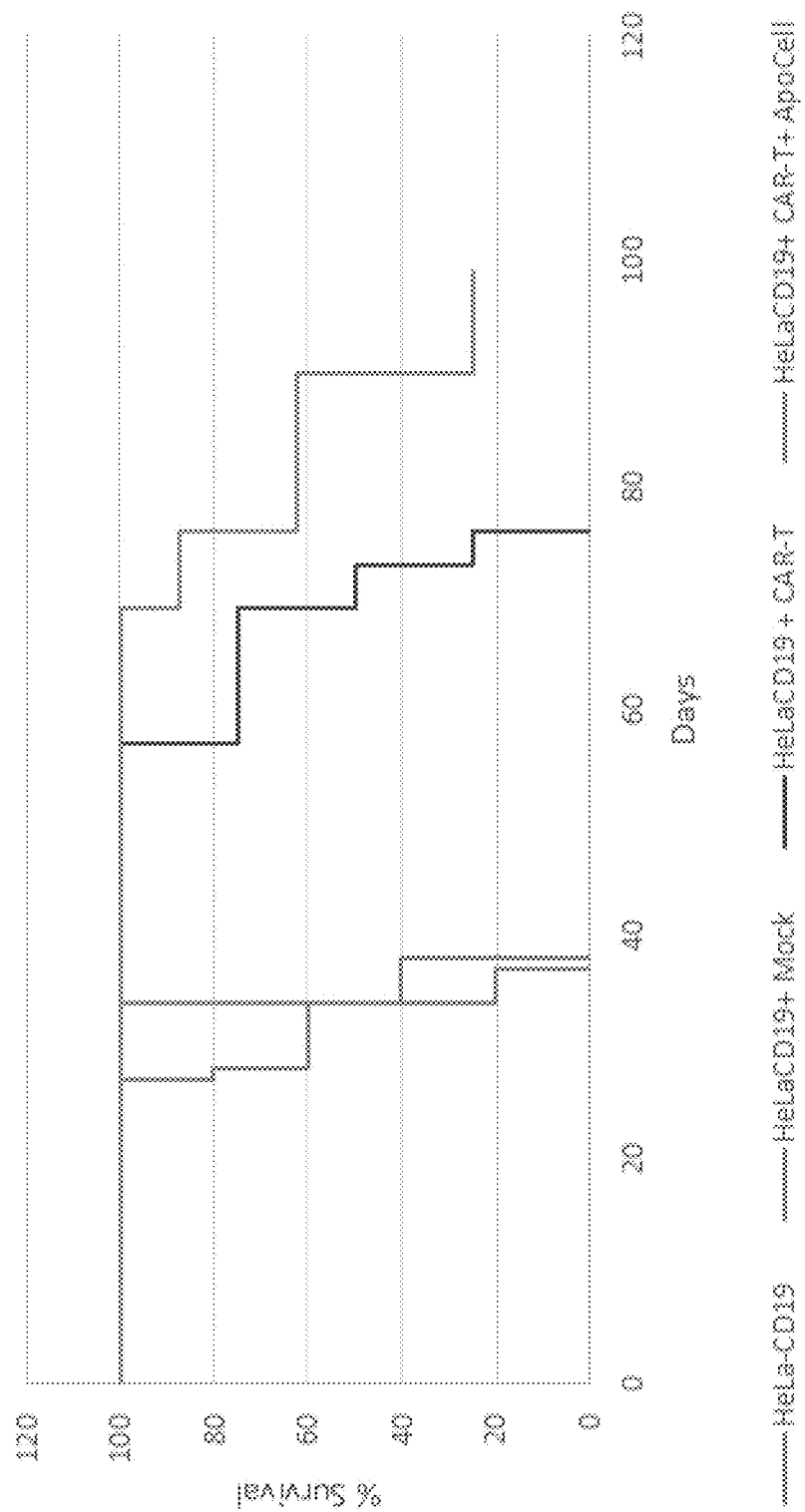

In the experiment wherein 2.2×10⁶ CAR-T positive cells were used, the same pattern of effect as seen with four-fold fewer CAR T-cells was observed (FIG. 20B). CAR-T treatment prolonged survival of mice with peritoneal HeLa-CD19 (p=0.0002). The effect was more significant in this experiment, probably due to the higher number of infused CAR T cells (2.2 versus 0.5×10⁶ CAR-T positive cells). Even with the more significant and prolonged effect, the early apoptotic cells had a synergistic effect and prolonged survival (p=0.0032). E/T ratios for CAR T were comparable in the presence/absence of apoptotic cells in vitro. Surprisingly, CAR T cell therapy given in the presence of apoptotic cells ameliorated survival of mice with a significant and reproducible addition of at least 12 days (p<0.0032, FIGS. 20A and 20B) in comparison to CAR therapy alone.

Conclusion:

CAR-T cell treatment prolonged survival of mice with peritoneal HeLa-CD19 cells Administration of irradiated early apoptotic cells one day before CAR-T had a synergistic effect and prolonged mice survival for more than 10 days (p<0.044, log-rank test), compared to CAR-T cell treatment alone.

The irradiated apoptotic cell infusion had a dramatic synergistic effect to CD19-specific CAR T cells in treating CD19-bearing Hela cells in SCID mice. In this example, similar results were observed to the results presented in Examples 5 and 6. By using irradiated apoptotic cells in this Example, compared with Examples 5 and 6, the possibility of a "graft versus leukemia effect" has been removed. Thus, this surprising synergistic effect appears to be mediated via the irradiated apoptotic cells provided.

CRS evolves from several factors, including tumor biology, interaction with monocytes/macrophages/dendritic cells, and as a response to the CAR T cell effect and expansion. Apoptotic cells decrease pro-inflammatory cytokines originating from innate immunity, and inhibit the IFN-γ effect on monocytes/macrophages/dendritic cells without harming IFN-γ levels or CAR-T cytotoxicity, and with significant increase in CAR-T cell efficacy. Unexpectedly, treatment with irradiated apoptotic cells complements CAR-T cell therapy, effectively extending the anti-cancer effect of the CAR-T cell therapy.

Example 9: Effect of Apoptotic Cells Treatment on a Non-Solid Tumor Model

Objective:

To test the effect of apoptotic cells on a non-solid tumor model where the cancer is widely spread and not localized or confined, in order to determine apoptotic cells efficacy on the survival in cancer.

Methods:

Raji Cells

Raji cells were purchased from ECACC (Cat. #: 85011429), and routinely cultured in complete medium (RPMI-1640 supplemented with 10% H.I. FBS, 1% Glutamax, 1% Penicillin/Streptomycin), and maintained at a concentration of 3×10⁵-3×10⁶ cells/ml.

Apoptotic cells were prepared as described in Example 1. Early apoptotic cells produced were at least 50% annexin V-positive and less than 5% PI-positive cells.

Non-Solid (Diffuse) Tumor Model

SCID mice received a single IV injection of 10⁵ Raji cells on day 1 of the experiment. A control group of SCID mice received a single IV injection of saline solution. (3 cohorts were tested; leukemia was induced in 2 cohorts using Raji cells, and 1 cohort was maintained as a control.)

Solid Tumor Model SCID mice will receive a single IP injection of 10⁵ Raji cells on day 1 of the experiment wherein control groups will receive a single IP injection of saline solution.

Apoptotic Cell Treatment

In a preliminary study, mice received an infusion of early apoptotic cells 6 days after the infusion of Raji cells. In later studies, the mice from one of the leukemic cohorts above received 3 infusions of early apoptotic cells (30×10⁶ cells) starting 6 days after the infusion of Raji cells.

Results

SCID mice have no T-cells and therefore no ability to recover from leukemia without therapy.

Figure 21:
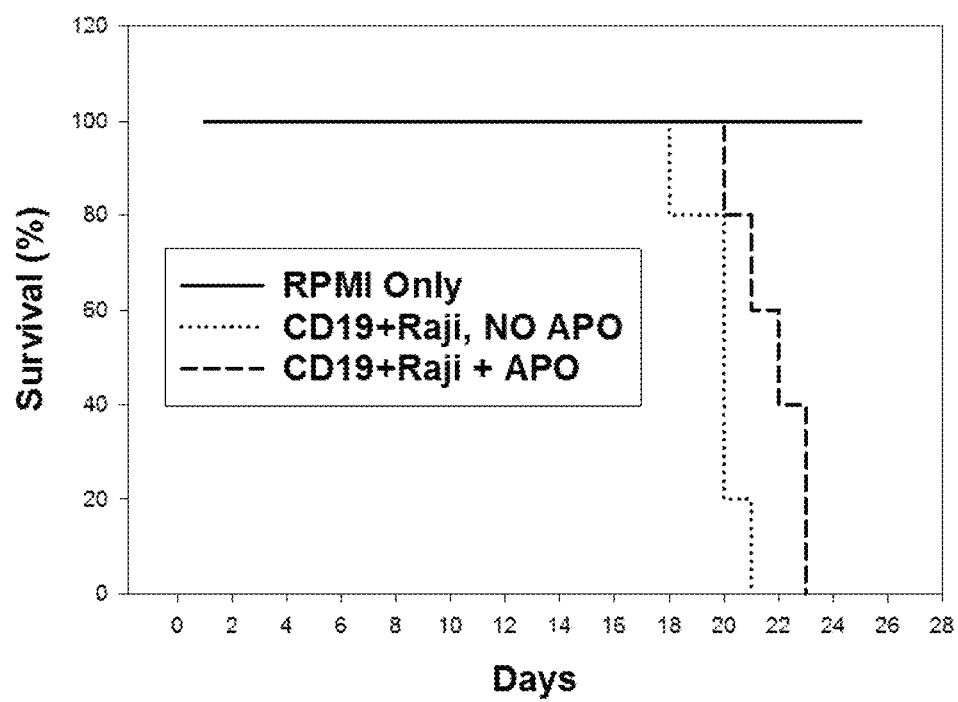
FIG. 21. Survival curves for in vivo diffuse tumor SCID mouse model. The curves show that administration of early apoptotic cells (APO; broad dashed lines - - - -) extended survival compared with mice not administered apoptotic cells (NO APO; dotted line • • • •), wherein control SCID mice showed 100% survival (solid line _____).

Surprising, in the preliminary study and as shown in FIG. 21, the apoptotic cell infusion (APO) 6 days after the infusion of Raji, significantly prolonged tumor free death in SCID injected with CD19+ Raji, compared with mice that did not receive an apoptotic cell infusion (NO APO).

Figure 22A:
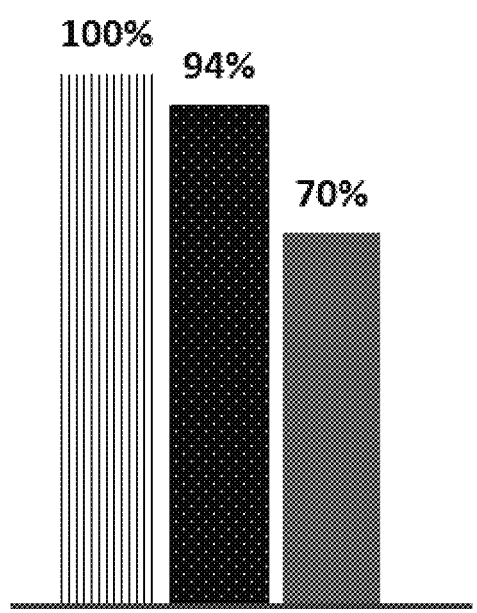
FIGS. 22A-22D. Apoptotic cell infusions increased the lifespan of leukemic mice and increased the number of mice attaining complete remission. Cohorts: No leukemia (Control-striped pattern); Leukemia+early apoptotic cells (spotted); Leukemia only (solid grey). n=51 in total (p<0.001) FIG. 22A. Apoptotic cell infusions increased the percentage of mice surviving through the expected life-span post leukemia induction.
Figure 22B:
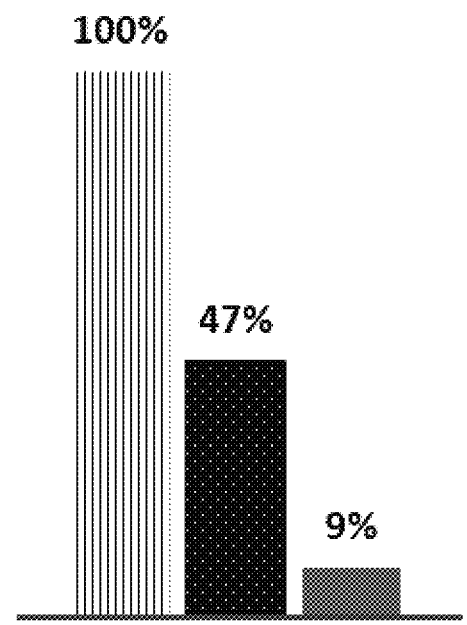
Figure 22C:
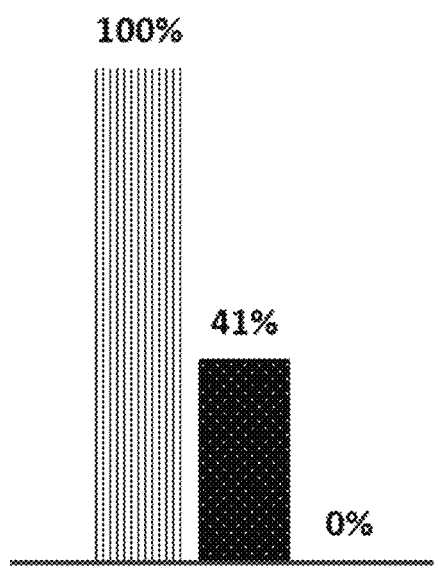
Figure 22D:
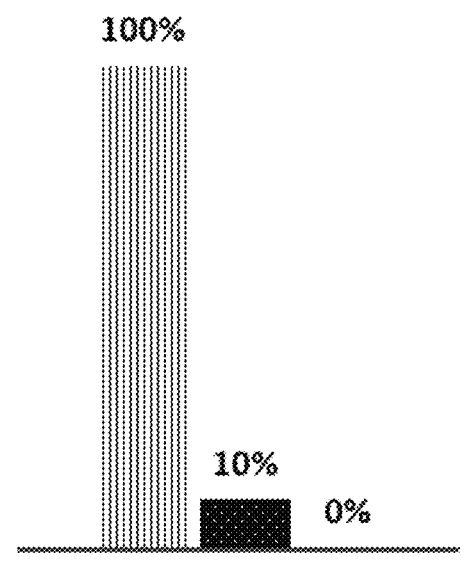

In the leukemic (NO APO) cohort, 70% of mice receiving Raji cells survived through their lifespan, compared to 94% of mice receiving both Raji cells and apoptotic cells (n=51 animals in total, p<0.001). As expected, 100% of control mice survived through their expected lifespan (FIG. 22A). In the leukemic cohort, 9% of mice receiving Raji cells and no apoptotic cells survived through up to 12% above the expected lifespan, compared to 47% of mice receiving both Raji cells and apoptotic cells (FIG. 22B). No mice receiving Raji cells and no apoptotic cells survived through greater than 30% of the expected lifespan, compared to 41% of mice receiving both Raji cells and apoptotic cells (FIG. 22C). No mice receiving Raji cells and no apoptotic cells attained complete remission, compared to 10% of mice receiving both Raji cells and apoptotic cells (FIG. 22D).

Conclusion:

Administration of an apoptotic cell infusion maintained and increased the lifespan of leukemic mice, wherein in certain instances mice administered early apoptotic cells attained complete remission (FIGS. 2 and 3A-3D).

Example 10: Effect of Combined Apoptotic Cell and Anti-CD20 mAb Treatment on a Diffuse Tumor Model Objective:

To test the effect of administering a combination of early apoptotic cells and anti-CD20 mAb on a diffuse (non-solid) tumor model, wherein the cancer is widely spread and not localized or confined, in order to determine the efficacy on survival of this combination therapy.

Raji cells, apoptotic cells, non-solid (diffuse) tumor model, solid tumor model, and apoptotic cell treatment were as described in Examples 1 and 9 above.

anti-CD20 mAb

Commercially available anti-CD20 mAb was acquired from Roche.

Anti-CD20 mAb Treatment

Mice received an IV infusion of 5 mg of anti-CD20 mAb.

Combined Apoptotic Cell and Anti-CD20 mAb Treatment

Starting at day 6 following Raji cell administration, mice received three IV infusions of $30 \times 10^6$ apoptotic cells each. In addition, mice received an IV infusion of 5 mg of anti-CD20 mAb.

Results

Figure 23A:
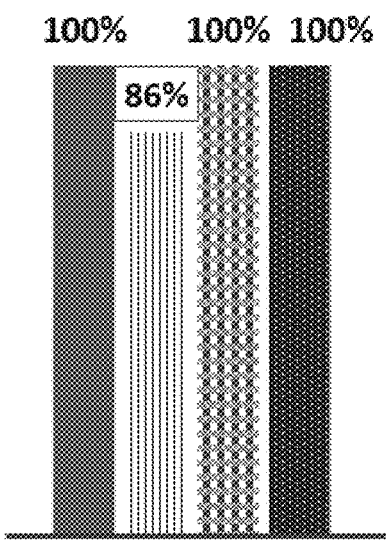
FIGS. 23A-23E. Apoptotic cell infusions increased the life-span of leukemic mice, increased the number of mice attaining complete remission, and enhanced the anti-CD20 monoclonal antibody (mAb) therapeutic effect. Cohorts: Leukemia only (solid grey); Leukemia+early apoptotic cells (striped pattern); Leukemia+anti-CD20 mAb (checkered); Leukemia+anti-CD20+early apoptotic cells (spotted). n=28 in total (p<0.002) FIG. 23A. Shows the percent (%) survival through the expected lifespan of mice following induction of leukemia with Raji cells.
Figure 23B:
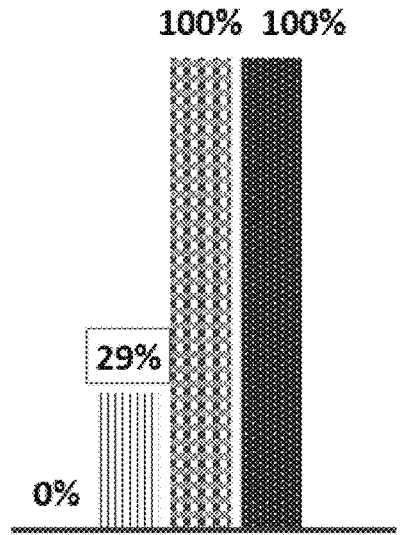
Figure 23C:
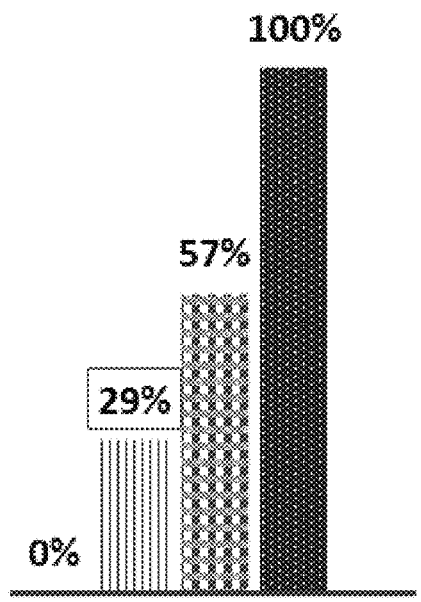
Figure 23D:
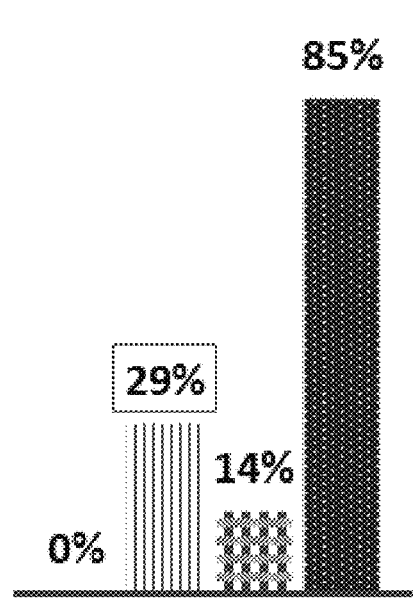
Figure 23E:
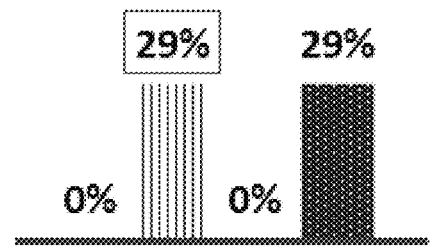

100% of mice receiving Raji cells, Raji cells+anti-CD20 mAb, and Raji cells+antiCD20+apoptotic cells survived through the expected lifespan of leukemic mice, compared to 86% of mice receiving both Raji cells and apoptotic cells (n=28 animals in total, p<0.0002) (FIG. 23A). No mice receiving Raji cells survived longer than 24% above the expected lifespan, compared to 29% of mice receiving both Raji cells+apoptotic cells, and 100% of mice receiving either Raji cells+anti-CD20 mAb or Raji cells+antiCD20+apoptotic cells (FIG. 23B). No mice receiving Raji cells survived longer than 59% above the expected lifespan, compared to 29% of mice receiving both Raji cells+apoptotic cells, 57% of mice receiving Raji cells+anti-CD20 mAb, and 100% of mice receiving Raji cells+antiCD20+apoptotic cells (FIG. 23C). No mice receiving Raji cells survived longer than 76% above the expected lifespan, compared to 29% of mice receiving both Raji cells+apoptotic cells, 14% of mice receiving Raji cells+anti-CD20 mAb, and 85% of mice receiving Raji cells+antiCD20+apoptotic cells (FIG. 23D). No mice receiving either Raji cells or Raji cells+anti-CD20 mAb survived longer than 100% above the expected lifespan of a mouse, compared to 29% of mice receiving either Raji cells+apoptotic cells or Raji cells+antiCD20+apoptotic cells (FIG. 23E).

Conclusion:

Apoptotic cell infusions increased the lifespan of leukemic mice, increased the number of mice attaining complete remission, and enhanced anti-CD20 mAb therapeutic effect (FIGS. 23A-23E).

Example II: Effect of ApoCell (Early Apoptotic Cells) on Leukemia/Lymphoma

Objective:

The work presented here had three main goals: (1) Evaluating the effect of ApoCell in a leukemia-lymphoma mouse model in terms of disease onset, progression, and ensuing death; (2) Assessing the distribution of tumor cells in a mouse model of leukemia-lymphoma after treatment with ApoCell; and (3) Assessing a possible synergistic effect of ApoCell and Rituximab (RtX) in the treatment of leukemia-lymphoma in SCID-Bg mice. As part of the work to meet these objectives, measurement of the survival of leukemic mice following ApoCell administration was measured. As well, the distribution of tumor cells was measured after treatment with ApoCell.

Methods:

Mice. Female SCID-Bg mice, 7 weeks-old (ENVIGO, Jerusalem, Israel), were injected intravenously with $0.1 \times 10^6$ Raji cells per mouse. Mice received 3 doses of $30 \times 10^6$ ApoCell intravenously on days 5, 8, and 11 of the experiment. For combinational therapy, mice received one dose (day 8) of RtX (2 or 5 mg/kg; Mabthera, Roche, Basel, Switzerland) 1.5 h after ApoCell administration.

Mice were followed daily and weighed twice a week. The endpoint was defined as death, or sacrifice due to the development of either of the following symptoms: paraplegia (lower body paralysis), loss of 20% from mouse start weight, lethargy, reduced mobility, or increased respiratory effort.

Survival analysis was performed according to the Kaplan-Meier method. Mice were kept in a specific-pathogen-free (SPF) animal facility in compliance with institutional Animal Care and Use Committee (IACUC) guidelines.

Raji Cell Line.

This human Burkitt's lymphoma cell line was purchased from the European Collection of Authenticated Cell Cultures (ECACC, Cat. #: 85011429), and routinely cultured in complete medium (RPMI-1640 supplemented with 10% heat inactivated FBS, 1% glutamax, 1% penicillin/streptomycin).

ApoCell.

Essentially, as described in Example 1. Briefly, an enriched mononuclear cell fraction was collected via leukapheresis from healthy, eligible donors. Following apheresis completion, cells were washed and resuspended with freezing media composed of PlasmaLyte A pH 7.4, 5% human serum albumin, 10% dimethyl sulfoxide (DMSO), 5% anticoagulant citrate dextrose solution formula A (ACD-A) and 0.5 U\ml heparin. Cells were then gradually frozen and transferred to liquid nitrogen for long-term storage.

For preparation of ApoCell, cryopreserved cells were thawed, washed and resuspended with apoptosis induction media, composed of RPMI 1640 supplemented with 2 mM L-glutamine and 10 mM hepes, 10% autologous plasma, 5% ACD-A, 0.5 U\ml heparin sodium and 50 µg/ml methylprednisolone. Cells were then incubated for 6 hours at 37° C. in 5% $CO_2$. At the end of incubation, cells were collected, washed and resuspended in Hartmann's solution using a cell processing system. ApoCell was centrifuged at 290 g, for 10 min at 2-8° C., and resuspended in Hartmann's solution for injection. Apoptosis and viability of ApoCell were determined using Annexin V and propidium iodide (PI, Medical & Biological Laboratories, Nagoya, Japan) using FCS express software.

Flow Cytometry.

Mouse spleen, liver, and bone marrow were collected from sacrificed mice (following deterioration of clinical signs, as defined above) and analyzed by flow-cytometry (FACSCalibur, BD, Franklin Lakes, N.J., USA) for the presence of the Raji tumor (anti-CD20).

Results:

Part A: ApoCell Delays Disease Onset and Ensuing Death in Leukemic Mice

Figure 24:
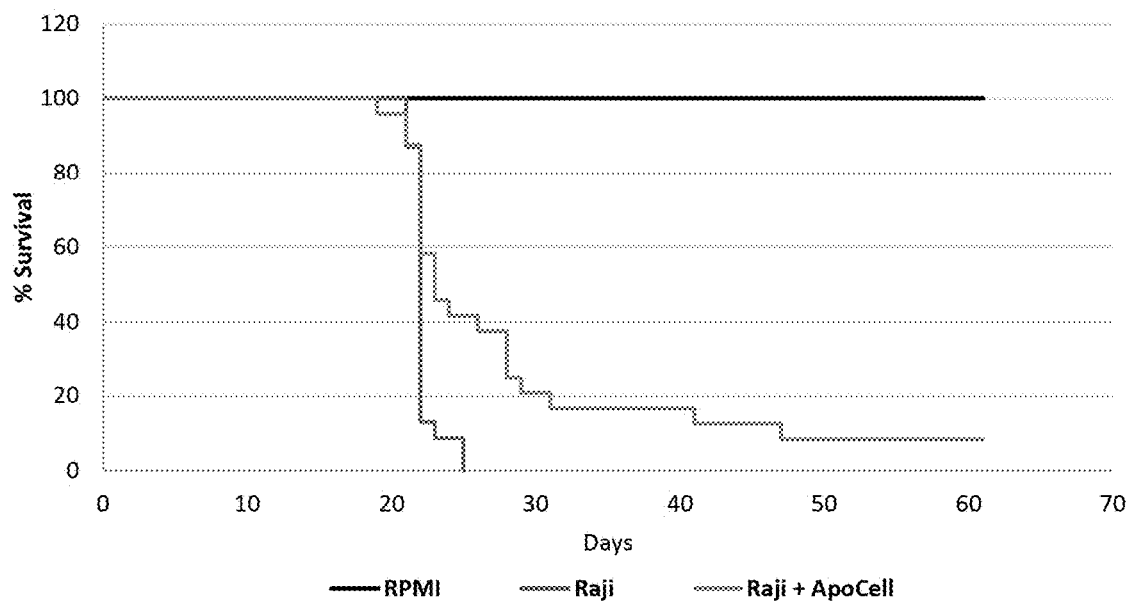
FIG. 24. Kaplan-Meier survival plot of SCID-Bg mice with Raji leukemia/lymphoma, receiving ApoCell. (RPMI group, n=15; Raji group, n=23; Raji+ApoCell group, n=24) RPMI (control)—Black; Raji only—Orange; Raji+ApoCell—Blue.

FIG. 24 is a Kaplan-Meier survival plot presenting 3 individual experiments (RPMI group, n=15; Raji group, n=23; Raji+ApoCell group, n=24). In each experiment, female SCID-Bg mice (7-8 weeks of age) were injected intravenously with $0.1 \times 10^6$ Raji cells and a control group was injected with RPMI. Subsequently, mice were administered with three doses of 30×10⁶ ApoCell by intravenous administration (IV), on days 5, 8, and 11. Mice were followed daily and weighed twice a week. Endpoint was defined as death, or sacrifice due to the development of either of the following symptoms: paraplegia (lower body paralysis), loss of 20% from mouse start weight, lethargy, reduced mobility, or increased respiratory effort. Experimental details are given in Table 11. Significant beneficial effect by ApoCell was seen (p=0.002, Log-rank (Mantel-Cox) test).

TABLE 11

Experimental details of FIG. A plot

| Group | Number of mice | Survival details | | Notes |
|---|---|---|---|---|
| | | Mean day of sacrifice | Range (days) | |
| RPMI | 15 | | | DFS* is shown for all mice |
| Raji | 23 | 22 | 21-25 | |
| Raji + ApoCell | 24 | 28 | 19->53 | 2 mice DFS* on day 53/60 (termination of experiment) |

*DFS = disease free survival

Figure 25A:
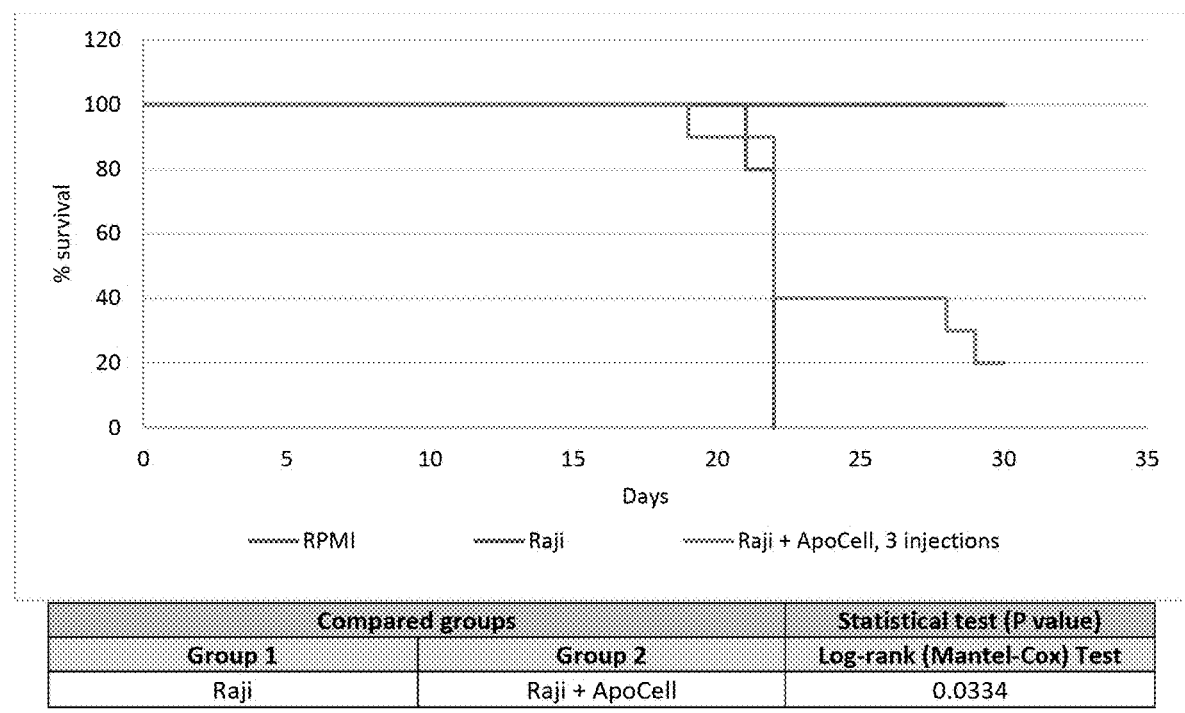
FIGS. 25A-25C. Kaplan-Meier survival plots.
Figure 25B:
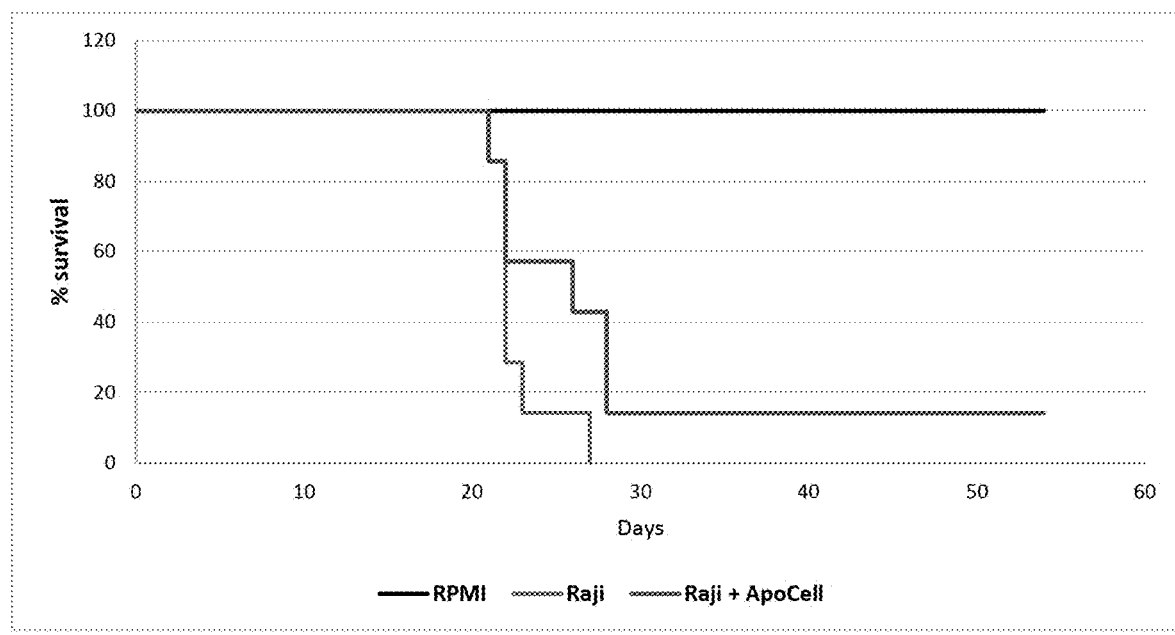
Figure 25C:
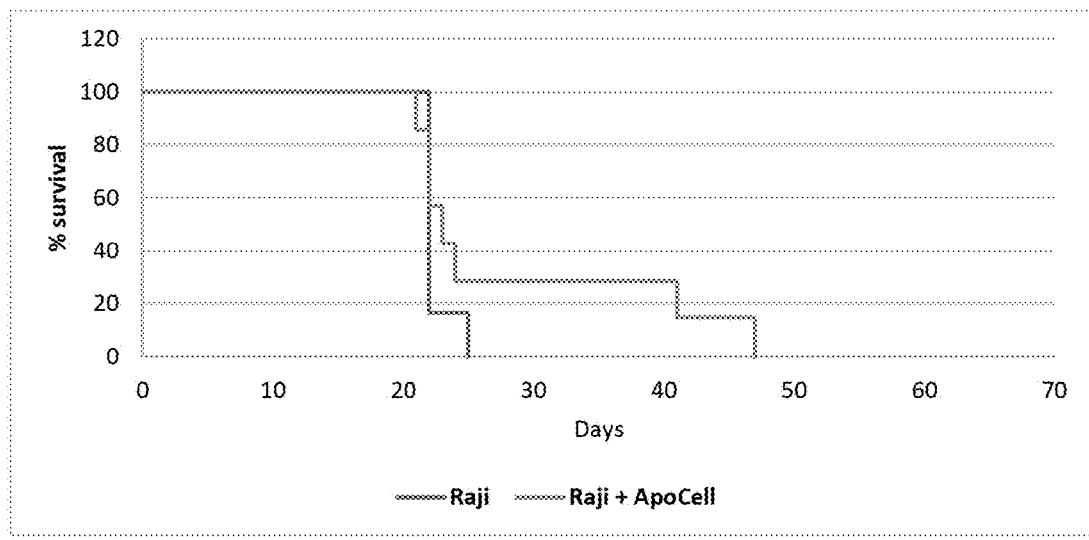

The data for the individual studies is presented in FIGS. 25A-25C.

As depicted above, mice treated with 3 doses of ApoCell after the administration of Raji cells had a slower disease progression, and died significantly later (p=0.0020) than untreated mice.

Leukemic mice treated with ApoCell had a significant delay in the onset of symptoms, demonstrated a slower disease progression, and died later than the control untreated mice. Interestingly, about 10 percent of the mice administered with Raji cells and ApoCell did not develop any of the expected symptoms characteristic in this leukemia/lymphoma model, and remained healthy until termination of the experiments (day 53 or 60).

ApoCell Reduce Tumor Load in Leukemic Mice

Upon sacrifice, following the deterioration of clinical signs as described above, organs of interest were collected for analysis, namely the liver, spleen, and bone-marrow. Cells of these target organs were analyzed by flow cytometry for the presence of human tumor cells (Raji cells are positive for CD20).

The data below (Table 12) describes the average percent cell population in target organs of the sacrificed mice from the 3 experiments described above; values of individual mice in each experiment can be found in Tables 13-18, which follow.

TABLE 12

Average percent of tumor population in Spleen, Bone Marrow and Liver (Flow cytometry)

| Tissue | Treatment | # of mice | % CD20⁺ cells (average ± SD) |
|---|---|---|---|
| Spleen | RPMI | 5 | 0 |
| | Raji | 10 | 0 |
| | Raji + ApoCell | 8 | 1.1 ± 3 |
| Bone-Marrow | RPMI | 5 | 0 |
| | Raji | 10 | 16.5 ± 8.8 |
| | Raji + ApoCell | 8 | 6.8 ± 9.2 (P = 0.02, t-test) |

TABLE 12-continued

Average percent of tumor population in Spleen, Bone Marrow and Liver (Flow cytometry)

| Tissue | Treatment | # of mice | % CD20⁺ cells (average ± SD) |
|---|---|---|---|
| Liver | RPMI | 5 | 0 |
| | Raji | 10 | 11.2 ± 12 |
| | Raji + ApoCell | 8 | 4.5 ± 7.5 (P = 0.06, t-test) |

In Vivo Experiment 011

FACS analysis of CD20+ cells in bone marrow, spleen, and liver:

One mouse receiving three doses of ApoCell was healthy when sacrificed on day 60.

Liver, spleen, and bone marrow cells were collected and analyzed by flow cytometry (FACSCalibur, BD) for the presence of human CD20-FITC (Biolegend, Cat. #302206); mIgG1-FITC (Biolegend, Cat. #400110).

In Vivo Experiment 019

FACS Analysis of Tumor Cells in Bone Marrow, Spleen, and Liver:

Mouse spleen, liver, and bone marrow cells were collected from mice who were sacrificed following clinical deterioration, as defined in the methods) and analyzed by flow cytometry (FACSCalibur, BD) for the presence of human CD20 (FITC).

The results of analysis of Spleen, Bone marrow, and Liver are presented in Tables 13-15 below.

TABLE 13

Spleen

| Mouse | Treatment | Day of sacrifice | CD20+ |
|---|---|---|---|
| A1 | RPMI | | 0 |
| A2 | | | 0 |
| A3 | | | 0 |
| B2 | Raji | 22 | 0 |
| B3 | | 22 | 0 |
| B5 | | 22 | 0 |
| B6 | | 22 | 0 |
| B2 (020) | | 25 | 0 |
| B3 (020) | | 25 | 0 |
| C1 | Raji + ApoCell | 28 | 0 |
| C2 | | 53 (healthy) | 8.7 |
| C4 | | 22 | 0 |
| C6 | | 22 | 0 |
| C7 | | 28 | 0 |

TABLE 14

Bone Marrow

| Mouse | Treatment | Day of sacrifice | CD20+ |
|---|---|---|---|
| A1 | RPMI | | 0 |
| A2 | | | 0 |
| A3 | | | 0 |
| B2 | Raji | 22 | 18.7 |
| B3 | | 22 | 11.3 |
| B5 | | 22 | 10.5 |
| B6 | | 22 | 14.5 |

TABLE 14-continued

Bone Marrow
Bone marrow

| Mouse | Treatment | Day of sacrifice | CD20+ |
|---|---|---|---|
| B2 (020) | | 25 | 21 |
| B3 (020) | | 25 | 0 |
| C1 | Raji + | 28 | 1 |
| C2 | ApoCell | 53 (healthy) | 0.5 |
| C4 | | 22 | 0.6 |
| C6 | | 22 | 17.5 |
| C7 | | 28 | 1.4 |

TABLE 15

Liver
Liver

| Mouse | Treatment | Day of sacrifice | CD20+ |
|---|---|---|---|
| A1 | RPMI | | 0 |
| A2 | | | 0 |
| A3 | | | 0 |
| B2 | Raji | 22 | 4.4 |
| B3 | | 22 | 6.5 |
| B5 | | 22 | 1.7 |
| B6 | | 22 | 5.4 |
| B2 (020) | | 25 | 26.4 |
| B3 (020) | | 25 | 5.9 |
| C1 | Raji + | 28 | 9.8 |
| C2 | Apo Cell | 53 (healthy) | 0.5 |
| C4 | | 22 | 3 |
| C6 | | 22 | 5 |
| C7 | | 28 | 22.7 |

In Vivo Experiment 023

Expression (%) of CD20 tumor cells in the spleen, bone marrow, and liver, as determine by flow cytometry. Mouse spleen, liver, and bone marrow were collected from sacrificed mice (following clinical deterioration, as defined in methods) and analyzed by flow cytometry (FACSCalibur, BD) for the presence of human CD20 (FITC). The results for Spleen, bone marrow, and liver for the individual mice are presented in Tables 16-18 below.

TABLE 16

Spleen
Spleen

| Treatment | Mouse | Day of sacrifice | CD20+ |
|---|---|---|---|
| Raji | B1 | 22 | 0 |
| | B2 | 25 | 0 |
| | B3 | 22 | 0 |
| | B4 | 22 | 0.2 |
| Raji + ApoCell | C1 | 22 | 0.2 |
| | C4 | 22 | 0.3 |
| | C5 | 41 | 0.1 |
| | C6 | 47 | 0 |
| Raji + RtX 2 mg/kg | E1 | 32 | 0 |
| | E2 | 32 | 0.7 |
| | E6 | 32 | 0 |

TABLE 16-continued

Spleen
Spleen

| Treatment | Mouse | Day of sacrifice | CD20+ |
|---|---|---|---|
| Raji + RtX 2 mg/kg + ApoCell | F1 | 40 | 0 |
| | F2 | 43 | 0.1 |
| | F4 | 35 | 0 |
| | F5 | 32 | 0 |
| | F6 | 35 | 0 |
| | F7 | 57 | 0.4 |
| Raji + RtX 5 mg/kg | G1 | 34 | 0 |
| | G3 | 34 | 0.1 |
| | G4 | 43 | 0 |
| | G5 | 40 | 0 |
| | G7 | 40 | 0.1 |
| Raji + RtX 5 mg/kg + ApoCell | H1 | 40 | 0.4 |
| | H3 | 36 | |
| | H4 | 36 | |
| | H5 | 40 | 0 |
| | H6 | 40 | 0 |
| | H7 | 53 | 0 |

TABLE 17

Bone Marrow
Bone marrow

| Treatment | Mouse | Day of sacrifice | CD20+ |
|---|---|---|---|
| Raji | B1 | 22 | 18 |
| | B2 | 25 | 22.5 |
| | B3 | 22 | 33.6 |
| | B4 | 22 | 14.9 |
| Raji + ApoCell | C1 | 22 | 24.3 |
| | C4 | 22 | 1.8 |
| | C5 | 41 | 7.8 |
| | C6 | 47 | 0 |
| Raji + RtX 2 mg/kg | E1 | 32 | 0.8 |
| | E2 | 32 | 3.1 |
| | E6 | 32 | 3 |
| Raji + RtX 2 mg/kg + ApoCell | F1 | 40 | 4.1 |
| | F2 | 43 | 0.4 |
| | F4 | 35 | 0.2 |
| | F5 | 32 | 0.8 |
| | F6 | 35 | 0.2 |
| | F7 | 57 | 0.4 |
| Raji + RtX 5 mg/kg | G1 | 34 | 2.1 |
| | G3 | 34 | 0.5 |
| | G4 | 43 | 4.3 |
| | G5 | 40 | 2.2 |
| | G7 | 40 | 2.6 |
| Raji + RtX 5 mg/kg + ApoCell | H1 | 40 | 0.9 |
| | H3 | 36 | 0 |
| | H4 | 36 | 0 |
| | H5 | 40 | 1.6 |
| | H6 | 40 | 1.3 |
| | H7 | 53 | 1.8 |

TABLE 18

Liver
Liver

| Treatment | Mouse | Day of sacrifice | CD20+ |
|---|---|---|---|
| Raji | B1 | 22 | 6.4 |
| | B2 | 25 | 42.6 |
| | B3 | 22 | 5 |
| | B4 | 22 | 8.1 |

TABLE 18-continued

Liver
Liver

| Treatment | Mouse | Day of sacrifice | CD20+ |
|---|---|---|---|
| Raji + ApoCell | C1 | 22 | 2.5 |
|  | C4 | 22 | 2.2 |
|  | C5 | 41 | 0.4 |
|  | C6 | 47 | 0 |
| Raji + RtX 2 mg/kg | E1 | 32 | 2.1 |
|  | E2 | 32 | 1.2 |
|  | E6 | 32 | 0.4 |
| Raji + RtX 2 mg/kg + ApoCell | F1 | 40 | 0 |
|  | F2 | 43 |  |
|  | F4 | 35 | 0 |
|  | F5 | 32 | 7.3 |
|  | F6 | 35 | 5 |
|  | F7 | 57 | 0 |
| Raji + RtX 5 mg/kg | G1 | 34 | 1 |
|  | G3 | 34 | 7.3 |
|  | G4 | 43 | 1.4 |
|  | G5 | 40 | 0.9 |
|  | G7 | 40 | 5.7 |
| Raji + RtX 5 mg/kg + ApoCell | H1 | 40 | 0.8 |
|  | H3 | 36 | 0.1 |
|  | H4 | 36 | 0 |
|  | H5 | 40 | 0.5 |
|  | H6 | 40 | 25.1 |
|  | H7 | 53 | 3.4 |

Preliminary Conclusions:

In conclusion, tumor distribution in the mouse organs correlated the beneficial effect seen in survival plots and was significantly reduced in bone-marrow and liver in treated mice.

Part B: Synergistic Effect of ApoCell and Rituximab (RtX) in the Treatment of Leukemia/Lymphoma Next, it was examined whether the ApoCell treatment was synergistic with other conventional treatments of leukemia/lymphoma by evaluating the combined effect of RtX and ApoCell on leukemic mice in two experiments.

Objectives:

Measurement of the survival of leukemic mice following RtX and ApoCell administration, and detect tumor cells in bone marrow, liver, and spleen in leukemic mice.

Methods:

The following work is a representative description of the results obtained in the combination therapy experiments (ApoCell and rtx). Briefly, female SCID-Beige mice were injected intravenously with $0.1 \times 10^6$ Raji cells (n=7 in all groups). Mice received three doses of $30 \times 10^6$ ApoCell intravenously on days 5, 8, and 12. On day 8, 1.5 h after ApoCell injection, the mice received a single IV dose of 2 or 5 mg/kg RtX. Mice were followed daily and weighted twice a week. The endpoint was defined as death, or sacrifice due to the development of one or more of the following symptoms: paraplegia (lower body paralysis), loss of 20% from starting weight, lethargy, reduced mobility, or increased respiratory effort.

Figure 26:
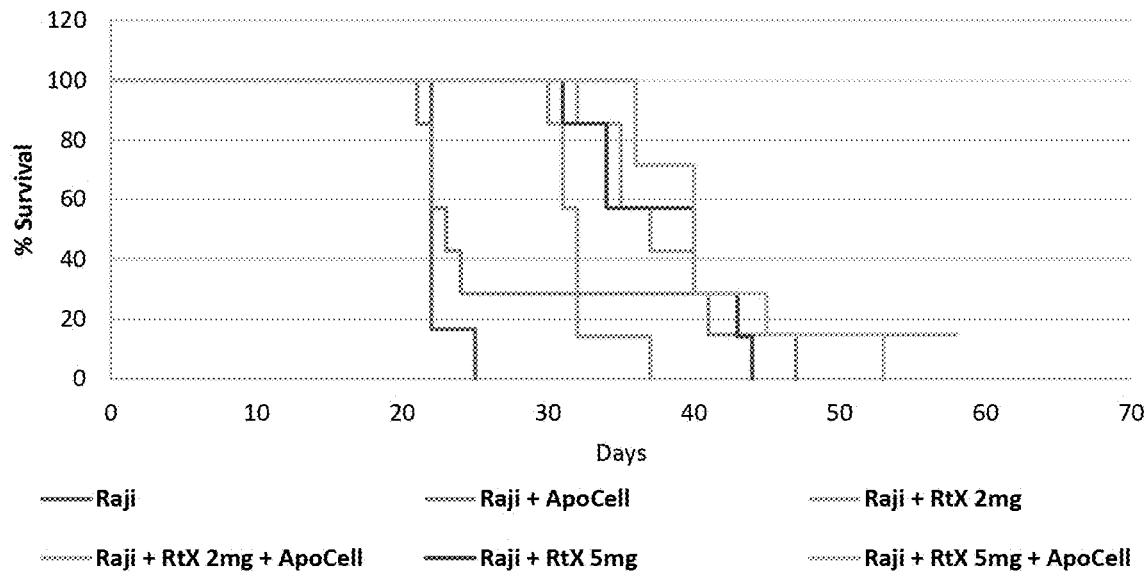
FIG. 26. Kaplan-Meier survival plot of SCID-Bg mice with Raji leukemia/lymphoma, receiving RtX and ApoCell. (Raji alone—orange; Raji+ApoCell—blue; Raji+RtX 2 mg—green; Raji+RtX 2 mg+ApoCell—yellow; Raji+RtX 5 mg—purple; Raji+RtX 5 mg+ApoCell—grey.)

Results:

As shown in FIG. 26, ApoCell had a beneficial effect corroborating the results presented in FIG. 24. Rituxan (RtX) alone had a superior effect to ApoCell both in 2 mg and 5 mg dosage but the combination of ApoCell and Rituxan had a synergistic effect at both in 2 mg (p=0.104) and in 5 mg dosage, although the synergistic effect seen in 5 mg did not reach statistical significance. Tumor distribution in the mouse organs correlated the beneficial effect (Table 19).

TABLE 19

Statistical analysis of the survival distributions (Log-rank (Mantel-Cox) test)

| Compared groups | | Statistical test (P value) Log-rank (Mantel-Cox) |
|---|---|---|
| Group 1 | Group 2 | Test |
| Raji | Raji + rtx (2 mg/Kg) | 0.0002 |
| Raji | Raji + rtx (2 mg/Kg) + ApoCell | 0.0002 |
| Raji | Raji + rtx (5 mg/Kg) | 0.0002 |
| Raji | Raji + rtx (5 mg/Kg) + ApoCell | 0.0002 |
| Raji + Rituxan (2 mg/Kg) | Raji + Rituxan (2 mg/Kg) + ApoCell | 0.0104 |

End of Experiment –Day 57

One mouse (Raji+RtX 2 mg/kg+ApoCell) was declared disease free upon termination of the experiment.

Figure 27:
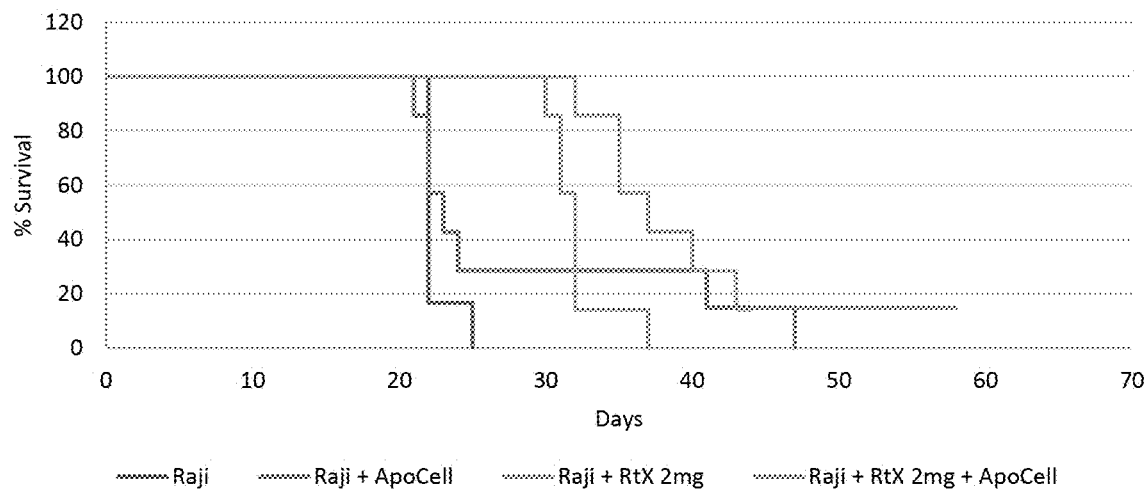
FIG. 27. Kaplan-Meier survival plot of SCID-Bg mice with Raji leukemia/lymphoma, receiving rtx and ApoCell. (Raji alone—orange; Raji+ApoCell—blue; Raji+RtX 2 mg—green; Raji+RtX 2 mg+ApoCell—yellow.)

The synergistic effect in one 2 mg RtX dose was measured in an additional experiment. As was clearly shown in this experiment (FIG. 27), the synergistic effect of ApoCell and RtX was again verified as significant (p=0.01).

As shown in Table 20, the spleen was not populated by tumor cells (0.1-0.3 represents background staining) and was used as a control. In contrast, bone marrow and liver were tumor targets. There was a reduced tumor population (Rajii-cells, as measured using CD20 marker) in bone marrow and liver following treatment by ApoCell and RtX separately, and the benefit increased when the two were given in combination; p=0.0034 () for Raji+rtx (2 mg/Kg)+ApoCell, and 0.0031 () for Raji+rtx (5 mg/Kg)+ApoCell (T-test. As expected, RtX significantly reduces tumor burden in the target organs of the leukemic mice. Interestingly, treatment with ApoCell alone reduced tumor cells in those organs to levels comparable to treatment with conventional RtX therapy.

TABLE 20

Average tumor cell population in the spleen, bone-marrow, and liver (flow cytometry)

| Tissue | Treatment | # of mice | CD20+ | Statistical test (P value) T-Test |
|---|---|---|---|---|
| Spleen | Raji | 7 | 0 | |
|  | Raji + ApoCell | 4 | 0.3 ± 0.4 | |
|  | Raji + rtx (2 mg/Kg) | 3 | 0.2 ± 0.4 | |
|  | Raji + rtx (2 mg/Kg) + ApoCell | 6 | 0.1 ± 0.1 | |
|  | Raji + rtx (5 mg/Kg) | 7 | 0 | |
|  | Raji + rtx (5 mg/Kg) + ApoCell | 4 | 0.1 ± 0.2 | |
| Bone Marrow | Raji | 6 | 18.3 ± 11 | |
|  | Raji + ApoCell | 4 | 8.5 ± 11 | |
|  | Raji + rtx (2 mg/Kg) | 3 | 2.3 ± 1.3 | |
|  | Raji + rtx (2 mg/Kg) + ApoCell | 6 | 1 ± 1.5 | 0.0034 (**) |
|  | Raji + rtx (5 mg/Kg) | 7 | 1.7 ± 1.5 | |
|  | Raji + rtx (5 mg/Kg) + ApoCell | 6 | 0.9 ± 0.8 | 0.0031 (**) |
| Liver | Raji | 6 | 15.7 ± 15.4 | |
|  | Raji + ApoCell | 4 | 1.3 ± 1.3 | |
|  | Raji + rtx (2 mg/Kg) | 3 | 1.2 ± 0.8 | |
|  | Raji + rtx (2 mg/Kg) + ApoCell | 5 | 2.5 ± 3.5 | |
|  | Raji + rtx (5 mg/Kg) | 7 | 3 ± 2.5 | |
|  | Raji + rtx (5 mg/Kg) + ApoCell | 7 | 4.4 ± 9.2 | |

Conclusion:

In summary, the survival plots (FIG. 24, FIG. 26, and FIG. 27) clearly demonstrate the beneficial effects of ApoCell and Rtx along as well as the synergistic effect of ApoCell and RtX in combination. Of note, when the conventional RtX treatment was combined with ApoCell, survival times increased significantly, regardless of the RtX dose, indicating a potent synergistic effect of the two therapies. A supporting clinical observation was the decrease in the of tumor cell population in the bone marrow and liver (Table 12).

Surprisingly, ApoCell preparation had a remarkably beneficial effect on disease progression and survival in a leukemic mouse model, independent of any other treatment. 10-20% of mice had prolonged survival in Kaplan-Meier analysis (FIG. 24, FIG. 26, and FIG. 27), and the tumor cell burden was reduced in the liver and bone marrow. Furthermore, there was a marked synergistic effect when ApoCell and RtX were administered in combination, further delaying disease onset and progression, and improving survival.

Example 12: Use of Pooled Apoptotic Cell Preparation in GVHD Leukemia/Lymphoma Models In the following preliminary work, the effect of the same infusion in GvHD leukemia/lymphoma models was examined. The safety and efficacy of an irradiated multiple donor single apoptotic cell infusion (a pooled mononuclear irradiated apoptotic cell preparation) for the prevention of acute GvHD in mice undergoing bone marrow transplantation (BMT) was examined. In this model, BMT rescued irradiated mice (80-100%).

The question regarding the possible loss of graft versus leukemia (GvL) effect arises in every successful treatment that potentially avoids high grade aGVHD, since this effect was found to correlate with the severity of GVHD.

Methods

Apoptotic cells were prepared as per Example 1 above, except that in the current experiments, preparation was done simultaneously from 4 donors. Following preparation from 4 donors, the cell preparations were combined at the last step (prior to irradiation), irradiated immediately after, and injected immediately after irradiation. Irradiation was at 25 Gy.

Results

Figure 28:
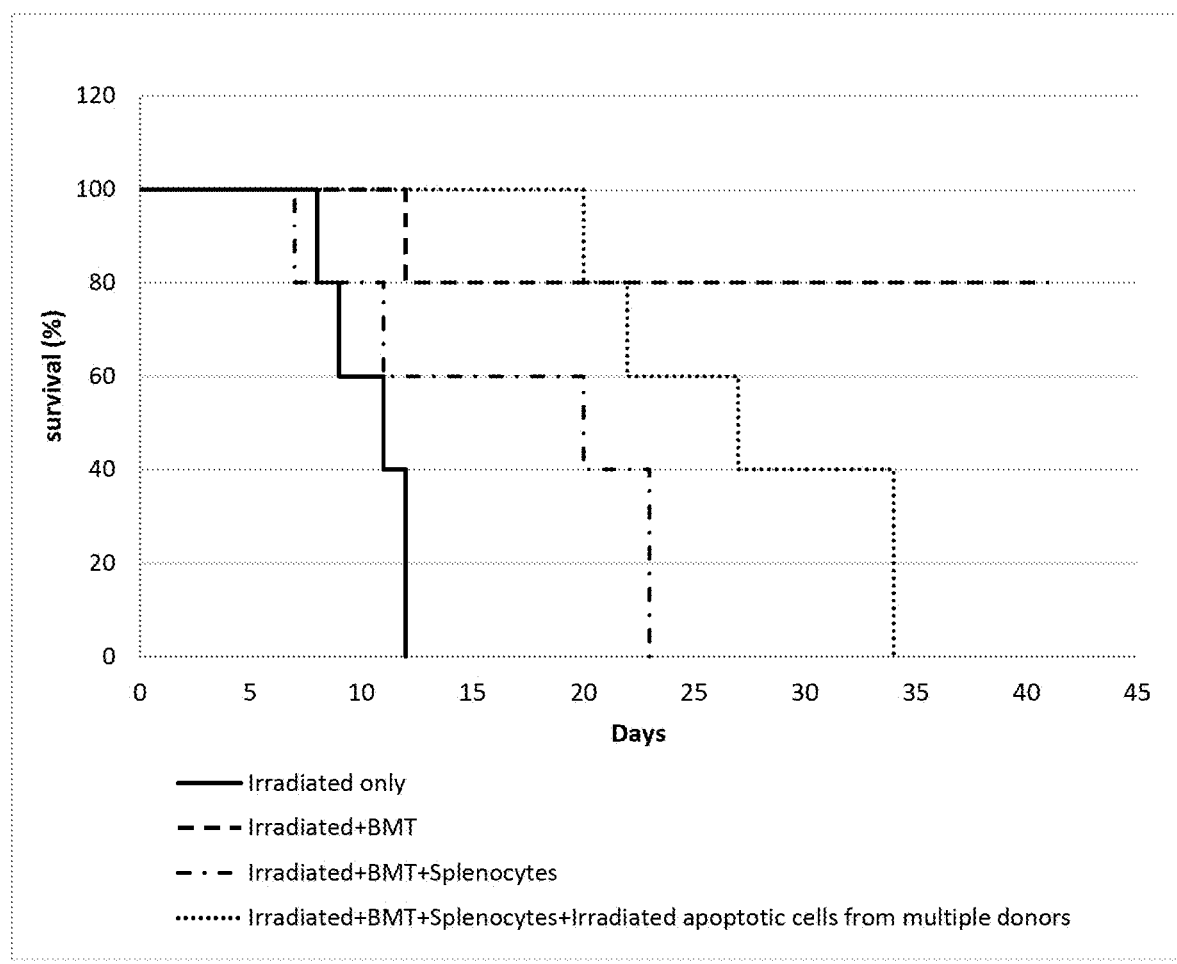
FIG. 28. Effect of Pooled ApoCell Preparation.
Figure 29:
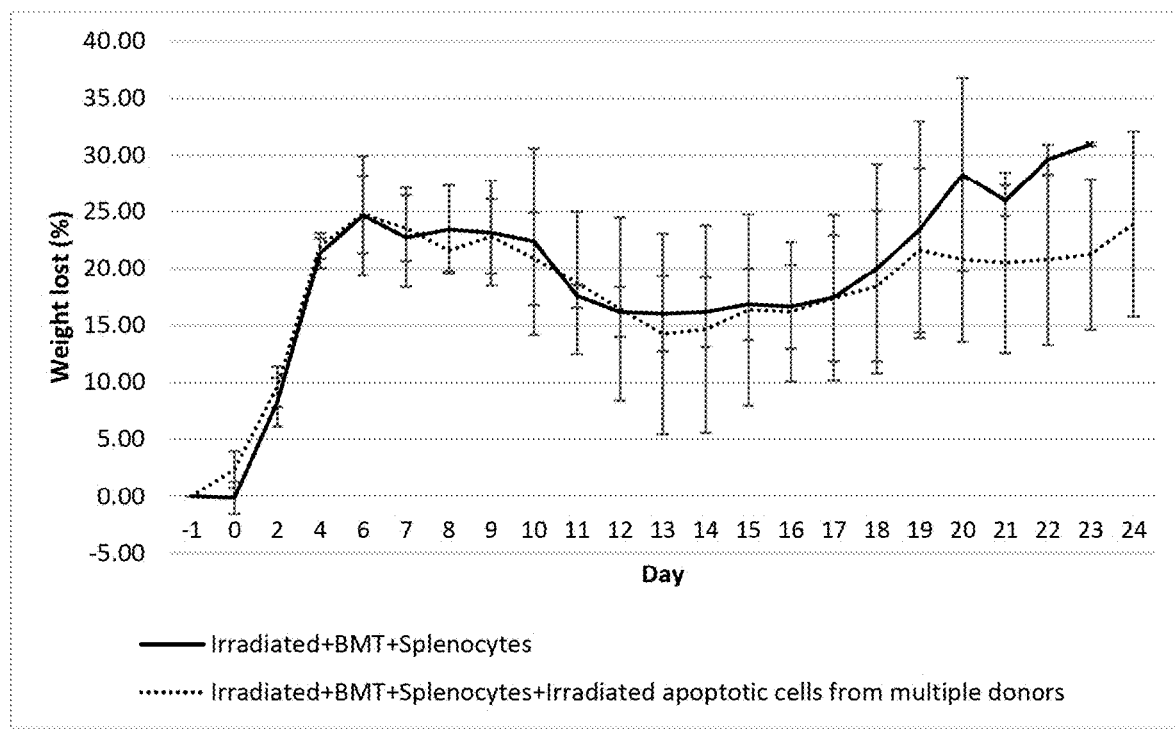
FIG. 29. Effect of Pooled ApoCell Preparation.

The two graphs presented in FIGS. 28 and 29, show the clear effect (p<0.01) of a single injection of apoptotic cell from multiple individual donors (dotted line), both on survival and weight loss. FIG. 28 is a Kaplan-Meier survival curve in a GvHD mouse model that was treated with a single dose irradiated apoptotic cells from multiple individual donors where survival was significantly ameliorated. FIG. 29 is percentage of weight loss of the 2 compared groups that follow and correlate with the findings of FIG. 28.

In summary, the single infusion of multiple-donor irradiated apoptotic cells successfully and significantly improved life expectancy in a mouse model of GvHD.

Example 13: Stability Criteria for Apoptotic Cells from Multiple Individual Donors The objective of this study is to develop stability criteria for apoptotic cells from multiple individual donors with comparability studies to non-irradiated HLA-matched apoptotic cells (Mevorach et al. (2014) Biology of Blood and Marrow Transplantation 20(1): 58-65; Mevorach et al. (2015) Biology of Blood and Marrow Transplantation 21(2): S339-S340).

Apoptotic cell final product preparations will be evaluated for cell number, viability, apoptotic phenotype and potency after storage at 2 to 8° C. for 8, 24, 48, and 60 hours with sampling at each time point. Apoptotic cell final product lots will be prepared following standard operating procedures (SOPs) (Example 1; Example 5) and batch records (BRs; i.e., specific manufacturing procedures). For potency evaluation, samples of early apoptotic cell preparation final product lots will be tested for inhibition of lipopolysaccharide (LPS) induced upregulation of MHC-II expression on immature dendritic cells (time points 0-24 h) or monocytes (time points 0-6) and will be performed according to SOPs and recorded on BR. These series of test will be performed on pooled and non-pooled products that are in preparations originating from multiple individual donors and from single donors, respectively.

In addition, flow cytometric analysis of CD3 (T cells), CD19 (B cells), CD14 (monocytes), $CD15^{high}$ (granulocytes) and CD56 (NK cells) will be documented. The aims of these studies are to demonstrate consistency with a narrow range of results. Preliminary results are consistent with these goals and no deviations from the SOP are noted and no technical problems are reported. However, further studies are needed in order to conclude the range and stability of effective treatment. Preliminary results show equivalence in all these parameters. Further, single donor stability studies showed stability at least through a 48 hour period (See, Example 1).

Example 14: Safety & Efficacy of Multiple Donor Irradiated Apoptotic Cells as Prophylaxis for Acute Graft-Versus-Host Disease Objective:

A phase 1/2a, multicenter, open-label study evaluating the safety, tolerability and preliminary efficacy of a single dose administration of irradiated apoptotic cells, from multi-, unmatched-donors, for the prevention of graft versus host disease in hematopoietic malignancies in human leukocyte antigen-matched, related and unrelated patients undergoing allogeneic hla-matched hematopoietic stem cell transplantation Primary Objective:

To determine safety and tolerability of multiple donor irradiated apoptotic cell treatment.

Secondary Objective:

To determine efficacy of irradiated apoptotic cells from multiple individual donors as prophylaxis measure for acute GVHD (aGVHD) in patients with hematopoietic malignancies scheduled to undergo hematopoietic stem cell transplantation (HSCT). For the purposes of this study, HSCT can be either bone marrow transplant (BMT) or peripheral blood stem cell transplantation (PBSCT).

Therapeutic Indication:

Graft vs. Host Disease (GVHD) post-transplantation in hematopoietic malignancies in human leukocyte antigen (HLA)-matched, related and unrelated patients Study Design:

This is an open labeled study, multi-center, phase-1/2a study in patients diagnosed with hematopoietic malignancies scheduled to undergo HSCT (either bone marrow transplantation or peripheral blood stem cell transplantation)

from an HLA-matched related or unrelated donor, following either full myeloablative or reduced intensity myeloablative conditioning regimens.

After a signing of informed consent by recipient patient, donors screening period and cell collection before initiating conditioning regimen, eligible recipient patients will be assigned (stratified by prophylactic treatment and related versus non-related transplant donors in 1:1 ratio to receive intravenous (IV) injection 12-36 hours prior to HSCT transplantation to either:

Investigational Arm:

single dose of $140 \times 10^6 \pm 20\%$ cell/kg from multiple individual donors of irradiated early apoptotic cells/kg body weight in phosphate buffer solution (PBS).

All patients will also be treated with the institutional standard of care (SOC) immunosuppressive regimen: cyclosporine/methotrexate or tacrolimus/methotrexate for full myeloablation and mycofenolate/cyclosporine or mycophenolate/tacrolinus for reduced intensity. Patients will be hospitalized as medically indicated.

Patients will be followed up for 180 days for the secondary efficacy endpoint and for 1 year for the primary safety and tertiary efficacy endpoints. Number of visits for patients participating in this study will be comparable to those customary for patients in their condition. For donor, study specific visit will be for apheresis procedure during the screening period.

As these patients have many underlying medical conditions and may experience symptoms compatible with aGVHD, it may be difficult to absolutely determine if toxicity is related to apoptotic cells or not although basic data exist from a former phase 1-2a study using apoptotic cells for GvHD prophylaxis (Mevorach et al. (2014) Biology of Blood and Marrow Transplantation 20(1): 58-65) Single Infusion of Donor Mononuclear Early Apoptotic Cells as Prophylaxis for Graft-versus-Host Disease in Myeloablative HLA-Matched Allogeneic Bone Marrow Transplantation: A Phase I/IIa Clinical Trial. BBMT 20(1)58-65).

Data Safety Monitoring Board (DSMB) will meet as specified in the DSMB charter, including at the time of the scheduled interim analysis (180 days) assuming no safety concerns were raised beforehand.

Study Procedures:

The study will comprise of screening, treatment and follow-up periods.

1. Screening Period (Day −60 to Day −2)

Potential recipient patients will sign informed consent prior to conduct of any study related procedures. The standard assessments before approval, will be performed by the transplantation center for the donor during the screening period and usually include: demographic data, medical history, HLA match status verification (no matching is needed), physical examination, height and weight, vital signs, pregnancy test (all women), hematology, blood chemistry, infectious disease screen, ECG and urinalysis.

The recipients (study patients) will undergo the following assessments during the screening period: demographic data, medical history, Karnofsky performance status, HLA match verification, physical exam, height and weight, vital signs, pregnancy test (all women), ECG, pulmonary function test, hematology, blood chemistry, coagulation markers, infectious disease screen, and urinalysis.

After the initial screening evaluations, if recipient is eligible to participate in the study, the recipient patient will be assigned on the first day of the conditioning regimen to receive single IV infusion of $140 \times 10^6 \pm 20\%$ cell/kg of multiple donor apoptotic cells. The conditioning regimen to be completed on the day before or day of Apoptotic Cell infusion scheduled for Study Day −1.

Apoptotic cell dosage will be calculated for each recipient patient and presumed apheresis collection number and number of donors will be decided accordingly.

For Peripheral Stem Cell Transplant Donors:

Between Days −6 to −1, the donor will receive one or more once daily injections of G-CSF to mobilize progenitor cells and on Day 0 will undergo apheresis to produce donor hematopoietic blood stem cells for transplantation. Preparation of the hematopoietic blood stem cells for bone marrow transplantation will be performed in accordance with the center's standard practice by trained hospital staff. The hematopoietic blood stem cells for HSCT will not be manipulated or T cell-depleted prior to administration.

For Bone Marrow Transplant Donors:

Bone marrow will harvested and prepared per center standard practice and will not be otherwise manipulated.

2. Treatment Day (Day −1)

On Day −1 (12-36 hours prior to HSCT), eligible patients will receive single IV infusion of either $140 \times 10^6 \pm 20\%$ cell/kg of multiple individual donors irradiated Early apoptotic Cells. Vital signs will be monitored every hour during infusion and every 4 hours for the first 24 hours afterwards. Treatment-related AEs will be assessed immediately following infusion.

On Day 0, patients will undergo hematopoietic stem cell transplantation according to local institution guidelines.

3. Short-Term Follow-Up Period (Day 0 to Day 180)

Patients will be followed-up to Study Day 180 for assessment of the primary endpoint safety and tolerability and secondary and tertiary endpoints: cumulative incidence of aGVHD grade II-IV ("modified Glucksberg" consensus based on Przepiorka et al cumulative incidence of any grade and high grade aGVHD, i.e., time to development of aGVHD, grades II-IV; any systemic treatment of GVHD, and the development of cGVHD.

The short term follow up visits will be daily while hospitalized for the transplantation (usually at least Days −1 to +14 or more) and weekly visits during the first 7 weeks after discharge; days +7, +14, +21. +28, +35, +42, and then on Days 60, 100, 140, and 180. The visit window will be ±5 days for each weekly visit (first 7 weeks) and ±5 days for biweekly or more visits during the subsequent follow up period up to 180 days.

Blood samples will be obtained on days 1, 3, 7, +7, +28, +42, 60, 100, 140 and 180 and examined for documentation of engraftment, immunological recovery, plasma and serum biomarkers ("Michigan") and cell subpopulations.

4. Long-Term Follow Up Period (Day 181 to Day 365/1 Year)

Patients will be followed for one year post-HSCT for the longer term secondary endpoints: non-relapse mortality and overall survival (OS), relapse incidence, leukemia free survival (LFS) and chronic GVHD. There will be at least two long-term follow-up visits, the last one being, 12±1 months following the HSCT.

Study Duration:

For each participating patient, the duration in the study will be up to 14 months as follows:

Screening Up to 60 days (2 months
Treatment 1 day
Follow-up 365 days (12 months) consisting of
Short-term: 180 days
Long-term +180 days Study Population:

A total of 25 patients diagnosed with hematologic malignancies scheduled to undergo HSCT (either bone marrow transplantation or peripheral blood stem cell transplantation), with at least 15 unrelated donors, following either myeloablative or reduced intensity conditioning regimens, per center standard practice will be included in this study and will be compared to historical controls.

Inclusion/Exclusion Criteria:

Recipient Patient Exclusion Criteria

1. Patients, Age >18, who are eligible for allogeneic HSCT for the following malignancies:

Acute myeloid or undifferentiated or biphenotypic, leukemia, in complete remission (any remission) or beyond but with <5% blasts by morphology in bone marrow.

Acute myeloid leukemia (AML) in complete remission if it has evolved from myelodysplastic syndrome (MDS) (there should be documented diagnosis of MDS at least 3 months prior to diagnosis of acute myeloid leukemia). Or evolved from polycythemia vera or essential thrombocytosis.

Acute lymphoblastic leukemia (ALL) in complete remission (any remission) with <5% blasts by morphology in bone marrow.

Chronic myeloid leukemia (CML) in chronic or accelerated phase

Myelodysplastic syndromes—refractory cytopenia with multilineage dysplasia (RCMD), RA (refractory anemia), RA with ringed sideroblast (RARS; all <5% blasts), RA with excess blasts (RAEB; 5 to 20% blasts).

The transplant donor and recipient patient must have at least an 8/8 HLA match at the HLA A, B, C, DQ, and DR loci and no antigen or allele mismatch. However the donor(s) of leukocytes for apoptotic cell formation is not restricted to HLA matching.

Performance status score of at least 70% at time of the screening visit (Karnofsky for adults and Lansky for recipient <16 years old.

Cardiac left ventricular ejection fraction ≥40% in adults within 4 weeks of initiation of conditioning; MUGA scan or cardiac ECHO required if prior anthracycline exposure or history of cardiac disease.

Pulmonary function test with DLCO$^1$, FEV1 (forced expiratory volume) and FVC (forced vital capacity) of ≥60% predicted.

$^1$Diffusing capacity of the lung for carbon monoxide

Oxygen saturation of at least 90% on room air.

Patients must have adequate organ function as defined below:

AST (SGOT)/ALT (SGPT)<3× upper limit of normal (ULN).

Serum creatinine <2.0 mg/dL (adults, >16 y) or <0.8 (1-2 y), <1(3-4 y), <1.2 (5-9 y), <1.6 (10-13 y), and 1.8 (14-15 y).

Serum bilirubin <3 mg/dL unless due to Gilbert's disease or hemolysis.

Signed written informed consent to participate in the study independently by patient, or guardian in the case of minors.

Ability to comply with the requirements of the study.

For duration of 4 weeks (from day −1), both female and male must agree to:

Use an acceptable method of birth control or be surgically sterile for the first month or more if there are BMT related restrictions.

To have a negative pregnancy test regardless of childbearing potential.

Recipient Patient Exclusion Criteria

All diseases eligible for HSCT not specified in the Inclusion Criteria.

Participation in an interventional investigational trial within 30 days of the screening visit.

Have progressive or poorly controlled malignancies.

If BMT plan include T-cell depleted allograft

If BMT plan include anti-thymocyte globulin (ATG) or alemtuzumab as part of immunosuppressive regimen or high dose Cyclophosphamide therapy for the prevention of GVHD after transplantation Uncontrolled infections including sepsis, pneumonia with hypoxemia, persistent bacteremia, or meningitis within two weeks of the screening visit.

Current known active acute or chronic infection with HBV or HCV.

Known human immunodeficiency virus (HIV) infection.

Patients with severe or symptomatic restrictive or obstructive lung disease or respiratory failure requiring ventilator support.

Patients with other concurrent severe and/or uncontrolled medical condition which could compromise participation in the study (i.e. active infection, uncontrolled diabetes, uncontrolled hypertension, congestive cardiac failure, unstable angina, ventricular arrhythmias, active ischemic heart disease, myocardial infarction within six months, chronic liver or renal disease, active upper gastrointestinal tract ulceration).

Any chronic or acute condition susceptible of interfering with the evaluation of investigational product effect.

Any form of substance abuse (including drug or alcohol abuse), psychiatric disorder or any chronic condition susceptible, in the opinion of the investigator, of interfering with the conduct of the study.

Organ allograft or previous history of stem cell transplantation (allogeneic only).

Breast feeding in women of childbearing potential.

Patients who are likely to be non-compliant or uncooperative during the study.

Investigational Product Route and Dosage Form

Apoptotic cells will be administered as an IV infusion of 140×10$^6$±20% cell/kg of irradiated multiple donor apoptotic cell product 12-36 hours prior to HSCT.

Apoptotic cells are a cell-based therapeutic composed of multiple individual donors apoptotic cells. The product contains allogeneic donor mononuclear enriched cells in the form of liquid suspension with at least 40% early apoptotic cells. The suspension is prepared from multiple individual donors with PBS solution in accordance with GMP regulations and should be stored at 2-8° C. until infusion. The final product will be in a total volume of 300-600 mL in an opaque transfer pack and will be irradiated with 25 Gy following preparation. Investigational product should be administered to the patient within 48 hours of completing the manufacturing process.

Safety Outcomes/Efficacy Endpoints/Outcome Measures
Primary:

Safety and tolerability endpoints include time to engraftment and a physical examination to determine adverse events, concomitant medications and safety laboratories on Day 180 and Day 360 (1 year). Further, it is expected that irradiated pooled apoptotic cell preparations will show a lack of in vitro and in vivo cell proliferation and lack of in vivo activation. Such a showing identifies the pooled apoptotic cell preparation as safe for use.

Secondary:

Cumulative incidence of aGVHD grade II-IV using "modified Glucksberg" consensus based on (Rowlings et al. 1997) IBMTR Severity Index for grading acute graft-versus-host disease: retrospective comparison with Glucksberg grade. Br J Haematol. 1997 June; 97(4):855-64) on Day 180

1-year non-relapse mortality and overall survival (OS)

1-year relapse incidence 1-year leukaemia free survival (LFS)

Maximum grade of aGVHD within the first 180 days

Cumulative incidence of grade III-IV aGVHD

Incidence of chronic GVHD according to (Jagasia et al., 2015) on Days 180 and 360 (1 year).

Any "systemic treatment" including corticosteroids (both used or not and cumulative dosage) for the treatment of aGvHD on Day 20 through Day 180

Immune reconstitution and function on Days +28, 100, 180 and 360 (1 year) in relation to T, B, NK, and Monocytes Major infection rate (including lung infiltrates, CMV reactivation and any other infections that require hospitalization) through Day 180 and 1 year.

Tertiary/Exploratory:

Percent of hospitalization days to total days at risk, or total days alive and out of the hospital. Or total hospitalization days till first discharge post transplantation.

Organ specific GVHD

T regs, CD4 Tcon, CD8, NK and B cells levels on Day 180

Statistical Analysis:

Study outcome will be compared to historical control with individuals with comparable baseline characteristics.

Descriptive statistics will be used to summarize outcome measures and baseline characteristics. In this analysis all available data will be presented with no imputation for any missing data. Subjects will contribute the data available up to the point of withdrawal or study completion or death. The descriptive statistics such as means, median, standard deviation, minimum and maximum will be used to summarize continuous variables. All subjects who receive the apoptotic cells infusion will be included in the safety analysis. Subjects who also receive the HSCT will be included in the efficacy analysis. As this study is exploratory in nature, ad hoc analyses are planned.

Sample Size Consideration

A total of 25 patients will be included at least 15 matched unrelated patients will be enrolled. Apoptotic cells (active will be given to all, stratifying on GVHD prophylaxis regimen, and related versus unrelated transplant donor.

Population Analysis Definition

All efficacy analyses will be conducted on the Intent-to-Treat (ITT) population and compared to adequate historical control. The safety population will be defined as all patients who receive a dose of study medication.

Statistical Methods

Patient, disease, and transplant characteristics will be described using frequencies and percentages or median (range) as appropriate.

Safety Analysis

Descriptive statistics will be used to summarize safety outcomes with focus on the AEs reported between study treatment infusion and HSCT procedure (24-30 hour window). No alterations in the conduct of the study will be initiated as a consequence of the DSMB review, including sample size adjustment. As such, no penalty adjustment in the overall Type I error as a consequence of the interim analysis will be required.

Secondary Endpoint Analysis

Grade II-IV aGVHD will be described using the cumulative incidence estimator with death prior to aGVHD as a competing event.

Neutrophil and platelet recovery, Grade III-IV aGVHD, chronic GVHD, infection, relapse, and transplant related mortality will be described using cumulative incidence with relapse as competing event for TRM and death as the competing event for all others. Overall survival and leukemia free survival will be described using the Kaplan-Meier estimator, and. The maximum grade of aGVHD within the first 180 days and the need for steroids at 180 days will be described using frequencies and percentages using the Mann-Whitney U-test and chi-square test respectively. Immune recovery of each cell subset and TREGs will be described at each time point using median and range Mann-Whitney tests.

Example 15: Comparison of Pooled Apoptotic Cell Preparation Vs. Single Donor Apoptotic Cell Preparation in GVHD Leukemia/Lymphoma Models Objective:

Compare the beneficial clinical effect of human early apoptotic cells obtained from a single donor on the severity of GvHD in a murine model of GvHD, to the clinical effect, if any, of human early apoptotic cells obtained from multiple individual donors on the severity of GvHD in the murine model of GvHD, wherein the multiple individual donors represented HLA-unmatched heterologous donors.

Example 12 above shows the beneficial effect of irradiated apoptotic cells pooled from multiple individual donors. The results shown in FIG. 28 and FIG. 29 were surprising as a skilled artisan may recognize that the multiple sources of unmatched cells may have increased the diversity of antigenicity of the cells, and thus would have expected a dramatic reduction in the clinical effect. Unexpectedly, the known, beneficial effect of early apoptotic cells on the reduction of GvHD severity, and therefore a prolongation of the number of days till mortality, was also alleviated by pooled unmatched early apoptotic cells (FIG. 28), which would purportedly have increased antigenicity due to the pooled multiple unmatched source cells.

An additional objective was to understand if there is a difference between the use of irradiated early apoptotic cells and non-irradiated apoptotic cells.

A skilled artisan would appreciate that unmatched, irradiated cells keep their antigenic profile as recognized by the APC mechanism and so by T-Cells of the host into which they have been infused. Accordingly, concerns when pooling heterologous unmatched populations of cells included cross-reactivity between the individual populations being pooled, mixed-cell lymphatic reactions of pooled populations, or T-cell immune reactions between pooled populations that could reduce or eliminate cells, or any combination thereof.

Methods

Mouse Model:

Female 7-9 week-old BALB/c mice (H-$2^d$) were used as recipients and female 8-9 week-old C57BL/6 mice (H-$2^b$) were used as donors in mismatched GVHD model. Recipients were total body irradiated at 850 cGy 24 hours before bone marrow and splenocyte transplantation. Donor bone-marrow cells were used for bone-marrow reconstitution. Bone marrow cells were extracted from the femoral and tibial bones with RPMI 1640. Red blood cells were lysed, then cells were washed and resuspended with PBS. Viability was assessed using trypan blue dye exclusion (>90% viability). Donor splenocytes were used for the induction of GVHD. Spleens were removed and homogenized and single cell suspension was obtained. Red blood cells were lysed and splenocytes were resuspended with PBS. At least 90% viable cells were assessed using trypan blue dye.

Early Apoptotic Cells:

Apoptotic cells were produced from mononuclear enriched cell fraction apheresis from healthy donors similar to Example 1. In brief:

Enriched fractions of mononuclear cells (MNCs) were obtained from healthy, eligible donors via leukapheresis procedure. Cells were collected via Spectra OPTIA® apheresis system from 12 liters of blood, in addition to 400-600 ml of autologous plasma. The estimated yield of the enriched mononuclear cell fraction from a donor was expected to be approximately $1.2$-$1.5 \times 10^{10}$ cells. Prior to leukapheresis procedure, donors are tested and confirmed negative to the below viral vectors:

1. Human Immunodeficiency virus (HIV), types 1 and 2;
2. Hepatitis B virus (HBV);
3. Hepatitis C virus (HCV);
4. Cytomegalovirus (CMV);
5. *Treponema pallidum* (syphilis);
6. Human T-lymphotropic virus (HTLV), types I and II Following cell collection, the cells were washed with RPMI and frozen as follows. The freezing formulation was composed of PlasmaLyte A for injection pH 7.4, 10% DMSO, 5% Human Serum Albumin and 5% Anticoagulant Citrate Dextrose solution inoculated with 10 U\ml heparin.

Freezing media was prepared in bags and the freezing procedure performed in a closed system under cGMP conditions.

Following leukapheresis procedure completion, enriched MNC fraction was washed with PlasmaLyte A and resuspended with ice-cold freezing media to a concentration of $50$-$65 \times 10^6$ cells\ml. Cells were then transferred to freezing bags, bags were transferred to pre-cooled aluminum cassettes and cassettes were transferred immediately to $-18$-($-25°$) C. for two hours.

Following the two hours, cassettes were transferred to $-80°$ C. for an additional 2 hours and then to long-term storage in liquid nitrogen ($>-135°$ C.).

Autologous plasma was divided to 50 gr aliquots. Plasma aliquots were transferred to $-80°$ C. for 2 hours and then to a long-term storage in $-18$-($-25°$) C.

For apoptosis induction cells were thawed and washed with pre-warmed RPMI1640 containing 10 mM Hepes buffer, 2 mM L-Glutamine and 5% Anticoagulant Citrate Dextrose solution inoculated with 10 U\ml heparin. After supernatant extraction cells were resuspended at final concentration of $5 \times 10^6$/ml in RPMI 1640 supplemented with 10 mM Hepes, 2 mM L-glutamine, with addition of 10% autologous plasma and. 50 µg\ml Methylprednisolone and 5% Anticoagulant Citrate Dextrose solution inoculated with 10 U\ml heparin. Cells are then transferred to cell culture bags, and incubated at humidified incubator 37° C., 5% $CO_2$ for 6 hours to stabilize apoptosis.

Following incubation cells were harvested, washed with PBS and resuspended in PBS.

Early apoptotic cell product was produced from one single donor or combined 10 different individual donors, in which case cells were combined just prior to irradiation. Since interference may occur between components in the multiple donor product, for example between living non-apoptotic cells, the early apoptotic cell product was subdivided and a sample of early apoptotic cells to be tested in vivo was irradiated with 2500 cGy prior to administration (sample F below), and stored at 2-8° C. until administration. Table 3 of Example 6 below presents details of the Annexin V positive/Propidium iodide negative ratio and cell surface markers of the early apoptotic cell product, establishing that consistency of apoptotic cells administered to mice is maintained. The final product was stable for 48 hours at 2-8° C.

On the day of transplantation, mice received $5 \times 10^6$ bone-marrow cells, $3 \times 10^6$ splenocytes and $30 \times 10^6$ single- or multiple-donor early apoptotic cell product, according to the following experimental design:

Irradiation Control
Reconstitution control –irradiation+Bone-Marrow transplantation (BM)
GVHD control–irradiation+Bone-Marrow and splenocyte transplantation
Single donor, irradiated–irradiation+Bone-Marrow and splenocyte transplantation+irradiated early apoptotic cell product from single donor
Single donor, non-irradiated–irradiation+Bone-Marrow and splenocyte transplantation+non-irradiated early apoptotic cell product from single donor
Multiple donor, irradiated–irradiation+Bone-Marrow and splenocyte transplantation+irradiated early apoptotic cell product from multiple donor
Multiple donor, non-irradiated–irradiation+Bone-Marrow and splenocyte transplantation+non-irradiated early apoptotic cell product from multiple individual donors.

Monitoring—Transplanted mice were tagged and survival was monitored. Body weight was assessed every two days for the first two weeks of the experiment and then every day. Loss of 35% from initial body weight was determined as primary end point and mice were sacrificed and survival curve was updated accordingly. Body weight results were comparable to those observed in Example 12 FIG. 29.

The severity of GVHD was assessed using a known scoring system (Cooke K R, et al. An experimental model of idiopathic pneumonia syndrome after bone marrow transplantation. I. The roles of minor H antigens and endotoxin. Blood. 1996; 8:3230-3239) that incorporates five clinical parameters: weight loss, posture (hunching), activity, fur texture and skin integrity. Mice were evaluated and graded from 0 to 2 for each criterion. By summation of the five clinical scores a clinical index value was generated (index number increases with the severity of GVHD).

Results

Figure 30:
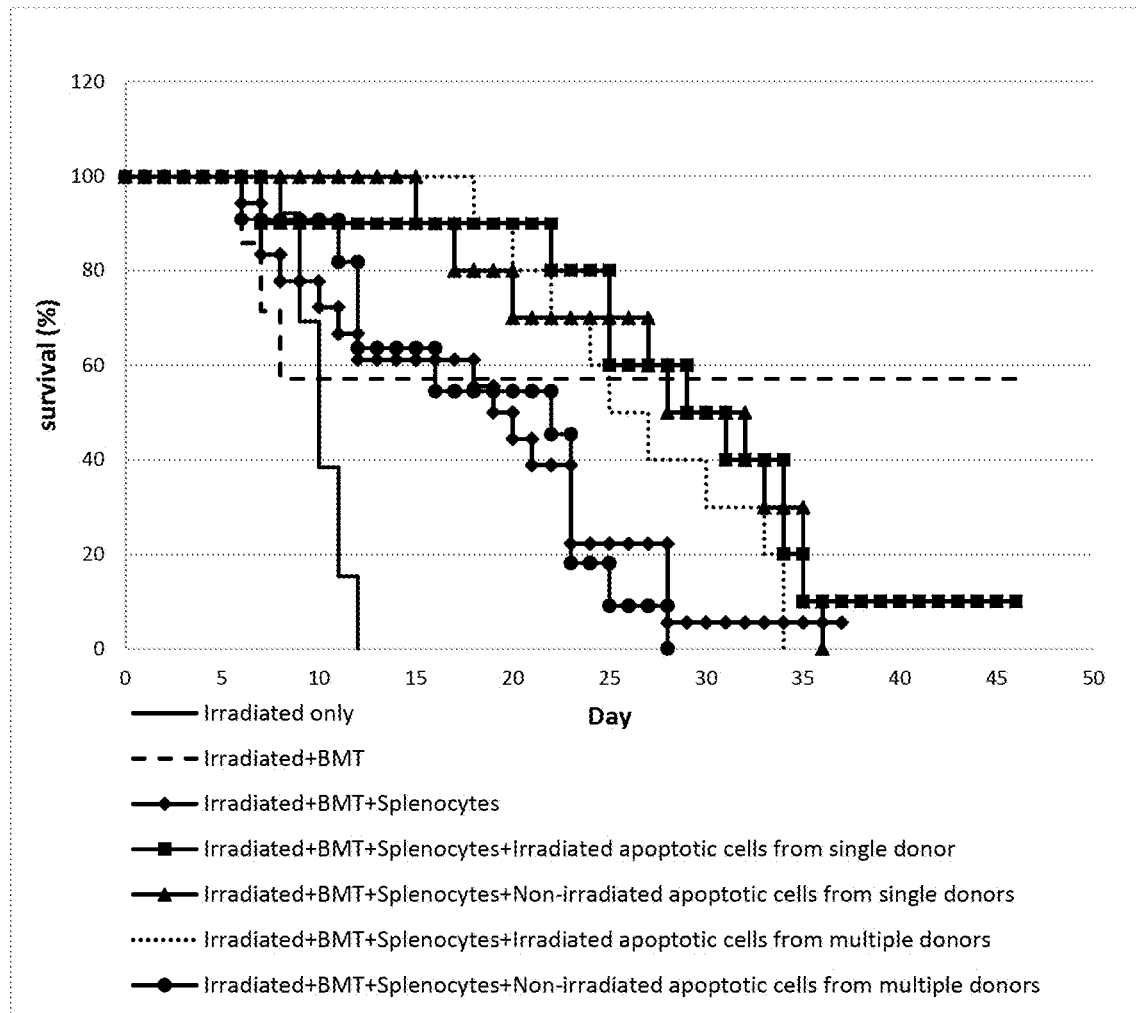
FIG. 30. Comparison of Single Donor versus Pooled ApoCell Preparation.

Percent survival of the different population of mice is presented graphically in FIG. 30. The irradiation only control mice died between day 8 and 12 (n=13), as expected from mice that did not receive bone marrow reconstitution. The majority of GVHD control mice (received bone-marrow and spleen) died between day 6 and 27. One mouse did not die (n=18). In bone-marrow reconstitution control group (BM) 3 out of 7 mice died between day 6 and 8. In the remaining mice, bone marrow was reconstituted by donor bone-marrow and mice remained alive (>50 days).

Single donor, non-irradiated mice died between day 15 and 36. Thus, as previously shown, single donor non-irradiated early apoptotic cells had a beneficial effect and survival was prolonged (p<0.01).

Single donor, irradiated mice died between day 7 and 35, one mouse remained disease free survival (>50 days). This demonstrated that single donor irradiated apoptotic cells also provided the beneficial effect with respect to GVHD. Thus, irradiation did not harm the immunomodulatory effect of early apoptotic cells. All had beneficial effect on survival in the GVHD murine model compared to GVHD control (p<0.01).

Non-irradiated multiple donor treatment did not provide a beneficial effect compared to GVHD control (n=11). Survival pattern was similar to GVHD control and mice died between day 6 and 28 (p=NS—not significant). Surprisingly and in contrast to the non-irradiated apoptotic cells, irradiated-multiple individual donor apoptotic cells (treatment F) (n=10) had a beneficial effect similar to single donor treatment, as compared with GVHD control. GVHD symptoms appeared significantly later and mice died between day 18 and 34 (p<0.01).

Irradiated-multiple individual donor (n=10), irradiated single donor (n=10) and non-irradiated single donor treatment (n=10) had similar survival patterns and no significant difference in effect on survival was observed between these three treatment groups.

The experiments indicated a clear effect of apoptotic cells infusion in GVHD induced mice. There was a significant prolonged survival effect for the treatments of irradiated multiple individual donors and irradiated- and non-irradiated single donor apoptotic cells.

Multiple donor treatment did not prolonged survival of mice when not irradiated but the irradiation of the apoptotic cell product prior to administration to mice improved results and treatment had close survival pattern as single-donor treatments.

As stated above, FIG. 30 shows, non-irradiated apoptotic cells obtained from multiple unmatched donors have significantly lower positive clinical effect on reduction in GvHD and mortality (% survival), as compared to (1) non-irradiated apoptotic cells obtained from single unmatched donors; (2) irradiated apoptotic cells obtained from single unmatched donors; and (3) irradiated apoptotic cells obtained from multiple unmatched donors. In addition, all three (non-irradiated early apoptotic cells, single donor; irradiated early apoptotic cells, single donor; and irradiated early apoptotic cells, multiple individual donors) have similar effects.

This data was surprising since the antigenicity of the non-irradiated apoptotic cells obtained from multiple individual donors was expected to be similar to that of irradiated apoptotic cells obtained from multiple individual donors, why would not both have similar hostile antigenic reaction with the implanted bone marrow, and why would both not be able to reduce GvHD and mortality rate?

If antigenicity is the main issue here, it was expected to see differences between the clinical effects of non-irradiated apoptotic cells obtained from single donor and irradiated apoptotic cells obtained from single donor. However the data does not show this difference.

One possibility is that the lack of efficacy of non-irradiated pooled apoptotic cell preparations prepared from multiple individual donors, resulted from cross-interaction between the individual mononuclear populations present in the pooled preparation. These interactions do not appear to be directly attributable to antigenicity towards the host, as irradiated cells maintain their antigenicity but the efficacy differed significantly from non-irradiated cells. Therefore, it appears that the cross-interaction in the pooled early apoptotic cell preparations receiving irradiation was unexpectedly eliminated and the host responded well to administration of the cells.

As shown, irradiated pooled donors had essentially the same effect as a single non irradiated donor.

Example 16: Effect of Irradiation on Final Apoptotic Cell Product

Apoptotic cells are increasingly used in novel therapeutic strategies because of their intrinsic immunomodulatory and anti-inflammatory properties. Early apoptotic cell preparations may contain as much as 20-40% viable cells (as measured by lack of PS exposure and no PI admission; Annexin V negative and Propidium iodide negative) of which some may be rendered apoptotic after use in a transfusion but some will remain viable. In the case of bone marrow transplantation from a matched donor, the viable cells do not represent a clinical issue as the recipient is already receiving many more viable cells in the actual transplant. However, in the case of a third party transfusion, (or fourth party or more as may be represented in a pooled mononuclear apoptotic cell preparation) use of an apoptotic cell population that includes viable cells may introduce a second GvHD inducer. Furthermore, the implication of irradiation on the immunomodulatory potential of early apoptotic cells has so far been not assessed. A skilled artisan may consider that additional irradiation of an early apoptotic cell population may lead cells to progress into later stages of apoptosis or necrosis. As this appears a particularly relevant question with regard to clinical applications, the experiments presented below were designed to address this issue, with at least one goal being to improve the biosafety of functional apoptotic cells.

Thus, the aim was to facilitate the clinical utilization of apoptotic cells for many indications wherein the potency of apoptotic cells may rely on a bystander effect rather than engraftment of the transplanted cells.

Objective:

Examine the effect of irradiation on early apoptotic cells, wherein irradiation occurs following induction of apoptosis.

Methods (in Brief):

The cells were collected according and early apoptotic cells were prepared essentially as described in Example 5.

Three separate early apoptotic cell batches were prepared on different dates (collections 404-1, 0044-1 and 0043-1).

Each final product was divided into three groups:

Untreated
2500 rad
4000 rad.

Following irradiation, early apoptotic cells were tested immediately (to) for cell count, AnnexinV positive-PI negative staining, cell surface markers (% population of different cell types) and potency (dendritic cells (DCs)). Following examination at to, early apoptotic cells were stored at 2-8° C. for 24 hours, and examined the next day using the same test panel ($t_{24\,h}$) (cell count, Annexin V positive-PI negative staining, and cell surface markers and potency).

Previously, a post-release potency assay was developed, which assesses the ability of donor mononuclear early apoptotic cells (Early apoptotic Cells) to induce tolerance (Mevorach et al, BBMT 2014 ibid). The assay is based on using flow cytometric evaluation of MHC-class II molecules (HLA-DR) and costimulatory molecule (CD86) expression on iDC membranes after exposure to LPS. As previously and repeatedly shown, tolerogenic DCs can be generated upon interaction with apoptotic cells (Verbovetsky et al., J Exp Med 2002, Krispin et al., Blood 2006), and inhibition of maturation of LPS-treated DCs (inhibition of DR and CD86 expression), occurs in a dose dependent manner During phase 1/2a of the early apoptotic cell clinical study, the post-release potency assay was conducted for each early apoptotic cell batch (overall results n=13) in order to evaluate the ability of each batch to induce tolerance (Results are shown in FIG. 1, Mevorach et al. (2014) Biology of Blood and Marrow Transplantation 20(1): 58-65).

DCs were generated for each early apoptotic cell batch from fresh buffy coat, collected from an unknown and unrelated healthy donor, and were combined with early apoptotic cells at different ratios (1:2, 1:4 and 1:8 DC:Early apoptotic Cells, respectively). After incubation with early apoptotic cells and exposure to LPS, potency was determined based on downregulation of DC membrane expression of either HLA DR or CD86 at one or more ratios of DC: early apoptotic cells. In all 13 assays, early apoptotic cells demonstrated a tolerogenic effect, which was seen with preparations at most DC: early apoptotic cells ratios, and for both markers, in a dose dependent manner Monocyte obtained immature DCs (iDCs) were generated from peripheral blood PBMCs of healthy donors and cultured in the presence of 1% autologous plasma, G-CSF and IL-4. iDCs were then pre-incubated for 2 hours at 1:2, 1:4 and 1:8 ratios with apoptotic cells either freshly prepared final product or final product stored at 2-8° C. for 24 hours. The two final products were examined simultaneously in order to determine whether storage affects potency ability of apoptotic cells. Following incubation, LPS was added to designated wells were left for additional 24 hours. At the end of incubation, iDCS were collected, washed and stained with both DC-sign and HLA-DR or CD86 in order to determine changes in expression. Cells were analyzed using flow cytometer and analysis performed using FCS-express software from DC-sign positive cells gate to assure analysis on DCs only.

FIGS. 31A and 31B and FIGS. 32A and 32B show potency test of irradiated pooled apoptotic cells compared to non-irradiated single donor cell.

Results:

Single Donor Preparations

Table 21 presents the comparative results of non-radiated and irradiated apoptotic cells; Average cell loss (%) at 24 hours; Annexin positive ($^+$) Propidium Iodide (PI) negative ($^-$)% at 0 hours and 24 hrs (% of early apoptotic cells; Annexin positive ($^+$) Propidium Iodide (PI) positive ($^+$) % at 0 hours and 24 hrs (% of late apoptotic cells); presence of cell surface antigens CD3 (T cells), CD19 (B cells), CD56 (NK cells), CD14 (monocytes), and CD15$^{high}$ (granulocyte), at 0 hours and 24 hours.

TABLE 21

| Final product description | Apoptotic Cell | Apoptotic Cell 2500 rad | Apoptotic Cell 4000 rad |
|---|---|---|---|
| An$^+$PI$^-$ t$_0$ (%) | 59.2 | 59.6 | 58.4 |
| Range (min-max) | (52.6-66.1) | (51.6-68.7) | (50.4-65.1) |
| An$^+$PI$^-$ t$_{24h}$ (%) | 62.6 | 68.1 | 66.7 |
| Range (min-max) | (53.6-76.3) | (52.0-81.3) | (52.9-77.1) |
| An$^+$PI$^+$ t$_0$ (%) | 4.9 | 6.0 | 6.1 |
| Range (min-max) | (3.2-7.0) | (5.2-7.4) | (4.0-9.1) |
| An$^+$PI$^+$ t$_{24h}$ (%) | 7.3 | 8.6 | 9.0 |
| Range (min-max) | (5.0-11.8) | (6.4-11.8) | (6.0-14.9) |
| CD3+ t$_0$ (%) | 56.9 | 58.3 | 57.5 |
| Range (min-max) | (47.4-66.3) | (48.8-67.7) | (48.6-66.4) |
| CD3+ t$_{24h}$ (%) | 56.8 | 57.1 | 56.6 |
| Range (min-max) | (49.6-64.0) | (48.0-66.1) | (49.7-63.4) |
| CD19+ t$_0$ (%) | 10.6 | 9.5 | 9.6 |
| Range (min-max) | (10.1-11.0) | (7.7-11.3) | (8.5-10.7) |
| CD19+ t$_{24h}$ (%) | 11.8 | 9.2 | 8.8 |
| Range (min-max) | (10.2-13.4) | (6.9-11.5) | (7.5-10.1) |
| CD56+ t$_0$ (%) | 12.2 | 13.0 | 14.4 |
| Range (min-max) | (7.0-17.3) | (7.6-18.4) | (21.2-7.6) |
| CD56+ t$_{24h}$ (%) | 12.9 | 14.1 | 17.1 |
| Range (min-max) | (8.8-13.4) | (10.4-17.8) | (10.0-24.1) |
| CD14+ t$_0$ (%) | 23.1 | 25.2 | 24.6 |
| Range (min-max) | (13.1-33.1) | (13.8-36.5) | (14.0-35.2) |
| CD14+ t$_{24h}$ (%) | 21.9 | 23.7 | 24.4 |
| Range (min-max) | (13.8-30.0) | (13.8-33.6) | (15.4-33.4) |
| CD15$^{high}$ t$_0$ (%) | 0.0 | 0.0 | 0.01 |
| Range (min-max) | | | |
| CD15$^{high}$ t$_{24h}$ (%) | 0.0 | 0.0 | 0.01 |
| Range (min-max) | | | (0.0-0.02) |

The results in Table 21 show that both non-irradiated apoptotic cells and irradiated apoptotic cells had comparable percentages of early (rows 2 and 3) and late (rows 4 and 5) apoptotic cells. Thus, 25 or 40 Gy irradiation did not accelerate the apoptotic or necrotic process induced prior to this high level of gamma-irradiation. Further, there was consistency between irradiated cell populations vs. control non-irradiated population with regard to cell type.

Figures 31A, 31B:
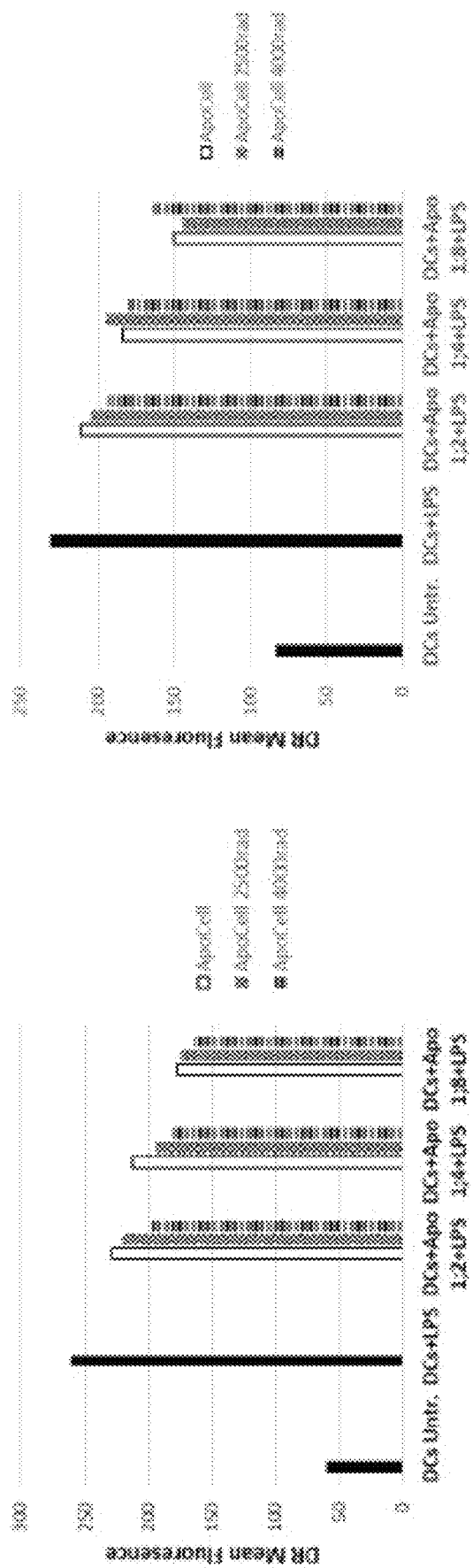
FIGS. 31A-31B. Potency Test.
Figures 32A, 32B:
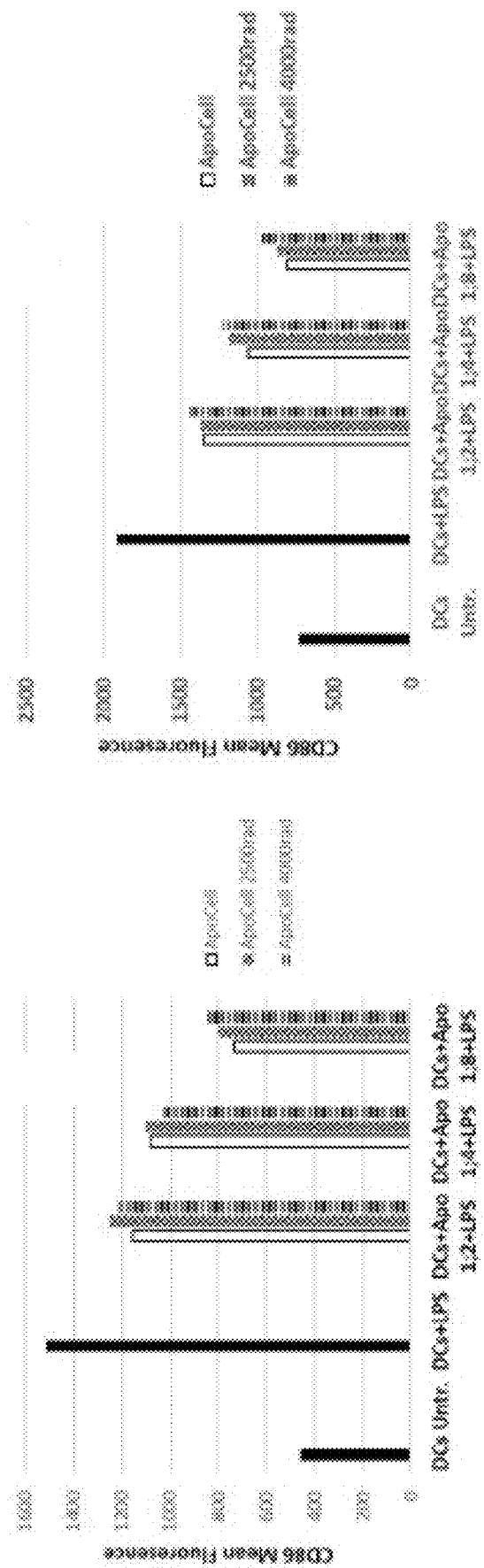
FIGS. 32A-32B. Potency Test.

The results of potency assays, presented in FIGS. 31A-31B (HLA-DR expression) and FIGS. 32A-32B (CD86 expression) show that there was no change in the immune modulatory capacity of fresh (FIG. 32A, FIG. 32A) and 24 hour-stored (FIG. 31B and FIG. 32B) irradiate apoptotic cells when compared with non-irradiated apoptotic cells.

In both FIGS. 31A-31B and FIGS. 32A-32B there is a clear upregulation in both HLA-DR and CD86 expression, following exposure to maturation agent LPS. Significant (p<0.01), dose-dependent down regulation of both co-stimulatory markers was observed in the presence of freshly prepared apoptotic cells both from a single donor or irradiated pooled donors. In addition, dose dependent down regulation was maintained in both markers in the presence of apoptotic cells stored at 2-8° C. for 24 hours, indicating final product stability and potency following 24 hours of storage.

Effect on dendritic cells, In order to test the immunomodulatory capacity of apoptotic cells a post release potency assay was used (Mevorach et al., (2014) BBMT, ibid). No change in immune modulatory assay in dendritic cells was observed. (Data not shown)

Effect on Mixed Lymphocyte Reaction (MLR).

In order to further test the immunomodulatory effect a standardized MLR assay was established. Here, co-cultivation of stimulator and responder cells, i.e. a MLR, yielded strong and reliable proliferation. Upon addition of non-irradiated apoptotic cells to the MLR, the lymphocyte proliferation was significantly reduced by >5-fold, clearly demonstrating cell inhibition of proliferation. Inhibition of lymphocyte proliferation in MLRs mediated by irradiated apoptotic cells was completely comparable. (Data not shown)

The next step was to evaluate in vivo, irradiated and non-irradiated apoptotic cells in a completely mismatched mouse model. As shown in FIGS. 28 and 29, irradiated and non-irradiated early apoptotic cell preparations had comparable in vivo beneficial effect.

Single Donor Preparations Conclusion:

In conclusion, irradiation of 25 Gy or 40 Gy did not significantly accelerate apoptosis or induced necrosis in populations of apoptotic cells. Significantly, these populations maintained the immunomodulatory effect of apoptotic cells both in vitro and in vivo.

Multiple Donor Preparations

Next, experiments were performed to verify that the phenomenon observed with single donor, third party preparation was also true for multiple third party donors. Unexpectedly, when using pooled individual donor apoptotic cell preparations, the beneficial effect of a single unmatched donor was lost (FIG. 30). This was not due to GvHD, as the beneficial effect of each donor separately was maintained (test results no shown). One possibility is that the beneficial effect of the early apoptotic cell preparation was lost due to the interaction of the individual donor cells among themselves. It was further examined whether this possible interaction of different donors could be avoided by gamma irradiation.

As shown in FIG. 30, the beneficial effect of a single donor was completely restored following gamma irradiation, wherein the irradiated multiple donor preparation and the single donor preparation (irradiated or non-irradiated) had similar survival patterns.

Conclusion:

It is shown here for the first time that surprisingly irradiation (and possibly any method leading to T-cell Receptor inhibition) not only avoided unwanted proliferation and activation of T-cells but also allowed for the beneficial effects of immune modulation when using a preparation of multiple donor third party apoptotic cells.

Example 17: Effect of Combined Apoptotic Cell and CAR-T Cell Treatment on a Solid Tumor Model Objective:

To test the effect of CAR-T cell therapy on a human peritoneal solid tumor model and evaluate any possible synergistic effect of apoptotic cell infusion on the CAR T-cell therapy anti-cancer action.

Methods

HeLa-CD19 Cell Line:

CD19-expressing HeLa cells were purchased from ProMab (ProMab, USA, cat. No. PM-Hela-CD19). In order to follow tumor growth in vivo, HeLa-CD19 were stably transduced with pLenti-PGK-VS-Luc-Neo (Addgene, USA, plasmid #21471) and single clones were isolated by flow cytometry cell sorter and cultured with 500 μg/ml G418 (Sigma-Aldrich, USA, cat. no. A1720-1G) as a selective agent. This cell line stably and continuously expresses the firefly luc gene under the PGK promoter. Genomic integration was verified by PCR and expression verified by flow cytometry and bioluminescent imaging (BLI) of the positive clones.

Cells were cultured in RPMI 1640 (Gibco, ThermoFisher Scientific, USA, cat. no. 31870-025) supplemented with 10% FBS (Gibco, ThermoFisher Scientific, South America, cat. no. 12657-029), 2 mM GlutaMAX (Gibco, ThermoFisher Scientific, USA, cat. no. 35050-038), and 100 U/ml Penicillin+100 U/ml Streptomycin (Gibco, ThermoFisher Scientific, USA, cat. no. 15140-122), referred to as "complete medium". HeLa-CD19 medium was further supplemented with 1 μg/ml puromycin (Sigma-Aldrich, USA, cat. no. P9620), as the selective antibiotics, during standard culturing.

For bioluminescent imaging, mice were injected i.p. with 150 mg/kg XenoLight D-luciferin (PerkinElmer, USA, cat. no. 122799) and anesthetized with 4% isoflurane. Ten minutes after injections, bioluminescence was captured using Caliper IVIS-Kinetics (PerkinElmer, USA) and Living Image software, v4.2 (PerkinElmer, USA).

CD19-Car-T Cells:

Fresh mononuclear cells (MNCs) fraction were isolated from the peripheral blood of healthy donors using Ficoll gradient. Cells were then gradually frozen and stored in liquid nitrogen until use. Following thawing, the cells were washed, and introduced with CD28+CD3+ beads (Miltenyi biotech) loaded per manufacturer instructions in a 1:2 bead: cell ratio, respectively. Cells were then incubated for 3 days in the presence of 300 U\ml recombinant human IL-2 (rhIL-2, Peprotech). 48 hours prior to MNCs infection, 293 Lenti-X cells (Clontech-Takara, 632180) were transfected with a $3^{rd}$ generation CD19-CAR plasmids (Creative Biolabs) using JetPrime reagent (Polyplus, 114-01) at 2:1 JetPrime: DNA ratio. 24 hours prior to infection, non-treated 24-well plates (SPL, BN30006) were coated with 7.5 ug\cm$^2$ of Retronectin (Takara-Clontech, T100A) according to manufacturer instructions. On the day of infection, virus-containing supernatant collected from the transfected 293 Lenti-X cells was filtered using 0.45 um filter (Millipore), transferred to the Retronectin-coated plates (0.75 ml of viral supernatant per well), and centrifuged according to manufacturer instructions. Activated T-cells were then added to the plates ($0.5 \times 10^6$ cells per well) and centrifuged as well at 290 g. Plates were then incubated for 60 hours in a humidified incubator. Following incubation, the cells were collected, residual adherent cells were detached using trypsin. Cells were washed twice with Hank's balanced salt solution (HBSS, Biological industries) supplemented with 2.5% Hepes buffer (Lonza). Cells were re-seeded in the presence of 300 U\ml rhIL-2, and diluted to a concentration of $1.0 \times 10^6$ every 48 hours with fresh media containing 300 U\ml rhIL-2. On day 12 following infection, cells were again activated with CD28+CD3+ beads in a 1:2 bead: cell ratio, respectively. Cells were incubated for additional two days, and then injected (in RPMI) to animals on day 14 following infection, a total of $10 \times 10^6$ cells per animal Mock-T cells (Mock-T) were prepared as the CAR-T cells with plasmid lacking the anti-CD19 region and injected as control. PCR and EGFR (Erbitux, Merck) expression were used for transduction efficacy. An in vitro cytotoxicity assay was used for functional test of CAR T cells.

Apoptotic Cells:

Enriched mononuclear cell fraction was collected via leukapheresis procedure from healthy, eligible human donors and prepared by as provided herein in Example 1 and gamma irradiated apoptotic cells, as produced herein (2000-6000 rad irradiation). The irradiated apoptotic cells used in this example are considered "over the shelf" (OTS), wherein the donor and recipient would not necessarily be HLA matched. In some embodiments, for methods of use herein, donor and recipient are not HLA matched. In some embodiments, for methods of use herein, donor and recipient are HLA matched. [Apoptosis and viability of apoptotic cells were determined using AnnexinV and PI staining (MBL, MA, USA), as described herein. Lack of proliferation was shown using Carboxyfluorescein succinimidyl ester (CFSE) staining and bead stimulation.

CFSE Staining:

Cells were brought to final concentration of $10 \times 10^6$ cells/mL with RPMI1640 and stained with 5 μM CFSE for 10 minutes at room temperature (RT) and protected from light with gentle tilting. Following incubation end time, staining reaction stopped with complete FBS for 1 minute. Cells were then washed twice in order to remove excess CFSE dye.

Cell Seeding:

Cells were brought to concentration of $1 \times 10^6$ cells/mL with culture media (RPMI1640 and Biotarget, supplemented with 2 mM L-Glutamine, 10 mM Hepes, 10% Heat inactivated FBS and 100 U/mL recombinant human IL-2). Cells were then seeded in 24 wells plates, 1 mL per well, either with or without CD3+CD28+ loading beads at 1:3 cell: beads ratio. Plates were incubated in an incubator (Enlivex Equipment number ENX01051) in the presence of 5% $CO_2$.

Sample Analysis:

Every 48 hours, each preparation was sampled, counted and analyzed via flow cytometer in order to access cell number and CFSE staining Preparations exceeded concentration of $1.5 \times 10^6$ cells/mL were diluted to $1 \times 10^6$ cells/mL with culture media. Preparations that did not exceeded $1.5 \times 10^6$ cells/mL were treated with culture media refreshment (0.3 mL of media was discarded and fresh culture media was added). Overall 4 testing points were performed throughout 8 days.

FACS Analysis of Subpopulations:

Peritoneal cells were evaluated by flow-cytometry (LSR-II, BD) for the following markers and isotype controls: mMHC-II-PE (12-5321), mCD19-FITC (11-0193), mCD11c-PE-Cy5.5 (35-0114), mF4/80-eFlour450 (48-4801), mCD11b-APC-eFlour780 (47-0112), rIgG2b-PE (12-4031), rIgG2 a-FITC (11-4321), Armenian-hamster IgG-PE-Cy5.5 (35-4888), rIgG2a-eFlour450 (48-4801), rIgG2b-APC-eFlour780 (47-4031), hCD19-APC (17-0198) and mIgG1-APC (17-4714) (eBiosciences).

Macrophages sub-population characterization was performed according to Ghosn et al. (PNAS 2010) Feb. 9, 2010. 107 (6) 2568-2573 and Casado et al. (PlosOne 2011) published Jul. 22, 2011. Briefly, non-CD19, non CD11c peritoneal cells were divided by their CD11b and F4/80 expression to Large Peritoneal Macrophages (LPM)—F4/80$^{high}$CD11b$^{pos}$, Small Peritoneal Macrophages (SPM)—F4/80$^{low}$CD11b$^{pos}$, and Granulocytes (Gra)—F4/80$^{low}$CD11b$^{neg}$ (Ghosn et al (2010 ibid). Casado et al. (2011 ibid) described the same macrophages sub-population slightly differently—non CD19, non CD11c, F4/80 positive cells were divided by their MHC-II and F4/80 expression to LPM—F4/80$^{high}$MHC-II$^{neg}$, SPM-F4/80$^{low}$MHC-II$^{pos}$, Gra-F4/80$^{low}$MHC-II$^{neg}$. Single-cell analyses of Tim4, MerTK, F4/80, CD11b, CCR2, Ly6c, CD206, CD64, C169, and CD74 were confirmed by FACS analysis. Resident peritoneal macrophages were identified based on expression levels of cell surface F4/80, CD11b, Tim4, and MerTK. Infiltrating macrophages were identified based on expression of cell surface CCR2, Ly6c, CD206, CD64, CD169, and CD74.

Luminex® Cytokine Analysis:

Human or mice cytokines were tested by Luminex cytokine analysis. Custom Multiplex kits were purchased from eBioscience (Vienna, Austria) or from R&D Systems (Minneapolis, USA).

For intra-peritoneal solid tumor model, SCID-Bg mice were injected intra-peritoneally (i.p) with 2 consecutive doses of $0.25 \times 10^6$ human HeLa-CD19-luciferase cells, on days 1 and 2 of the experiment. Mice also received $10 \times 10^6$ human apoptotic cells (irradiated as described above, 2000-6000 rad irradiation) or vehicle, on day 9; and $10 \times 10^6$ CD19-CAR-T (third generation) cells or mock T cells on day 10. Mice were weighted twice a week and monitored daily for clinical signs and peritoneal fluid accumulations. In some experiments, pre-scheduled sacrifices were performed to characterize cell and macrophage sub-population profile. The rest of the mice were kept for survival analysis. Survival endpoint was defined by a score based on severe peritoneal fluid accumulation manifested as enlarged and tense abdomen, and reduced mobility or increased respiratory effort. These clinical findings correlated to large accumulation of HeLa cells in the peritoneum. Survival analysis was performed according to the Kaplan-Meier Log rank statistical test.

Figure 33:
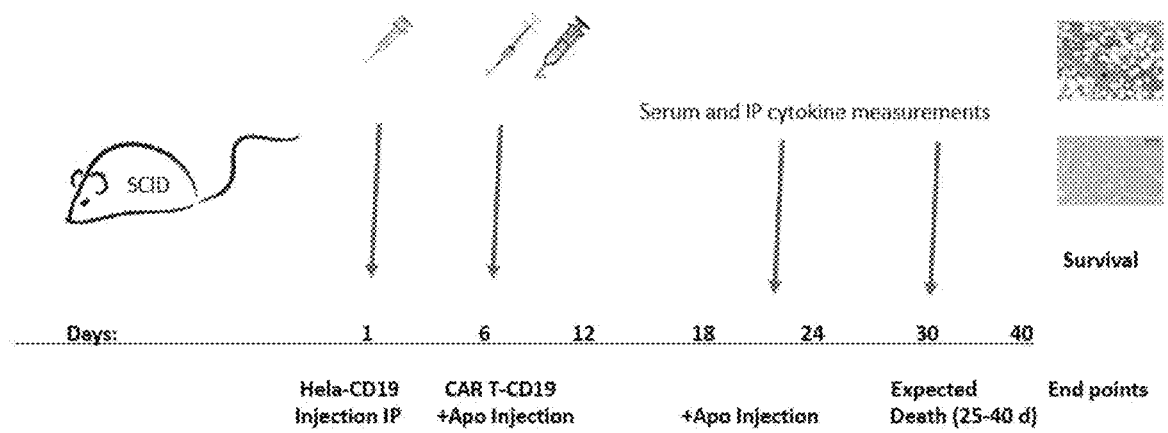
FIG. 33. Schematic of Example 17 experiment scheme showing the general flow of treatment of a solid tumor by CAR T-CD19 and ApoCell administration, and the cell pathology at the end point.

Treatment:

FIG. 33 presents an experimental scheme.

Results

Figure 34A:
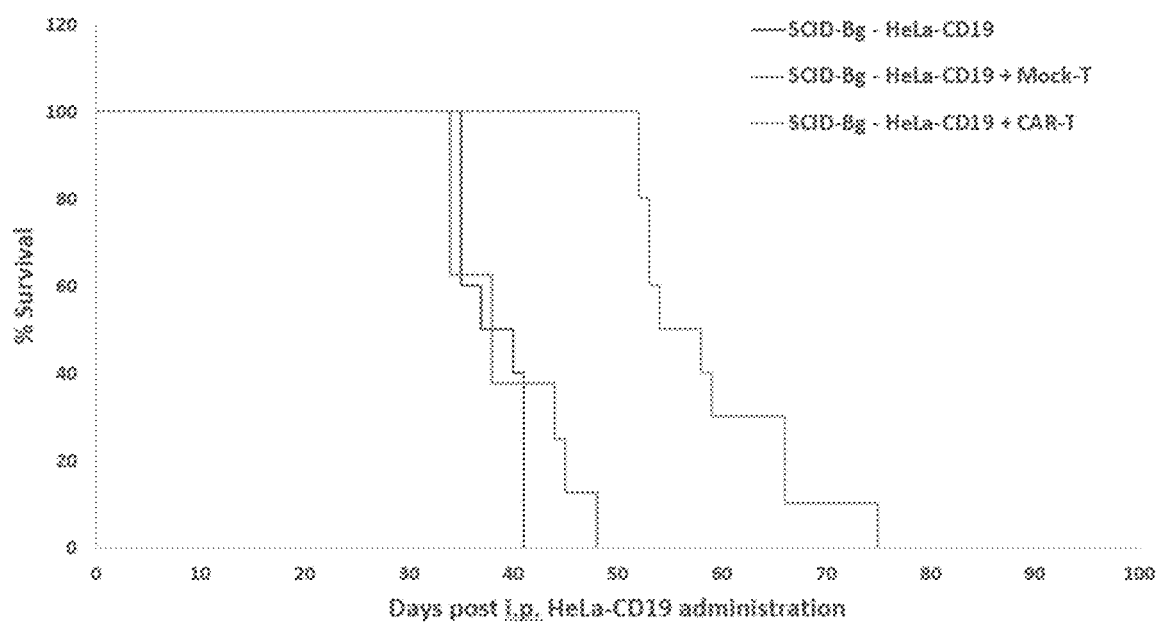
FIGS. 34A-34D. Survival following CAR T-cell therapy alone or with co-administration of apoptotic cells.
Figure 34B:
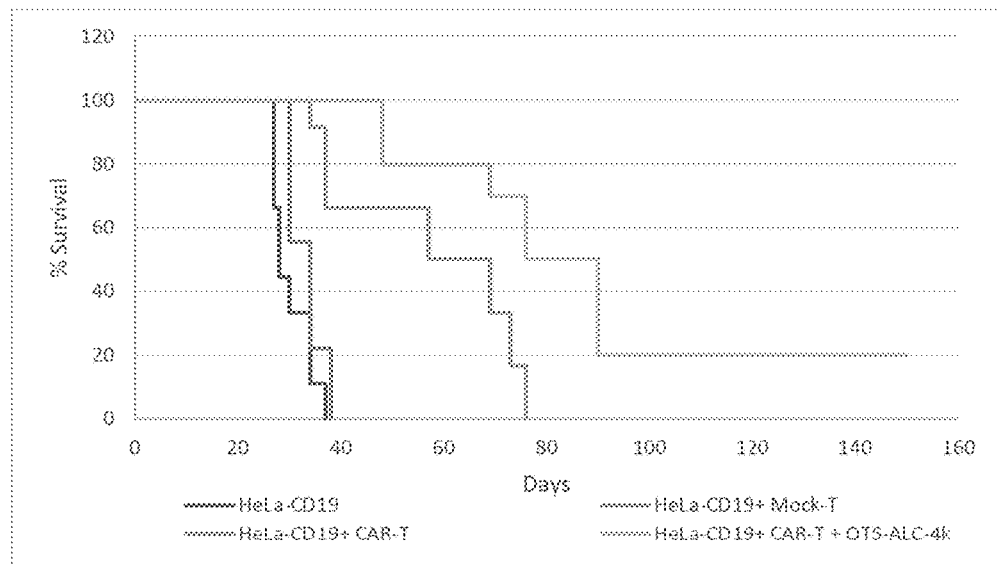
Figure 34C:
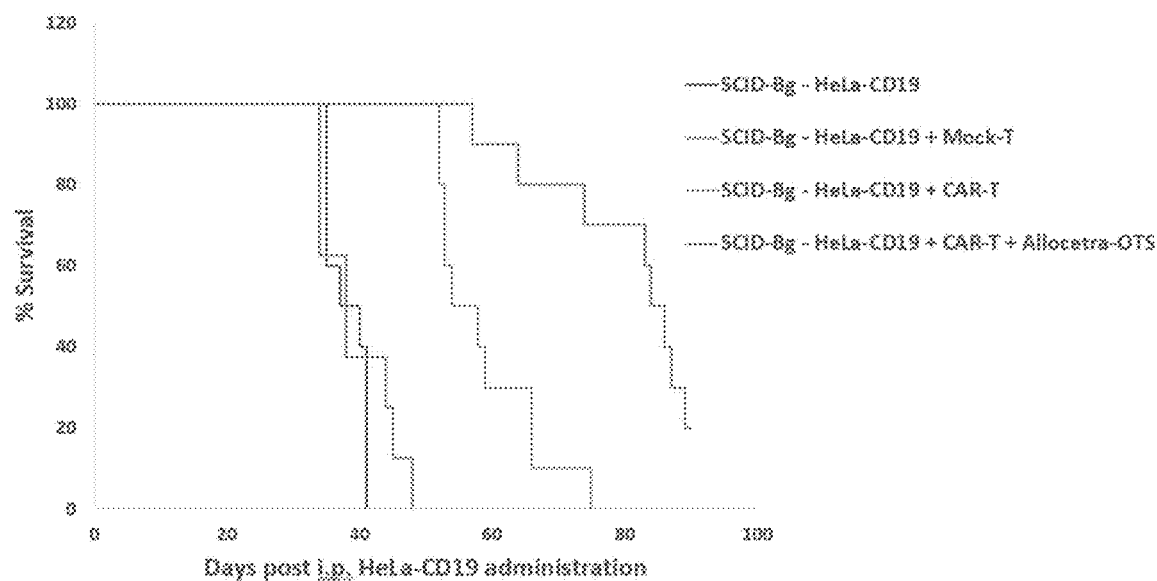
Figure 34D:
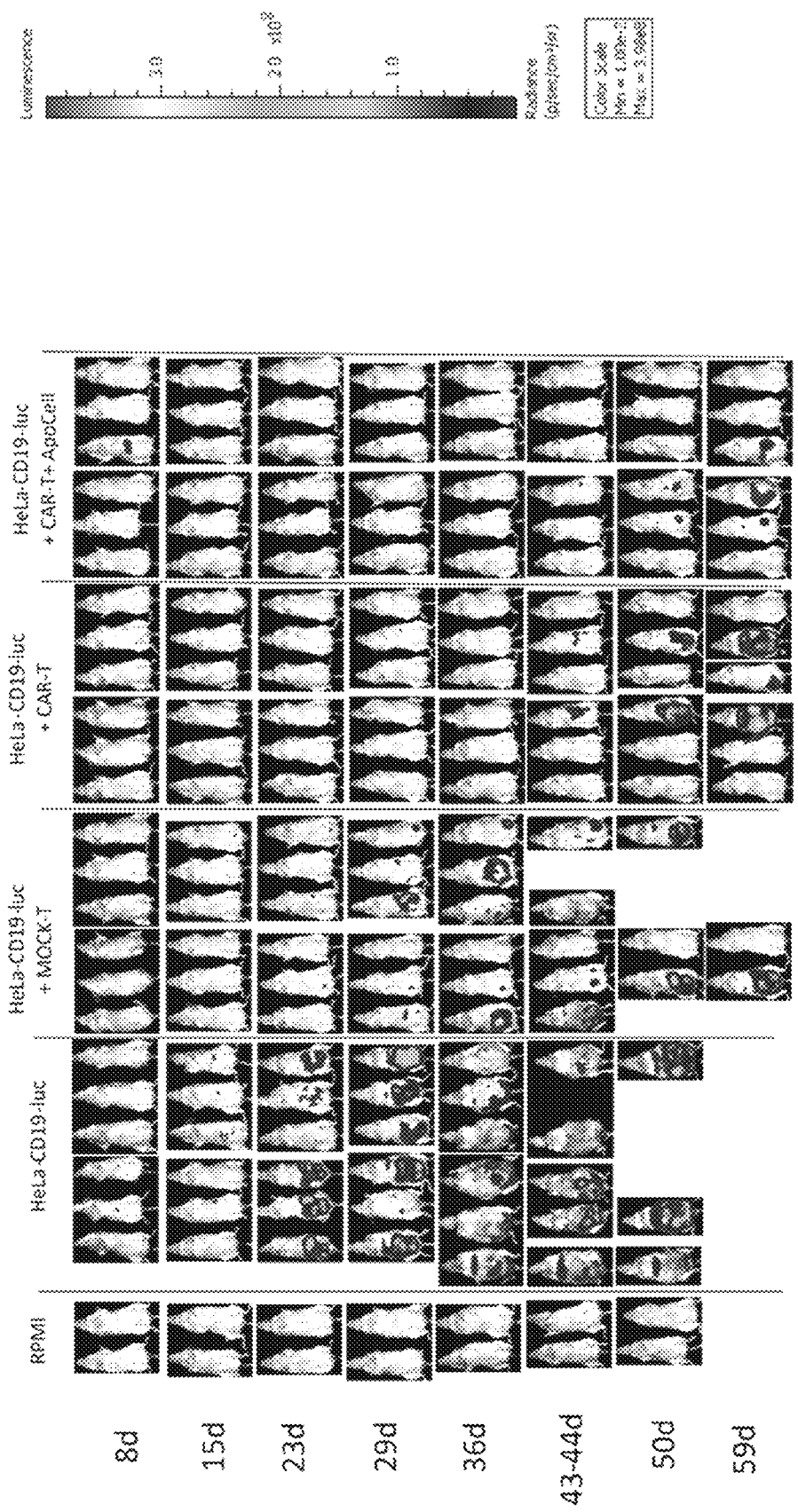

In this model mice survived about 30±5 days (27-37) and died from the formation of a solid tumor in the peritoneal cavity followed by accumulation of bloody peritoneal fluid and clinical deterioration. Mock treatment showed no significant amelioration of the solid tumor or change of mouse survival (34±4 days; range 30-38). CAR T cell therapy alone significantly ameliorated mouse survival to 55±11 (range 34-76, p<0.05) (FIG. 34A). However, when mice received co-administration of apoptotic cells and CAR T cells, a further significant increase in survival was seen, with survival reaching 70±20 days (range 48-90, P<0.05) when compared to CAR T cell alone. Furthermore, 2/10 mice were disease free for 150 days (end of experiment). FIG. 34B (representative of 5 separate experiments) shows survival curves of peritoneal solid tumor Hela-CD19 under control and treatment conditions. FIG. 34C presents survival curves showing that apoptotic cells (Allocetra-OTS) dramatically enhanced CAR T anti-cancer function. FIG. 34C shows progression of tumor as visualized by an in vivo imaging system (IVIS), representative of the results used for the survival curves of FIG. 34B. Spread of the tumor can be visualized as early as day 15 (Hela-CD19-Luc) whereas mice treated with CAR do not show any tumor spread until day 43. When mice received apoptotic cells, most mice do not show tumor spread until day 50 and tumor size (see scale for correlation) is clearly smaller as reflected in survival curve (FIG. 34B).

Figure 35A:
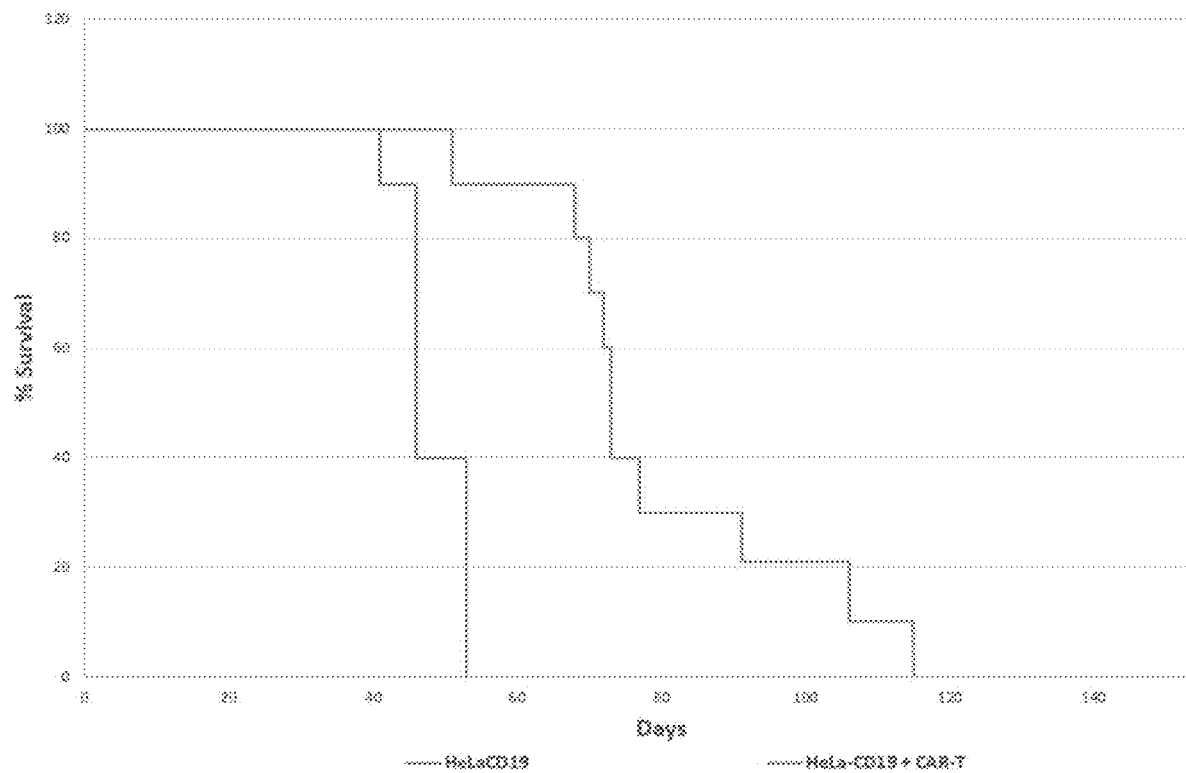
FIGS. 35A-35B. Survival following CAR T-cell therapy alone or with co-administration of apoptotic cells.
Figure 35B:
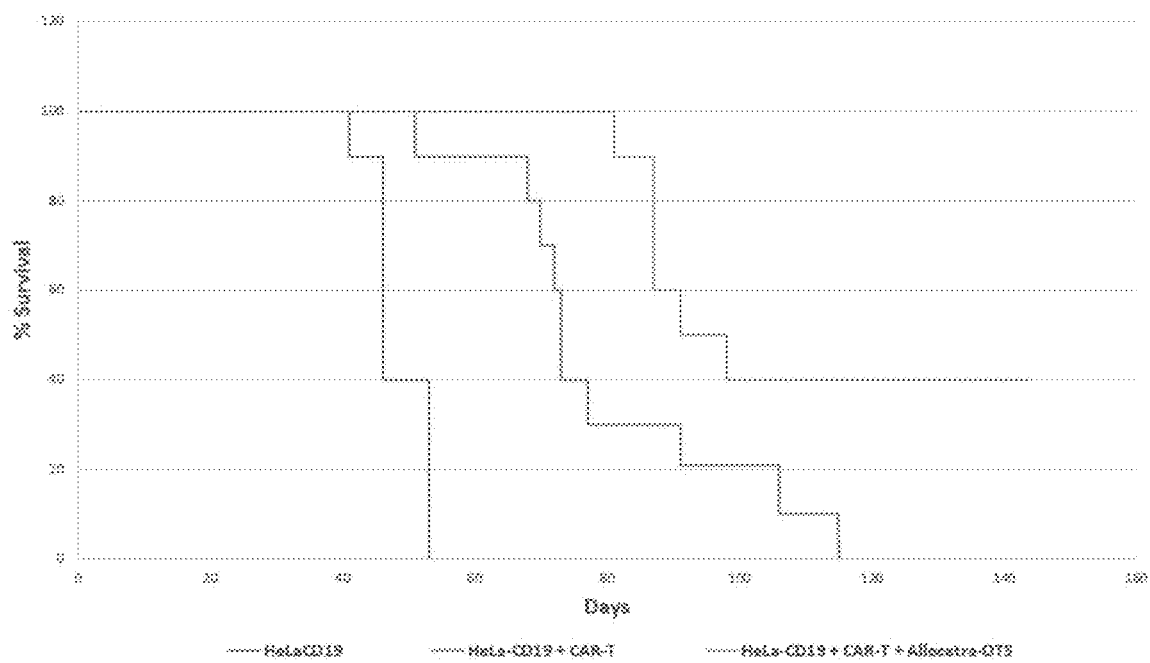

FIGS. 35A and 35B provide addition evidence of enhancement of the effect of CART cells by co-administration with early apoptotic cells (Allocetra-OTS), wherein survival of mice bearing a tumor burden was extended with addition of apoptotic cell administration. SCID-Bg mice were injected intra-peritoneally with human HeLa-CD19-luciferase cells, followed by CD19-CAR T cells, wherein administration of CAR-T cells increased the percent survival and extended the life expectancy of the mice (FIG. 35A). A similar experiment, wherein SCID-Bg mice were injected intra-peritoneally with human HeLa-CD19-luciferase cells, followed by CD19-CAR T cells, with or without apoptotic cells (Allocetra-OTS) showed an even greater increased percentage of survival over time, wherein some mice (HeLa-CD19+ CAR-T+apoptotic cells) were still alive at 140 days (FIG. 35B).

Figure 36A:
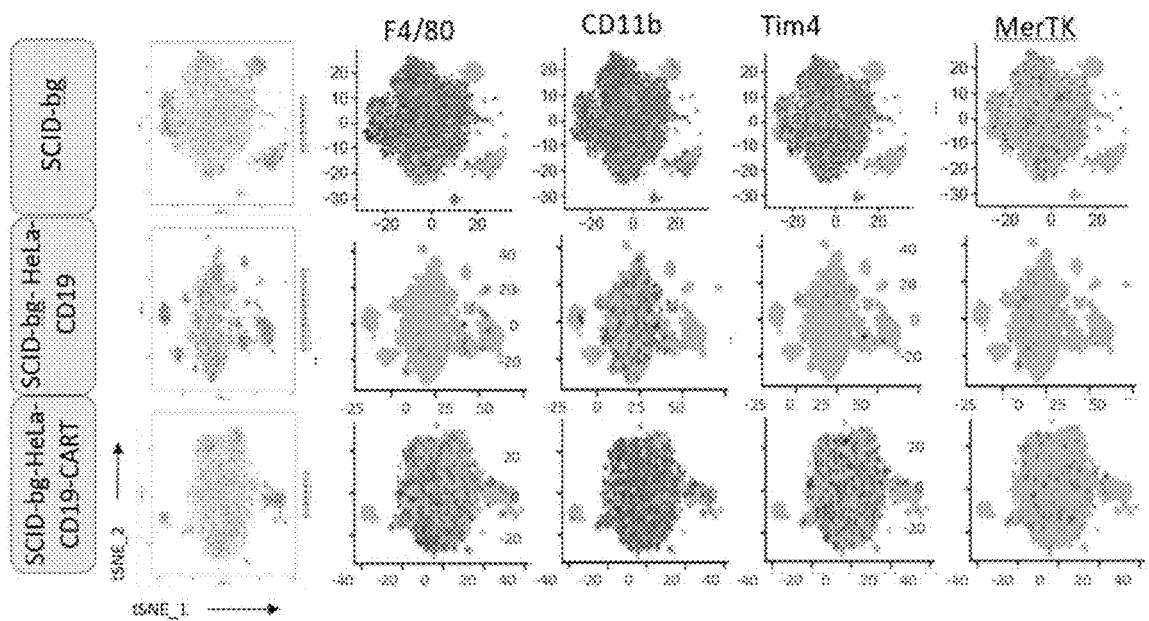
FIGS. 36A-36C. FACS analysis of macrophages.
Figure 36B:
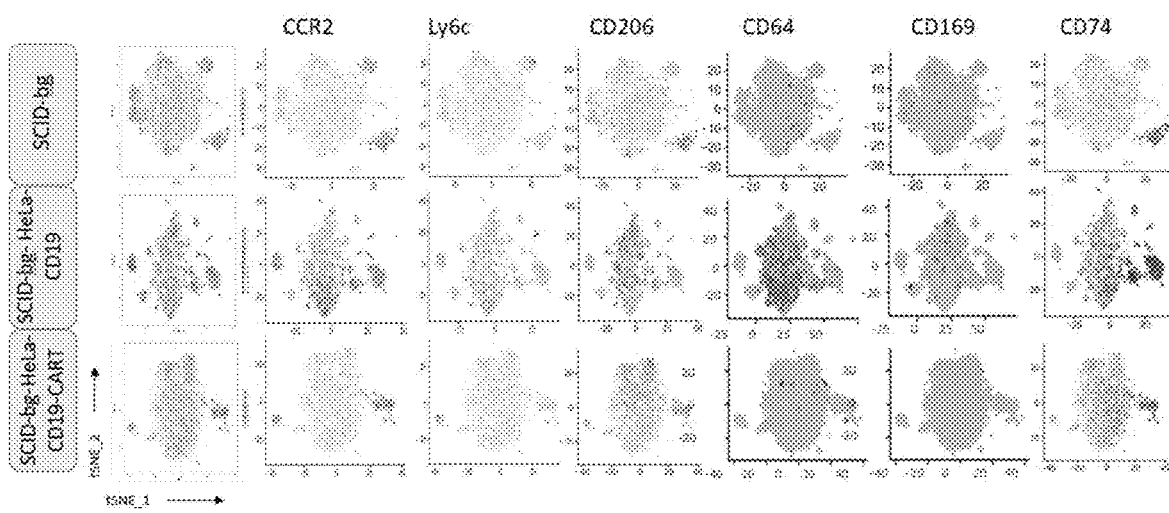
Figure 36C:
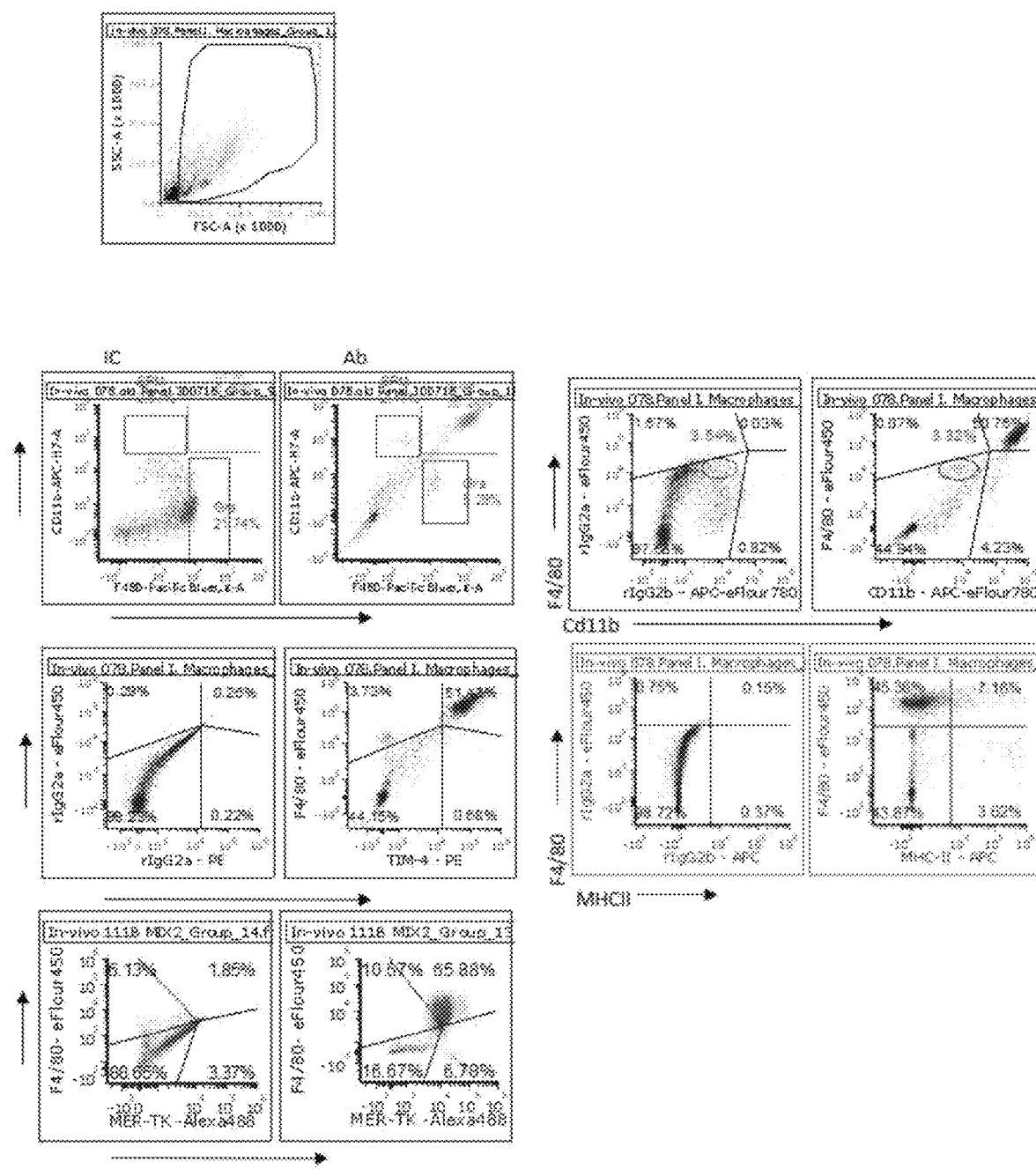

Analysis of the macrophage subpopulations over the course of treatment revealed surprising results. FIG. 36A shows that based on the expression of the residential peritoneal macrophage signature of markers F4/80, CD11b, Tim4, and MerTK, resident macrophages disappear during tumor progression (compare the top (no tumor) and middle (Hela-CD19 tumor) rows). Surprisingly, treatment with CAR-T cells resulted in the reappearance of resident macrophages (bottom row +CART). Concurrently, measure of the expression of tumor associated macrophage (TAM) signature markers CCR2, Ly6c, CD206, CD64, CD169, and CD74 (FIG. 36B) showed that TAM appeared during tumor progression (compare the top (no tumor) and middle (Hela-CD19 tumor) rows). Treatment with CART cells resulted in the reduction and disappearance of these TAM (bottom row +CART). Resident macrophages in SCID mice were identified as mostly large peritoneal macrophages (LPM) (FIG. 36C). The results shown in FIGS. 36A-36C show that all of the F4/80$^{high}$ cells are CD11b positive, and that only 13.5% of the F4/80$^{high}$ cells were MHCII positive. Thus, the population of resident macrophages in SCID mice were F4/80$^{high}$/TIM4$^+$, MHCII$^{low}$, MerTK$^+$/CD11b$^+$, and during tumor progression this population disappears, and TAM, monocytes, and dendritic cells appear. Treatment with CAR T-cells reverses this effect, wherein resident macrophages reappear, and TAM disappear.

Figure 37:
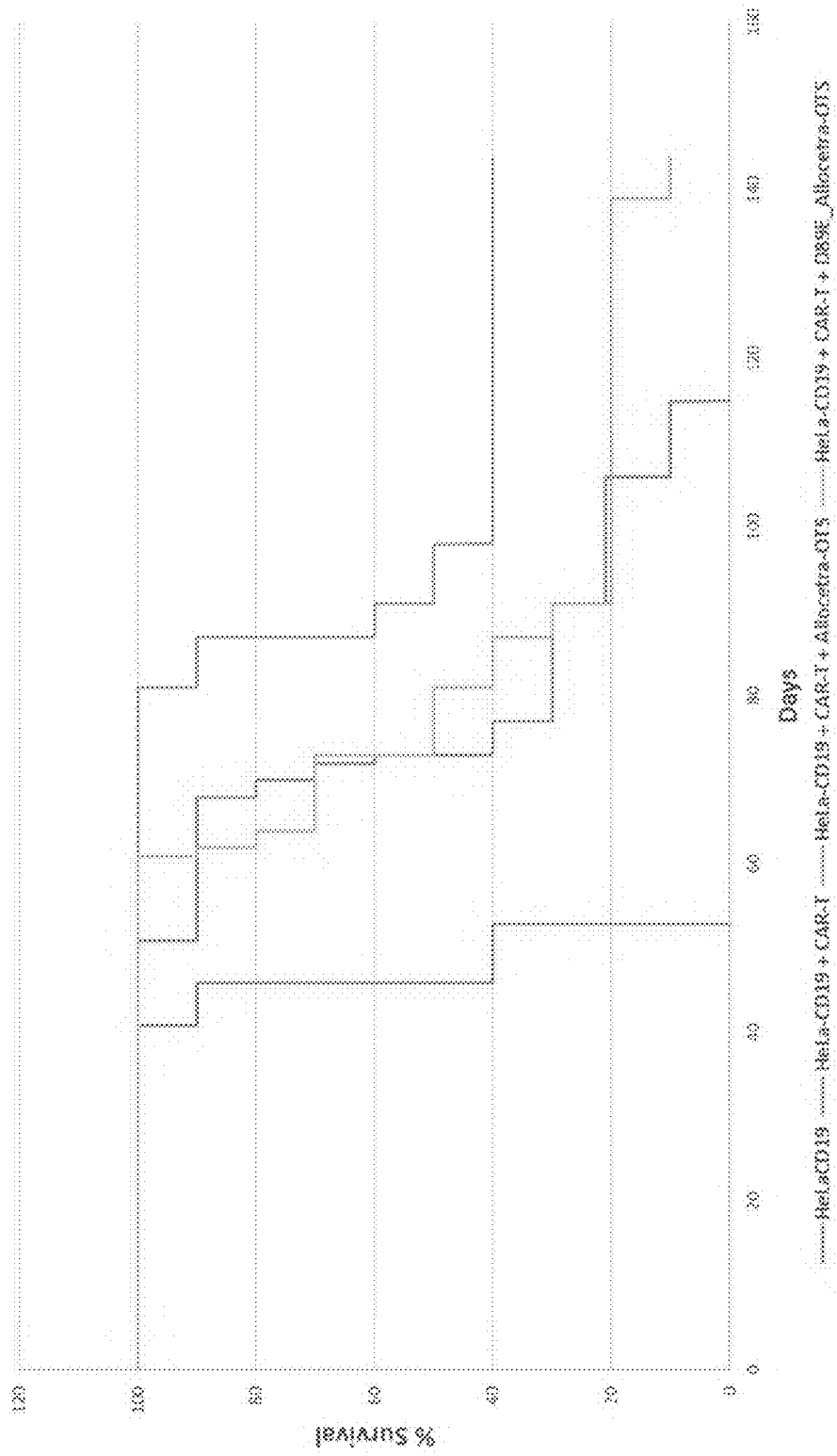
FIG. 37. Percent (%) curves following CAR T-cell therapy alone or with co-administration of apoptotic cells or opsonized apoptotic cells. The figure shows survival curves of peritoneal solid tumor Hela-CD19, treated by CAR T-cell therapy alone or CAR T-cell therapy plus co-administration of apoptotic cells or opsonized apoptotic cells. (SCID-Bg-HeLa-CD19: control no treatment; SCID-Bg-HeLa-CD19+ CAR-T: includes treatment with CAR T-cells; SCID-Bg-Hela-CD19+CAR-T+Allocetra-OTS: treatment was with CAR T-cells and "off the shelf" apoptotic cells irradiated with 4000 rad; SCID-Bg-Hela-CD19+CAR-T+D89E_Allocetra-OTS: treatment was with CAR T-cells and "off the shelf" opsonized apoptotic cells irradiated with 4000 rad).

To address the role of the resident macrophages present following CAR T cell, SCID-Bg mice were injected intraperitoneally with human HeLa-CD19-luciferase cells, followed by CD19-CAR T cells, with or without apoptotic cells (Allocetra-OTS), or opsonized apoptotic cells (D89E_Allocetra-OTS) that avoids clearance of apoptotic cells by resident macrophages. The results unexpectedly showed that in the absence of clearance of administered apoptotic cells (Hela-CD19+ CAR-T+D89E_Allocetra-OTS) the percent survival of mice bearing a tumor burden was reduced to almost the level seen with CAR T cell administration alone (Hela-CD19+CAR-T) (FIG. 37). This result suggests resident macrophages may, in some embodiments, be an effective tool during cancer therapy, wherein resident macrophage markers could be targeted to trigger resident macrophage activation following CAR T-cell administration.

Summary:

As discussed, Chimeric Antigen Receptor (CAR) T cell therapy is a novel and innovative immunotherapy. CAR-T cells are genetically engineered T cells, carrying MHC independent specific antigen receptor and co-stimulatory molecule which can activate an immune response to a cancer specific antigen. This therapy showed great results in hematological malignancies but could not achieve a similar efficacy in solid tumors both hematological and non-hematological. Likely reasons for this failure may be lack of antigens, poor trafficking, and hostile tumor microenvironment. Here, the effect of CAR T cell therapy on human peritoneal solid tumor model in SCID mice was demonstrated, wherein the synergistic effect of apoptotic cell infusion on the anti-cancer action of CAR T-cell therapy was significant.

The results presented here, show that mice survived 30±5 days, and mock treatment non significantly ameliorated their survival to 34±4 days. CAR T cell therapy significantly ameliorated their survival to 55±11 days. Single-cell analysis confirmed by flow cytometry revealed that resident macrophages that were associated with anti-tumor activity, completely disappeared during tumor progression, and reappeared during successful CAR T therapy. Apoptotic cells injected during tumor progression were able to stabilize the presence of macrophages, as confirmed by single cell and flow cytometry analysis, and synergize with the anti-tumor CAR-T cell effect, resulting in significantly increased anti-tumor macrophage population and increased survival to 75±10 days ($p<0.05$).

While certain features disclosed herein have been illustrated and described herein, many modifications, substitutions, changes, and equivalents will now occur to those of ordinary skill in the art. It is, therefore, to be understood that the appended claims are intended to cover all such modifications and changes as fall within the true spirit disclosed herein.

What is claimed is:

1. A method of treating a cancer or a tumor in a subject, wherein said tumor or cancer comprises a metastasis of the tumor or cancer and wherein said method of treating slows, reduces, inhibits, or eliminates metastatic spread of a cancer or tumor in the subject, said method comprising a step of administering a composition comprising a mononuclear-enriched early apoptotic cell population to said subject, wherein said mononuclear-enriched early apoptotic cell population comprises peripheral blood mononuclear cells and analysis shows the population is ≥40% AnnexinV+ and ≤15% propidium iodide+, and wherein said method further comprises an additional immune therapy comprising administrating a composition comprising CAR T-cells, wherein said method slows, reduces, inhibits, or eliminates metastatic spread of the cancer or tumor in said subject, or any combination thereof, compared with a subject not administered the compositions comprising the mononuclear-enriched early apoptotic cell population and the CAR T-cells.

2. The method of claim 1, wherein the size or the growth rate or a combination thereof, of said cancer or tumor is reduced.

3. The method of claim 1, wherein the survival of said subject is increased.

4. The method of claim 1, wherein said early apoptotic cell population comprises
decreased non-quiescent non-apoptotic cells, suppressed cellular activation of any living non-apoptotic cells, or reduced proliferation of any living non-apoptotic cells, or any combination thereof.

5. The method of claim 1, wherein said early apoptotic cell population comprises an irradiated and pooled population of early apoptotic cells, wherein said irradiation is post induction of apoptosis.

6. The method of claim 1, wherein said subject is a human subject.

7. The method of claim 1, wherein said cancer or tumor comprises a solid tumor.

8. The method of claim 1, wherein said administering comprises a single infusion of said early apoptotic cell population.

9. The method of claim 1, wherein said administering comprises multiple infusions of said apoptotic cell population.

10. The method of claim 1, further comprising administering, a chemotherapeutic agent or an immune modulator to said subject, or any combination thereof.

11. The method of claim 10, wherein said a chemotherapeutic agent, or an immune modulator is administered prior to, concurrent with, or following administration of said early apoptotic cells.

12. The method of claim 1, wherein said method increases the efficacy of said CAR T-cells, compared with a subject administered CAR T-cells and not administered early apoptotic cells.

13. The method of claim 1, wherein said method comprises a first-line therapy.

14. The method of claim 1, wherein said method comprises an adjuvant therapy.

15. The method of claim 1, wherein said method reduces the minimal residual disease, increases remission, increases remission duration, reduces tumor relapse rate, or any combination thereof.

16. The method of claim 1, wherein said composition comprising CAR T cells is administered prior to, concurrent with, or following administration of said early apoptotic cells.

17. The method of claim 4, wherein said early apoptotic cell population comprises an irradiated population of early apoptotic cells, wherein said irradiation is post induction of apoptosis.

* * * * *